US012616744B2

(12) United States Patent
Emini et al.

(10) Patent No.: US 12,616,744 B2
(45) **Date of Patent: *May 5, 2026**

(54) IMMUNOGENIC COMPOSITIONS COMPRISING CONJUGATED CAPSULAR SACCHARIDE ANTIGENS AND USES THEREOF

(71) Applicant: Pfizer Inc., New York, NY (US)

(72) Inventors: Emilio Anthony Emini, Dresher, PA (US); Wendy Jo Watson, Blue Bell, PA (US); Avvari Krishna Prasad, Chapel Hill, NC (US); Mingming Han, Holly Springs, NC (US); Jin-Hwan Kim, Suffern, NY (US); Jianxin Gu, Paramus, NJ (US); Yu-ying Yang, Stamford, CT (US); Rajesh Kumar Kainthan, Tappan, NY (US); David Cooper, Monroe, NY (US); Michael William Pride, Staten Island, NY (US); Kathrin Ute Jansen, New York, NY (US)

(73) Assignee: PFIZER INC., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/531,055

(22) Filed: Dec. 6, 2023

(65) Prior Publication Data

US 2024/0374699 A1 Nov. 14, 2024

Related U.S. Application Data

(60) Division of application No. 17/194,224, filed on Mar. 6, 2021, now Pat. No. 11,872,274, which is a division of application No. 16/899,738, filed on Jun. 12, 2020, now Pat. No. 11,090,375, which is a continuation of application No. 15/286,696, filed on Oct. 6, 2016, now Pat. No. 11,160,855, which is a division of application No. 14/597,488, filed on Jan. 15, 2015, now Pat. No. 9,492,559.

(60) Provisional application No. 61/929,547, filed on Jan. 21, 2014.

(51) Int. Cl.

| | |
|---|---|
| ***A61K 39/09*** | (2006.01) |
| ***A61K 47/64*** | (2017.01) |
| *A61K 39/00* | (2006.01) |

(52) U.S. Cl.

CPC .......... *A61K 39/092* (2013.01); *A61K 47/646* (2017.08); *A61K 2039/55505* (2013.01); *A61K 2039/6037* (2013.01); *A61K 2039/70* (2013.01); *Y02A 50/30* (2018.01)

(58) Field of Classification Search

CPC .................................................... A61K 39/092

See application file for complete search history.

(56) References Cited

U.S. PATENT DOCUMENTS

| | | | | |
|---|---|---|---|---|
| 5,623,057 | A | 4/1997 | Kniskern et al. | |
| 5,855,901 | A | 1/1999 | Malcolm | |
| 7,217,791 | B2 | 5/2007 | Chen et al. | |
| 8,192,746 | B2 | 6/2012 | Caulfield et al. | |
| 9,981,029 | B2 | 5/2018 | Park et al. | |
| 11,090,375 | B2 * | 8/2021 | Emini | A61K 47/646 |
| 11,160,855 | B2 * | 11/2021 | Emini | A61K 39/092 |
| 11,872,274 | B2 * | 1/2024 | Emini | A61K 39/092 |
| 2007/0110762 | A1 | 5/2007 | Jessouroun et al. | |
| 2007/0253984 | A1 | 11/2007 | Khandke et al. | |
| 2008/0069835 | A1 | 3/2008 | Boutriau et al. | |
| 2009/0010959 | A1 | 1/2009 | Biemans et al. | |
| 2010/0074922 | A1 | 3/2010 | Biemans et al. | |
| 2010/0209450 | A1 | 8/2010 | Biemans et al. | |
| 2012/0276137 | A1 | 11/2012 | Freese et al. | |
| 2012/0301502 | A1 | 11/2012 | Caulfield et al. | |
| 2012/0321658 | A1 | 12/2012 | Biemans et al. | |
| 2015/0231225 | A1 | 8/2015 | Shin et al. | |

FOREIGN PATENT DOCUMENTS

| | | | |
|---|---|---|---|
| CN | 101590224 | A | 12/2009 |
| CN | 101785857 | B | 7/2010 |
| CN | 102068690 | A | 5/2011 |
| CN | 101024079 | B | 2/2012 |
| IN | 1330/MUM/2010 | B | 2/2013 |
| WO | 1996/040225 | A1 | 12/1996 |
| WO | 2003/051392 | A2 | 6/2003 |
| WO | 2007/000314 | A2 | 1/2007 |
| WO | 2007/000327 | A1 | 1/2007 |

(Continued)

OTHER PUBLICATIONS

Breukels, M., et al.,"Pneumococcal Conjugate Vaccine Primes for Polysaccharide-Inducible IgG2 Antibody Response in Children with Recurrent Otitis Media Acuta," Journal of Infectious Diseases, 1999, 179:1152-6.

Brief for Appellant (Pfizer Inc.) in appeals from PTAB in Case Nos. IPR2017-02131, IPR2017-02132, IPR2017-02136, IPR2017-02138, IPR2018-00187 to Court of Appeals for the Federal Circuit in *Pfizer Inc.* v. *Sanofi Pasteur Inc.* (Case No. 19-1871, filed Jul. 18, 2022; including addendum, 525 pages).

Brief for Appellant (Pfizer Inc.) in appeals from PTAB in Case Nos. IPR2017-02131, IPR2017-02132, IPR2018-00187 to Court of Appeals for the Federal Circuit in *Pfizer Inc.* v. *Sanofi Pasteur Inc.* (Case No. 24-2199, filed Jan. 22, 2025; including addendum, 254 pages).

(Continued)

*Primary Examiner* — Albert M Navarro

(57) ABSTRACT

The present invention relates to new immunogenic compositions comprising conjugated *Streptococcus pneumoniae* capsular saccharide antigens (glycoconjugates) and uses thereof. Immunogenic compositions of the present invention will typically comprise at least one glycoconjugate from a *S. pneumoniae* serotype not found in PREVNAR®, SYNFLORIX® and/or PREVNAR 13®. The invention also relates to vaccination of human subjects, in particular infants and elderly, against pneumococcal infections using said novel immunogenic compositions.

19 Claims, 16 Drawing Sheets

Specification includes a Sequence Listing.

(56) References Cited

FOREIGN PATENT DOCUMENTS

| | | | |
|---|---|---|---|
| WO | 2007/000341 | A2 | 1/2007 |
| WO | 2007/000342 | A2 | 1/2007 |
| WO | 2007/000343 | A2 | 1/2007 |
| WO | 2007/071710 | A2 | 6/2007 |
| WO | 2007/127665 | A2 | 11/2007 |
| WO | 2008/079732 | A2 | 7/2008 |
| WO | 2009/000824 | A2 | 12/2008 |
| WO | 2010/080484 | A1 | 7/2010 |
| WO | 2011/110241 | A1 | 9/2011 |
| WO | 2014/038879 | A1 | 3/2014 |
| WO | 2014/060385 | A1 | 4/2014 |
| WO | 2014/060389 | A2 | 4/2014 |
| WO | 2015/175355 | A1 | 11/2015 |

OTHER PUBLICATIONS

Croxtall, J., and Keating, G., "Pneumococcal Polysaccharide Protein D-Conjugate Vaccine (Synflorix; PHiD-CV)," Pediatric Drugs, 2009, 11(5): 349-357.

Dagan, R. et al., "Safety and immunogenicity of tetravalent pneumococcal vaccines containing 6B, 14, 19F and 23F polysaccharides conjugated to either tetanus toxoid or diphtheria toxoid in young infants and their booster ability by native polysaccharide antigens," Pediatric Infectious Disease Journal, 1997, 16(11):18pages.

Dagan, R., et al., "Reduction of Nasopharyngeal Carriage of Pneumococci during the Second Year of Life by a Heptavalent Conjugate Pneumococcal Vaccine," Journal of Infectious Diseases, 1996, 174:1271-8.

Fedson, D., et al, "Pneumococcal polysaccharide vaccination for adults: new perspectives for Europe," Expert Review of Vaccines, 2011, 10(8):1143-1167.

Givon-Lavi, N., et al., "Immunogenicity of Alternative Regimens of the Conjugated 7-Valent Pneumococcal Vaccine," Pediatric Infectious Disease Journal, 2010, 29(8):756-762.

Gruber, W., et al., "Development and clinical evaluation of Prevnar 13, a 13-valent pneumocococcal CRM197 conjugate vaccine," Annals of the NY Academy of Sciences, 2012, 1263:15-26.

Opinion of the Court of Appeals for the Federal Circuit in *Pfizer Inc.* v. *Sanofi Pasteur Inc.* (Case No. 19-1871, decided Mar. 5, 2024; appeals from PTAB in Case Nos. IPR2017-02131, IPR2017-02132, IPR2017-02136, IPR2017-02138, IPR2018-00187; 20 pages).

Pace, D. "Glycoconjugate vaccines," Expert Opinion on Biological Therapy, 2013, 13(1):11-33.

Pobre, K., et al., "Carrier priming or suppression: Understanding carrier priming enhancement of anti-polysaccharide antibody response to conjugate vaccines," Vaccine, 2014, 32:1423-1430.

Poolman, J. et al., "The history of pneumococcal conjugate vaccine development: dose selection," Expert Review of Vaccines, 2014, 12(12):1379-1394.

PTAB Final Written Decision on Remand Denying Patent Owner's Motion to Amend as to Proposed Substitute Claims 48 and 49 in *Sanofi Pasteur Inc.* v. *Pfizer Inc.* (Case Nos. IPR2017-02131, IPR2017-02132, IPR2018-00187, filed Jun. 10, 2024; 35 pages).

Public Assessment Report for Prevnar 13 in connection with review of application for marketing authorization of Prevnar 13 by the Thailand Food and Drug Administration (document undated).

Response to Notices of Opposition filed by Patent Owner (Pfizer Inc.) in Opposition against EP 3096785 B1 Jan. 3, 2022; 32 pages.

WHO Expert Committee on Biological Standardization, Technical Report Series 977, 60th Report, Copyright 2013, 242 pages.

Written Submission Before Oral Proceedings filed by Patent Owner (Pfizer Inc.) in Opposition against EP 3096785 B1 Oct. 2, 2024; 13 pages.

* cited by examiner

→4)-β-D-Glc*p*A-(1→4)-β-D-Glc*p*-(1→4)-α-D-Glc*p*-(1→4)-α-D-Gal*p*-(1→

MW ($H^+$) = 662.553 $C_{24}H_{38}O_{21}$

MW ($Na^+$) = 684.534 $C_{24}H_{37}O_{21}Na_1$

Mw (Na) = 950.7

Ac (100%) Ac (50%) at positions 4, 6 of β-D-Gal*p*; Ac (60%) Ac (50%) at positions 2, 3 of α-D-Glc*p*

[→3)-β-D-Gal*p*-(1→4)-β-D-Glc*p*-(1→6)-α-D-Glc*p*-(1→4)-α-D-Gal*p*-(1→]$_n$

4 ← $OPO_3^-$-1-D-glycerol

R = Ac (C6 = 55%, C4 = 12%, C3 = 12%, C2 = 6%)

Ac= Acetyl

→6)-D-Glcp NAc-β-(1→3)-D-Galp-β-(1→4)-D-Glcp-β-(1→

D-Galp-α-(1→2)-D-Galp(3-OPO$_3$-R$^1$)-β-(1→4

R$^1$ = CH(CH$_2$OH)$_2$

$C_{37}H_{61}NNaO_{31}P$, MW=1069.8

Pn 33F

→3)-β-D-Galp-(1→3)-α-D-Galp-(1→3)-β-D-Galf-(1→3)-β-D-Glcp-(1→5)-β-D-Galf-(1→

2 ← α-D-Galp (on α-D-Galp)

2 ← $Ac_{0.5}$ (on β-D-Galf)

SEQUENCE LISTING

```
Sequence total quantity: 40
SEQ ID NO: 1            moltype = DNA  length = 21
FEATURE                 Location/Qualifiers
misc_feature            1..21
                        note = "A class" CpG oligonucleotide
source                  1..21
                        mol_type = other DNA
                        organism = synthetic construct
SEQUENCE: 1
ggggacgacg tcgtgggggg g                                            21

SEQ ID NO: 2            moltype = DNA  length = 21
FEATURE                 Location/Qualifiers
misc_feature            1..21
                        note = "A class" CpG oligonucleotide
source                  1..21
                        mol_type = other DNA
                        organism = synthetic construct
SEQUENCE: 2
ggggacgacg tcgtgggggg g                                            21

SEQ ID NO: 3            moltype = DNA  length = 21
FEATURE                 Location/Qualifiers
misc_feature            1..21
                        note = "B class" CpG oligonucleotide
source                  1..21
                        mol_type = other DNA
                        organism = synthetic construct
SEQUENCE: 3
tcgtcgtttt tcggtgcttt t                                            21

SEQ ID NO: 4            moltype = DNA  length = 21
FEATURE                 Location/Qualifiers
misc_feature            1..21
                        note = "B class" CpG oligonucleotide
source                  1..21
                        mol_type = other DNA
                        organism = synthetic construct
SEQUENCE: 4
tcgtcgtttt tcggtcgttt t                                            21
```

-continued

```
SEQ ID NO: 5            moltype = DNA  length = 24
FEATURE                 Location/Qualifiers
misc_feature            1..24
                        note = "B class" CpG oligonucleotide
source                  1..24
                        mol_type = other DNA
                        organism = synthetic construct
SEQUENCE: 5
tcgtcgtttt gtcgttttgt cgtt                                        24

SEQ ID NO: 6            moltype = DNA  length = 24
FEATURE                 Location/Qualifiers
misc_feature            1..24
                        note = "B class" CpG oligonucleotide
source                  1..24
                        mol_type = other DNA
                        organism = synthetic construct
SEQUENCE: 6
tcgtcgtttc gtcgttttgt cgtt                                        24

SEQ ID NO: 7            moltype = DNA  length = 24
FEATURE                 Location/Qualifiers
misc_feature            1..24
                        note = "B class" CpG oligonucleotide
source                  1..24
                        mol_type = other DNA
                        organism = synthetic construct
SEQUENCE: 7
tcgtcgtttt gtcgtttttt tcga                                        24

SEQ ID NO: 8            moltype = DNA  length = 21
FEATURE                 Location/Qualifiers
misc_feature            1..21
                        note = B-Class oligonucleotide
source                  1..21
                        mol_type = other DNA
                        organism = synthetic construct
SEQUENCE: 8
tcgtcgtttt tcggtgcttt t                                           21

SEQ ID NO: 9            moltype = DNA  length = 21
FEATURE                 Location/Qualifiers
misc_feature            1..21
                        note = B-Class oligonucleotide
source                  1..21
                        mol_type = other DNA
                        organism = synthetic construct
SEQUENCE: 9
tcgtcgtttt tcggtcgttt t                                           21

SEQ ID NO: 10           moltype = DNA  length = 24
FEATURE                 Location/Qualifiers
misc_feature            1..24
                        note = B-Class oligonucleotide
source                  1..24
                        mol_type = other DNA
                        organism = synthetic construct
SEQUENCE: 10
tcgtcgtttt gtcgttttgt cgtt                                        24

SEQ ID NO: 11           moltype = DNA  length = 24
FEATURE                 Location/Qualifiers
misc_feature            1..24
                        note = B-Class oligonucleotide
source                  1..24
                        mol_type = other DNA
                        organism = synthetic construct
SEQUENCE: 11
tcgtcgtttc gtcgttttgt cgtt                                        24

SEQ ID NO: 12           moltype = DNA  length = 24
FEATURE                 Location/Qualifiers
misc_feature            1..24
                        note = B-Class oligonucleotide
source                  1..24
                        mol_type = other DNA
                        organism = synthetic construct
SEQUENCE: 12
tcgtcgtttt gtcgtttttt tcga                                        24
```

```
SEQ ID NO: 13          moltype = DNA  length = 22
FEATURE                Location/Qualifiers
misc_feature           1..22
                       note = C class CpG Oligonucleotide
source                 1..22
                       mol_type = other DNA
                       organism = synthetic construct
SEQUENCE: 13
tcgcgtcgtt cggcgcgcgc cg                                          22

SEQ ID NO: 14          moltype = DNA  length = 23
FEATURE                Location/Qualifiers
misc_feature           1..23
                       note = C class CpG Oligonucleotide
source                 1..23
                       mol_type = other DNA
                       organism = synthetic construct
SEQUENCE: 14
tcgtcgacgt tcggcgcgcg ccg                                         23

SEQ ID NO: 15          moltype = DNA  length = 21
FEATURE                Location/Qualifiers
misc_feature           1..21
                       note = C class CpG Oligonucleotide
source                 1..21
                       mol_type = other DNA
                       organism = synthetic construct
SEQUENCE: 15
tcggacgttc ggcgcgcgcc g                                           21

SEQ ID NO: 16          moltype = DNA  length = 19
FEATURE                Location/Qualifiers
misc_feature           1..19
                       note = C class CpG Oligonucleotide
source                 1..19
                       mol_type = other DNA
                       organism = synthetic construct
SEQUENCE: 16
tcggacgttc ggcgcgccg                                              19

SEQ ID NO: 17          moltype = DNA  length = 20
FEATURE                Location/Qualifiers
misc_feature           1..20
                       note = C class CpG Oligonucleotide
source                 1..20
                       mol_type = other DNA
                       organism = synthetic construct
SEQUENCE: 17
tcgcgtcgtt cggcgcgccg                                             20

SEQ ID NO: 18          moltype = DNA  length = 20
FEATURE                Location/Qualifiers
misc_feature           1..20
                       note = C class CpG Oligonucleotide
source                 1..20
                       mol_type = other DNA
                       organism = synthetic construct
SEQUENCE: 18
tcgacgttcg gcgcgcgccg                                             20

SEQ ID NO: 19          moltype = DNA  length = 18
FEATURE                Location/Qualifiers
misc_feature           1..18
                       note = C class CpG Oligonucleotide
source                 1..18
                       mol_type = other DNA
                       organism = synthetic construct
SEQUENCE: 19
tcgacgttcg gcgcgccg                                               18

SEQ ID NO: 20          moltype = DNA  length = 18
FEATURE                Location/Qualifiers
misc_feature           1..18
                       note = C class CpG Oligonucleotide
source                 1..18
                       mol_type = other DNA
                       organism = synthetic construct
SEQUENCE: 20
```

```
tcgcgtcgtt cggcgccg                                                18

SEQ ID NO: 21          moltype = DNA  length = 22
FEATURE                Location/Qualifiers
misc_feature           1..22
                       note = C class CpG Oligonucleotide
source                 1..22
                       mol_type = other DNA
                       organism = synthetic construct
SEQUENCE: 21
tcgcgacgtt cggcgcgcgc cg                                           22

SEQ ID NO: 22          moltype = DNA  length = 22
FEATURE                Location/Qualifiers
misc_feature           1..22
                       note = C class CpG Oligonucleotide
source                 1..22
                       mol_type = other DNA
                       organism = synthetic construct
SEQUENCE: 22
tcgtcgtttt cggcgcgcgc cg                                           22

SEQ ID NO: 23          moltype = DNA  length = 22
FEATURE                Location/Qualifiers
misc_feature           1..22
                       note = C class CpG Oligonucleotide
source                 1..22
                       mol_type = other DNA
                       organism = synthetic construct
SEQUENCE: 23
tcgtcgtttt cggcggccgc cg                                           22

SEQ ID NO: 24          moltype = DNA  length = 24
FEATURE                Location/Qualifiers
misc_feature           1..24
                       note = C class CpG Oligonucleotide
source                 1..24
                       mol_type = other DNA
                       organism = synthetic construct
SEQUENCE: 24
tcgtcgtttt acggcgccgt gccg                                         24

SEQ ID NO: 25          moltype = DNA  length = 23
FEATURE                Location/Qualifiers
misc_feature           1..23
                       note = C class CpG Oligonucleotide
source                 1..23
                       mol_type = other DNA
                       organism = synthetic construct
SEQUENCE: 25
tcgtcgtttt cggcgcgcgc cgt                                          23

SEQ ID NO: 26          moltype = DNA  length = 22
FEATURE                Location/Qualifiers
misc_feature           1..22
                       note = C-Class oligonucleotides
source                 1..22
                       mol_type = other DNA
                       organism = synthetic construct
SEQUENCE: 26
tcgcgtcgtt cggcgcgcgc cg                                           22

SEQ ID NO: 27          moltype = DNA  length = 23
FEATURE                Location/Qualifiers
misc_feature           1..23
                       note = C-Class oligonucleotide
source                 1..23
                       mol_type = other DNA
                       organism = synthetic construct
SEQUENCE: 27
tcgtcgacgt tcggcgcgcg ccg                                          23

SEQ ID NO: 28          moltype = DNA  length = 21
FEATURE                Location/Qualifiers
misc_feature           1..21
                       note = C-Class oligonucleotide
source                 1..21
                       mol_type = other DNA
                       organism = synthetic construct
```

-continued

```
SEQUENCE: 28
tcggacgttc ggcgcgcgcc g                                            21

SEQ ID NO: 29          moltype = DNA  length = 19
FEATURE                Location/Qualifiers
misc_feature           1..19
                       note = C-Class oligonucleotide
source                 1..19
                       mol_type = other DNA
                       organism = synthetic construct
SEQUENCE: 29
tcggacgttc ggcgcgccg                                               19

SEQ ID NO: 30          moltype = DNA  length = 20
FEATURE                Location/Qualifiers
misc_feature           1..20
                       note = C-Class oligonucleotide
source                 1..20
                       mol_type = other DNA
                       organism = synthetic construct
SEQUENCE: 30
tcgcgtcgtt cggcgcgccg                                              20

SEQ ID NO: 31          moltype = DNA  length = 20
FEATURE                Location/Qualifiers
misc_feature           1..20
                       note = C-Class oligonucleotide
source                 1..20
                       mol_type = other DNA
                       organism = synthetic construct
SEQUENCE: 31
tcgacgttcg gcgcgcgccg                                              20

SEQ ID NO: 32          moltype = DNA  length = 18
FEATURE                Location/Qualifiers
misc_feature           1..18
                       note = C-Class oligonucleotide
source                 1..18
                       mol_type = other DNA
                       organism = synthetic construct
SEQUENCE: 32
tcgacgttcg gcgcgccg                                                18

SEQ ID NO: 33          moltype = DNA  length = 18
FEATURE                Location/Qualifiers
misc_feature           1..18
                       note = C-Class oligonucleotide
source                 1..18
                       mol_type = other DNA
                       organism = synthetic construct
SEQUENCE: 33
tcgcgtcgtt cggcgccg                                                18

SEQ ID NO: 34          moltype = DNA  length = 22
FEATURE                Location/Qualifiers
misc_feature           1..22
                       note = C-Class oligonucleotide
source                 1..22
                       mol_type = other DNA
                       organism = synthetic construct
SEQUENCE: 34
tcgcgacgtt cggcgcgcgc cg                                           22

SEQ ID NO: 35          moltype = DNA  length = 22
FEATURE                Location/Qualifiers
misc_feature           1..22
                       note = C-Class oligonucleotide
source                 1..22
                       mol_type = other DNA
                       organism = synthetic construct
SEQUENCE: 35
tcgtcgtttt cggcgcgcgc cg                                           22

SEQ ID NO: 36          moltype = DNA  length = 22
FEATURE                Location/Qualifiers
misc_feature           1..22
                       note = C-Class oligonucleotide
source                 1..22
                       mol_type = other DNA
```

-continued

```
                        organism = synthetic construct
SEQUENCE: 36
tcgtcgtttt cggcggccgc cg                                              22

SEQ ID NO: 37           moltype = DNA  length = 24
FEATURE                 Location/Qualifiers
misc_feature            1..24
                        note = C-Class oligonucleotide
source                  1..24
                        mol_type = other DNA
                        organism = synthetic construct
SEQUENCE: 37
tcgtcgtttt acggcgccgt gccg                                            24

SEQ ID NO: 38           moltype = DNA  length = 23
FEATURE                 Location/Qualifiers
misc_feature            1..23
                        note = C-Class oligonucleotide
source                  1..23
                        mol_type = other DNA
                        organism = synthetic construct
SEQUENCE: 38
tcgtcgtttt cggcgcgcgc cgt                                             23

SEQ ID NO: 39           moltype = DNA  length = 23
FEATURE                 Location/Qualifiers
misc_feature            1..23
                        note = P class CpG oligonucleotide
source                  1..23
                        mol_type = other DNA
                        organism = synthetic construct
SEQUENCE: 39
tcgtcgacga tcggcgcgcg ccg                                             23

SEQ ID NO: 40           moltype = DNA  length = 23
FEATURE                 Location/Qualifiers
misc_feature            1..23
                        note = P class CpG oligonucleotide
source                  1..23
                        mol_type = other DNA
                        organism = synthetic construct
SEQUENCE: 40
tcgtcgacga tcggcgcgcg ccg                                             23
```

IMMUNOGENIC COMPOSITIONS COMPRISING CONJUGATED CAPSULAR SACCHARIDE ANTIGENS AND USES THEREOF

CROSS REFERENCE TO RELATED APPLICATION

This application is a divisional application of U.S. application Ser. No. 17/194,224, filed Mar. 6, 2021, issued as U.S. Pat. No. 11,872,274, which is a divisional of U.S. application Ser. No. 16/899,738, filed Jun. 12, 2020, issued as U.S. Pat. No. 11,090,375, which is a continuation of U.S. application Ser. No. 15/286,696, filed Oct. 6, 2016, issued as U.S. Pat. No. 11,160,855, which is a divisional of U.S. application Ser. No. 14/597,488, filed Jan. 15, 2015, issued as U.S. Pat. No. 9,492,559, which claims the priority benefit of U.S. Provisional Application No. 61/929,547, filed Jan. 21, 2014, the entireties of which are hereby incorporated by reference herein.

REFERENCE TO SEQUENCE LISTING

This application includes an electronically submitted Sequence Listing XML file named "PC072040E Sequence Listing.xml" created on Dec. 6, 2023 and having a size of 51,967 bytes. The material in the Sequence Listing XML file "PC072040E Sequence Listing.xml" is part of the specification and is incorporated by reference herein in its entirety.

FIELD OF THE INVENTION

The present invention relates to new immunogenic compositions comprising conjugated capsular saccharide antigens (glycoconjugates) and uses thereof. Immunogenic compositions of the present invention will typically comprise glycoconjugates, wherein the saccharides are derived from serotypes of *Streptococcus pneumoniae*. The invention also relates to vaccination of human subjects, in particular infants and elderly, against pneumococcal infections using said novel immunogenic compositions.

BACKGROUND OF THE INVENTION

Infections caused by pneumococci are a major cause of morbidity and mortality all over the world. Pneumonia, febrile bacteraemia and meningitis are the most common manifestations of invasive pneumococcal disease, whereas bacterial spread within the respiratory tract may result in middle-ear infection, sinusitis or recurrent bronchitis. Compared with invasive disease, the non-invasive manifestations are usually less severe, but considerably more common.

In Europe and the United States, pneumococcal pneumonia is the most common community-acquired bacterial pneumonia, estimated to affect approximately 100 per 100,000 adults each year. The corresponding figures for febrile bacteraemia and meningitis are 15-19 per 100000 and 1-2 per 100,000, respectively. The risk for one or more of these manifestations is much higher in infants and elderly people, as well as immune compromised persons of any age. Even in economically developed regions, invasive pneumococcal disease carries high mortality; for adults with pneumococcal pneumonia the mortality rate averages 10%-20%, whilst it may exceed 50% in the high-risk groups. Pneumonia is by far the most common cause of pneumococcal death worldwide.

The etiological agent of pneumococcal diseases, *Streptococcus pneumoniae* (pneumococcus), is a Gram-positive encapsulated coccus, surrounded by a polysaccharide capsule. Differences in the composition of this capsule permit serological differentiation between about 91 capsular types, some of which are frequently associated with pneumococcal disease, others rarely. Invasive pneumococcal infections include pneumonia, meningitis and febrile bacteremia; among the common non-invasive manifestations are otitis media, sinusitis and bronchitis.

Pneumococcal conjugate vaccines (PCVs) are pneumococcal vaccines used to protect against disease caused by *S. pneumoniae* (pneumococcus). There are currently three PCV vaccines available on the global market: PREVNAR® (called PREVENAR® in some countries) (heptavalent vaccine), SYNFLORIX® (a decavalent vaccine) and PREVNAR 13® (tridecavalent vaccine).

The recent development of widespread microbial resistance to essential antibiotics and the increasing number of immunocompromised persons underline the need for pneumococcal vaccines with even broader protection.

In particular, there is a need to address remaining unmet medical need for coverage of pneumococcal disease due to serotypes not found in PREVNAR 13® and potential for serotype replacement over time. The specific serotypes causing disease beyond the 13 in PREVNAR 13® vary by region, population, and may change overtime due to acquisition of antibiotic resistance, pneumococcal vaccine introduction and secular trends of unknown origin. There is a need for immunogenic compositions that can be used to induce an immune response against additional *Streptococcus pneumoniae* serotypes in humans and in particular in children less than 2 years old.

An object of the new immunogenic compositions of the present invention is to provide for appropriate protection against *S. pneumoniae* serotypes not found in PREVNAR 13®. In one aspect, an object of the immunogenic compositions of the present invention is to provide for appropriate protection against *S. pneumoniae* serotypes not found in PREVNAR® (heptavalent vaccine), SYNFLORIX® and/or PREVNAR 13® while maintaining an immune response against serotypes currently covered by said vaccines.

SUMMARY OF THE INVENTION

The present invention relates to an immunogenic composition comprising at least one glycoconjugate selected from the group consisting of a glycoconjugate from *S. pneumoniae* serotype 15B, a glycoconjugate from *S. pneumoniae* serotype 22F, a glycoconjugate from *S. pneumoniae* serotype 33F, a glycoconjugate from *S. pneumoniae* serotype 12F, a glycoconjugate from *S. pneumoniae* serotype 10A, a glycoconjugate from *S. pneumoniae* serotype 11A and a glycoconjugate from *S. pneumoniae* serotype 8.

In one aspect, the invention provides an immunogenic composition comprising at least one glycoconjugate from *S. pneumoniae* serotype 15B, at least one glycoconjugate from *S. pneumoniae* serotype 22F and at least one glycoconjugate from *S. pneumoniae* serotype 33F.

In another aspect the invention provides an immunogenic composition comprising at least one glycoconjugate from *S. pneumoniae* serotype 15B, at least one glycoconjugate from *S. pneumoniae* serotype 22F, at least one glycoconjugate from *S. pneumoniae* serotype 33F, at least one glycoconjugate from *S. pneumoniae* serotype 12F, at least one glycoconjugate from *S. pneumoniae* serotype 10A, at least one glycoconjugate from *S. pneumoniae* serotype 11A and at least one glycoconjugate from *S. pneumoniae* serotype 8.

In an aspect the above immunogenic composition further comprises glycoconjugates from *S. pneumoniae* serotypes 4, 6B, 9V, 14, 18C, 19F and 23F.

In another aspect the above immunogenic composition further comprises glycoconjugates from *S. pneumoniae* serotypes 1, 5 and 7F.

In another aspect the above immunogenic composition further comprises glycoconjugates from *S. pneumoniae* serotypes 6A and 19A.

In another aspect the above immunogenic composition further comprises glycoconjugates from *S. pneumoniae* serotype 3.

In another aspect the above immunogenic composition further comprises glycoconjugates from *S. pneumoniae* serotype 2, 9N, 17F, 20 and/or 15C.

In an aspect the above immunogenic composition does not comprise capsular saccharide from *S. pneumoniae* serotype 9N, 9A and/or 9L.

In an aspect the above immunogenic composition is a 8, 9, 10, 11, 12, 13, 14, 15, 16, 17, 18, 19 or 20-valent pneumococcal conjugate composition. In an aspect the above immunogenic composition is a 7, 8, 9, 10, 11, 12, 13, 14, 15, 16, 17, 18, 19, 20, 21, 22, 23, 24 or 25-valent pneumococcal conjugate composition.

In an aspect the glycoconjugates are individually conjugated to a carrier protein selected form the group consisting of DT (Diphtheria toxin), TT (tetanus toxoid), $CRM_{197}$, other DT mutants, PD (*Haemophilus influenzae* protein D), or immunologically functional equivalents thereof.

In one aspect, the invention provides a container filled with any of the immunogenic composition defined in the present document.

In one aspect, the invention provides any of the immunogenic composition defined in the present document for use as a medicament, in particular for use as a vaccine.

In one aspect, the invention provides a method of preventing, treating or ameliorating an infection, disease or condition associated with *S. pneumoniae* in a subject, comprising administering to the subject an immunologically effective amount of any of the immunogenic composition defined in the present document.

FIGURES

Figure 11:
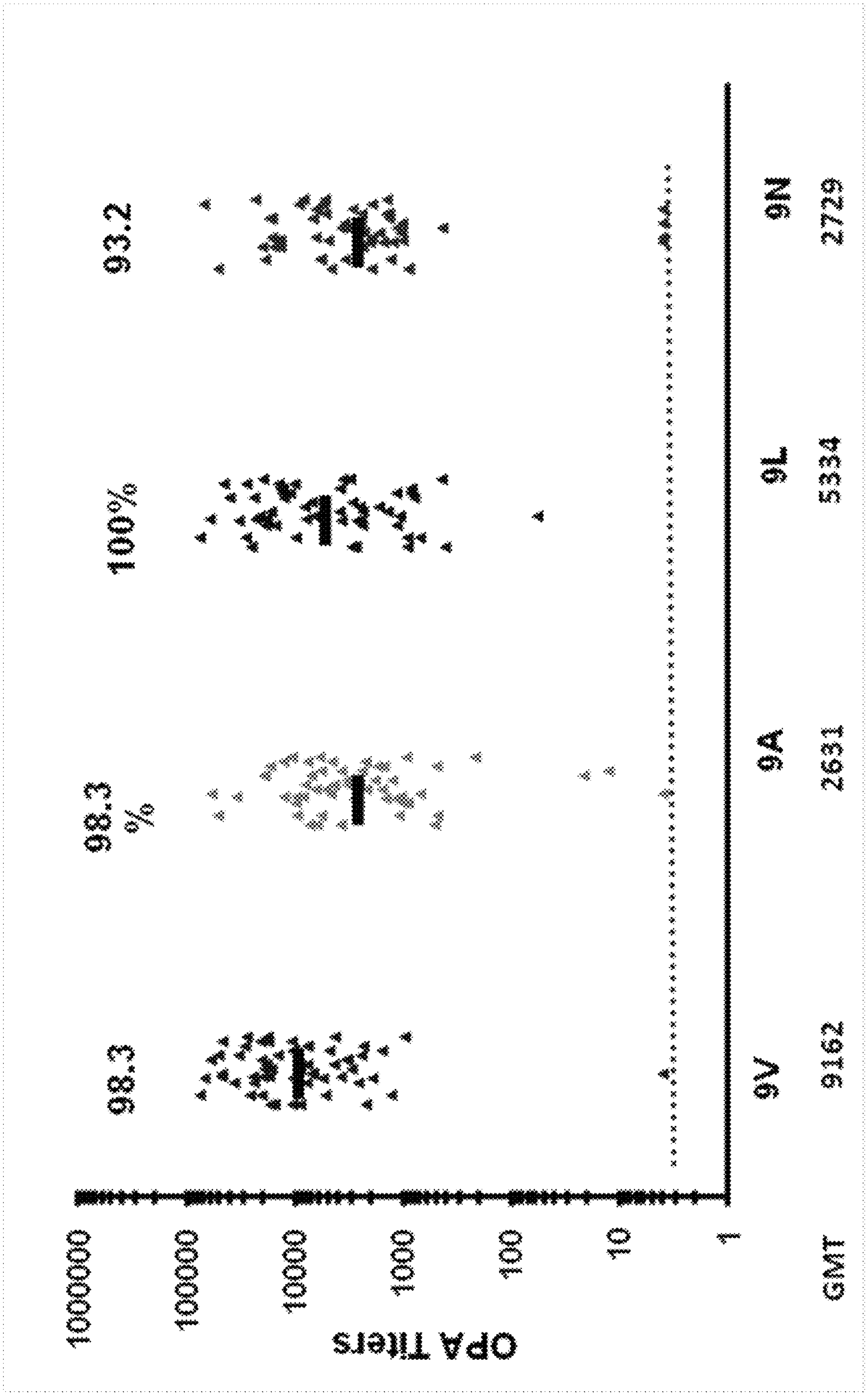

FIG. 11 Cross-Functional OPA Responses. A subset of 59 sera from adults vaccinated with a 13 valent Pneumococcal Conjugate Vaccine (US Study 6115A1-004; ClinicalTrials.gov Identifier: NCT00427895) was assessed in OPAs for the presence of functional antibodies against serotypes 9V, 9A, 9L, and 9N. The percent of samples with OPA positive titer (i.e., ≥1:8) is indicated above each group. Geometric mean titers (GMT) are listed in the x axis below each group.

Figure 12:
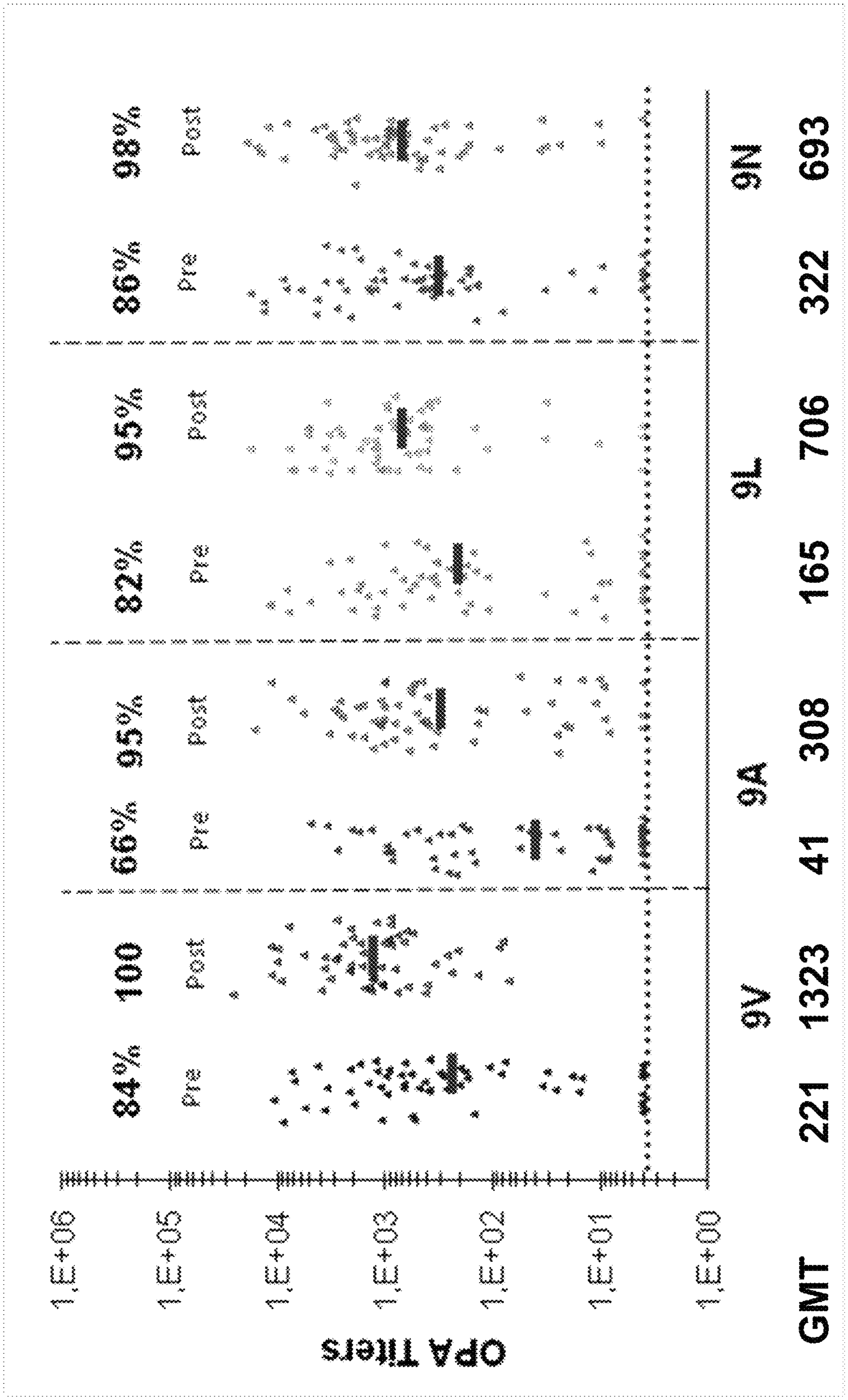

FIG. 12 Cross-Functional OPA Responses of Sixty-six Matched pre/post Sera. A subset of 66 matched pre- and post-vaccinated serum panel from adults vaccinated with a 13 valent Pneumococcal Conjugate Vaccine (study 6115A1-3005; ClinicalTrials.gov Identifier: NCT00546572) were assessed in OPAs for the presence of functional antibodies against serotypes 9V, 9A, 9L, and 9N. The percent of samples with OPA positive titer (i.e., ≥1:8) is indicated above each group. Geometric mean titers (GMT) are listed in the x axis below each group.

Figure 13:
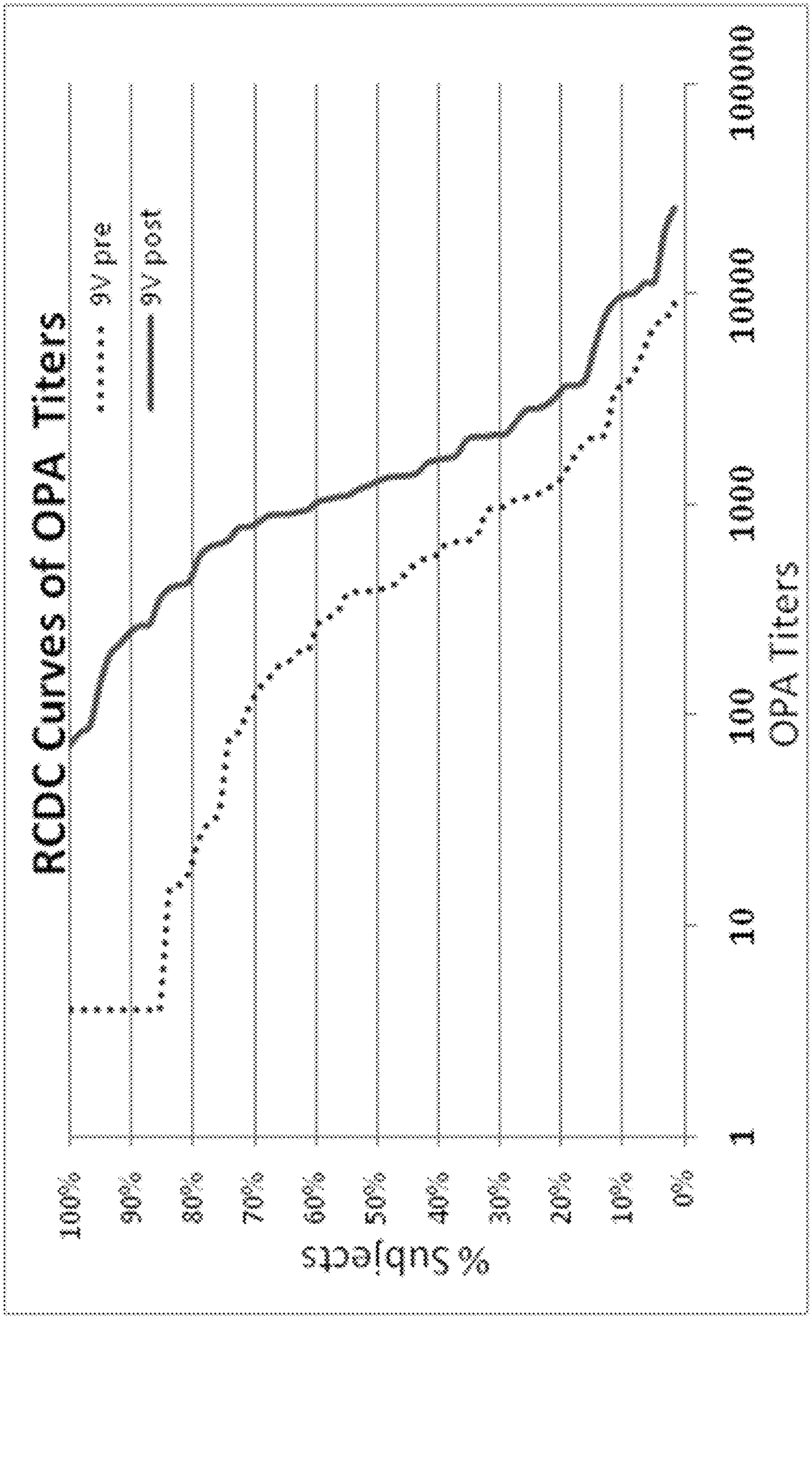

FIG. 13 Reverse cumulative distribution curves (RCDC) of pre and post Immunization-pneumococcal serotype 9V (Pn9V).

Reverse cumulative distribution curves of OPA titers to serotype 9V from a matched pre- and post-vaccination serum panel (N=66) vaccinated with a 13 valent Pneumococcal Conjugate Vaccine (study 6115A1-3005; ClinicalTrials.gov Identifier: NCT00546572). The plots represent the percent of sera with OPA positive titer (i.e., ≥1:8).

Figure 14:
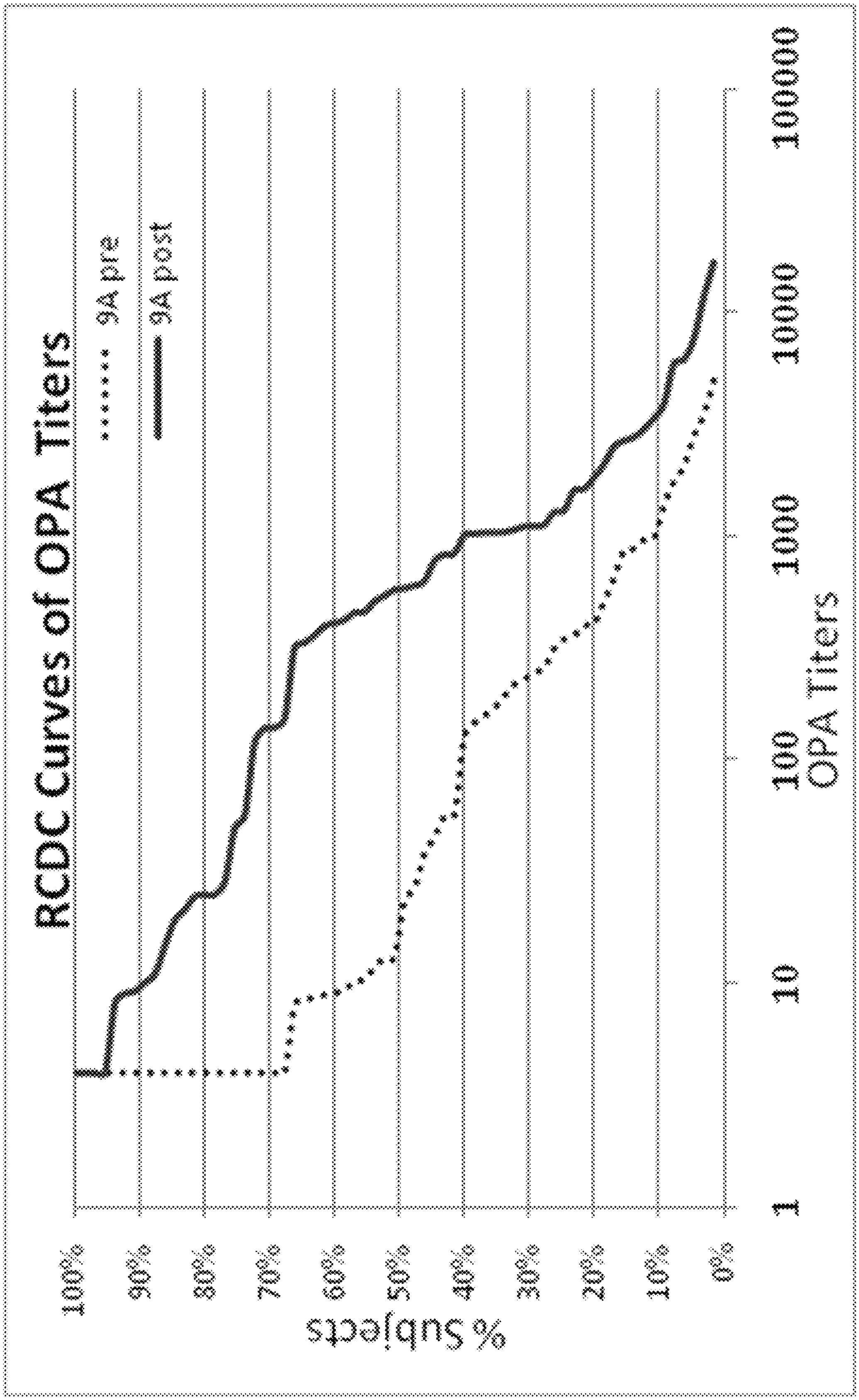

FIG. 14 Reverse cumulative distribution curves (RCDC) of pre and post Immunization-pneumococcal serotype 9A (Pn9A).

Reverse cumulative distribution curves of OPA titers to serotype 9A from a matched pre- and post-vaccination serum panel (N=66) vaccinated with a 13 valent Pneumococcal Conjugate Vaccine (study 6115A1-3005; ClinicalTrials.gov Identifier: NCT00546572). The plots represent the percent of sera with OPA positive titer (i.e., ≥1:8).

Figure 15:
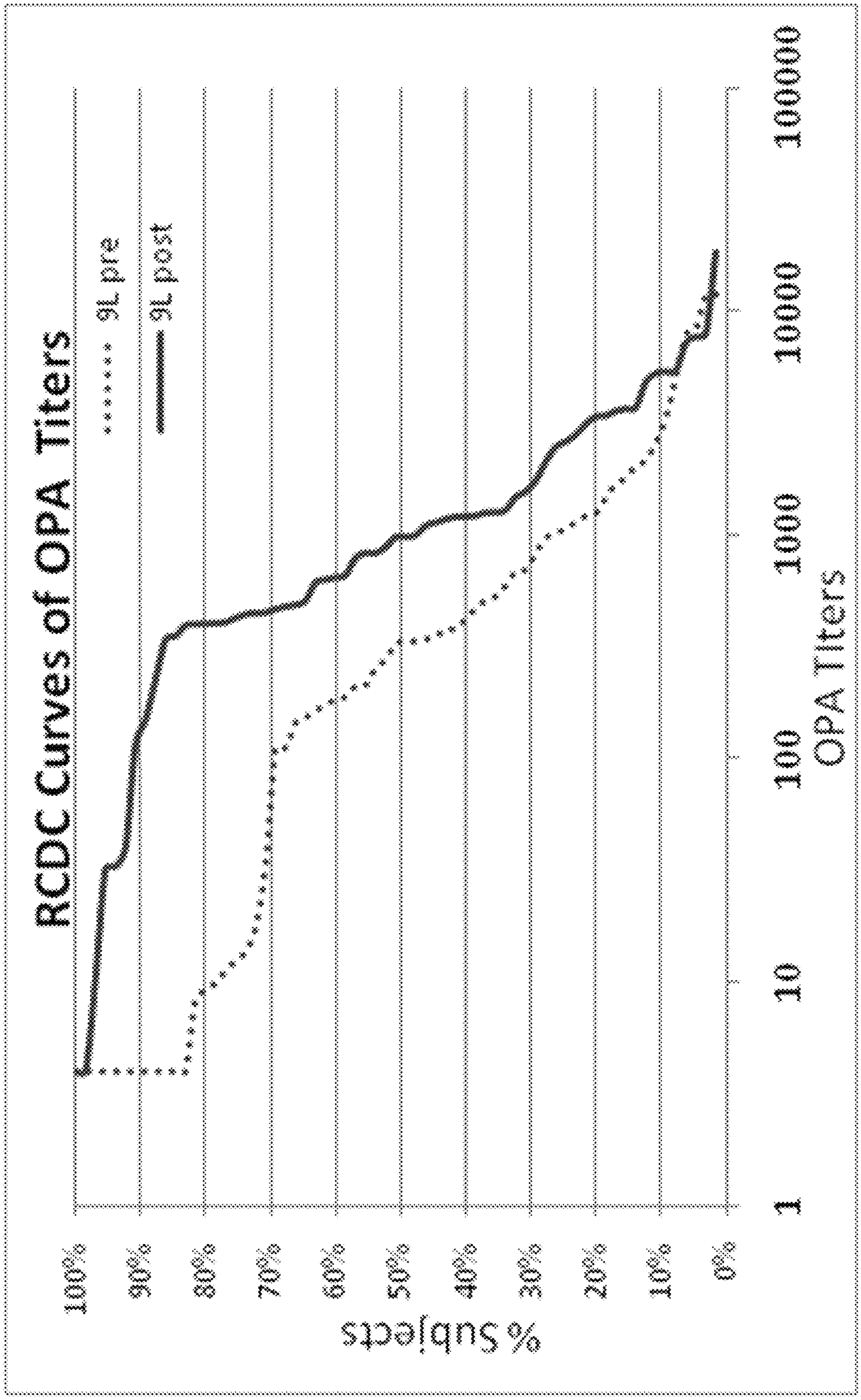

FIG. 15 Reverse cumulative distribution curves (RCDC) of pre and post Immunization-pneumococcal serotype 9L (Pn9L).

Reverse cumulative distribution curves of OPA titers to serotype 9L from a matched pre- and post-vaccination serum panel (N=66) vaccinated with a 13 valent Pneumococcal Conjugate Vaccine (study 6115A1-3005; ClinicalTrials.gov Identifier: NCT00546572). The plots represent the percent of sera with OPA positive titer (i.e., ≥1:8).

Figure 16:
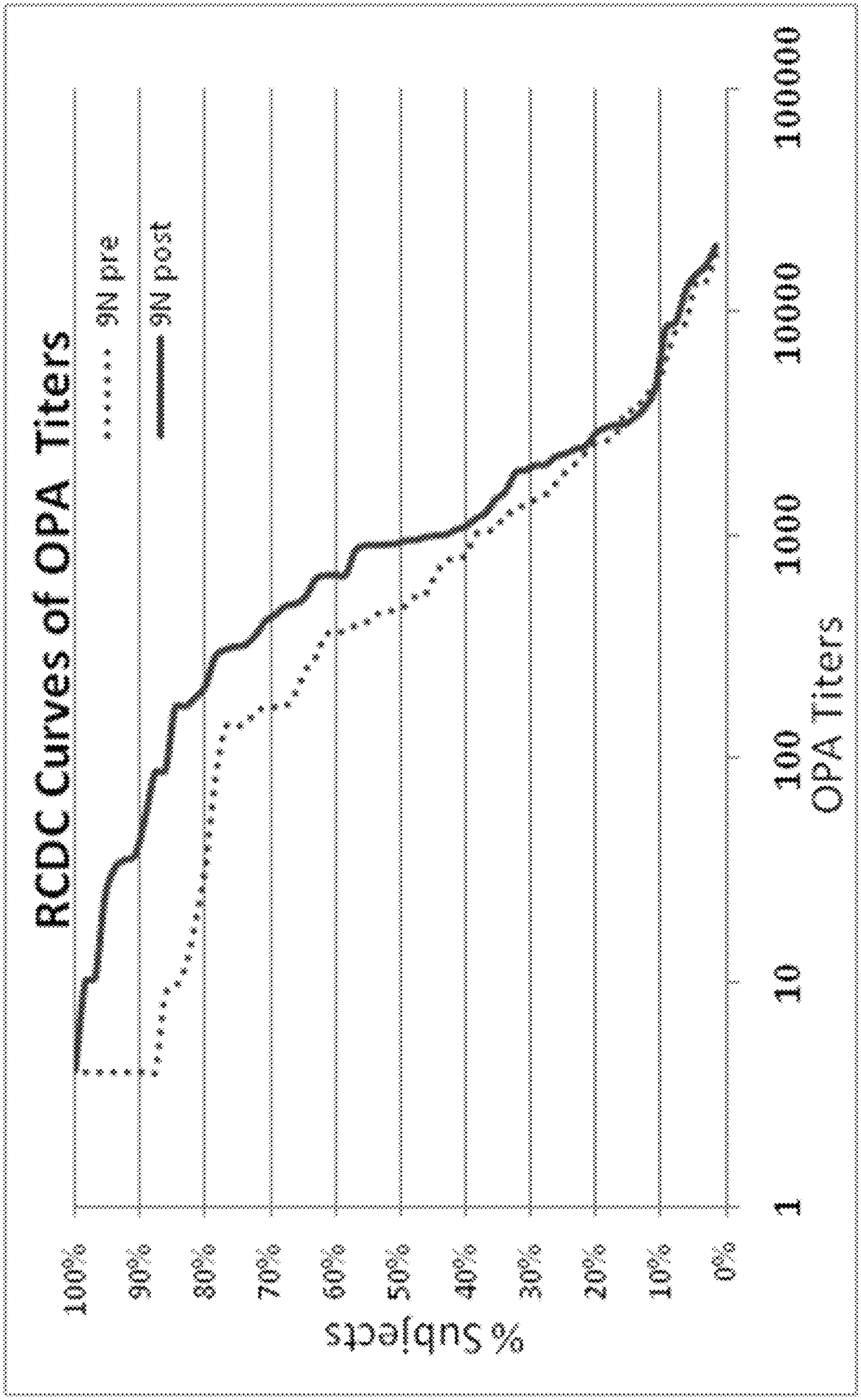

FIG. 16 Reverse cumulative distribution curves (RCDC) of pre and post Immunization-pneumococcal serotype 9N (Pn9N).

Reverse cumulative distribution curves of OPA titers to serotype 9N from a matched pre- and post-vaccination serum panel (N=66) vaccinated with a 13 valent Pneumococcal Conjugate Vaccine (study 6115A1-3005; ClinicalTrials.gov Identifier: NCT00546572). The plots represent the percent of sera with OPA positive titer (i.e., 1:8).

1 Immunogenic Compositions of the Invention

Immunogenic compositions of the present invention will typically comprise conjugated capsular saccharide antigens (also named glycoconjugates), wherein the saccharides are derived from serotypes of *S. pneumoniae*.

Preferably, the number of *S. pneumoniae* capsular saccharides can range from 8 different serotypes (or "v", valences) to 20 different serotypes (20v). In one embodiment there are 8 different serotypes. In one embodiment there are 9 different serotypes. In one embodiment there are 10 different serotypes. In one embodiment there are 11 different serotypes. In one embodiment there are 12 different serotypes. In one embodiment there are 13 different serotypes. In one embodiment there are 14 different serotypes. In one embodiment there are 15 different serotypes. In one embodiment there are 16 different serotypes. In an embodiment there are 17 different serotypes. In an embodiment there are 18 different serotypes. In an embodiment there are 19 different serotypes. In an embodiment there are 20 different serotypes. The capsular saccharides are conjugated to a carrier protein to form glycoconjugates as described here below.

If the protein carrier is the same for 2 or more saccharides in the composition, the saccharides could be conjugated to the same molecule of the protein carrier (carrier molecules having 2 or more different saccharides conjugated to it) [see for instance WO2004/083251].

In a preferred embodiment though, the saccharides are each individually conjugated to different molecules of the protein carrier (each molecule of protein carrier only having one type of saccharide conjugated to it). In said embodiment, the capsular saccharides are said to be individually conjugated to the carrier protein.

For the purposes of the invention the term 'glycoconjugate' indicates a capsular saccharide linked covalently to a carrier protein. In one embodiment a capsular saccharide is linked directly to a carrier protein. In a second embodiment a bacterial saccharide is linked to a protein through a spacer/linker.

1.1 Carrier Protein of the Invention

A component of the glycoconjugate of the invention is a carrier protein to which the saccharide is conjugated. The terms "protein carrier" or "carrier protein" or "carrier" may be used interchangeably herein. Carrier proteins should be amenable to standard conjugation procedures.

In a preferred embodiment, the carrier protein of the glycoconjugates is selected in the group consisting of: DT (Diphtheria toxin), TT (tetanus toxoid) or fragment C of TT, $CRM_{197}$ (a nontoxic but antigenically identical variant of diphtheria toxin), other DT mutants (such as CRM176, CRM228, CRM45 (Uchida et al. (1973) J. Biol. Chem. 218:3838-3844), CRM9, CRM102, CRM103 or CRM107; and other mutations described by Nicholls and Youle in Genetically Engineered Toxins, Ed: Frankel, Marcel Dekker Inc. (1992); deletion or mutation of Glu-148 to Asp, Gln or Ser and/or Ala 158 to Gly and other mutations disclosed in U.S. Pat. Nos. 4,709,017 and 4,950,740; mutation of at least one or more residues Lys 516, Lys 526, Phe 530 and/or Lys 534 and other mutations disclosed in U.S. Pat. Nos. 5,917,017 and 6,455,673; or fragment disclosed in U.S. Pat. No. 5,843,711, pneumococcal pneumolysin (ply) (Kuo et al. (1995) Infect Immun 63:2706-2713) including ply detoxified in some fashion, for example dPLY-GMBS (WO 2004/081515, WO 2006/032499) or dPLY-formol, PhtX, including PhtA, PhtB, PhtD, PhtE (sequences of PhtA, PhtB, PhtD or PhtE are disclosed in WO 00/37105 and WO 00/39299) and fusions of Pht proteins, for example PhtDE fusions, PhtBE fusions, Pht A-E (WO 01/98334, WO 03/054007, WO 2009/000826), OMPC (meningococcal outer membrane protein), which is usually extracted from *Neisseria meningitidis* serogroup B (EP0372501), PorB (from *N. meningitidis*), PD (*Haemophilus influenzae* protein D; see, e.g., EP0594610 B), or immunologically functional equivalents thereof, synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al. (2001) Eur J Immunol 31:3816-3824) such as N19 protein (Baraldoi et al. (2004) Infect Immun 72:4884-4887) pneumococcal surface protein PspA (WO 02/091998), iron uptake proteins (WO 01/72337), toxin A or B of *Clostridium difficile* (WO 00/61761), transferrin binding proteins, pneumococcal adhesion protein (PsaA), recombinant *Pseudomonas aeruginosa* exotoxin A (in particular non-toxic mutants thereof (such as exotoxin A bearing a substitution at glutamic acid 553 (Douglas et al. (1987) J. Bacteriol. 169(11): 4967-4971)). Other proteins, such as ovalbumin, keyhole limpet hemocyanin (KLH), bovine serum albumin (BSA) or purified protein derivative of tuberculin (PPD) also can be used as carrier proteins. Other suitable carrier proteins include inactivated bacterial toxins such as cholera toxoid (e.g., as described in WO 2004/083251), *Escherichia coli* LT, *E. coli* ST, and exotoxin A from *P. aeruginosa.*

In a preferred embodiment, the carrier protein of the glycoconjugates is independently selected from the group consisting of TT, DT, DT mutants (such as $CRM_{197}$), *H. influenzae* protein D, PhtX, PhtD, PhtDE fusions (particularly those described in WO 01/98334 and WO 03/054007), detoxified pneumolysin, PorB, N19 protein, PspA, OMPC, toxin A or B of *C. difficile* and PsaA.

In an embodiment, the carrier protein of the glycoconjugates of the invention is DT (Diphtheria toxoid). In another embodiment, the carrier protein of the glycoconjugates of the invention is TT (tetanus toxoid).

In another embodiment, the carrier protein of the glycoconjugates of the invention is PD (*H. influenzae* protein D; see, e.g., EP0594610 B).

In a preferred embodiment, the capsular saccharides of the invention are conjugated to $CRM_{197}$ protein. The $CRM_{197}$ protein is a nontoxic form of diphtheria toxin but is immunologically indistinguishable from the diphtheria toxin. $CRM_{197}$ is produced by *Corynebacterium diphtheriae* infected by the nontoxigenic phage $\beta 197^{tox-}$ created by nitrosoguanidine mutagenesis of the toxigenic corynephage beta (Uchida et al. (1971) Nature New Biology 233:8-11). The $CRM_{197}$ protein has the same molecular weight as the diphtheria toxin but differs therefrom by a single base change (guanine to adenine) in the structural gene. This single base change causes an amino acid substitution (glutamic acid for glycine) in the mature protein and eliminates the toxic properties of diphtheria toxin. The $CRM_{197}$ protein is a safe and effective T-cell dependent carrier for saccharides. Further details about $CRM_{197}$ and production thereof can be found, e.g., in U.S. Pat. No. 5,614,382.

In an embodiment, the capsular saccharides of the invention are conjugated to $CRM_{197}$ protein or the A chain of $CRM_{197}$ (see CN103495161). In an embodiment, the capsular saccharides of the invention are conjugated the A chain of $CRM_{197}$ obtained via expression by genetically recombinant *E. coli* (see CN103495161). In an embodiment, the capsular saccharides of the invention are all conjugated to $CRM_{197}$. In an embodiment, the capsular saccharides of the invention are all conjugated to the A chain of $CRM_{197}$.

Accordingly, in frequent embodiments, the glycoconjugates of the invention comprise $CRM_{197}$ as the carrier protein, wherein the capsular polysaccharide is covalently linked to $CRM_{197}$.

1.2 Capsular Saccharide of the Invention

The term "saccharide" throughout this specification may indicate polysaccharide or oligosaccharide and includes both. In frequent embodiments, the saccharide is a polysaccharide, in particular a *S. pneumoniae* capsular polysaccharide.

Capsular polysaccharides are prepared by standard techniques known to those of ordinary skill in the art.

In the present invention, capsular polysaccharides may be prepared, e.g., from serotypes 1, 3, 4, 5, 6A, 6B, 7F, 8, 9V, 10A, 11A, 12F, 14, 15B, 18C, 19A, 19F, 22F, 23F and 33F of *S. pneumoniae*. Typically capsular polysaccharides are produced by growing each *S. pneumoniae* serotype in a medium (e.g., in a soy-based medium), the polysaccharides are then prepared from the bacteria culture. Bacterial strains of *S. pneumoniae* used to make the respective polysaccharides that are used in the glycoconjugates of the invention may be obtained from established culture collections or clinical specimens.

The population of the organism (each *S. pneumoniae* serotype) is often scaled up from a seed vial to seed bottles and passaged through one or more seed fermentors of increasing volume until production scale fermentation volumes are reached. At the end of the growth cycle the cells are lysed and the lysate broth is then harvested for downstream (purification) processing (see for example WO 2006/110381, WO 2008/118752, and U.S. Patent App. Pub. Nos. 2006/0228380, 2006/0228381, 2008/0102498 and 2008/0286838).

The individual polysaccharides are typically purified through centrifugation, precipitation, ultra-filtration, and/or column chromatography (see for example WO 2006/110352 and WO 2008/118752).

Purified polysaccharides may be activated (e.g., chemically activated) to make them capable of reacting (e.g., with the eTEC spacer) and then incorporated into glycoconjugates of the invention, as further described herein.

*S. pneumoniae* capsular polysaccharides comprise repeating oligosaccharide units which may contain up to 8 sugar residues.

In an embodiment, capsular saccharide of the invention may be one oligosaccharide unit or a shorter than native length saccharide chain of repeating oligosaccharide units. In an embodiment, capsular saccharide of the invention is one repeating oligosaccharide unit of the relevant serotype.

In an embodiment, capsular saccharide of the invention may be oligosaccharides. Oligosaccharides have a low number of repeat units (typically 5-15 repeat units) and are typically derived synthetically or by hydrolysis of polysaccharides.

Preferably though, all of the capsular saccharides of the present invention and in the immunogenic compositions of the present invention are polysaccharides. High molecular weight capsular polysaccharides are able to induce certain antibody immune responses due to the epitopes present on the antigenic surface. The isolation and purification of high molecular weight capsular polysaccharides is preferably contemplated for use in the conjugates, compositions and methods of the present invention.

In some embodiments, the purified polysaccharides before conjugation have a molecular weight of between 10 kDa and 4,000 kDa. In other such embodiments, the polysaccharide has a molecular weight of between 50 kDa and 4,000 kDa. In further such embodiments, the polysaccharide has a molecular weight of between 50 kDa and 3,500 kDa; between 50 kDa and 3,000 kDa; between 50 kDa and 2,500 kDa; between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 100 kDa and 4,000 kDa; between 100 kDa and 3,500 kDa; 100 kDa and 3,000 kDa; 100 kDa and 2,500 kDa; 100 kDa and 2,000 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 4,000 kDa; between 200 kDa and 3,500 kDa; between 200 kDa and 3,000 kDa; between 200 kDa and 2,500 kDa; between 200 kDa and 2,000 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa. Any whole number integer within any of the above ranges is contemplated as an embodiment of the disclosure.

A polysaccharide can become slightly reduced in size during normal purification procedures. Additionally, as described herein, polysaccharide can be subjected to sizing techniques before conjugation. Mechanical or chemical sizing maybe employed. Chemical hydrolysis maybe conducted using acetic acid. Mechanical sizing maybe conducted using High Pressure Homogenization Shearing. The molecular weight ranges mentioned above refer to purified polysaccharides before conjugation (e.g., before activation).

In a preferred embodiment the purified polysaccharides, are capsular polysaccharide from serotypes 1, 3, 4, 5, 6A, 6B, 7F, 8, 9V, 10A, 11A, 12F, 14, 15B, 18C, 19A, 19F, 22F, 23F or 33F of *S. pneumoniae*, wherein the capsular polysaccharide has a molecular weight falling within one of the molecular weight ranges as described here above.

As used herein, the term "molecular weight" of polysaccharide or of carrier protein-polysaccharide conjugate refers to molecular weight calculated by size exclusion chromatography (SEC) combined with multiangle laser light scattering detector (MALLS).

In some embodiments, the pneumococcal saccharides from serotypes 9V, 18C, 11A, 15B, 22F and/or 33F of the invention are O-acetylated. In some embodiments, the pneumococcal saccharides from serotypes 9V, 11A, 15B, 22F and/or 33F of the invention are O-acetylated.

The purified polysaccharides described herein are chemically activated to make the saccharides capable of reacting with the carrier protein. These pneumococcal conjugates are prepared by separate processes and formulated into a single dosage formulation as described below.

1.2.1 Pneumococcal Polysaccharide from *S. pneumoniae* serotypes 1, 3, 4, 5, 6A, 6B, 7F, 9V, 14, 18C, 19A, 19F and 23F Capsular saccharides from *S. pneumoniae* serotypes 1, 3, 4, 5, 6A, 6B, 7F, 9V, 14, 18C, 19A, 19F and 23F may be prepared by standard techniques known to those of ordinary skill in the art (see for example WO 2006/110381). Capsular polysaccharides can be produced by growing each *S. pneumoniae* serotype in a medium; at the end of the growth cycle the cells are lysed and the lysate broth is then harvested for downstream (purification) processing. The individual polysaccharides are typically purified through centrifugation, precipitation, ultra-filtration, and/or column chromatography (see for example WO 2006/110352 and WO 2008/118752). Purified polysaccharides may be further processed as further described herein to prepare glycoconjugates of the invention. In some embodiments, the purified polysaccharides from *S. pneumoniae* serotypes 1, 3, 4, 5, 6A, 6B, 7F, 9V, 14, 18C, 19A, 19F and/or 23F before conjugation have a molecular weight of between 10 kDa and 4,000 kDa. In other such embodiments, the polysaccharide has a molecular weight of between 50 kDa and 4,000 kDa; between 50 kDa and 3,000 kDa or between 50 kDa and 2,000 kDa. In further such embodiments, the polysaccharide has a molecular weight of between 50 kDa and 3,500 kDa; between 50 kDa and 3,000 kDa; between 50 kDa and 2,500 kDa; between 50 kDa and 2,000 kDa; 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 100 kDa and 4,000 kDa; between 100 kDa and 3,500 kDa; between 100 kDa and 3,000 kDa; between 100 kDa and 2,500 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 4,000 kDa; between 200 kDa and 3,500 kDa; between 200 kDa and 3,000 kDa; between 200 kDa and 2,500 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa. Any whole number integer within any of the above ranges is contemplated as an embodiment of the disclosure.

A polysaccharide can become slightly reduced in size during normal purification procedures. Additionally, as described herein, polysaccharide can be subjected to sizing techniques before conjugation. The molecular weight ranges mentioned above refer to purified polysaccharides before conjugation (e.g., before activation) after an eventual sizing step.

In some embodiments, the pneumococcal saccharides from serotypes 9V and/or 18C of the invention are O-acetylated. In some embodiments, the pneumococcal saccharide from serotype 9V of the invention is O-acetylated and the pneumococcal saccharide from serotype 18C of the invention is de-O-acetylated.

1.2.2 Pneumococcal Polysaccharide Serotype 8

Figure 1:
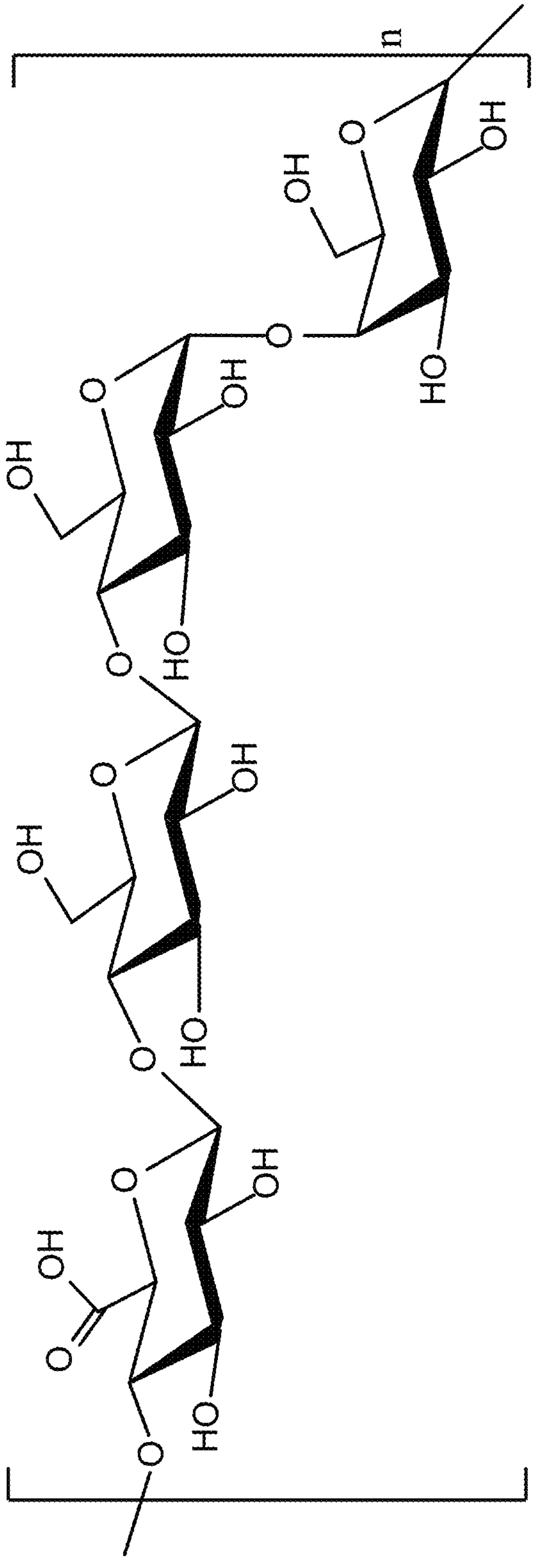
FIG. 1 shows a repeating polysaccharide structure of *S. pneumoniae* serotype 8 (Pn-8) capsular polysaccharide.

The polysaccharide repeating unit of serotype 8 consists of a linear tetrasaccharide unit with one glucuronic acid (GlcpA), two glucopyranoses (Glcp) and one galactopyranose (Galp) (Jones et al. (1957) The Journal of the American Chemical Society. 79(11):2787-2793). All four monosaccharides are linked via 1,4-linkages as shown at FIG. 1.

Serotype 8 saccharides can be obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/118752). In addition, they can be produced using synthetic protocols.

Serotype 8 *S. pneumoniae* strains may be obtained from established culture collections (such as for example the Streptococcal Reference Laboratory (Centers for Disease Control and Prevention, Atlanta, GA)) or clinical specimens.

In some embodiments, the purified polysaccharides from *S. pneumoniae* serotype 8 before conjugation have a molecular weight of between 10 kDa and 2,000 kDa. In one embodiment, the capsular polysaccharide has a molecular weight of between 50 kDa and 1,000 kDa. In another embodiment, the capsular polysaccharide has a molecular weight of between 70 kDa and 900 kDa. In another embodiment, the capsular polysaccharide has a molecular weight of between 100 kDa and 800 kDa.

In further embodiments, the capsular polysaccharide has a molecular weight of 100 kDa to 600 kDa; 100 kDa to 500 kDa; 100 kDa to 400 kDa; 150 kDa to 600 kDa; 150 kDa to 500 kDa; 150 kDa to 400 kDa; 200 kDa to 600 kDa; 200 kDa to 500 kDa; 200 kDa to 400 kDa; 250 kDa to 600; 250 kDa to 500 kDa; 250 kDa to 400 kDa; 250 kDa to 350 kDa; 300 kDa to 600 kDa; 300 kDa to 500 kDa; 300 kDa to 400 kDa; 400 kDa to 600 kDa; 500 kDa to 600 kDa; and similar desired molecular weight ranges. Any whole number integer within any of the above ranges is contemplated as an embodiment of the disclosure.

A polysaccharide can become slightly reduced in size during normal purification procedures. Additionally, as described herein, polysaccharide can be subjected to sizing techniques before conjugation. The molecular weight ranges mentioned above refer to purified polysaccharides before conjugation (e.g., before activation) after an eventual sizing step.

1.2.3 Pneumococcal Polysaccharide Serotype 10A

Figure 2:
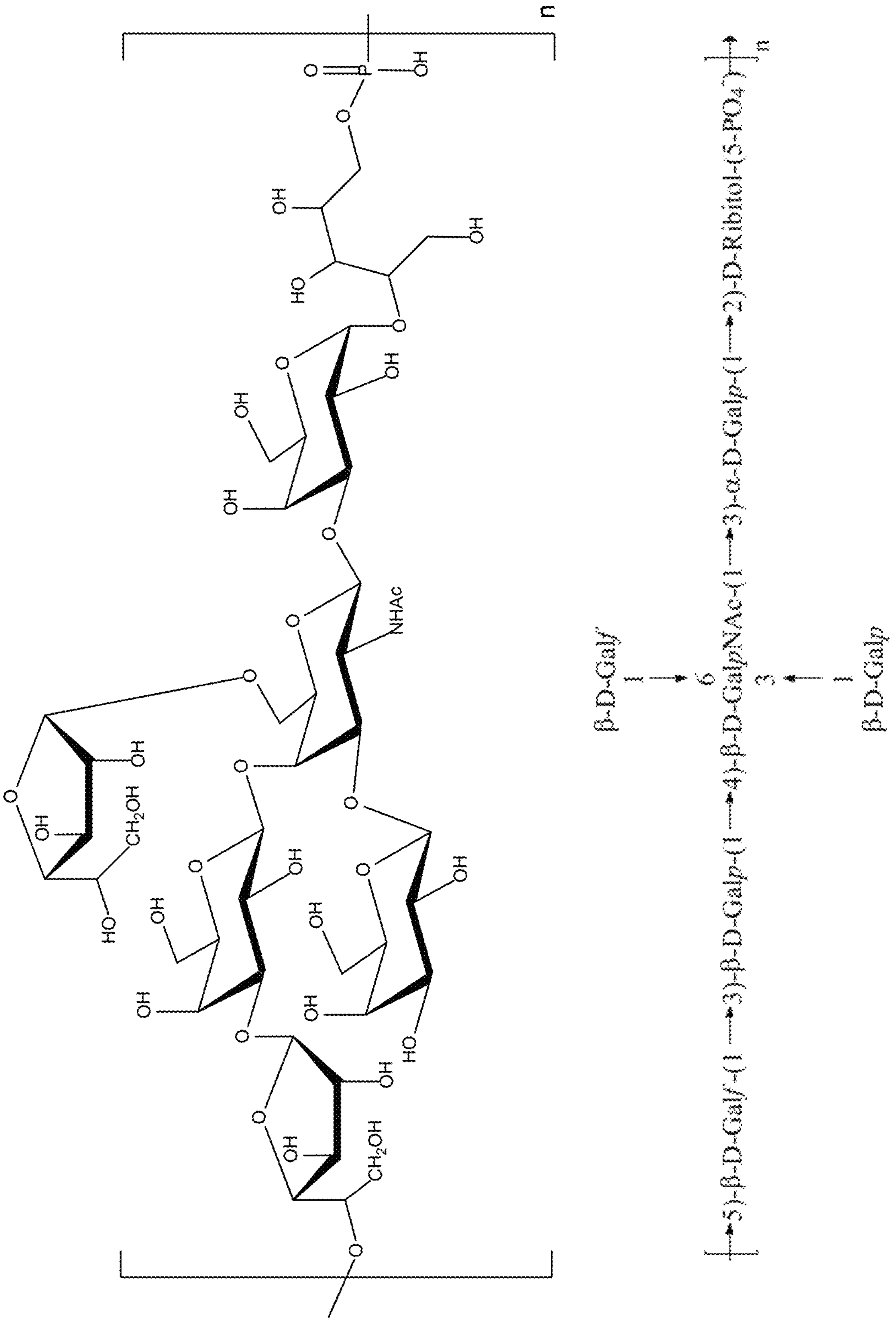
FIG. 2 shows a repeating polysaccharide structure of *S. pneumoniae* serotype 10A (Pn-10A) capsular polysaccharide.

The polysaccharide repeating unit of serotype 10A consists of a branched hexasaccharide repeat unit with two galactofuranoses ($Gal_f$), three galactopyranoses ($Gal_p$), one N-acetylgalactosamine ($Gal_pNAc$) and a backbone phosphoribitol (Jones, C. (1995) Carbohydrate Research 269(1):175-181). There are two branching monosaccharides at the β-GalpNAc moiety (a β-3-Galp and a β-6-Galf) as shown at FIG. 2.

Serotype 10A saccharides can be obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/118752). In addition, they can be produced using synthetic protocols.

Serotype 10A *S. pneumoniae* strains may be obtained from established culture collections (such as for example the Streptococcal Reference Laboratory (Centers for Disease Control and Prevention, Atlanta, GA)) or clinical specimens.

In some embodiments, the purified polysaccharides from *S. pneumoniae* serotype 10A before conjugation have a molecular weight of between 10 kDa and 2,000 kDa. In one embodiment, the capsular polysaccharide has a molecular weight of between 50 kDa and 1,000 kDa. In another embodiment, the capsular polysaccharide has a molecular weight of between 70 kDa and 900 kDa. In another embodiment, the capsular polysaccharide has a molecular weight of between 100 kDa and 800 kDa.

In further embodiments, the capsular polysaccharide has a molecular weight of 100 kDa to 600 kDa; 100 kDa to 500 kDa; 100 kDa to 400 kDa; 150 kDa to 600 kDa; 150 kDa to 500 kDa; 150 kDa to 400 kDa; 200 kDa to 600 kDa; 200 kDa to 500 kDa; 200 kDa to 400 kDa; 250 kDa to 600 kDa; 250 kDa to 500 kDa; 250 kDa to 400 kDa; 250 kDa to 350 kDa; 300 kDa to 600 kDa; 300 kDa to 500 kDa; 300 kDa to 400 kDa; 400 kDa to 600 kDa; 500 kDa to 600 kDa; and similar desired molecular weight ranges. Any whole number integer within any of the above ranges is contemplated as an embodiment of the disclosure.

A polysaccharide can become slightly reduced in size during normal purification procedures. Additionally, as described herein, polysaccharide can be subjected to sizing techniques before conjugation. The molecular weight ranges mentioned above refer to purified polysaccharides before conjugation (e.g., before activation) after an eventual sizing step.

1.2.4 Pneumococcal Polysaccharide Serotype 11A

Figure 3:
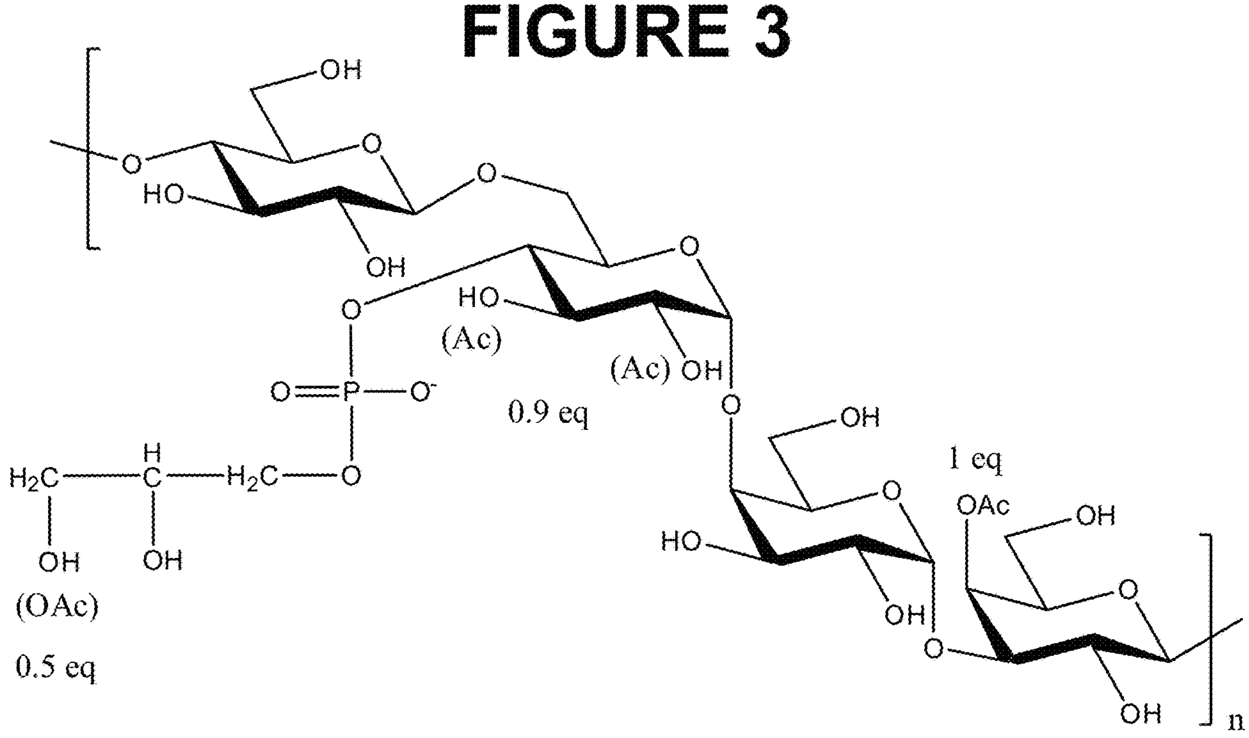
FIG. 3 shows a repeating polysaccharide structure of *S. pneumoniae* serotype 11A (Pn-11A) capsular polysaccharide.

The polysaccharide repeating unit of serotype 11A consists of a linear tetrasaccharide backbone (two galactopyranoses ($Gal_p$) and two glucopyranose ($Glc_p$) and a pendent phosphoglycerol (Richards et al. (1988) Adv. Exp. Med. Biol. 228:595-597), as shown at FIG. 3. The polysaccharide is O-acetylated at multiple locations and, based on the reported data in the literature (Calix et al. (2011) J Bacteriol. 193(19):5271-5278), the total amount of O-acetylation in 11A polysaccharide is about 2.6 O-acetyl groups per polysaccharide repeat unit.

Serotype 11A saccharides can be obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/118752). In addition, they can be produced using synthetic protocols.

Serotype 11A *S. pneumoniae* strains may be obtained from established culture collections (such as for example the Streptococcal Reference Laboratory (Centers for Disease Control and Prevention, Atlanta, GA)) or clinical specimens.

The isolated serotype 11A capsular polysaccharide obtained by purification of serotype 11A polysaccharide from the *S. pneumoniae* lysate and optionally sizing of the purified polysaccharide may be characterized by different attributes including, for example, the molecular weight (MW) and the mM of acetate per mM of said serotype 11A capsular polysaccharide.

In some embodiments, the purified polysaccharides from *S. pneumoniae* serotype 11A before conjugation have a molecular weight of between 10 kDa and 2,000 kDa. In one embodiment, the capsular polysaccharide has a molecular weight of between 50 kDa and 1,000 kDa. In another embodiment, the capsular polysaccharide has a molecular weight of between 70 kDa and 900 kDa. In another embodiment, the capsular polysaccharide has a molecular weight of between 100 kDa and 800 kDa.

In further embodiments, the capsular polysaccharide has a molecular weight of 100 kDa to 600 kDa; 100 kDa to 500 kDa; 100 kDa to 400 kDa; 100 kDa to 300 kDa; 100 kDa to 200 kDa; 150 kDa to 600 kDa; 150 kDa to 500 kDa; 150 kDa to 400 kDa; 150 kDa to 300 kDa; 150 kDa to 200 kDa; 200 kDa to 600 kDa; 200 kDa to 500 kDa; 200 kDa to 400 kDa; 250 kDa to 600 kDa; 250 kDa to 500 kDa; 250 kDa to 400 kDa; 250 kDa to 350 kDa; 300 kDa to 600 kDa; 300 kDa to 500 kDa; 300 kDa to 400 kDa; 400 kDa to 600 kDa; 500 kDa to 600 kDa; and similar desired molecular weight ranges. Any whole number integer within any of the above ranges is contemplated as an embodiment of the disclosure.

A polysaccharide can become slightly reduced in size during normal purification procedures. Additionally, as described herein, polysaccharide can be subjected to sizing techniques before conjugation. The molecular weight ranges mentioned above refer to purified polysaccharides before conjugation (e.g., before activation) after an eventual sizing step.

In an embodiment, the size of the purified serotype 11A polysaccharide is reduced by high pressure homogenization. High pressure homogenization achieves high shear rates by pumping the process stream through a flow path with sufficiently small dimensions. The shear rate is increased by using a larger applied homogenization pressure, and exposure time can be increased by recirculating the feed stream through the homogenizer.

The high pressure homogenization process is particularly appropriate for reducing the size of the purified serotype 11A polysaccharide while preserving the structural features of the polysaccharide, such as the presence of O-acetyl groups.

The presence of O-acetyl in a purified, isolated or activated serotype 11A capsular polysaccharide or in a serotype 11A polysaccharide-carrier protein conjugate is expressed as the number of mM of acetate per mM of said polysaccharide or as the number of O-acetyl group per polysaccharide repeating unit.

In a preferred embodiment, the purified polysaccharides from *S. pneumoniae* serotype 11A has at least 0.2, 0.4, 0.6, 0.8, 1.0, 1.2, 1.4 or 1.6, μmol acetate per μmol of said serotype 11A capsular polysaccharide.

1.2.5 Pneumococcal Polysaccharide Serotype 12F

Figure 4:
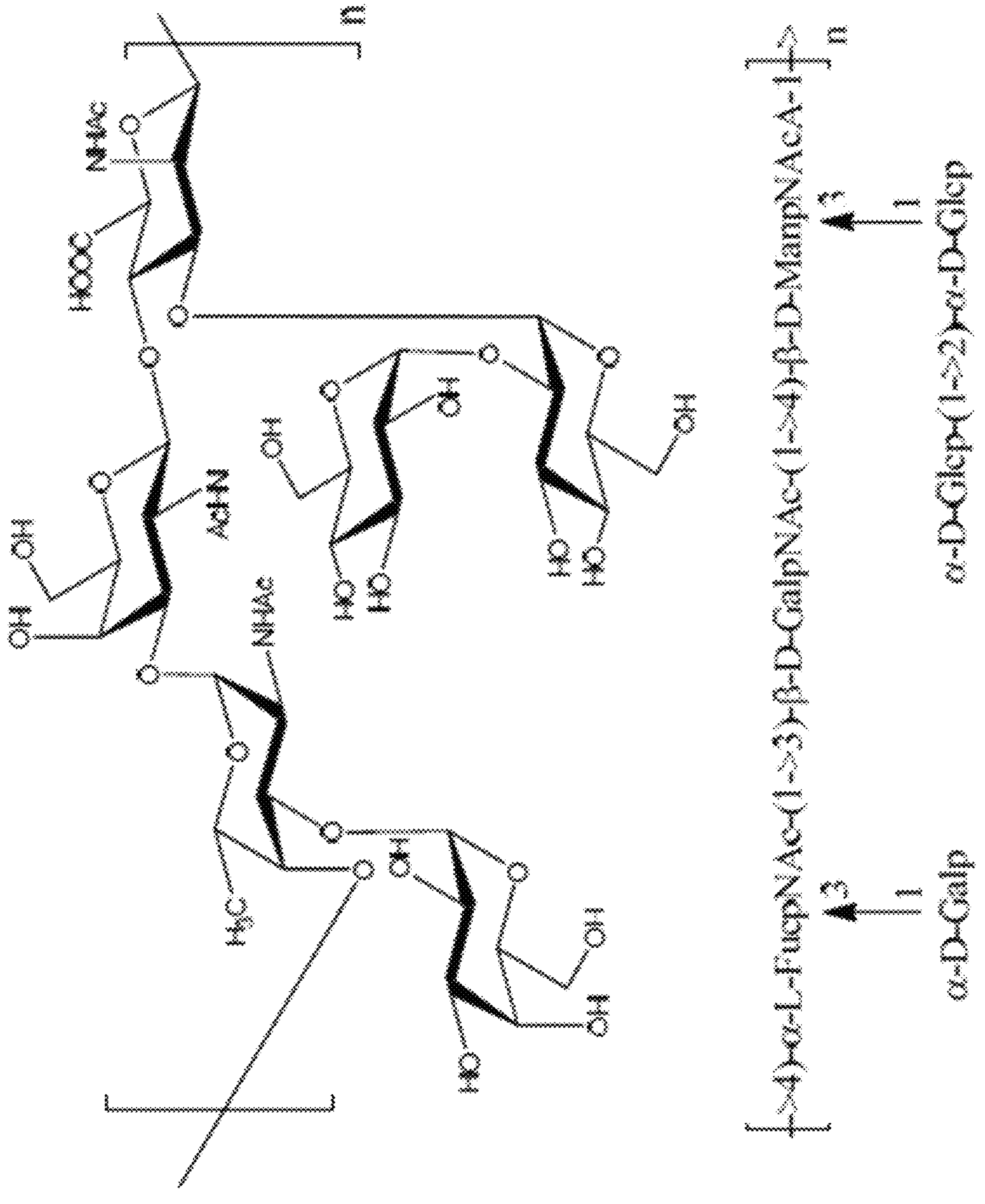
FIG. 4 shows a repeating polysaccharide structure of *S. pneumoniae* serotype 12F (Pn-12F) capsular polysaccharide.

The polysaccharide repeating unit of serotype 12F consists of a linear trisaccharide backbone (one N-acetylfucosamine ($Fuc_pNAc$), one N-acetylgalactosamine (GalpNAc) and one N-acetylmannuronic acid ($Man_pNAcA$)) with two branches: a pendant α-galactopyranose ($Gal_p$) linked at C3 of $Fuc_pNAc$ and an α-$Glc_p$-(1→2)-α-$Glc_p$ disaccharide branch linked at C3 of $Man_pNAcA$ (Leontein et al. (1983) Carbohydrate Research 114(2):257-266.) as shown at FIG. 4.

Serotype 12F *Streptococcus pneumoniae* strains may be obtained from established culture collections (such as for example the Streptococcal Reference Laboratory (Centers for Disease Control and Prevention, Atlanta, GA)) or clinical specimens.

Capsular saccharides from *S. pneumoniae* serotype 12F are prepared by standard techniques known to those of ordinary skill in the art. Typically capsular polysaccharides are produced by growing each *S. pneumoniae* serotype in a medium (e.g., in a soy-based medium), the polysaccharides are then prepared from the bacteria culture. The population of the organism (*S. pneumoniae* serotype 12F) is often scaled up from a seed vial to seed bottles and passaged through one or more seed fermentors of increasing volume until production scale fermentation volumes are reached. At the end of the growth cycle the cells are lysed and the lysate broth is then harvested for downstream (purification) processing (see for example WO 2006/110381 and WO 2008/118752, U.S. Patent App. Pub. Nos. 2006/0228380, 2006/0228381, 2008/0102498 and US2008/0286838). The polysaccharides are typically purified through centrifugation, precipitation, ultra-filtration, and/or column chromatography (see for example WO 2006/110352 and WO 2008/118752).

Purified polysaccharides from serotype 12F may be activated (e.g., chemically activated) to make them capable of reacting and then incorporated into glycoconjugates of the invention, as further described herein.

In some embodiments, the purified polysaccharides from *S. pneumoniae* serotype 12F before conjugation have a molecular weight of between 10 kDa and 2,000 kDa. In one embodiment, the capsular polysaccharide has a molecular weight of between 50 kDa and 1,000 kDa. In another embodiment, the capsular polysaccharide has a molecular weight of between 50 kDa and 300 kDa. In another embodiment, the capsular polysaccharide has a molecular weight of between 70 kDa and 300 kDa. In further embodiments, the capsular polysaccharide has a molecular weight of 90 kDa to 250 kDa; 90 kDa to 150 kDa; 90 kDa to 120 kDa; 80 kDa to 120 kDa; 70 kDa to 100 kDa; 70 kDa to 110 kDa; 70 kDa to 120 kDa; 70 kDa to 130 kDa; 70 kDa to 140 kDa; 70 kDa to 150 kDa; 70 kDa to 160 kDa; 80 kDa to 110 kDa; 80 kDa to 120 kDa; 80 kDa to 130 kDa; 80 kDa to 140 kDa; 80 kDa to 150 kDa; 80 kDa to 160 kDa; 90 kDa to 110 kDa; 90 kDa to 120 kDa; 90 kDa to 130 kDa; 90 kDa to 140 kDa; 90 kDa to 150 kDa; 90 kDa to 160 kDa; 100 kDa to 120 kDa; 100 kDa to 130 kDa; 100 kDa to 140 kDa; 100 kDa to 150 kDa; 100 kDa to 160 kDa; and similar desired molecular weight ranges. Any whole number integer within any of the above ranges is contemplated as an embodiment of the disclosure.

A polysaccharide can become slightly reduced in size during normal purification procedures. Additionally, as described herein, polysaccharide can be subjected to sizing techniques before conjugation. The molecular weight ranges mentioned above refer to purified polysaccharides before conjugation (e.g., before activation) after an eventual sizing step.

1.2.6 Pneumococcal Polysaccharide Serotype 15B

Figure 5:
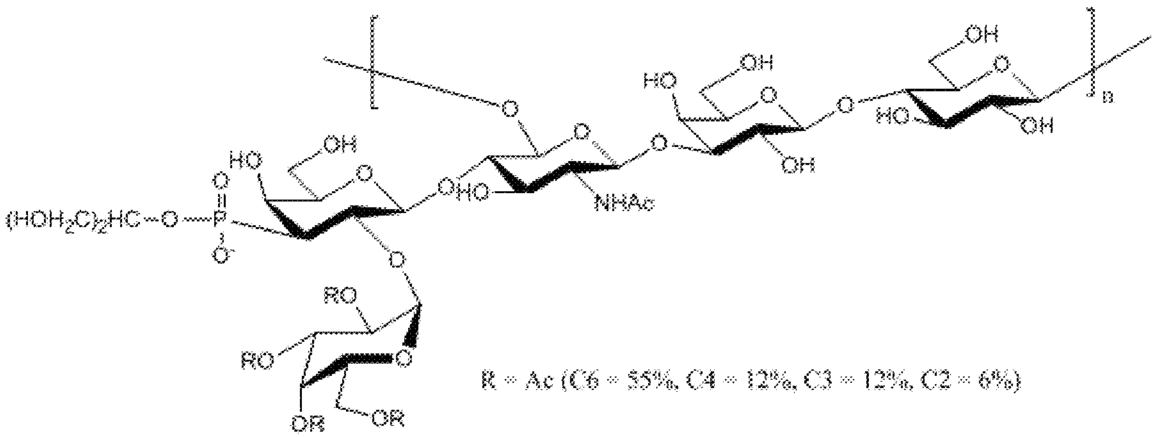
FIG. 5 shows a repeating polysaccharide structure of *S. pneumoniae* serotype 15B (Pn-15B) capsular polysaccharide.

As shown at FIG. 5, the polysaccharide repeating unit of serotype 15B consists of a branched trisaccharide backbone (one N-acetylglucosamine ($Glc_pNAc$), one galactopyranose ($Gal_p$) and one glucopyranose ($Glc_p$)) with an $\alpha Gal_p$-$\beta Gal_p$ disaccharide branch linked to the C4 hydroxyl group of $Glc_pNAc$. The phosphoglycerol is linked to the C3 hydroxyl group of the $\beta Gal_p$ residue in the disaccharide branch (Jones et al. (2005) Carbohydrate Research 340(3):403-409). Capsular polysaccharide from serotype 15C serotype has the identical backbone structure as serotype 15B but lacks the O-acetylation.

Serotype 15B polysaccharides can be obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/118752). They can also be produced using synthetic protocols known to the man skilled in the art.

Serotype 15B *S. pneumoniae* strains may be obtained from established culture collections (such as for example the American Type Culture Collection (ATCC, Manassas, VA USA) (e.g., deposit strain No. ATCC10354) or the Streptococcal Reference Laboratory (Centers for Disease Control and Prevention, Atlanta, GA USA)) or from clinical specimens.

The bacterial cells are grown in a medium, preferably in a soy based medium. Following fermentation of bacterial cells that produce *S. pneumoniae* serotype 15B capsular polysaccharides, the bacterial cells are lysed to produce a cell lysate. The serotype 15B polysaccharide may then be isolated from the cell lysate using purification techniques known in the art, including the use of centrifugation, depth filtration, precipitation, ultra-filtration, treatment with activate carbon, diafiltration and/or column chromatography (see, for example, U.S. Patent App. Pub. Nos. 2006/0228380, 2006/0228381, 2007/0184071, 2007/0184072, 2007/0231340, and 2008/0102498 and WO 2008/118752). The purified serotype 15B capsular polysaccharide can then be used for the preparation of immunogenic conjugates.

The isolated serotype 15B capsular polysaccharide obtained by purification of serotype 15B polysaccharide from the *S. pneumoniae* lysate and optionally sizing of the purified polysaccharide can be characterized by different parameters including, for example, the molecular weight (MW), the mM of acetate per mM of said serotype 15B capsular polysaccharide and the mM of glycerol per mM of said serotype 15B capsular polysaccharide.

Preferably, in order to generate 15B conjugates with advantageous filterability characteristics and/or yields, sizing of the polysaccharide to a target molecular weight range is performed prior to the conjugation to a carrier protein. Advantageously, the size of the purified serotype 15B polysaccharide is reduced while preserving critical features of the structure of the polysaccharide such as for example the presence of O-acetyl groups. Preferably, the size of the purified serotype 15B polysaccharide is reduced by mechanical homogenization.

In a preferred embodiment, the size of the purified serotype 15B polysaccharide is reduced by high pressure homogenization. High pressure homogenization achieves high shear rates by pumping the process stream through a flow path with sufficiently small dimensions. The shear rate is increased by using a larger applied homogenization pressure, and exposure time can be increased by recirculating the feed stream through the homogenizer.

The high pressure homogenization process is particularly appropriate for reducing the size of the purified serotype 15B polysaccharide while preserving the structural features of the polysaccharide, such as the presence of O-acetyl groups.

In a preferred embodiment, the isolated serotype 15B capsular polysaccharide has a molecular weight between 5 kDa and 500 kDa, between 50 kDa and 500 kDa, between 50 kDa and 450 kDa, between 100 kDa and 400 kDa, and between 100 kDa and 350 kDa. In a preferred embodiment, the isolated serotype 15B capsular polysaccharide has a molecular weight between 100 kDa and 350 kDa. In a preferred embodiment, the isolated serotype 15B capsular polysaccharide has a molecular weight between 100 kDa and 300 kDa. In a preferred embodiment, the isolated serotype 15B capsular polysaccharide has a molecular weight between 150 kDa and 300 kDa. In a preferred embodiment, the isolated serotype 15B capsular polysaccharide has a molecular weight between 150 kDa and 350 kDa. In further embodiments, the capsular polysaccharide has a molecular weight of 100 kDa to 500 kDa; 100 kDa to 400 kDa; 100 kDa to 300 kDa; 100 kDa to 200 kDa; 150 kDa to 500 kDa; 150 kDa to 400 kDa; 150 kDa to 300 kDa; 150 kDa to 200 kDa; 200 kDa to 500 kDa; 200 kDa to 400 kDa; 250 kDa to 500 kDa; 250 kDa to 400 kDa; 250 kDa to 350 kDa; 300 kDa to 500 kDa; 300 kDa to 400 kDa; and similar desired molecular weight ranges. Any whole number integer within any of the above ranges is contemplated as an embodiment of the disclosure.

Serotype 15B polysaccharide is O-acetylated and the total amount of O-acetylation is approximately 0.8-0.9 O-acetyl groups per polysaccharide repeating unit. The degree of O-acetylation of the polysaccharide can be determined by any method known in the art, for example, by proton NMR (see for example Lemercinier et al. (1996) Carbohydrate Research 296:83-96; Jones et al. (2002) J. Pharmaceutical and Biomedical Analysis 30:1233-1247; WO 2005/033148 and WO 00/56357). Another commonly used method is described in Hestrin, S. (1949) J. Biol. Chem. 180:249-261. Preferably, the presence of O-acetyl groups is determined by ion-HPLC analysis.

The presence of O-acetyl in a purified, isolated or activated serotype 15B capsular polysaccharide or in a serotype 15B polysaccharide-carrier protein conjugate is expressed as the number of mM of acetate per mM of said polysaccharide or as the number of O-acetyl group per polysaccharide repeating unit.

In a preferred embodiment, the isolated serotype 15B capsular polysaccharide comprises at least 0.1, 0.2, 0.3, 0.4, 0.5, 0.6, 0.7 or 0.8 mM acetate per mM of said serotype 15B capsular polysaccharide. In a preferred embodiment, the isolated serotype 15B capsular polysaccharide comprises at least 0.5, 0.6 or 0.7 mM acetate per mM of said serotype 15B capsular polysaccharide. In a preferred embodiment, the isolated serotype 15B capsular polysaccharide comprises at least 0.6 mM acetate per mM of said serotype 15B capsular polysaccharide. In a preferred embodiment, the isolated serotype 15B capsular polysaccharide comprises at least 0.7 mM acetate per mM of said serotype 15B capsular polysaccharide.

The presence of glycerolphosphate side chains is determined by measurement of glycerol using high performance anion exchange chromatography with pulsed amperometric detection (HPAEC-PAD) after its release by treatment of the polysaccharide with hydrofluoric acid (HF). The presence of glycerol in a purified, isolated or activated serotype 15B polysaccharide or in a serotype 15B polysaccharide-carrier protein conjugate is expressed as the number of mM of glycerol per mM of serotype 15B polysaccharide.

In a preferred embodiment, the isolated serotype 15B capsular polysaccharide comprises at least 0.1, 0.2, 0.3, 0.4, 0.5, 0.6, 0.7 or 0.8 mM glycerol per mM of said serotype 15B capsular polysaccharide. In a preferred embodiment, the isolated serotype 15B capsular polysaccharide comprises at least 0.5, 0.6 or 0.7 mM glycerol per mM of said serotype 15B capsular polysaccharide. In a preferred embodiment, the isolated serotype 15B capsular polysaccharide comprises at least 0.6 mM glycerol per mM of said serotype 15B capsular polysaccharide. In a preferred embodiment, the isolated serotype 15B capsular polysaccharide comprises at least 0.7 mM glycerol per mM of said serotype 15B capsular polysaccharide.

In a preferred embodiment, the isolated serotype 15B capsular polysaccharide has a molecular weight between 100 kDa and 350 kDa and comprises at least 0.6 mM acetate per mM of said serotype 15B capsular polysaccharide.

In a preferred embodiment, the isolated serotype 15B capsular polysaccharide has a molecular weight between 100 kDa and 350 kDa and comprises at least 0.6 mM glycerol per mM of said serotype 15B capsular polysaccharide.

In a preferred embodiment, the isolated serotype 15B capsular polysaccharide has a molecular weight between 150 kDa and 300 kDa and comprises at least 0.6 mM acetate per mM of said serotype 15B capsular polysaccharide.

In a preferred embodiment, the isolated serotype 15B capsular polysaccharide has a molecular weight between 150 kDa and 300 kDa and comprises at least 0.6 mM glycerol per mM of said serotype 15B capsular polysaccharide.

In a preferred embodiment, the isolated serotype 15B capsular polysaccharide has a molecular weight between 150 kDa and 350 kDa and comprises at least 0.6 mM acetate per mM of said serotype 15B capsular polysaccharide.

In a preferred embodiment, the isolated serotype 15B capsular polysaccharide has a molecular weight between 150 kDa and 350 kDa and comprises at least 0.6 mM glycerol per mM of said serotype 15B capsular polysaccharide.

In a preferred embodiment, the isolated serotype 15B capsular polysaccharide comprises at least 0.6 mM acetate per mM of said serotype 15B capsular polysaccharide and at least 0.6 mM glycerol per mM of said serotype 15B capsular polysaccharide.

In a preferred embodiment, the isolated serotype 15B capsular polysaccharide has a molecular weight between 100 kDa and 350 kDa and comprises at least 0.6 mM acetate per mM of said serotype 15B capsular polysaccharide and at least 0.6 mM glycerol per mM of said serotype 15B capsular polysaccharide.

In a preferred embodiment, the isolated serotype 15B capsular polysaccharide has a molecular weight between 150 kDa and 300 kDa and comprises at least 0.6 mM acetate per mM of said serotype 15B capsular polysaccharide and at least 0.6 mM glycerol per mM of said serotype 15B capsular polysaccharide.

In a preferred embodiment, the isolated serotype 15B capsular polysaccharide has a molecular weight between 150 kDa and 350 kDa and comprises at least 0.6 mM acetate per mM of said serotype 15B capsular polysaccharide and at least 0.6 mM glycerol per mM of said serotype 15B capsular polysaccharide.

1.2.7 Pneumococcal Polysaccharide Serotype 22F

Figure 6:
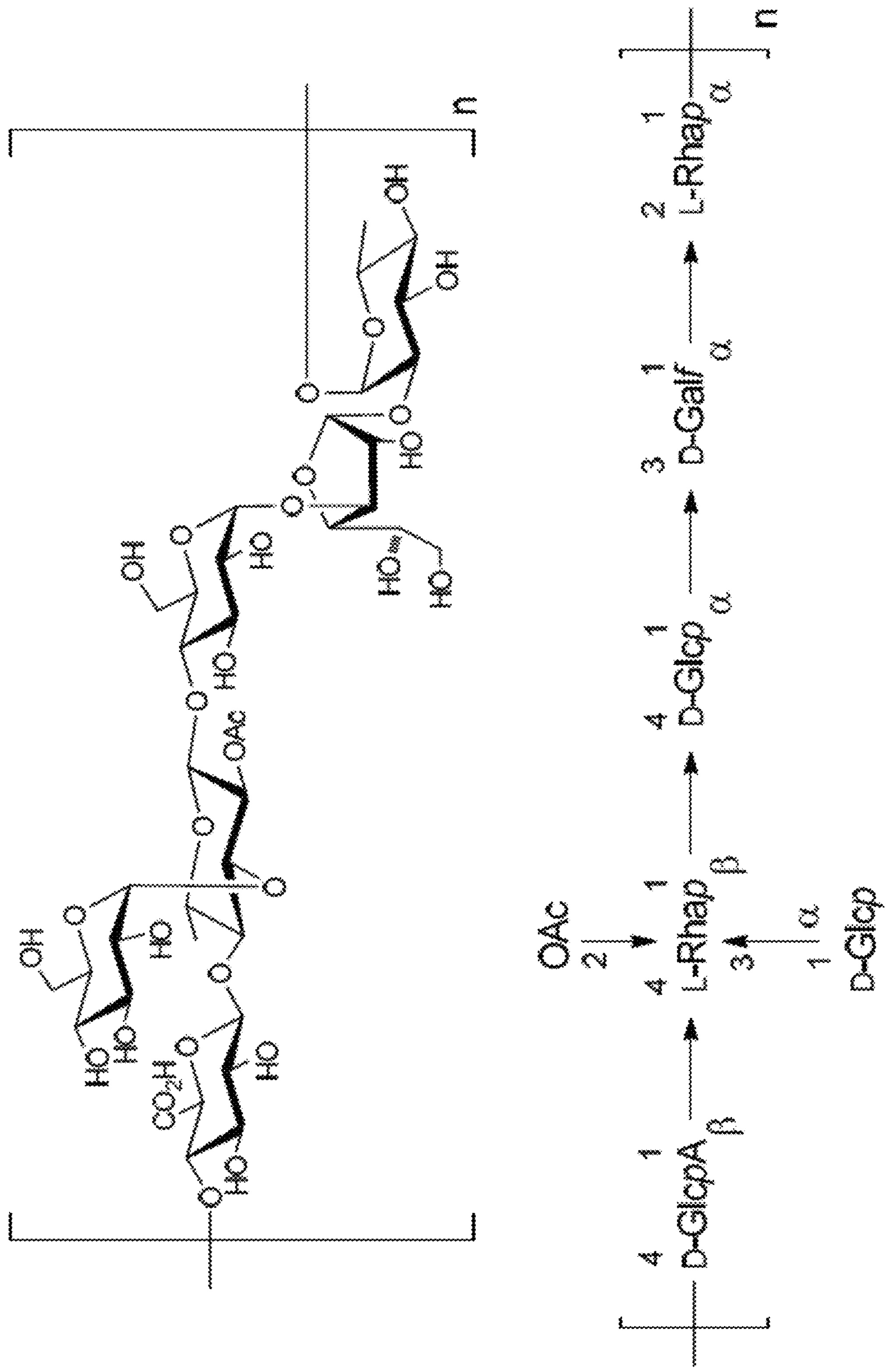
FIG. 6 shows a repeating polysaccharide structure of *S. pneumoniae* serotype 22F (Pn-22F) capsular polysaccharide.

As shown at FIG. 6, the polysaccharide repeating unit of serotype 22F consists of a branched pentasaccharide backbone (one glucuronic acid ($Glc_pA$), one glucopyranose ($Glc_p$), one galactofuranose ($Gal_f$) and two rhamnopyranoses ($Rha_p$)) with a $\alpha Glc_p$ branch linked to the C3 hydroxyl group of $\beta Rha_p$ (Richards et al. (1989) Canadian Journal of Chemistry 67(6):1038-1050). Approximately 80% of the C2 hydroxyl groups of the $\beta Rha_p$ residue in the polysaccharide repeating unit are O-acetylated.

Serotype 22F polysaccharides can be obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/118752). In addition, they can be produced using synthetic protocols.

Serotype 22F *S. pneumoniae* strains may be obtained from established culture collections (such as for example the Streptococcal Reference Laboratory (Centers for Disease Control and Prevention, Atlanta, GA)) or clinical specimens.

The isolated serotype 22F capsular polysaccharide obtained by purification of serotype 22F polysaccharide from the *S. pneumoniae* lysate and optionally sizing of the purified polysaccharide can be characterized by different parameters including, for example, the molecular weight (MW) and the mM of acetate per mM of said serotype 22F capsular polysaccharide.

Preferably, in order to generate serotype 22F conjugates with advantageous filterability characteristics and/or yields, sizing of the polysaccharide to a target molecular weight range is performed prior to the conjugation to a carrier protein. Advantageously, the size of the purified serotype 22F polysaccharide is reduced while preserving critical features of the structure of the polysaccharide such as for example the presence of O-acetyl group. Preferably, the size of the purified serotype 22F polysaccharide is reduced by mechanical homogenization.

In a preferred embodiment, the size of the purified polysaccharide is reduced by high pressure homogenization. High pressure homogenization achieves high shear rates by pumping the process stream through a flow path with sufficiently small dimensions. The shear rate is increased by using a larger applied homogenization pressure, and exposure time can be increased by recirculating the feed stream through the homogenizer.

The high pressure homogenization process is particularly appropriate for reducing the size of the purified serotype 22F polysaccharide while preserving the structural features of the polysaccharide, such as the presence of O-acetyl groups.

In some embodiments, the purified polysaccharides from *S. pneumoniae* serotype 22F before conjugation have a molecular weight of between 10 kDa and 2,000 kDa. In one embodiment, the capsular polysaccharide has a molecular weight of between 50 kDa and 1,000 kDa. In another embodiment, the capsular polysaccharide has a molecular weight of between 70 kDa to 900 kDa. In another embodiment, the capsular polysaccharide has a molecular weight of between 100 kDa to 800 kDa. In another embodiment, the capsular polysaccharide has a molecular weight of between 200 kDa to 600 kDa. In another embodiment, the capsular polysaccharide has a molecular weight of between 400 kDa to 700 kDa.

In further embodiments, the capsular polysaccharide has a molecular weight of 100 kDa to 1,000 kDa; 100 kDa to 900 kDa; 100 kDa to 800 kDa; 100 kDa to 700 kDa; 100 kDa to 600 kDa; 100 kDa to 500 kDa; 100 kDa to 400 kDa; 100 kDa to 300 kDa; 150 kDa to 1,000 kDa; 150 kDa to 900 kDa; 150 kDa to 800 kDa; 150 kDa to 700 kDa; 150 kDa to 600 kDa; 150 kDa to 500 kDa; 150 kDa to 400 kDa; 150 kDa to 300 kDa; 200 kDa to 1,000 kDa; 200 kDa to 900 kDa; 200 kDa to 800 kDa; 200 kDa to 700 kDa; 200 kDa to 600 kDa; 200 kDa to 500 kDa; 200 kDa to 400 kDa; 200 kDa to 300 kDa; 250 kDa to 1,000 kDa; 250 kDa to 900 kDa; 250 kDa to 800 kDa; 250 kDa to 700 kDa; 250 kDa to 600 kDa; 250 kDa to 500 kDa; 250 kDa to 400 kDa; 250 kDa to 350 kDa; 300 kDa to 1,000 kDa; 300 kDa to 900 kDa; 300 kDa to 800 kDa; 300 kDa to 700 kDa; 300 kDa to 600 kDa; 300 kDa to 500 kDa; 300 kDa to 400 kDa; 400 kDa to 1,000 kDa; 400 kDa to 900 kDa; 400 kDa to 800 kDa; 400 kDa to 700 kDa; 400 kDa to 600 kDa; 500 kDa to 600 kDa; and similar desired molecular weight ranges. Any whole number integer within any of the above ranges is contemplated as an embodiment of the disclosure.

A polysaccharide can become slightly reduced in size during normal purification procedures. Additionally, as described hereabove, 22F polysaccharide can be subjected to sizing techniques before conjugation. The molecular weight ranges mentioned above refer to purified polysaccharides before conjugation (e.g., before activation) after an eventual sizing step.

The degree of O-acetylation of the polysaccharide can be determined by any method known in the art, for example, by proton NMR (Lemercinier et al. (1996) Carbohydrate Research 296:83-96; Jones et al. (2002) J. Pharmaceutical and Biomedical Analysis 30:1233-1247; WO 2005/033148 and WO 00/56357). Another commonly used method is described in Hestrin, S. (1949) J. Biol. Chem. 180:249-261. Preferably, the presence of O-acetyl groups is determined by ion-HPLC analysis.

The presence of O-acetyl in a purified, isolated or activated serotype 22F capsular polysaccharide or in a serotype 22F polysaccharide-carrier protein conjugate is expressed as the number of mM of acetate per mM of said polysaccharide or as the number of O-acetyl group per polysaccharide repeating unit.

In a preferred embodiment, the purified polysaccharides from *S. pneumoniae* serotype 22F has at least 0.2, 0.4, 0.6, 0.8, 1, 1.2, 1.4 or 1.6, μmol acetate per μmol of said serotype 22F capsular polysaccharide.

1.2.8 Pneumococcal Polysaccharide Serotype 33F

Figure 7:
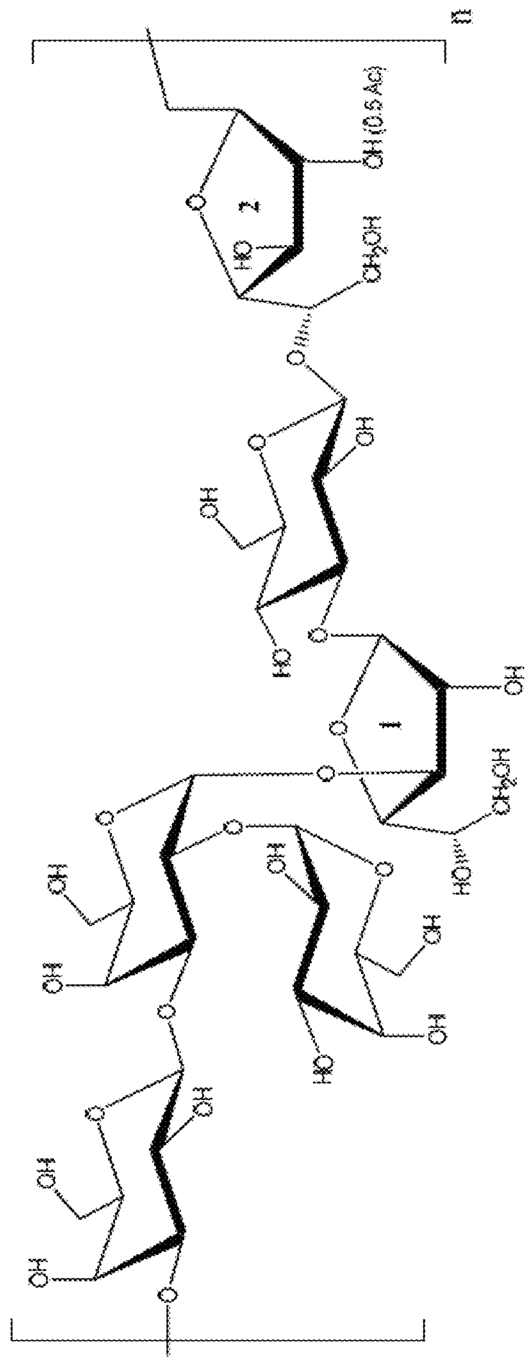
FIG. 7 shows a repeating polysaccharide structure of *S. pneumoniae* serotype 33F (Pn-33F) capsular polysaccharide.

As shown at FIG. 7, the polysaccharide repeating unit of serotype 33F consists of a branched pentasaccharide backbone (two galactopyranoses ($Gal_p$), two galactofuranoses ($Gal_f$) and one glucopyranose ($Glc_p$) with a terminal $\alpha Gal_p$ linked to the C2 hydroxyl group of $\alpha Gal_p$ residue within the backbone (Lemercinier et al. (2006) Carbohydrate Research 341(1):68-74.). It has been reported in the literature that the C2 hydroxyl group of the backbone 3-R-$Gal_f$ residue is O-acetylated.

Serotype 33F polysaccharides can be obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/118752). In addition, they can be produced using synthetic protocols.

Serotype 33F *S. pneumoniae* strains may be obtained from established culture collections (such as for example the Streptococcal Reference Laboratory (Centers for Disease Control and Prevention, Atlanta, GA)) or clinical specimens.

Purified polysaccharides from serotype 33F may be activated (e.g., chemically activated) to make them capable of reacting and then incorporated into glycoconjugates of the invention, as further described herein.

The isolated serotype 33F capsular polysaccharide obtained by purification of serotype 33F polysaccharide from the *S. pneumoniae* lysate and optionally sizing of the purified polysaccharide can be characterized by different parameters including, for example, the molecular weight and the mM of acetate per mM of said serotype 33F capsular polysaccharide.

In some embodiments, the purified polysaccharides from *S. pneumoniae* serotype 33F before conjugation have a molecular weight of between 10 kDa and 2,000 kDa. In other such embodiments, the saccharide has a molecular weight of between 50 kDa and 2,000 kDa. In further such embodiments, the saccharide has a molecular weight of between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa. Any whole number integer within any of the above ranges is contemplated as an embodiment of the disclosure.

A polysaccharide can become slightly reduced in size during normal purification procedures. Additionally, as described herein, polysaccharide can be subjected to sizing techniques before conjugation. The molecular weight ranges mentioned above refer to purified polysaccharides before conjugation (e.g., before activation) after an eventual sizing step.

The presence of O-acetyl in a purified, isolated or activated serotype 33F capsular polysaccharide or in a serotype 33F polysaccharide-carrier protein conjugate is expressed as the number of mM of acetate per mM of said polysaccharide or as the number of O-acetyl group per polysaccharide repeating unit.

In a preferred embodiment, the purified polysaccharides from *S. pneumoniae* serotype 33F has at least 0.2, 0.4, 0.6, 0.8, 1.0, 1.2, 1.4 or 1.6, μmol acetate per μmol of said serotype 33F capsular polysaccharide.

1.3 Glycoconjugates of the Invention

The purified saccharides are chemically activated to make the saccharides (i.e., activated saccharides) capable of reacting with the carrier protein. Once activated, each capsular saccharide is separately conjugated to a carrier protein to form a glycoconjugate. In one embodiment, each capsular saccharide is conjugated to the same carrier protein. The chemical activation of the saccharides and subsequent conjugation to the carrier protein can be achieved by the activation and conjugation methods disclosed herein.

1.3.1 Glycoconjugates from *S. pneumoniae* serotype 1, 3, 4, 5, 6A, 6B, 7F, 9V, 14, 18C, 19A, 19F and 23F Capsular polysaccharides from serotypes 1, 3, 4, 5, 6A, 6B, 7F, 9V, 14, 18C, 19A, 19F and 23F of *S. pneumoniae* are prepared by standard techniques known to those of ordinary skill in the art (see for example WO 2006/110381, WO 2008/118752, WO 2006/110352, and U.S. Patent App. Pub. Nos. 2006/0228380, 2006/0228381, 2008/0102498 and 2008/0286838).

In an embodiment, the polysaccharides are activated with 1-cyano-4-dimethylamino pyridinium tetrafluoroborate (CDAP) to form a cyanate ester. The activated polysaccharide is then coupled directly or via a spacer (linker) group to an amino group on the carrier protein (preferably $CRM_{197}$). For example, the spacer could be cystamine or cysteamine to give a thiolated polysaccharide which could be coupled to the carrier via a thioether linkage obtained after reaction with a maleimide-activated carrier protein (for example using N-[γ-maleimidobutyrloxy]succinimide ester (GMBS)) or a haloacetylated carrier protein (for example using iodoacetimide, N-succinimidyl bromoacetate (SBA; SIB), N-succinimidyl(4-iodoacetyl)aminobenzoate (SIAB), sulfo-succinimidyl(4-iodoacetyl)aminobenzoate (sulfo-SIAB), N-succinimidyl iodoacetate (SIA) or succinimidyl 3-[bromoacetamido]proprionate (SBAP)). Preferably, the cyanate ester (optionally made by CDAP chemistry) is coupled with hexane diamine or adipic acid dihydrazide (ADH) and the amino-derivatised saccharide is conjugated to the carrier protein (e.g., $CRM_{197}$) using carbodiimide (e.g., EDAC or EDC) chemistry via a carboxyl group on the protein carrier. Such conjugates are described for example in WO 93/15760, WO 95/08348 and WO 96/29094.

Other suitable techniques for conjugation use carbodiimides, hydrazides, active esters, norborane, p-nitrobenzoic acid, N-hydroxysuccinimide, S-NHS, EDC, TSTU. Many are described in International Patent Application Publication No. WO 98/42721. Conjugation may involve a carbonyl linker which may be formed by reaction of a free hydroxyl group of the saccharide with 1,1'-carbonyldiimidazole (CDI) (see Bethell et al. (1979) J. Biol. Chem. 254:2572-2574; Hearn et al. (1981) J. Chromatogr. 218:509-518) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

In an preferred embodiment, at least one of capsular polysaccharides from serotypes 1, 3, 4, 5, 6A, 6B, 7F, 9V, 14, 18C, 19A, 19F and 23F of *S. pneumoniae* is conjugated to the carrier protein by reductive amination (such as described in U.S. Patent Appl. Pub. Nos. 2006/0228380, 2007/0231340, 2007/0184071 and 2007/0184072, WO 2006/110381, WO 2008/079653, and WO 2008/143709). In a preferred embodiment, the capsular polysaccharides from serotypes 1, 3, 4, 5, 6A, 6B, 7F, 9V, 14, 18C, 19A, 19F and 23F of *S. pneumoniae* are all conjugated to the carrier protein by reductive amination.

Reductive amination involves two steps, (1) oxidation of the polysaccharide, (2) reduction of the activated polysaccharide and a carrier protein to form a conjugate. Before oxidation, the polysaccharide is optionally hydrolyzed. Mechanical or chemical hydrolysis may be employed. Chemical hydrolysis may be conducted using acetic acid. The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate).

In an embodiment the capsular polysaccharide from serotype 1, 3, 4, 5, 6A, 6B, 7F, 9V, 14, 18C, 19A, 19F or 23F of *S. pneumoniae* is oxidized in the presence of metaperiodate, preferably in the presence of sodium periodate ($NaIO_4$). In another embodiment the capsular polysaccharides from serotypes 1, 3, 4, 5, 6A, 6B, 7F, 9V, 14, 18C, 19A, 19F and 23F of *S. pneumoniae* is oxydized in the presence of orthoperiodate, preferably in the presence of periodic acid.

Following the oxidation step of the polysaccharide, the polysaccharide is said to be activated and is referred to as "activated polysaccharide" here below. The activated polysaccharide and the carrier protein may be lyophilised (freeze-dried), either independently (discrete lyophilization) or together (co-lyophilized). In one embodiment the activated polysaccharide and the carrier protein are co-lyophilized. In another embodiment the activated polysaccharide and the carrier protein are lyophilized independently.

In one embodiment the lyophilization takes place in the presence of a non-reducing sugar, possible non-reducing sugars include sucrose, trehalose, raffinose, stachyose, melezitose, dextran, mannitol, lactitol and palatinit.

The second step of the conjugation process is the reduction of the activated polysaccharide and a carrier protein to form a conjugate (so-called reductive amination), using a reducing agent. Reducing agents which are suitable include the cyanoborohydrides, such as sodium cyanoborohydride, borane-pyridine, or borohydride exchange resin. In one embodiment the reducing agent is sodium cyanoborohydride.

In an embodiment, the reduction reaction is carried out in aqueous solvent, in another embodiment the reaction is carried out in aprotic solvent. In an embodiment, the reduction reaction is carried out in DMSO (dimethylsulfoxide) or in DMF (dimethylformamide) solvent. The DMSO or DMF solvent may be used to reconstitute the activated polysaccharide and carrier protein which has been lyophilized.

At the end of the reduction reaction, there may be unreacted aldehyde groups remaining in the conjugates, these may be capped using a suitable capping agent. In one embodiment this capping agent is sodium borohydride ($NaBH_4$). Following the conjugation (the reduction reaction and optionally the capping), the glycoconjugates may be purified. The glycoconjugates maybe purified by diafiltration and/or ion exchange chromatography and/or size exclusion chromatography. In an embodiment, the glycoconjugates are purified by diafiltration or ion exchange chromatography or size exclusion chromatography. In one embodiment the glycoconjugates are sterile filtered.

In some embodiments, the glycoconjugate from *S. pneumoniae* serotypes 9V and/or 18C comprise a saccharide which has a degree of O-acetylation of between 10% and 100%, between 20% and 100%, between 30% and 100%, between 40% and 100%, between 50% and 100%, between 60% and 100%, between 70% and 100%, between 75% and 100%, between 80% and 100%, between 90% and 100%, between 50% and 90%, between 60% and 90%, between 70% and 90% or between 80% and 90%. In other embodiments, the degree of O-acetylation is ≥10%, ≥20%, ≥30%, ≥40%, ≥50%, ≥60%, ≥70%, ≥80%, or ≥90%, or about 100%.

In some embodiments, the glycoconjugate from *S. pneumoniae* serotypes 9V and/or 18C of the invention are O-acetylated. In some embodiments, the glycoconjugate from *S. pneumoniae* serotype 9V is O-acetylated and the glycoconjugate from *S. pneumoniae* serotype 18C is de-O-acetylated.

1.3.2 Glycoconjugates from *S. pneumoniae* Serotype 22F

In an embodiment, the serotype 22F glycoconjugates are obtained by activating polysaccharide with 1-cyano-4-dimethylamino pyridinium tetrafluoroborate (CDAP) to form a cyanate ester. The activated polysaccharide may be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide, SIB, SIAB, sulfo-SIAB, SIA, or SBAP). Preferably, the cyanate ester (optionally made by CDAP chemistry) is coupled with hexane diamine or adipic acid dihydrazide (ADH) and the amino-derivatised saccharide is conjugated to the carrier protein using carbodiimide (e.g., EDAC or EDC) chemistry via a carboxyl group on the protein carrier. Such conjugates are described for example in WO 93/15760, WO 95/08348 and WO 96/29094.

Other suitable techniques use carbodiimides, hydrazides, active esters, norborane, p-nitrobenzoic acid, N-hydroxysuccinimide, S-NHS, EDC, TSTU. Many are described in International Patent Application Publication No. WO 98/42721. Conjugation may involve a carbonyl linker which may be formed by reaction of a free hydroxyl group of the saccharide with CDI (see Bethell et al. (1979) J. Biol. Chem. 254:2572-2574; Hearn et al. (1981) J. Chromatogr. 218:509-518) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

In preferred embodiments, the serotype 22F glycoconjugates of the invention are prepared using reductive amination. Reductive amination involves two steps, (1) oxidation of the polysaccharide to generate aldehyde functionalities from vicinal diols in individual hexasaccharide unit, (2) reduction of the activated polysaccharide and a carrier protein (e.g., $CRM_{197}$) to form a conjugate.

Preferably, before oxidation, sizing of the serotype 22F polysaccharide to a target molecular weight (MW) range is performed. Advantageously, the size of the purified serotype 22F polysaccharide is reduced while preserving critical features of the structure of the polysaccharide such as for example the presence of O-acetyl groups. Preferably, the size of the purified serotype 22F polysaccharide is reduced by mechanical homogenization (see section 1.2.7 above).

In an embodiment, serotype polysaccharide is activated (oxidized) by a process comprising the step of:

(a) reacting isolated serotype 22F polysaccharide with an oxidizing agent;

(b) quenching the oxidation reaction by addition of a quenching agent resulting in an activated serotype 22F polysaccharide.

In a preferred embodiment, the oxidizing agent is periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate). In a preferred embodiment, the oxidizing agent is sodium periodate. In a preferred embodiment, the periodate used for the oxidation of serotype 22F polysaccharide is metaperiodate. In a preferred embodiment the periodate used for the oxidation of serotype 22F polysaccharide is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

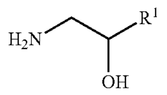

(I)

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid.

In one embodiment, the quenching agent is an amino acid. In such embodiments, said amino acid may be selected from serine, threonine, cysteine, cystine, methionine, proline, hydroxyproline, tryptophan, tyrosine, and histidine.

In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms.

Preferably, the quenching agent is a compound of formula (II):

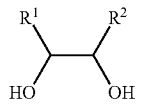

(II)

wherein $R^1$ and $R^2$ are each independently selected from H, methyl, ethyl, propyl or isopropyl.

In a preferred embodiment, the quenching agent is glycerol, ethylene glycol, propan-1,2-diol, butan-1,2-diol or butan-2,3-diol, or ascorbic acid. In a preferred embodiment, the quenching agent is butan-2,3-diol.

In a preferred embodiment, the isolated serotype 22F polysaccharide is activated by a process comprising the step of:

(a) reacting isolated serotype 22F polysaccharide with periodate;

(b) quenching the oxidation reaction by addition of butan-2,3-diol resulting in an activated serotype 22F polysaccharide.

Following the oxidation step of the polysaccharide, the polysaccharide is said to be activated and is referred to as "activated polysaccharide" here below.

In a preferred embodiment, the activated serotype 22F polysaccharide is purified. The activated serotype 22F polysaccharide is purified according to methods known to the man skilled in the art such as gel permeation chromatography (GPC), dialysis or ultrafiltration/diafiltration. For example, the activated 22F polysaccharide is purified by concentration and diafiltration using an ultrafiltration device.

In a preferred embodiment the degree of oxidation of the activated serotype 22F polysaccharide is between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotype 22F polysaccharide is between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

In a preferred embodiment, the activated serotype 22F polysaccharide has a molecular weight between 25 kDa and 1,000 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa. In an embodiment, the activated serotype 22F polysaccharide has a molecular weight between 300 kDa and 800 kDa. In an embodiment, the activated serotype 22F polysaccharide has a molecular weight between 400 kDa and 600 kDa. In a preferred embodiment, the activated serotype 22F polysaccharide has a molecular weight between 400 kDa and 600 kDa and a degree of oxidation between 10 and 25, between 10 and 20, between 12 and 20 or between 14 and 18. In a preferred embodiment, the activated serotype 22F polysaccharide has a molecular weight between 400 kDa and 600 kDa and a degree of oxidation between 10 and 20.

In a preferred embodiment, the activated serotype 22F polysaccharide comprises at least 0.1, 0.2, 0.3, 0.4, 0.5, 0.6 or 0.7 or about 0.8 mM acetate per mM serotype 22F polysaccharide. In a preferred embodiment, the activated serotype 22F polysaccharide comprises at least 0.5, 0.6 or 0.7 mM acetate per mM serotype 22F polysaccharide. In a preferred embodiment, the activated serotype 22F polysaccharide comprises at least 0.6 mM acetate per mM serotype 22F polysaccharide. In a preferred embodiment, the activated serotype 22F polysaccharide comprises at least 0.7 mM acetate per mM serotype 22F polysaccharide.

In a preferred embodiment, the activated serotype 22F polysaccharide has a molecular weight between 400 kDa and 800 kDa and comprises at least 0.6 mM acetate per mM serotype 22F polysaccharide.

In a preferred embodiment, the activated serotype 22F polysaccharide has a molecular weight between 400 kDa and 800 kDa, a degree of oxidation between 12 and 20 and comprises at least 0.6 mM acetate per mM serotype 22F polysaccharide.

The activated polysaccharide and/or the carrier protein may be lyophilised (freeze-dried), either independently (discrete lyophilization) or together (co-lyophilized).

In an embodiment, the activated serotype 22F polysaccharide is lyophilized, optionally in the presence of saccharide. In a preferred embodiment, the saccharide is selected from sucrose, trehalose, raffinose, stachyose, melezitose, dextran, mannitol, lactitol and palatinit. In a preferred embodiment, the saccharide is sucrose. In one embodiment, the lyophilized activated polysaccharide is then compounded with a solution comprising the carrier protein.

In another embodiment the activated polysaccharide and the carrier protein are co-lyophilised. In such embodiments, the activated serotype 22F polysaccharide is compounded with the carrier protein and lyophilized optionally in the presence of a saccharide. In a preferred embodiment, the saccharide is selected from sucrose, trehalose, raffinose, stachyose, melezitose, dextran, mannitol, lactitol and palatinit. In a preferred embodiment, the saccharide is sucrose. The co-lyophilized polysaccharide and carrier protein can then be resuspended in solution and reacted with a reducing agent.

The second step of the conjugation process is the reduction of the activated polysaccharide and a carrier protein to form a conjugate (reductive amination), using a reducing agent.

The activated serotype 22F polysaccharide can be conjugated to a carrier protein by a process comprising the step of:

(c) compounding the activated serotype 22F polysaccharide with a carrier protein; and (d) reacting the compounded activated serotype 22F polysaccharide and carrier protein with a reducing agent to form a serotype 22F polysaccharide-carrier protein conjugate.

In an embodiment, the reduction reaction is carried out in aqueous solvent, in another embodiment the reaction is carried out in aprotic solvent. In an embodiment, the reduction reaction is carried out in DMSO (dimethylsulfoxide) or in DMF (dimethylformamide)) solvent. The DMSO or DMF solvent may be used to reconstitute the activated polysaccharide and carrier protein which has been lyophilised.

The conjugation of activated serotype 22F polysaccharide with a protein carrier by reductive amination in dimethylsulfoxide (DMSO) is suitable to preserve the O-acetyl content of the polysaccharide as compared, for example, to reductive amination in aqueous phase where the level of O-acetylation of the polysaccharide may be significantly reduced. Therefore in a preferred embodiment, step (c) and step (d) are carried out in DMSO.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^i$PrN-$BH_3$, benzylamine-$BH_3$ or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotype 22F polysaccharide to the carrier protein, the glycoconjugate can be purified (enriched with respect to the amount of polysaccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

In some embodiments, the serotype 22F glycoconjugates of the present invention comprise a saccharide having a molecular weight of between 10 kDa and 2,000 kDa. In other such embodiments, the saccharide has a molecular weight of between 50 kDa and 1,000 kDa. In other such embodiments, the saccharide has a molecular weight of between 70 kDa and 900 kDa. In other such embodiments, the saccharide has a molecular weight of between 100 kDa and 800 kDa. In other such embodiments, the saccharide has a molecular weight of between 200 kDa and 600 kDa. In further such embodiments, the saccharide has a molecular weight of 100 kDa to 1,000 kDa; 100 kDa to 900 kDa; 100 kDa to 800 kDa; 100 kDa to 700 kDa; 100 kDa to 600 kDa; 100 kDa to 500 kDa; 100 kDa to 400 kDa; 100 kDa to 300 kDa; 150 kDa to 1,000 kDa; 150 kDa to 900 kDa; 150 kDa to 800 kDa; 150 kDa to 700 kDa; 150 kDa to 600 kDa; 150 kDa to 500 kDa; 150 kDa to 400 kDa; 150 kDa to 300 kDa; 200 kDa to 1,000 kDa; 200 kDa to 900 kDa; 200 kDa to 800 kDa; 200 kDa to 700 kDa; 200 kDa to 600 kDa; 200 kDa to 500 kDa; 200 kDa to 400 kDa; 200 kDa to 300 kDa; 250 kDa to 1,000 kDa; 250 kDa to 900 kDa; 250 kDa to 800 kDa; 250 kDa to 700 kDa; 250 kDa to 600 kDa; 250 kDa to 500 kDa; 250 kDa to 400 kDa; 250 kDa to 350 kDa; 300 kDa to 1000 kDa; 300 kDa to 900 kDa; 300 kDa to 800 kDa; 300 kDa to 700 kDa; 300 kDa to 600 kDa; 300 kDa to 500 kDa; 300 kDa to 400 kDa; 400 kDa to 1,000 kDa; 400 kDa to 900 kDa; 400 kDa to 800 kDa; 400 kDa to 700 kDa; 400 kDa to 600 kDa; 500 kDa to 600 kDa. Any whole number integer within any of the above ranges is contemplated as an embodiment of the disclosure. In some such embodiments, the serotype 22F glycoconjugates are prepared using reductive amination. In some embodiments, the serotype 22F glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the serotype 22F glycoconjugate has a molecular weight of between 500 kDa and 10,000 kDa. In other embodiments, the serotype 22F glycoconjugate has a molecular weight of between 1,000 kDa and 8,000 kDa. In still other embodiments, the serotype 22F glycoconjugate has a molecular weight of between 2,000 kDa and 8,000 kDa or between 3,000 kDa and 7,000 kDa. In further embodiments, the serotype 22F glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotype 22F glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the serotype 22F glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa. The molecular weight of the glycoconjugate is measured by SEC-MALLS. Any whole number integer within any of the above ranges is contemplated as an embodiment of the disclosure.

In a preferred embodiment, the serotype 22F glycoconjugate of the invention comprises at least 0.1, 0.2, 0.3, 0.4, 0.5, 0.6 or 0.7 or about 0.8 mM acetate per mM serotype 22F polysaccharide. In a preferred embodiment, the glycoconjugate comprises at least 0.5, 0.6 or 0.7 mM acetate per mM serotype 22F polysaccharide. In a preferred embodiment, the glycoconjugate comprises at least 0.6 mM acetate per mM serotype 22F polysaccharide. In a preferred embodiment, the glycoconjugate comprises at least 0.7 mM acetate per mM serotype 22F polysaccharide.

In a preferred embodiment, the ratio of mM acetate per mM serotype 22F polysaccharide in the glycoconjugate to mM acetate per mM serotype 22F polysaccharide in the isolated polysaccharide is at least 0.6, 0.65, 0.7, 0.75, 0.8, 0.85, 0.9, or 0.95. In a preferred embodiment, the ratio of mM acetate per mM serotype 22F polysaccharide in the glycoconjugate to mM acetate per mM serotype 22F polysaccharide in the isolated polysaccharide is at least 0.7. In a preferred embodiment, the ratio of mM acetate per mM serotype 22F polysaccharide in the glycoconjugate to mM acetate per mM serotype 22F polysaccharide in the isolated polysaccharide is at least 0.9.

In a preferred embodiment, the ratio of mM acetate per mM serotype 22F polysaccharide in the glycoconjugate to mM acetate per mM serotype 22F polysaccharide in the activated polysaccharide is at least 0.6, 0.65, 0.7, 0.75, 0.8, 0.85, 0.9, or 0.95. In a preferred embodiment, the ratio of mM acetate per mM serotype 22F polysaccharide in the glycoconjugate to mM acetate per mM serotype 22F polysaccharide in the activated polysaccharide is at least 0.7. In a preferred embodiment, the ratio of mM acetate per mM serotype 22F polysaccharide in the glycoconjugate to mM acetate per mM serotype 22F polysaccharide in the activated polysaccharide is at least 0.9.

Another way to characterize the serotype 22F glycoconjugates of the invention is by the number of lysine residues in the carrier protein (e.g., $CRM_{197}$) that become conjugated to the saccharide which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered compared to the $CRM_{197}$ protein starting material used to generate the conjugate materials. In a preferred embodiment, the degree of conjugation of the serotype 22F glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotype 22F glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotype 22F glycoconjugate of the invention is between 4 and 7. In some such embodiments, the carrier protein is $CRM_{197}$.

The serotype 22F glycoconjugates of the invention may also be characterized by the ratio (weight/weight) of saccharide to carrier protein. In some embodiments, the ratio of serotype 22F polysaccharide to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of serotype 22F capsular polysaccharide to carrier protein in the conjugate is between 0.9 and 1.1. In some such embodiments, the carrier protein is $CRM_{197}$.

The serotype 22F glycoconjugates and immunogenic compositions of the invention may contain free saccharide that is not covalently conjugated to the carrier protein, but is nevertheless present in the glycoconjugate composition. The free saccharide may be noncovalently associated with (i.e., noncovalently bound to, adsorbed to, or entrapped in or with) the glycoconjugate.

In a preferred embodiment, the serotype 22F glycoconjugate comprises less than about 50%, 45%, 40%, 35%, 30%, 25%, 20% or 15% of free serotype 22F polysaccharide compared to the total amount of serotype 22F polysaccharide. In a preferred embodiment the serotype 22F glycoconjugate comprises less than about 40% of free serotype 22F polysaccharide compared to the total amount of serotype 22F polysaccharide. In a preferred embodiment the serotype 22F glycoconjugate comprises less than about 25% of free serotype 22F polysaccharide compared to the total amount of serotype 22F polysaccharide. In a preferred embodiment the serotype 22F glycoconjugate comprises less than about 20% of free serotype 22F polysaccharide compared to the total amount of serotype 22F polysaccharide. In a preferred embodiment the serotype 22F glycoconjugate comprises less than about 15% of free serotype 22F polysaccharide compared to the total amount of serotype 22F polysaccharide.

The serotype 22F glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the serotype 22F glycoconjugate has a $K_d$ below or equal to 0.3 in a CL-4B column. In a preferred embodiment, at least 40% of the glycoconjugate has a $K_d$ below or equal to 0.3 in a CL-4B column. In a preferred embodiment, at least 45%, 50%, 55%, 60%, 65%, 70%, 75%, 80%, or 85% of the serotype 22F glycoconjugate has a $K_d$ below or equal to 0.3 in a CL-4B column. In a preferred embodiment, at least 60% of the serotype 22F glycoconjugate has a $K_d$ below or equal to 0.3 in a CL-4B column. In a preferred embodiment, between 50% and 80% of the serotype 22F glycoconjugate has a $K_d$ below or equal to 0.3 in a CL-4B column. In a preferred embodiment, between 65% and 80% of the serotype 22F glycoconjugate has a $K_d$ below or equal to 0.3 in a CL-4B column.

1.3.3 Glycoconjugates from *S. pneumoniae* serotype 33F

In an embodiment, the serotype 33F glycoconjugates are obtained by activating polysaccharide with 1-cyano-4-dimethylamino pyridinium tetrafluoroborate (CDAP) to form a cyanate ester. The activated polysaccharide may be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide, SIB, SIAB, sulfo-SIAB, SIA, or SBAP). Preferably, the cyanate ester (optionally made by CDAP chemistry) is coupled with hexane diamine or adipic acid dihydrazide (ADH) and the amino-derivatised saccharide is conjugated to the carrier protein using carbodiimide (e.g., EDAC or EDC) chemistry via a carboxyl group on the protein carrier. Such conjugates are described for example in WO 93/15760, WO 95/08348 and WO 96/29094.

Other suitable techniques use carbodiimides, hydrazides, active esters, norborane, p-nitrobenzoic acid, N-hydroxysuccinimide, S-NHS, EDC, TSTU. Many are described in International Patent Application Publication No. WO 98/42721. Conjugation may involve a carbonyl linker which may be formed by reaction of a free hydroxyl group of the saccharide with CDI (see Bethell et al. (1979) J. Biol. Chem. 254:2572-2574; Hearn et al. (1981) J. Chromatogr. 218:509-518) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

In certain embodiments, the serotype 33F glycoconjugates of the invention are prepared using reductive amination. In such embodiment, the serotype 33F glycoconjugates of the invention maybe prepared using reductive amination in aqueous phase (RAC/aqueous). Reductive amination in aqueous phase has been successfully applied to produce pneumococcal conjugate vaccine (see, e.g., WO 2006/110381). Preferably though, when using reductive amination, the serotype 33F glycoconjugates are prepared via reductive amination in DMSO (RAC/DMSO). In view of the challenges associated with the preservation of O-acetyl functionality using RAC/aqueous process, reductive amination in DMSO is preferred. RAC/DMSO has been successfully applied to produce pneumococcal conjugate vaccine (see, e.g., WO 2006/110381).

In preferred embodiments, the serotype 33F glycoconjugates of the invention are prepared using eTEC conjugation (hereinafter "serotype 33F eTEC linked glycoconjugates"), such as described at Examples 1, 2 and 3 and in WO 2014/027302. Said 33F glycoconjugates comprise a saccharide covalently conjugated to a carrier protein through one or more eTEC spacers, wherein the saccharide is covalently conjugated to the eTEC spacer through a carbamate linkage, and wherein the carrier protein is covalently conjugated to the eTEC spacer through an amide linkage. The eTEC linked glycoconjugates of the invention may be represented by the general formula (III):

(III)

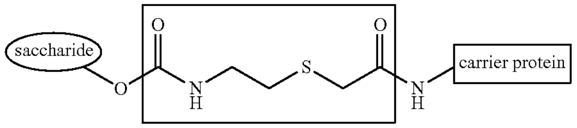

wherein the atoms that comprise the eTEC spacer are contained in the central box.

The eTEC spacer includes seven linear atoms (i.e., —$C(O)NH(CH_2)_2SCH_2C(O)$—) and provides stable thioether and amide bonds between the saccharide and carrier protein. Synthesis of the eTEC linked glycoconjugate involves reaction of an activated hydroxyl group of the saccharide with the amino group of a thioalkylamine reagent, e.g., cystamine or cysteamine or a salt thereof, forming a carbamate linkage to the saccharide to provide a thiolated saccharide. Generation of one or more free sulfhydryl groups is accomplished by reaction with a reducing agent to provide an activated thiolated saccharide. Reaction of the free sulfhydryl groups of the activated thiolated saccharide with an activated carrier protein having one or more α-haloacetamide groups on amine containing residues generates a thioether bond to form the conjugate, wherein the carrier protein is attached to the eTEC spacer through an amide bond.

In serotype 33F glycoconjugates of the invention, the saccharide may be a polysaccharide or an oligosaccharide. The carrier protein may be selected from any suitable carrier as described herein or known to those of skill in the art. In frequent embodiments, the saccharide is a polysaccharide. In some such embodiments, the carrier protein is $CRM_{197}$. In some such embodiments, the eTEC linked glycoconjugate comprises a *S. pneumoniae* serotype 33F capsular polysaccharide.

In particularly preferred embodiments, the eTEC linked glycoconjugate comprises a Pn-33F capsular polysaccharide, which is covalently conjugated to $CRM_{197}$ through an eTEC spacer (serotype 33F eTEC linked glycoconjugates).

In some embodiments, the serotype 33F glycoconjugates of the present invention comprise a saccharide having a molecular weight of between 10 kDa and 2,000 kDa. In other such embodiments, the saccharide has a molecular weight of between 50 kDa and 2,000 kDa. In further such embodiments, the saccharide has a molecular weight of between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa. Any whole number integer within any of the above ranges is contemplated as an embodiment of the disclosure.

In some embodiments, the serotype 33F glycoconjugate of the invention has a molecular weight of between 50 kDa and 20,000 kDa. In other embodiments, the serotype 33F glycoconjugate has a molecular weight of between 500 kDa and 10,000 kDa. In other embodiments, the serotype 33F glycoconjugate has a molecular weight of between 200 kDa and 10,000 kDa. In still other embodiments, the serotype 33F glycoconjugate has a molecular weight of between 1,000 kDa and 3,000 kDa.

In further embodiments, the serotype 33F glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; between 2,000 kDa and 3,000 kDa; between 3,000 kDa and 20,000 kDa; between 3,000 kDa and 15,000 kDa; between 3,000 kDa and 12,500 kDa; between 3,000 kDa and 10,000 kDa; between 3,000 kDa and 9,000 kDa; between 3,000 kDa and 8,000 kDa; between 3,000 kDa and 7,000 kDa; between 3,000 kDa and 6,000 kDa; between 3,000 kDa and 5,000 kDa or between 3,000 kDa and 4,000 kDa. Any whole number integer within any of the above ranges is contemplated as an embodiment of the disclosure.

Another way to characterize the serotype 33F glycoconjugates of the invention is by the number of lysine residues in the carrier protein (e.g., $CRM_{197}$) that become conjugated to the saccharide, which can be characterized as a range of conjugated lysines (degree of conjugation).

In a preferred embodiment, the degree of conjugation of the serotype 33F glycoconjugate of the invention is between 2 and 20, between 4 and 16, between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotype 33F glycoconjugate of the invention is about 2, about 3, about 4, about 5, about 6, about 7, about 8, about 9, about 10, about 11, about 12, about 13, about 14, about 15, about 16, about 17, about 18, about 19 or about 20. In a preferred embodiment, the degree of conjugation of the serotype 33F glycoconjugate of the invention is between 4 and 16. In some such embodiments, the carrier protein is $CRM_{197}$.

In a preferred embodiment, the carrier protein comprises $CRM_{197}$, which contains 39 lysine residues. In some such embodiments, the $CRM_{197}$ may comprise 4 to 16 lysine residues out of 39 covalently linked to the saccharide. Another way to express this parameter is that about 10% to about 41% of $CRM_{197}$ lysines are covalently linked to the saccharide. In another such embodiment, the $CRM_{197}$ may comprise 2 to 20 lysine residues out of 39 covalently linked to the saccharide. Another way to express this parameter is that about 5% to about 50% of $CRM_{197}$ lysines are covalently linked to the saccharide. In some embodiments, the $CRM_{197}$ may comprise about 4, about 5, about 6, about 7, about 8, about 9, about 10, about 11, about 12, about 13, about 14, about 15, or about 16 lysine residues out of 39 covalently linked to the saccharide.

In frequent embodiments, the carrier protein is covalently conjugated to an eTEC spacer through an amide linkage to one or more &-amino groups of lysine residues on the carrier protein. In some such embodiments, the carrier protein comprises 2 to 20 lysine residues covalently conjugated to the saccharide. In other such embodiments, the carrier protein comprises 4 to 16 lysine residues covalently conjugated to the saccharide.

The serotype 33F glycoconjugates of the invention may also be characterized by the ratio (weight/weight) of saccharide to carrier protein. In some embodiments, the saccharide to carrier protein ratio (w/w) is between 0.2 and 4.0 (e.g., about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the saccharide to carrier protein ratio (w/w) is between 1.0 and 2.5. In further embodiments, the saccharide to carrier protein ratio (w/w) is between 0.4 and 1.7. In some such embodiments, the carrier protein is $CRM_{197}$.

The frequency of attachment of the saccharide chain to a lysine on the carrier protein is another parameter for characterizing the serotype 33F glycoconjugates of the invention. For example, in some embodiments, at least one covalent linkage between the carrier protein and the polysaccharide occurs for every 4 saccharide repeat units of the polysaccharide. In another embodiment, the covalent linkage between the carrier protein and the polysaccharide occurs at least once in every 10 saccharide repeat units of the polysaccharide. In another embodiment, the covalent linkage between the carrier protein and the polysaccharide occurs at least once in every 15 saccharide repeat units of the polysaccharide. In a further embodiment, the covalent linkage between the carrier protein and the polysaccharide occurs at least once in every 25 saccharide repeat units of the polysaccharide.

In frequent embodiments, the carrier protein is $CRM_{197}$ and the covalent linkage via an eTEC spacer between the $CRM_{197}$ and the polysaccharide occurs at least once in every 4, 10, 15 or 25 saccharide repeat units of the polysaccharide.

In other embodiments, the conjugate comprises at least one covalent linkage between the carrier protein and saccharide for every 5 to 10 saccharide repeat units; every 2 to 7 saccharide repeat units; every 3 to 8 saccharide repeat units; every 4 to 9 saccharide repeat units; every 6 to 11 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; every 4 to 25 saccharide repeat units or every 2 to 25 saccharide repeat units. In frequent embodiments, the carrier protein is $CRM_{197}$.

In another embodiment, at least one linkage between carrier protein and saccharide occurs for every 2, 3, 4, 5, 6, 7, 8, 9, 10, 11, 12, 13, 14, 15, 16, 17, 18, 19, 20, 21, 22, 23, 24 or 25 saccharide repeat units of the polysaccharide. In an embodiment, the carrier protein is $CRM_{197}$. Any whole number integer within any of the above ranges is contemplated as an embodiment of the disclosure.

An important consideration during conjugation is the development of conditions that permit the retention of potentially sensitive non-saccharide substituent functional groups of the individual components, such as O-Acyl, phosphate or glycerol phosphate side chains that may form part of the saccharide epitope.

In one embodiment, the serotype 33F glycoconjugates of the invention comprise a saccharide which has a degree of O-acetylation between 10% and 100%. In some such embodiments, the saccharide has a degree of O-acetylation between 50% and 100%. In other such embodiments, the saccharide has a degree of O-acetylation between 75% and 100%. In further embodiments, the saccharide has a degree of O-acetylation greater than or equal to 70% (≥70%).

In a preferred embodiment, the serotype 33F glycoconjugate of the invention comprises at least 0.1, 0.2, 0.3, 0.4, 0.5, 0.6, 0.7 or 0.8 mM acetate per mM serotype 33F capsular polysaccharide. In a preferred embodiment, the glycoconjugate comprises at least 0.5, 0.6 or 0.7 mM acetate per mM serotype 33F capsular polysaccharide. In a preferred embodiment, the glycoconjugate comprises at least 0.6 mM acetate per mM serotype 33F capsular polysaccharide. In a preferred embodiment, the glycoconjugate comprises at least 0.7 mM acetate per mM serotype 33F capsular polysaccharide. In a preferred embodiment, the presence of O-acetyl groups is determined by ion-HPLC analysis.

In a preferred embodiment, the ratio of mM acetate per mM serotype 33F polysaccharide in the glycoconjugate to mM acetate per mM serotype 33F polysaccharide in the isolated polysaccharide is at least 0.6, 0.65, 0.7, 0.75, 0.8, 0.85, 0.9, or 0.95. In a preferred embodiment, the ratio of mM acetate per mM serotype 33F polysaccharide in the glycoconjugate to mM acetate per mM serotype 33F polysaccharide in the isolated polysaccharide is at least 0.7. In a preferred embodiment, the ratio of mM acetate per mM serotype 33F polysaccharide in the glycoconjugate to mM acetate per mM serotype 33F polysaccharide in the isolated polysaccharide is at least 0.9.

In a preferred embodiment, the ratio of mM acetate per mM serotype 33F polysaccharide in the glycoconjugate to mM acetate per mM serotype 33F polysaccharide in the activated polysaccharide is at least 0.6, 0.65, 0.7, 0.75, 0.8, 0.85, 0.9, or 0.95. In a preferred embodiment, the ratio of mM acetate per mM serotype 33F polysaccharide in the glycoconjugate to mM acetate per mM serotype 33F polysaccharide in the activated polysaccharide is at least 0.7. In a preferred embodiment, the ratio of mM acetate per mM serotype 33F polysaccharide in the glycoconjugate to mM acetate per mM serotype 33F polysaccharide in the activated polysaccharide is at least 0.9.

The serotype 33F glycoconjugates and immunogenic compositions of the invention may contain free saccharide that is not covalently conjugated to the carrier protein, but is nevertheless present in the glycoconjugate composition. The free saccharide may be noncovalently associated with (i.e., noncovalently bound to, adsorbed to, or entrapped in or with) the glycoconjugate.

In some embodiments, the serotype 33F glycoconjugates of the invention comprise less than about 50%, 45%, 40%, 35%, 30%, 25%, 20%, 15%, 10% or 5% of free serotype 33F polysaccharide compared to the total amount of serotype 33F polysaccharide.

Preferably, serotype 33F the glycoconjugate comprises less than 15% free saccharide, more preferably less than 10% free saccharide, and still more preferably, less than 5% of free saccharide. In a preferred embodiment the serotype 33F glycoconjugate comprises less than about 25% of free serotype 33F polysaccharide compared to the total amount of serotype 33F polysaccharide. In a preferred embodiment the serotype 33F glycoconjugate comprises less than about 20% of free serotype 33F polysaccharide compared to the total amount of serotype 33F polysaccharide. In a preferred embodiment the serotype 33F glycoconjugate comprises less than about 15% of free serotype 33F polysaccharide compared to the total amount of serotype 33F polysaccharide.

In certain preferred embodiments, the invention provides a serotype 33F glycoconjugate having one or more of the following features alone or in combination: the polysaccharide has a molecular weight of between 50 kDa and 2,000 kDa; the glycoconjugate has a molecular weight of between 500 kDa to 10,000 KDa; the carrier protein comprises 2 to 20 lysine residues covalently linked to the saccharide; the saccharide to carrier protein ratio (w/w) is between 0.2 and 4.0; the glycoconjugate comprises at least one covalent linkage between the carrier protein and the polysaccharide for every 4, 10, 15 or 25 saccharide repeat units of the polysaccharide; the saccharide has a degree of O-acetylation between 75% and 100%; the conjugate comprises less than about 15% free polysaccharide relative to total polysaccharide; the carrier protein is $CRM_{197}$.

The serotype 33F glycoconjugates may also be characterized by their molecular size distribution ($K_d$). Size exclusion chromatography media (CL-4B) can be used to determine the relative molecular size distribution of the conjugate, as mentioned above.

In an embodiment, at least 15% of the serotype 33F glycoconjugates of the invention have a $K_d$ below or equal to 0.3 in a CL-4B column. In an embodiment, at least 15%, 20%, 25%, 30%, 35%, 40%, 45%, 50%, 60%, 70%, 80% or 90% of the serotype 33F glycoconjugates of the invention have a $K_d$ below or equal to 0.3 in a CL-4B column.

In a preferred embodiment, at least 35% of the serotype 33F glycoconjugates of the invention have a $K_d$ below or equal to 0.3 in a CL-4B column. In preferred embodiments, at least 40%, 45%, 50%, 55%, 60%, 65%, 70%, 75%, 80%, or 85% of the serotype 33F glycoconjugates of the invention have a $K_d$ below or equal to 0.3 in a CL-4B column. In a preferred embodiment, at least 60% of the serotype 33F glycoconjugates of the invention have a $K_d$ below or equal to 0.3 in a CL-4B column. In a preferred embodiment, at least 70% of the serotype 33F glycoconjugates of the invention have a $K_d$ below or equal to 0.3 in a CL-4B column.

In a preferred embodiment, between 40% and 90% of the serotype 33F glycoconjugates have a $K_d$ below or equal to 0.3 in a CL-4B column. In a preferred embodiment, between 50% and 90% of the serotype 33F glycoconjugates have a $K_d$ below or equal to 0.3 in a CL-4B column. In a preferred embodiment, between 65% and 80% of the serotype 33F glycoconjugates have a $K_d$ below or equal to 0.3 in a CL-4B column.

1.3.4 Glycoconjugates from *S. pneumoniae* Serotype 15B

In an embodiment, the serotype 15B glycoconjugates are obtained by activating polysaccharide with 1-cyano-4-dimethylamino pyridinium tetrafluoroborate (CDAP) to form a cyanate ester. The activated polysaccharide may be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide, SIB, SIAB, sulfo-SIAB, SIA, or SBAP). Preferably, the cyanate ester (optionally made by CDAP chemistry) is coupled with hexane diamine or adipic acid dihydrazide (ADH) and the amino-derivatised saccharide is conjugated to the carrier protein using carbodiimide (e.g., EDAC or EDC) chemistry via a carboxyl group on the protein carrier. Such conjugates are described for example in WO 93/15760, WO 95/08348 and WO 96/29094.

Other suitable techniques use carbodiimides, hydrazides, active esters, norborane, p-nitrobenzoic acid, N-hydroxysuccinimide, S-NHS, EDC, TSTU. Many are described in International Patent Application Publication No. WO 98/42721. Conjugation may involve a carbonyl linker which may be formed by reaction of a free hydroxyl group of the saccharide with CDI (see Bethell et al. (1979) J. Biol. Chem. 254:2572-2574; Hearn et al. (1981) J. Chromatogr. 218:509-518) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

In preferred embodiments, the serotype 15B glycoconjugates of the invention are prepared using reductive amination. Reductive amination involves two steps, (1) oxidation of the polysaccharide to generate aldehyde functionalities from vicinal diols in individual hexasaccharide unit, (2) reduction of the activated polysaccharide and a carrier protein to form a conjugate.

Preferably, before oxidation, sizing of the serotype 15B polysaccharide to a target molecular weight (MW) range is performed. Advantageously, the size of the purified serotype 15B polysaccharide is reduced while preserving critical features of the structure of the polysaccharide such as for example the presence of O-acetyl groups. Preferably, the size of the purified serotype 15B polysaccharide is reduced by mechanical homogenization (see section 1.2.6 above).

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate). In a preferred embodiment the periodate used for the oxidation of serotype 15B capsular polysaccharide is metaperiodate. In a preferred embodiment the periodate used for the oxidation of serotype 15B capsular polysaccharide is sodium metaperiodate.

In a preferred embodiment, the polysaccharide is reacted with 0.01 to 10.0, 0.05 to 5.0, 0.1 to 1.0, 0.5 to 1.0, 0.7 to 0.8, 0.05 to 0.5, 0.1 to 0.3 molar equivalents of oxidizing agent. In a preferred embodiment, the polysaccharide is reacted with about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95 molar equivalents of oxidizing agent. In a preferred embodiment, the polysaccharide is reacted with about 0.15 molar equivalents of oxidizing agent. In a preferred embodiment, the polysaccharide is reacted with about 0.25 molar equivalents of oxidizing agent. In a preferred embodiment, the polysaccharide is reacted with about 0.5 molar equivalents of oxidizing agent. In a preferred embodiment, the polysaccharide is reacted with about 0.6 molar equivalents of oxidizing agent. In a preferred embodiment, the polysaccharide is reacted with about 0.7 molar equivalents of oxidizing agent.

In a preferred embodiment, the duration of the reaction is between 1 hour and 50 hours, between 10 hours and 30 hours, between 15 hours and 20 hours, between 15 hours and 17 hours or about 16 hours.

In a preferred embodiment, the temperature of the reaction is maintained between 15° C. and 45° C., between 15° C. and 30° C., between 20° C. and 25° C. In a preferred embodiment, the temperature of the reaction is maintained at about 23° C.

In a preferred embodiment, the oxidation reaction is carried out in a buffer selected from sodium phosphate, potassium phosphate, 2-(N-morpholino)ethanesulfonic acid (MES) or Bis-Tris. In a preferred embodiment, the buffer is potassium phosphate.

In a preferred embodiment, the buffer has a concentration of between 1 mM and 500 mM, between 1 mM and 300 mM, or between 50 mM and 200 mM. In a preferred embodiment the buffer has a concentration of about 100 mM.

In a preferred embodiment, the oxidation reaction is carried out at a pH between 4.0 and 8.0, between 5.0 and 7.0, or between 5.5 and 6.5. In a preferred embodiment, the pH is about 6.0.

In preferred embodiment, the activated serotype 15B capsular polysaccharide is obtained by reacting 0.5 mg/mL to 5 mg/mL of isolated serotype 15B capsular polysaccharide with 0.2 to 0.3 molar equivalents of periodate at a temperature between 20° C. and 25° C.

In a preferred embodiment, the activated serotype 15B capsular polysaccharide is purified. The activated serotype 15B capsular polysaccharide is purified according to methods known to the man skilled in the art, such as gel permeation chromatography (GPC), dialysis or ultrafiltration/diafiltration. For example, the activated capsular polysaccharide is purified by concentration and diafiltration using an ultrafiltration device. In a preferred embodiment, the degree of oxidation of the activated serotype 15B capsular polysaccharide is between 2 and 20, between 2 and 15, between 2 and 10, between 2 and 5, between 5 and 20, between 5 and 15, between 5 and 10, between 10 and 20, between 10 and 15, or between 15 and 20. In a preferred embodiment the degree of oxidation of the activated serotype 15B capsular polysaccharide is between 2 and 10, between 4 and 8, between 4 and 6, between 6 and 8, between 6 and 12, between 8 and 12, between 9 and 11, between 10 and 16, between 12 and 16, between 14 and 18, between 16 and 20, between 16 and 18, or between 18 and 20.

In a preferred embodiment, the activated serotype 15B capsular polysaccharide has a molecular weight between 5 kDa and 500 kDa, between 50 kDa and 500 kDa, between 50 kDa and 450 kDa, between 100 kDa and 400 kDa, between 100 kDa and 350 kDa. In a preferred embodiment, the activated serotype 15B capsular polysaccharide has a molecular weight between 100 kDa and 350 kDa. In a preferred embodiment, the activated serotype 15B capsular polysaccharide has a molecular weight between 100 kDa and 300 kDa. In a preferred embodiment, the activated serotype 15B capsular polysaccharide has a molecular weight between 100 kDa and 250 kDa.

In a preferred embodiment, the activated serotype 15B capsular polysaccharide comprises at least 0.1, 0.2, 0.3, 0.4, 0.5, 0.6, 0.7 or 0.8 mM acetate per mM of said serotype 15B capsular polysaccharide. In a preferred embodiment, the activated serotype 15B capsular polysaccharide comprises at least 0.5, 0.6 or 0.7 mM acetate per mM of said serotype 15B capsular polysaccharide. In a preferred embodiment, the activated serotype 15B capsular polysaccharide comprises at least 0.6 mM acetate per mM of said serotype 15B capsular polysaccharide. In a preferred embodiment, the activated serotype 15B capsular polysaccharide comprises at least 0.7 mM acetate per mM of said serotype 15B capsular polysaccharide.

In a preferred embodiment, the activated serotype 15B capsular polysaccharide comprises at least 0.1, 0.2, 0.3, 0.4, 0.5, 0.6, 0.7 or 0.8 mM glycerol per mM of said serotype 15B capsular polysaccharide. In a preferred embodiment, the activated serotype 15B capsular polysaccharide comprises at least 0.5, 0.6 or 0.7 mM glycerol per mM of said serotype 15B capsular polysaccharide. In a preferred embodiment, the activated serotype 15B capsular polysaccharide comprises at least 0.6 mM glycerol per mM of said serotype 15B capsular polysaccharide. In a preferred embodiment, the activated serotype 15B capsular polysaccharide comprises at least 0.7 mM glycerol per mM of said serotype 15B capsular polysaccharide.

In a preferred embodiment, the activated serotype 15B capsular polysaccharide has a molecular weight between 100 kDa and 250 kDa and comprises at least 0.6 mM acetate per mM of said serotype 15B capsular polysaccharide.

In a preferred embodiment, the activated serotype 15B capsular polysaccharide has a molecular weight between 100 kDa and 250 kDa and comprises at least 0.6 mM glycerol per mM of said serotype 15B capsular polysaccharide.

In a preferred embodiment, the activated serotype 15B capsular polysaccharide comprises at least 0.6 mM acetate per mM of said serotype 15B capsular polysaccharide and at least 0.6 mM glycerol per mM of said serotype 15B capsular polysaccharide.

In a preferred embodiment, the activated serotype 15B capsular polysaccharide has a molecular weight between 100 kDa and 250 kDa and comprises at least 0.6 mM acetate per mM of said serotype 15B capsular polysaccharide and at least 0.6 mM glycerol per mM of said serotype 15B capsular polysaccharide.

In an embodiment, the activated serotype 15B capsular polysaccharide is lyophilized, optionally in the presence of saccharide. In a preferred embodiment, the saccharide is selected from sucrose, trehalose, raffinose, stachyose, melezitose, dextran, mannitol, lactitol and palatinit. In a preferred embodiment, the saccharide is sucrose. The lyophilized activated capsular polysaccharide can then be compounded with a solution comprising the carrier protein.

In another embodiment, the activated serotype 15B capsular polysaccharide is compounded with the carrier protein and lyophilized optionally in the presence of a saccharide. In a preferred embodiment, the saccharide is selected from sucrose, trehalose, raffinose, stachyose, melezitose, dextran, mannitol, lactitol and palatinit. In a preferred embodiment, the saccharide is sucrose. The co-lyophilized polysaccharide and carrier protein can then be resuspended in solution and reacted with a reducing agent.

The activated serotype 15B capsular polysaccharide can be conjugated to a carrier protein by a process comprising the step of:

(a) compounding the activated serotype 15B capsular polysaccharide with a carrier protein, and
(b) reacting the compounded activated serotype 15B capsular polysaccharide and carrier protein with a reducing agent to form a serotype 15B capsular polysaccharide-carrier protein conjugate.

The conjugation of activated serotype 15B capsular polysaccharide with a protein carrier by reductive amination in dimethylsulfoxide (DMSO) is suitable to preserve the O-acetyl content of the polysaccharide as compared for example to reductive amination in aqueous solution where the level of O-acetylation of the polysaccharide is significantly reduced. In a preferred embodiment, step (a) and step (b) are carried out in DMSO.

In a preferred embodiment, step (a) comprises dissolving lyophilized serotype 15B capsular polysaccharide in a solution comprising a carrier protein and DMSO. In a preferred embodiment, step (a) comprises dissolving co-lyophilized serotype 15B capsular polysaccharide and carrier protein in DMSO.

When steps (a) and (b) are carried out in aqueous solution, steps (a) and (b) are carried out in a buffer, preferably selected from PBS, MES, HEPES, Bis-tris, ADA, PIPES, MOPSO, BES, MOPS, DIPSO, MOBS, HEPPSO, POPSO, TEA, EPPS, Bicine or HEPB, at a pH between 6.0 and 8.5, between 7.0 and 8.0 or between 7.0 and 7.5. In a preferred embodiment the buffer is PBS. In a preferred embodiment the pH is about 7.3.

In a preferred embodiment, the concentration of activated serotype 15B capsular polysaccharide in step (b) is between 0.1 mg/mL and 10 mg/mL, between 0.5 mg/mL and 5 mg/mL, or between 0.5 mg/mL and 2 mg/mL. In a preferred embodiment, the concentration of activated serotype 15B capsular polysaccharide in step (b) is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 mg/mL.

In a preferred embodiment the initial input ratio (weight by weight) of activated serotype 15B capsular polysaccharide to carrier protein is between 5:1 and 0.1:1, between 2:1 and 0.1:1, between 2:1 and 1:1, between 1.5:1 and 1:1, between 0.1:1 and 1:1, between 0.3:1 and 1:1, or between 0.6:1 and 1:1.

In a preferred embodiment the initial input ratio of activated serotype 15B capsular polysaccharide to carrier protein is about 0.6:1 to 1:1. In another preferred embodiment the initial input ratio of activated serotype 15B capsular polysaccharide to carrier protein is about 0.6:1 to 1.5:1. Such initial input ratio is particularly suitable to obtain low levels of free polysaccharide in the glycoconjugate.

In a preferred embodiment the initial input ratio of activated serotype 15B capsular polysaccharide to carrier protein is about 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1 or 2:1.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMeiPrN-BH3, benzylamine-BH3 or 5-ethyl-2-methylpyridine borane (PEMB). In a preferred embodiment, the reducing agent is sodium cyanoborohydride. In a preferred embodiment, the reducing agent is sodium 2-Picoline Borane.

In a preferred embodiment, the quantity of reducing agent used in step (b) is between about 0.1 and 10.0 molar equivalents, between 0.5 and 5.0 molar equivalents, or between 1.0 and 2.0 molar equivalents. In a preferred embodiment, the quantity of reducing agent used in step (b) is about 1.0, 1.1, 1.2, 1.3, 1.4, 1.5, 1.6, 1.7, 1.8, 1.9 or 2.0 molar equivalents.

In a preferred embodiment, the duration of step (b) is between 1 hour and 60 hours, between 10 hours and 50 hours, between 40 hours and 50 hours, or between 42 hours and 46 hours. In a preferred embodiment, the duration of step (b) is about 44 hours.

In a preferred embodiment, the temperature of the reaction in step (b) is maintained between 10° C. and 40° C., between 15° C. and 30° C. or between 20° C. and 26° C. In a preferred embodiment, the temperature of the reaction in step (b) is maintained at about 23° C.

In a preferred embodiment, the process for the preparation of a glycoconjugate comprising *S. pneumoniae* serotype 15B capsular polysaccharide covalently linked to a carrier protein further comprises a step (step (c)) of capping unreacted aldehyde (quenching) by addition of $NaBH_4$.

In a preferred embodiment, the quantity of $NaBH_4$ used in step (c) is between 0.1 and 10 molar equivalents, between 0.5 and 5.0 molar equivalents or between 1.0 and 3.0 molar equivalents. In a preferred embodiment, the quantity of $NaBH_4$ used in step (c) is about 2 molar equivalents.

In a preferred embodiment, the duration of step (c) is between 0.1 hours and 10 hours, 0.5 hours and 5 hours, or between 2 hours and 4 hours. In a preferred embodiment, the duration of step (c) is about 3 hours.

In a preferred embodiment, the temperature of the reaction in step (c) is maintained between 15° C. and 45° C., between 15° C. and 30° C. or between 20° C. and 26° C. In a preferred embodiment, the temperature of the reaction in step (c) is maintained at about 23° C.

In a preferred embodiment the yield of the conjugation step is greater than 50%, 55%, 60%, 65%, 70%, 75%, 80%, 85% or 90%. In a preferred embodiment the yield of the conjugation step (step b) is greater than 60%. In a preferred embodiment the yield of the conjugation step (step b) is greater than 70%. The yield is the amount of serotype 15B polysaccharide in the conjugate×100)/amount of activated polysaccharide used in the conjugation step.

In a preferred embodiment, the process for the preparation of a glycoconjugate comprising *S. pneumoniae* serotype 15B capsular polysaccharide covalently linked to a carrier protein comprises the steps of:

(a) sizing purified serotype 15B polysaccharide by high pressure homogenization;
(b) reacting the sized serotype 15B polysaccharide with an oxidizing agent;

(c) compounding the activated serotype 15B polysaccharide with a carrier protein;

(d) reacting the compounded activated serotype 15B polysaccharide and carrier protein with a reducing agent to form a serotype 15B polysaccharide-carrier protein conjugate; and (e) capping unreacted aldehyde (quenching) by addition of $NaBH_4$.

In a preferred embodiment the yield of the conjugation step (step d) of the above process is greater than 50%, 55%, 60%, 65%, 70%, 75%, 80%, 85% or 90%. In a preferred embodiment the yield of the conjugation step (step d) is greater than 60%. In a preferred embodiment the yield of the conjugation step (step d) is greater than 70%. The yield is the amount of serotype 15B polysaccharide in the conjugate× 100)/amount of activated polysaccharide used in the conjugation step.

After conjugation of the serotype 15B capsular polysaccharide to the carrier protein, the polysaccharide-protein conjugate can be purified (enriched with respect to the amount of polysaccharide-protein conjugate) by a variety of techniques known to the skilled person. These techniques include dialysis, concentration/diafiltration operations, tangential flow filtration, precipitation/elution, column chromatography (DEAE or hydrophobic interaction chromatography), and depth filtration.

In an embodiment the carrier protein is as defined at section 1.1. In an embodiment the carrier protein is selected in the group consisting of: DT (Diphtheria toxin), TT (tetanus toxoid), $CRM_{197}$, other DT mutants, PD (*Haemophilus influenzae* protein D), or immunologically functional equivalents thereof. In an embodiment the carrier protein is $CRM_{197}$.

In some embodiments, the serotype 15B glycoconjugates of the present invention are conjugated to the carrier protein (e.g., $CRM_{197}$) and comprise a saccharide having a molecular weight of between 5 kDa and 1,500 kDa. In other such embodiments, the saccharide has a molecular weight of between 10 kDa and 1,500 kDa. In further such embodiments, the saccharide has a molecular weight of between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 250 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 250 kDa; between 200 kDa and 1,500 kDa; between 200 kDa and 1,250 kDa; between 200 kDa and 1,000 kDa; between 200 kDa and 750 kDa; or between 200 kDa and 500 kDa; or between 200 kDa and 400 kDa. Any whole number integer within any of the above ranges is contemplated as an embodiment of the disclosure. In some embodiments, the serotype 15B glycoconjugate of the invention has a molecular weight of between 50 kDa and 20,000 kDa. In some embodiments, the serotype 15B glycoconjugate of the invention has a molecular weight of between 1,000 kDa and 20,000 kDa In a preferred embodiment, the serotype 15B glycoconjugate of the invention has a molecular weight between 3,000 kDa and 20,000 kDa, between 5,000 kDa and 10,000 kDa, between 5,000 kDa and 20,000 kDa, between 8,000 kDa and 20,000 kDa, between 8,000 kDa and 16,000 kDa or between 10,000 kDa and 16,000 kDa.

In further embodiments, the serotype 15B glycoconjugate of the invention has a molecular weight of about 1,000 kDa, about 1,500 kDa, about 2,000 kDa, about 2,500 kDa, about 3,000 kDa, about 3,500 kDa, about 4,000 kDa, about 4,500 kDa, about 5,000 kDa, about 5,500 kDa, about 6,000 kDa, about 6,500 kDa, about 7,000 kDa, about 7,500 kDa, about 8,000 kDa, about 8,500 kDa, about 9,000 kDa, about 9,500 kDa about 10,000 kDa, about 10,500 kDa, about 11,000 kDa, about 11,500 kDa, about 12,000 kDa, about 12,500 kDa, about 13,000 kDa, about 13,500 kDa, about 14,000 kDa, about 14,500 kDa, about 15,000 kDa, about 15,500 kDa, about 16,000 kDa, about 16,500 kDa, about 17,000 kDa, about 17,500 kDa, about 18,000 kDa, about 18,500 kDa about 19,000 kDa, about 19,500 kDa or about 20,000 kDa.

In further embodiments, the serotype 15B glycoconjugate of the invention has a molecular weight of between 1,000 kDa and 20,000 kDa; between 1,000 kDa and 15,000 kDa; between 1,000 kDa and 10,000 kDa; between 1,000 kDa and 7,500 kDa; between 1,000 kDa and 5,000 kDa; between 1,000 kDa and 4,000 kDa; between 1,000 kDa and 3,000 kDa; between 2,000 kDa and 20,000 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotype 15B glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 3,000 kDa and 4,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa or between 4,000 kDa and 5,000 kDa. In further embodiments, the serotype 15B glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate is measured by SEC-MALLS. Any whole number integer within any of the above ranges is contemplated as an embodiment of the disclosure. In an embodiment, said serotype 15B glycoconjugates are prepared using reductive amination.

The serotype 15B glycoconjugates of the invention may also be characterized by the ratio (weight/weight) of saccharide to carrier protein. In a preferred embodiment, the ratio (weight by weight) of serotype 15B capsular polysaccharide to carrier protein in the conjugate is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9 or about 3.0). In a preferred embodiment, the ratio of serotype 15B capsular polysaccharide to carrier protein in the conjugate is between 0.4 and 2. In a preferred embodiment, the ratio of serotype 15B capsular polysaccharide to carrier protein in the conjugate is between 0.5 and 2.0, 0.5 and 1.5, 0.5 and 1.0, 1.0 and 1.5, 1.0 and 2.0. In a preferred embodiment, the ratio of serotype 15B capsular polysaccharide to carrier protein in the conjugate is between 0.7 and 0.9.

The serotype 15B glycoconjugates and immunogenic compositions of the invention may contain free saccharide that is not covalently conjugated to the carrier protein, but is nevertheless present in the glycoconjugate composition. The free saccharide may be noncovalently associated with (i.e., noncovalently bound to, adsorbed to, or entrapped in or with) the glycoconjugate.

In a preferred embodiment, the serotype 15B glycoconjugate of the invention comprises less than about 50%, 45%, 40%, 35%, 30%, 25%, 20% or 15% of free serotype 15B capsular polysaccharide compared to the total amount of serotype 15B capsular polysaccharide. In a preferred embodiment the serotype 15B glycoconjugate of the invention comprises less than about 25% of free serotype 15B capsular polysaccharide compared to the total amount of serotype 15B capsular polysaccharide. In a preferred embodiment the serotype 15B glycoconjugate of the invention comprises less than about 20% of free serotype 15B capsular polysaccharide compared to the total amount of serotype 15B capsular polysaccharide. In a preferred embodiment the serotype 15B glycoconjugates of the invention comprises less than about 15% of free serotype 15B capsular polysaccharide compared to the total amount of serotype 15B capsular polysaccharide.

The serotype 15B glycoconjugates may also be characterized by their molecular size distribution ($K_d$). Size exclusion chromatography media (CL-4B) can be used to determine the relative molecular size distribution of the conjugate, as mentioned above.

In a preferred embodiment, at least 20% of the serotype 15B glycoconjugates of the invention have a $K_d$ below or equal to 0.3 in a CL-4B column. In a preferred embodiment, at least 30% of the immunogenic conjugate has a $K_d$ below or equal to 0.3 in a CL-4B column. In a preferred embodiment, at least 40% of the serotype 15B glycoconjugates of the invention have a $K_d$ below or equal to 0.3 in a CL-4B column. In a preferred embodiment, at least 45%, 50%, 55%, 60%, 65%, 70%, 75%, 80%, or 85% of the serotype 15 glycoconjugates of the invention have a $K_d$ below or equal to 0.3 in a CL-4B column. In a preferred embodiment, at least 60% of the serotype 15B glycoconjugates of the invention have a $K_d$ below or equal to 0.3 in a CL-4B column. In a preferred embodiment, at least 70% of the serotype 15B glycoconjugates of the invention have a $K_d$ below or equal to 0.3 in a CL-4B column.

In a preferred embodiment, between 40% and 90% of the serotype 15B glycoconjugates have a $K_d$ below or equal to 0.3 in a CL-4B column. In a preferred embodiment, between 50% and 90% of the serotype 15B glycoconjugates have a $K_d$ below or equal to 0.3 in a CL-4B column. In a preferred embodiment, between 65% and 80% of the serotype 15B glycoconjugates have a $K_d$ below or equal to 0.3 in a CL-4B column.

In a preferred embodiment, the serotype 15B glycoconjugate of the invention comprises at least 0.1, 0.2, 0.3, 0.4, 0.5, 0.6, 0.7 or 0.8 mM acetate per mM serotype 15B capsular polysaccharide. In a preferred embodiment, the glycoconjugate comprises at least 0.5, 0.6 or 0.7 mM acetate per mM serotype 15B capsular polysaccharide. In a preferred embodiment, the glycoconjugate comprises at least 0.6 mM acetate per mM serotype 15B capsular polysaccharide. In a preferred embodiment, the glycoconjugate comprises at least 0.7 mM acetate per mM serotype 15B capsular polysaccharide. In a preferred embodiment, the presence of O-acetyl groups is determined by ion-HPLC analysis.

In a preferred embodiment, the ratio of mM acetate per mM serotype 15B capsular polysaccharide in the serotype 15B glycoconjugate to mM acetate per mM serotype 15B capsular polysaccharide in the isolated polysaccharide is at least 0.6, 0.65, 0.7, 0.75, 0.8, 0.85, 0.9, or 0.95. In a preferred embodiment, the ratio of mM acetate per mM serotype 15B capsular polysaccharide in the serotype 15B glycoconjugate to mM acetate per mM serotype 15B capsular polysaccharide in the isolated polysaccharide is at least 0.7. In a preferred embodiment, the ratio of mM acetate per mM serotype 15B capsular polysaccharide in the serotype 15B glycoconjugate to mM acetate per mM serotype 15B capsular polysaccharide in the isolated polysaccharide is at least 0.9. In a preferred embodiment, the presence of O-acetyl groups is determined by ion-HPLC analysis.

In a preferred embodiment, the ratio of mM acetate per mM serotype 15B capsular polysaccharide in the serotype 15B glycoconjugate to mM acetate per mM serotype 15B capsular polysaccharide in the activated polysaccharide is at least 0.6, 0.65, 0.7, 0.75, 0.8, 0.85, 0.9, or 0.95. In a preferred embodiment, the ratio of mM acetate per mM serotype 15B capsular polysaccharide in the serotype 15B glycoconjugate to mM acetate per mM serotype 15B capsular polysaccharide in the activated polysaccharide is at least 0.7. In a preferred embodiment, the ratio of mM acetate per mM serotype 15B capsular polysaccharide in the serotype 15B glycoconjugate to mM acetate per mM serotype 15B capsular polysaccharide in the activated polysaccharide is at least 0.9. In a preferred embodiment, the presence of O-acetyl groups is determined by ion-HPLC analysis.

In a preferred embodiment, the serotype 15B glycoconjugate of the invention comprises at least 0.1, 0.2, 0.3, 0.4, 0.5, 0.6, 0.7 or 0.8 mM glycerol per mM serotype 15B capsular polysaccharide. In a preferred embodiment, the serotype 15B glycoconjugate of the invention comprises at least 0.5, 0.6 or 0.7 mM glycerol per mM serotype 15B capsular polysaccharide. In a preferred embodiment, the serotype 15B glycoconjugate of the invention comprises at least 0.6 mM glycerol per mM serotype 15B capsular polysaccharide. In a preferred embodiment, the serotype 15B glycoconjugate of the invention comprises at least 0.7 mM glycerol per mM serotype 15B capsular polysaccharide.

Another way to characterize the serotype 15B glycoconjugates of the invention is by the number of lysine residues in the carrier protein (e.g., $CRM_{197}$) that become conjugated to the saccharide which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered compared to the $CRM_{197}$ protein starting material used to generate the conjugate materials.

In a preferred embodiment, the degree of conjugation of the serotype 15B glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotype 15B glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotype 15B glycoconjugate of the invention is between 2 and 5.

1.3.5 Glycoconjugates from *S. pneumoniae* Serotype 12F

In the glycoconjugates from *S. pneumoniae* serotype 12F of the present invention, the saccharide is selected from the group consisting of a polysaccharide and an oligosaccharide, and the carrier protein is selected from any suitable carrier as described herein or known to those of skill in the art. In some preferred embodiments, the saccharide is a polysaccharide from serotype 12F *S. pneumoniae.*

In an embodiment, glycoconjugates from *S. pneumoniae* serotype 12F are prepared using CDAP. The polysaccharides are activated with 1-cyano-4-dimethylamino pyridinium tetrafluoroborate (CDAP) to form a cyanate ester. The activated polysaccharide is then coupled directly or via a spacer (linker) group to an amino group on the carrier protein (preferably $CRM_{197}$). For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide, SIB, SIAB, sulfo-SIAB, SIA, or SBAP). Preferably, the cyanate ester (optionally made by CDAP chemistry) is coupled with hexane diamine or adipic acid dihydrazide (ADH) and the amino-derivatised saccharide is conjugated to the carrier protein (e.g., $CRM_{197}$) using carbodiimide (e.g., EDAC or EDC) chemistry via a carboxyl group on the protein carrier.

Other techniques for conjugation use carbodiimides, hydrazides, active esters, norborane, p-nitrobenzoic acid, N-hydroxysuccinimide, S-NHS, EDC, TSTU. Many are described in International Patent Application Publication No. WO 98/42721. Conjugation may involve a carbonyl linker which may be formed by reaction of a free hydroxyl group of the saccharide with CDI (see Bethell et al. (1979) J. Biol. Chem. 254:2572-2574; Hearn et al. (1981) J. Chromatogr. 218:509-518) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

In an embodiment, capsular polysaccharides from serotypes 12F *S. pneumoniae* are conjugated to the carrier protein by reductive amination. Reductive amination involves two steps, (1) oxidation of the polysaccharide to generate aldehyde functionalities from vicinal diols in individual hexasaccharide unit, (2) reduction of the activated polysaccharide and a carrier protein to form a conjugate.

Before oxidation, the serotype 12F polysaccharide is optionally hydrolized (sized). Mechanical or chemical hydrolysis maybe employed. Chemical hydrolysis maybe conducted using acetic acid.

In an embodiment, the oxidizing agent is periodate. The term "periodate" includes both periodate and periodic acid (see below).

In a preferred embodiment, the oxidizing agent is 2,2,6,6-tetramethyl-1-piperidinyloxy (TEMPO) free radical and N-Chlorosuccinimide (NCS) as the cooxidant. In such embodiment, the glycoconjugates from *S. pneumoniae* serotype 12F are prepared using 2,2,6,6-tetramethyl-1-piperidinyloxy (TEMPO) free radical to oxidize primary alcohols of the saccharide to aldehydes using N-Chlorosuccinimide (NCS) as the cooxidant (hereinafter "TEMPO/NCS oxidation"), such as described at Example 7 and in WO 2014/097099. Therefore in one aspect, the glycoconjugates from *S. pneumoniae* serotype 12F are obtainable by a method comprising the steps of: a) reacting a 12F saccharide with 2,2,6,6-tetramethyl-1-piperidinyloxy (TEMPO) and N-chlorosuccinimide (NCS) in an aqueous solvent to produce an activated saccharide; and b) reacting the activated saccharide with a carrier protein comprising one or more amine groups (hereinafter "TEMPO/NCS-reductive amination"). In one aspect, the glycoconjugates from *S. pneumoniae* serotype 12F are obtained by said method. In an embodiment, the degree of oxidation of the activated 12F saccharide ranges from 1 to 50, from 1 to 40, from 1 to 30, from 1 to 20, from 1 to 10, from 1 to 5, from 3 to 40, from 3 to 30, from 3 to 20, from 3 to 10, from 4 to 40, from 4 to 30, from 4 to 20, from 4 to 10, from 5 to 30, from 5 to 25, from 5 to 20, from 5 to 10, from 6 to 50, from 6 to 40, from 6 to 30, from 6 to 20, from 6 to 15, from 6 to 14, from 6 to 13, from 6 to 12, from 6 to 11, from 6 to 10, from 7 to 40, from 7 to 30, from 7 to 20, from 7 to 15, from 7 to 14, from 7 to 13, from 7 to 12, from 7 to 11, from 7 to 10, from 8 to 40, from 8 to 30, from 8 to 20, from 8 to 15, from 8 to 14, from 8 to 13, from 8 to 13, from 8 to 12, from 8 to 11, from 8 to 10, from 9 to 40, from 9 to 30, from 9 to 20, from 9 to 15, from 10 to 40, from 10 to 30, from 10 to 20, or from 10 to 15. In a further aspect, the degree of oxidation of the activated saccharide is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. Preferably, the carrier protein is $CRM_{197}$.

In an embodiment, prior to step a), the 12F saccharide is hydrolyzed to a molecular weight ranging from 100 kDa to 400 kDa. For example, in one aspect, the molecular weight ranges from 100 kDa to 350 kDa, from 100 kDa to 300 kDa, from 100 kDa to 250 kDa, from 100 kDa to 200 kDa, from 100 kDa to 150 kDa, from 200 kDa to 400 kDa, from 200 kDa to 350 kDa, from 200 kDa to 300 kDa, from 200 kDa to 250 kDa, from 300 kDa to 400 kDa, or from 300 kDa to 350 kDa.

In a further aspect, the method further comprises the step of purifying the activated polysaccharide prior to step b). In a further aspect, the methods further comprise the step of adding a reducing agent following step b). In one aspect, the reducing agent is $NaCNBH_3$. In a further aspect, the methods further comprise the step of adding $NaBH_4$ following the addition of $NaCNBH_3$. In a further aspect, the method comprises a purification step following the addition of $NaBH_4$.

In another aspect, the present disclosure provides a glycoconjugate from *S. pneumoniae* serotype 12F produced, or obtainable by any of the methods disclosed hereabove. For example, in one aspect the present disclosure provides a glycoconjugate from *S. pneumoniae* serotype 12F comprising a saccharide conjugated to a carrier protein that is produced or obtainable by the method comprising the steps of: a) reacting a saccharide with 2,2,6,6-tetramethyl-1-piperidinyloxy (TEMPO) and N-chlorosuccinimide (NCS) in an aqueous solvent to produce an activated saccharide; and b) reacting the activated saccharide with a carrier protein comprising one or more amine groups.

In one embodiment, the glycoconjugate from *S. pneumoniae* serotype 12F of the present invention has a molecular weight of between about 50 kDa and about 20,000 kDa. In another embodiment, the glycoconjugate has a molecular weight of between about 200 kDa and about 10,000 kDa. In another embodiment, the glycoconjugate from *S. pneumoniae* serotype 12F has a molecular weight of between about 500 kDa and about 5,000 kDa. In one embodiment, the glycoconjugate from *S. pneumoniae* serotype 12F has a molecular weight of between about 1,000 kDa and about 3,000 kDa. In other embodiments the glycoconjugate from *S. pneumoniae* serotype 12F has a molecular weight of between about 600 kDa and about 2,800 kDa; between about 700 kDa and about 2,700 kDa; between about 1,000 kDa and about 2,000 kDa; between about 1,800 kDa and about 2,500 kDa; between about 1,100 kDa and about 2,200 kDa; between about 1,900 kDa and about 2,700 kDa; between about 1,200 kDa and about 2,400 kDa; between about 1,700 kDa and about 2,600 kDa; between about 1,300 kDa and about 2,600 kDa; between about 1,600 kDa and about 3,000 kDa.

In further embodiments, the serotype 12F glycoconjugate of the invention has a molecular weight of between 1,000 kDa and 20,000 kDa; between 1,000 kDa and 15,000 kDa; between 1,000 kDa and 10,000 kDa; between 1,000 kDa and 7,500 kDa; between 1,000 kDa and 5,000 kDa; between 1,000 kDa and 4,000 kDa; between 1,000 kDa and 3,000 kDa; between 2,000 kDa and 20,000 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa. Any whole number integer within any of the above ranges is contemplated as an embodiment of the disclosure. In some such embodiments, the carrier protein is $CRM_{197}$. In some such embodiments, the serotype 12F glycoconjugate is conjugated to the carrier protein by TEMPO/NCS-reductive amination.

Another way to characterize the serotype 12F glycoconjugates of the invention is by the number of lysine residues in the carrier protein (e.g., $CRM_{197}$) that become conjugated to the saccharide, which can be characterized as a range of conjugated lysines (degree of conjugation).

In a preferred embodiment, the degree of conjugation of the serotype 12F glycoconjugate of the invention is between 2 and 20, between 4 and 16, between 4 and 15, between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotype 12F glycoconjugate of the invention is about 2, about 3, about 4, about 5, about 6, about 7, about 8, about 9, about 10, about 11, about 12, about 13, about 14, about 15, about 16, about 17, about 18, about 19 or about 20.

The number of lysine residues in the carrier protein conjugated to the saccharide may also be expressed as a molar ratio. For example, in a glycoconjugate where 4 to 15 lysine residues of $CRM_{197}$ are covalently linked to the saccharide, the molar ratio of conjugated lysines to $CRM_{197}$ in the glycoconjugate is between about 10:1 to about 40:1. In an immunogenic composition where 2 to 20 lysine residues of $CRM_{197}$ are covalently linked to the saccharide, the molar ratio of conjugated lysines to $CRM_{197}$ in the glycoconjugate is between about 5:1 and about 50:1. In one embodiment, in the glycoconjugate from *S. pneumoniae* serotype 12F of the present invention the molar ratio of conjugated lysines to carrier protein is from about 10:1 to about 25:1. In some such embodiments, the carrier protein is $CRM_{197}$. In some embodiments, the $CRM_{197}$ may comprise about 4, 5, 6, 7, 8, 9, 10, 11, 12, 13, 14, 15, or 16 lysine residues out of 39 covalently linked to the saccharide. In some such embodiments, the serotype 12F glycoconjugate is conjugated to the carrier protein by TEMPO/NCS-reductive amination. In one embodiment, the saccharide to carrier protein ratio (w/w) is between 0.2 and 4 in the glycoconjugate from *S. pneumoniae* serotype 12F (e.g., about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In another embodiment, the saccharide to carrier protein ratio (w/w) is between 1.1 and 1.7 in the glycoconjugate from *S. pneumoniae* serotype 12F. In other embodiments, the saccharide to carrier protein ratio (w/w) is between 0.8 and 1.8 (e.g., about 0.8, about 0.9, about 1.0, about 1.1, about 1.2, about 1.3, about 1.4, about 1.5, about 1.6, about 1.7 or about 1.8). In some such embodiments, the carrier protein is $CRM_{197}$. In some such embodiments, the carrier protein is $CRM_{197}$. In some such embodiments, the serotype 12F glycoconjugate is conjugated to the carrier protein by TEMPO/NCS-reductive amination.

The frequency of attachment of the saccharide chain to a lysine on the carrier protein is another parameter for characterizing the serotype 12F glycoconjugates of the disclosure. For example, in one embodiment, there is at least one covalent linkage between the carrier protein and the polysaccharide for every 100 saccharide repeat units of the polysaccharide. In one embodiment, there is at least one covalent linkage between the carrier protein and the polysaccharide for every 50 saccharide repeat units of the polysaccharide. In one embodiment, there is at least one covalent linkage between the carrier protein and the polysaccharide for every 25 saccharide repeat units of the polysaccharide. In another embodiment, the covalent linkage between the carrier protein and the polysaccharide occurs at least once in every 4 saccharide repeat units of the polysaccharide. In another embodiment, the covalent linkage between the carrier protein and the polysaccharide occurs at least once in every 10 saccharide repeat units of the polysaccharide. In a further embodiment, the covalent linkage between the carrier protein and the polysaccharide occurs at least once in every 15 saccharide repeat units of the polysaccharide. In frequent embodiments, the carrier protein is $CRM_{197}$ and the covalent linkage between the $CRM_{197}$ and the polysaccharide occurs at least once in every 4, 10, 15 or 25 saccharide repeat units of the polysaccharide.

In other embodiments, the conjugate comprises at least one covalent linkage between the carrier protein and saccharide for every 5 to 10 saccharide repeat units; every 2 to 7 saccharide repeat units; every 3 to 8 saccharide repeat units; every 4 to 9 saccharide repeat units; every 6 to 11 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; every 4 to 25 saccharide repeat units or every 2 to 25 saccharide repeat units. In frequent embodiments, the carrier protein is $CRM_{197}$.

In another embodiment, at least one linkage between $CRM_{197}$ and saccharide occurs for every 2, 3, 4, 5, 6, 7, 8, 9, 10, 11, 12, 13, 14, 15, 16, 17, 18, 19, 20, 21, 22, 23, 24 or 25 saccharide repeat units of the polysaccharide. In some such embodiments, the serotype 12F glycoconjugate is conjugated to the carrier protein by TEMPO/NCS-reductive amination.

In one embodiment, the glycoconjugate from *S. pneumoniae* serotype 12F of the invention comprises at least one covalent linkage between the carrier protein and the polysaccharide for every 25 saccharide repeat units of the polysaccharide. In another embodiment, the covalent linkage between the carrier protein and the polysaccharide occurs at least once in every 4 saccharide repeat units of the polysaccharide. In another embodiment, the covalent linkage between the carrier protein and the polysaccharide occurs at least once in every 10 saccharide repeat units of the polysaccharide. In a further embodiment, the covalent linkage between the carrier protein and the polysaccharide occurs at least once in every 15 saccharide repeat units of the polysaccharide. In some such embodiments, the serotype 12F glycoconjugate is conjugated to the carrier protein by TEMPO/NCS-reductive amination.

The serotype 12F glycoconjugates and immunogenic compositions of the invention may contain free saccharide that is not covalently conjugated to the carrier protein, but is nevertheless present in the glycoconjugate composition. The free saccharide may be noncovalently associated with (i.e., noncovalently bound to, adsorbed to, or entrapped in or with) the glycoconjugate.

In some embodiments, the serotype 12F glycoconjugates of the invention comprise less than about 50%, 45%, 40%, 35%, 30%, 25%, 20%, 15%, 10% or 5% of free serotype 12F polysaccharide compared to the total amount of serotype 12F polysaccharide. In one embodiment, the glycoconjugate from *S. pneumoniae* serotype 12F comprises less than about 50% of free serotype 12F polysaccharide compared to the total amount of serotype 12F polysaccharide. In one embodiment, the glycoconjugate from *S. pneumoniae* serotype 12F comprises less than about 45% of free serotype 12F polysaccharide compared to the total amount of serotype 12F polysaccharide. In another embodiment, the glycoconjugate comprises less than about 30% of free serotype 12F polysaccharide compared to the total amount of serotype 12F polysaccharide. In another embodiment, the glycoconjugate from *S. pneumoniae* serotype 12F comprises less than about 20% of free serotype 12F polysaccharide compared to the total amount of serotype 12F polysaccharide. In a further embodiment, the glycoconjugate comprises less than about 10% of free serotype 12F polysaccharide compared to the total amount of serotype 12F polysaccharide. In another embodiment, the glycoconjugate from *S. pneumoniae* serotype 12F comprises less than about 5% of free serotype 12F polysaccharide compared to the total amount of serotype 12F polysaccharide. In some such embodiments, the serotype 12F glycoconjugate is conjugated to the carrier protein by TEMPO/NCS-reductive amination.

In some embodiments, the serotype 12F glycoconjugate of the present invention comprises a saccharide having a molecular weight of between 10 kDa and 2,000 kDa. In other such embodiments, the saccharide has a molecular weight of between 50 kDa and 2,000 kDa. In further such embodiments, the saccharide has a molecular weight of between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa; or between 200 kDa and 400 kDa. In some such embodiments, the serotype 12F glycoconjugate is conjugated to the carrier protein by TEMPO/NCS-reductive amination.

The serotype 12F glycoconjugates may also be characterized by their molecular size distribution ($K_d$). Size exclusion chromatography media (CL-4B) can be used to determine the relative molecular size distribution of the conjugate, as mentioned above.

In a preferred embodiment, at least 35% of the serotype 12F glycoconjugates of the invention have a $K_d$ below or equal to 0.3 in a CL-4B column. In a preferred embodiment, at least 40%, 45%, 50%, 55%, 60%, 65%, 70%, 75%, 80%, or 85% of the serotype 12F glycoconjugates of the invention have a $K_d$ below or equal to 0.3 in a CL-4B column. In a preferred embodiment, at least 60% of the serotype 12F glycoconjugates of the invention have a $K_d$ below or equal to 0.3 in a CL-4B column. In a preferred embodiment, at least 70% of the serotype 12F glycoconjugates of the invention have a $K_d$ below or equal to 0.3 in a CL-4B column.

In a preferred embodiment, between 40% and 90% of the serotype 12F glycoconjugates have a $K_d$ below or equal to 0.3 in a CL-4B column. In a preferred embodiment, between 50% and 90% of the serotype 12F glycoconjugates have a $K_d$ below or equal to 0.3 in a CL-4B column. In a preferred embodiment, between 65% and 80% of the serotype 12F glycoconjugates have a $K_d$ below or equal to 0.3 in a CL-4B column.

1.3.6 Glycoconjugates from *S. pneumoniae* Serotype 10A

In an embodiment, the serotype 10A glycoconjugates are obtained by activating polysaccharide with 1-cyano-4-dimethylamino pyridinium tetrafluoroborate (CDAP) to form a cyanate ester. The activated polysaccharide may be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide, SIB, SIAB, sulfo-SIAB, SIA, or SBAP). Preferably, the cyanate ester (optionally made by CDAP chemistry) is coupled with hexane diamine or adipic acid dihydrazide (ADH) and the amino-derivatised saccharide is conjugated to the carrier protein using carbodiimide (e.g., EDAC or EDC) chemistry via a carboxyl group on the protein carrier. Such conjugates are described for example in WO 93/15760, WO 95/08348 and WO 96/29094.

Other suitable techniques use carbodiimides, hydrazides, active esters, norborane, p-nitrobenzoic acid, N-hydroxysuccinimide, S-NHS, EDC, TSTU. Many are described in International Patent Application Publication No. WO 98/42721. Conjugation may involve a carbonyl linker which may be formed by reaction of a free hydroxyl group of the saccharide with CDI (See Bethell et al. (1979) J. Biol. Chem. 254:2572-2574; Hearn et al. (1981) J. Chromatogr. 218:509-518) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

In preferred embodiments, the serotype 10A glycoconjugates of the invention are prepared using reductive amination. Reductive amination involves two steps, (1) oxidation of the polysaccharide to generate aldehyde functionalities from vicinal diols in individual hexasaccharide unit, (2) reduction of the activated polysaccharide and a carrier protein to form a conjugate.

Before oxidation, the serotype 10A polysaccharide is optionally hydrolized (sized). Mechanical or chemical hydrolysis maybe employed. Chemical hydrolysis maybe conducted using acetic acid.

In an embodiment, serotype polysaccharide is activated (oxidized) by a process comprising the step of:

(a) reacting isolated serotype 10A polysaccharide with an oxidizing agent;

(b) quenching the oxidation reaction by addition of a quenching agent resulting in an activated serotype 10A polysaccharide.

In a preferred embodiment, the oxidizing agent is periodate. For the purpose of the present invention, the term "periodate" includes both periodate and periodic acid, the term also includes both metaperiodate ($IO_4^-$) and orthoperiodate ($IO_6^{5-}$) and the various salts of periodate (e.g., sodium periodate and potassium periodate). In a preferred embodiment, the oxidizing agent is sodium periodate. In a preferred embodiment, the periodate used for the oxidation of serotype 10A polysaccharide is metaperiodate. In a preferred embodiment the periodate used for the oxidation of serotype 10A polysaccharide is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

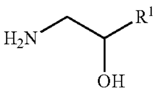

(I)

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid.

In one embodiment, the quenching agent is an amino acid. In such embodiments, said amino acid may be selected from serine, threonine, cysteine, cystine, methionine, proline, hydroxyproline, tryptophan, tyrosine, and histidine.

In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms.

Preferably, the quenching agent is a compound of formula (II):

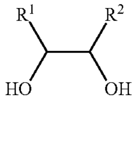

(II)

wherein $R^1$ and $R^2$ are each independently selected from H, methyl, ethyl, propyl or isopropyl.

In a preferred embodiment, the quenching agent is glycerol, ethylene glycol, propan-1,2-diol, butan-1,2-diol or butan-2,3-diol, ascorbic acid. In a preferred embodiment, the quenching agent is butan-2,3-diol.

In preferred embodiment, the isolated serotype 10A polysaccharide is activated by a process comprising the step of:

(a) reacting isolated serotype 10A polysaccharide with periodate;

(b) quenching the oxidation reaction by addition of butan-2,3-diol resulting in an activated serotype 10A polysaccharide.

Following the oxidation step of the polysaccharide, the polysaccharide is said to be activated and is referred to an "activated polysaccharide" hereinafter.

In a preferred embodiment, the activated serotype 10A polysaccharide is purified. The activated serotype 10A polysaccharide is purified according to methods known to the man skilled in the art, such as gel permeation chromatography (GPC), dialysis or ultrafiltration/diafiltration. For example, the activated 10A polysaccharide is purified by concentration and diafiltration using an ultrafiltration device.

In a preferred embodiment the degree of oxidation of the activated serotype 10A polysaccharide is between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotype 10A polysaccharide is between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

In a preferred embodiment, the activated serotype 10A polysaccharide has a molecular weight between 50 kDa and 400 kDa, between 50 kDa and 350 kDa, between 50 kDa and 300 kDa, between 50 kDa and 250 kDa, between 50 kDa and 200 kDa, between 100 kDa and 300 kDa, between 100 kDa and 250 kDa or between 100 kDa and 200 kDa. In a preferred embodiment, the activated serotype 10A polysaccharide has a molecular weight between 50 kDa and 300 kDa. In a preferred embodiment, the activated serotype 10A polysaccharide has a molecular weight between 100 kDa and 200 kDa. In a preferred embodiment, the activated serotype 10A polysaccharide has a molecular weight between 100 kDa and 200 kDa and a degree of oxidation between 5 and 20, between 5 and 15, between 8 and 14, between 8 and 12 or between 9 and 11. In a preferred embodiment, the activated serotype 10A polysaccharide has a molecular weight between 100 kDa and 200 kDa and a degree of oxidation between 9 and 11.

The activated polysaccharide and/or the carrier protein may be lyophilised (freeze-dried), either independently (discrete lyophilization) or together (co-lyophilized).

In an embodiment, the activated serotype 10A polysaccharide is lyophilized, optionally in the presence of saccharide. In a preferred embodiment, the saccharide is selected from sucrose, trehalose, raffinose, stachyose, melezitose, dextran, mannitol, lactitol and palatinit. In a preferred embodiment, the saccharide is sucrose. In one embodiment, the lyophilized activated polysaccharide is then compounded with a solution comprising the carrier protein.

In another embodiment the activated polysaccharide and the carrier protein are co-lyophilised. In such embodiments, the activated serotype 10A polysaccharide is compounded with the carrier protein and lyophilized optionally in the presence of a saccharide. In a preferred embodiment, the saccharide is selected from sucrose, trehalose, raffinose, stachyose, melezitose, dextran, mannitol, lactitol and palatinit. In a preferred embodiment, the saccharide is sucrose. The co-lyophilized polysaccharide and carrier protein can then be resuspended in solution and reacted with a reducing agent.

The second step of the conjugation process is the reduction of the activated polysaccharide and a carrier protein to form a conjugate (reductive amination), using a reducing agent.

The activated serotype 10A polysaccharide can be conjugated to a carrier protein by a process comprising the step of:

(c) compounding the activated serotype 10A polysaccharide with a carrier protein; and (d) reacting the compounded activated serotype 10A polysaccharide and carrier protein with a reducing agent to form a serotype 10A polysaccharide-carrier protein conjugate.

In an embodiment, the reduction reaction is carried out in aqueous solvent, in another embodiment the reaction is carried out in aprotic solvent. In an embodiment, the reduction reaction is carried out in DMSO (dimethylsulfoxide) or in DMF (dimethylformamide) solvent. The DMSO or DMF solvent may be used to reconstitute the activated polysaccharide and carrier protein which has been lyophilised.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMeiPrN-BH3, benzylamine-BH3 or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotype 10A polysaccharide to the carrier protein, the glycoconjugate can be purified (enriched with respect to the amount of polysaccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

In some embodiments, the serotype 10A glycoconjugates of the present invention comprise a saccharide having a molecular weight of between 10 kDa and 2,000 kDa. In other such embodiments, the saccharide has a molecular weight of between 50 kDa and 2,000 kDa. In further such embodiments, the saccharide has a molecular weight of between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa; or between 200 kDa and 400 kDa. In some such embodiments, the serotype 10A glycoconjugates are prepared using reductive amination.

In some embodiments, the serotype 10A glycoconjugate of the invention has a molecular weight of between 50 kDa and 20,000 kDa. In other embodiments, the serotype 10A glycoconjugate has a molecular weight of between 50 kDa and 15,000 kDa. In other embodiments, the serotype 10A glycoconjugate has a molecular weight of between 500 kDa and 15,000 kDa, between 500 kDa and 10,000 kDa; between 2,000 kDa and 10,000 kDa; or between 3,000 kDa and 8,000 kDa. In other embodiments, the serotype 10A glycoconjugate has a molecular weight of between 1,000 kDa and 10,000 kDa. In other embodiments, the serotype 10A glycoconjugate has a molecular weight of between 1000 kDa and 8,000 kDa. In still other embodiments, the serotype 10A glycoconjugate has a molecular weight of between 2,000 kDa and 8,000 kDa or between 3,000 kDa and 7,000 kDa. In further embodiments, the serotype 10A glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotype 10A glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa. In further embodiments, the serotype 10A glycoconjugate of the invention has a molecular weight of between 5,000 kDa and 20,000 kDa; between 5,000 kDa and 15,000 kDa; between 5,000 kDa and 10,000 kDa or between 5,000 kDa and 7,500 kDa. In further embodiments, the serotype 10A glycoconjugate of the invention has a molecular weight of between 6,000 kDa and 20,000 kDa; between 6,000 kDa and 15,000 kDa; between 6,000 kDa and 10,000 kDa or between 6,000 kDa and 7,500 kDa. In further embodiments, the serotype 10A glycoconjugate of the invention has a molecular weight of between 7,000 kDa and 20,000 kDa; between 7,000 kDa and 15,000 kDa; between 7,000 kDa and 10,000 kDa or between 7,000 kDa and 8,000 kDa. In further embodiments, the serotype 10A glycoconjugate of the invention has a molecular weight of between 8,000 kDa and 20,000 kDa; between 8,000 kDa and 15,000 kDa; or between 8,000 kDa and 10,000 kDa.

Any whole number integer within any of the above ranges is contemplated as an embodiment of the disclosure. The molecular weight of the glycoconjugate is measured by SEC-MALLS.

Another way to characterize the serotype 10A glycoconjugates of the invention is by the number of lysine residues in the carrier protein (e.g., $CRM_{197}$) that become conjugated to the saccharide which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered compared to the $CRM_{197}$ protein starting material used to generate the conjugate materials.

In a preferred embodiment, the degree of conjugation of the serotype 10A glycoconjugate is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In a preferred embodiment, the degree of conjugation of the serotype 10A glycoconjugate is between 6 and 8. In a preferred embodiment, the carrier protein is $CRM_{197}$ The serotype 10A glycoconjugates of the invention may also be characterized by the ratio (weight/weight) of saccharide to carrier protein. In some embodiments, the saccharide to carrier protein ratio (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9 or about 3.0). In a preferred embodiment, the ratio of serotype 10A saccharide to carrier protein in the conjugate is between 0.5 and 2.0, 0.5 and 1.5, 0.5 and 1.0, 1.0 and 1.5 or 1.0 and 2.0. In a preferred embodiment, the ratio of serotype 10A polysaccharide to carrier protein in the conjugate is between 0.8 and 1.4. In a preferred embodiment, the ratio of serotype 10A capsular polysaccharide to carrier protein in the conjugate is between 0.8 and 1.2 (e.g., about 0.8, about 0.9 about 1.0, about 1.1, or about 1.2). In some such embodiments, the carrier protein is $CRM_{197}$.

The serotype 10A glycoconjugates and immunogenic compositions of the invention may contain free saccharide that is not covalently conjugated to the carrier protein, but is nevertheless present in the glycoconjugate composition. The free saccharide may be noncovalently associated with (i.e., noncovalently bound to, adsorbed to, or entrapped in or with) the glycoconjugate.

In some embodiments, the serotype 10A glycoconjugates of the invention comprise less than about 50% free saccharide, less than about 45% free saccharide, less than about 40% free saccharide, less than about 35% free saccharide, less than about 30% free saccharide, less than about 25% free saccharide, less than about 20% free saccharide, less than about 15% free saccharide, less than about 10% free saccharide, or less than about 5% free saccharide relative to the total amount of 10A saccharide. Preferably, serotype 10A the glycoconjugate comprises less than 15% free saccharide, more preferably less than 10% free saccharide, and still more preferably, less than 5% of free saccharide.

The serotype 10A glycoconjugates may also be characterized by their molecular size distribution ($K_d$). Size exclusion chromatography media (CL-4B) can be used to determine the relative molecular size distribution of the conjugate, as mentioned above.

In a preferred embodiment, at least 30% of the serotype 10A glycoconjugates of the invention have a $K_d$ below or equal to 0.3 in a CL-4B column. In a preferred embodiment, at least 40% of the serotype 10A glycoconjugates of the invention have a $K_d$ below or equal to 0.3 in a CL-4B column. In a preferred embodiment, at least 45%, 50%, 55%, 60%, 65%, 70%, 75%, 80%, or 85% of the serotype 10A glycoconjugates of the invention have a $K_d$ below or equal to 0.3 in a CL-4B column. In a preferred embodiment, at least 60% of the serotype 10A glycoconjugates have a $K_d$ below or equal to 0.3 in a CL-4B column. In a preferred embodiment, between 50% and 80% of the serotype 10A glycoconjugates of the invention have a $K_d$ below or equal to 0.3 in a CL-4B column.

1.3.7 Glycoconjugates from *S. pneumoniae* Serotype 11A

In an embodiment, the serotype 11A glycoconjugates are obtained by activating polysaccharide with 1-cyano-4-dimethylamino pyridinium tetrafluoroborate (CDAP) to form a cyanate ester. The activated polysaccharide may be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide, SIB, SIAB, sulfo-SIAB, SIA, or SBAP). Preferably, the cyanate ester (optionally made by CDAP chemistry) is coupled with hexane diamine or adipic acid dihydrazide (ADH) and the amino-derivatised saccharide is conjugated to the carrier protein using carbodiimide (e.g., EDAC or EDC) chemistry via a carboxyl group on the protein carrier. Such conjugates are described for example in WO 93/15760, WO 95/08348 and WO 96/29094.

Other suitable techniques use carbodiimides, hydrazides, active esters, norborane, p-nitrobenzoic acid, N-hydroxysuccinimide, S-NHS, EDC, TSTU. Many are described in International Patent Application Publication No. WO 98/42721. Conjugation may involve a carbonyl linker which may be formed by reaction of a free hydroxyl group of the saccharide with CDI (see Bethell et al. (1979). Biol. Chem. 254:2572-2574; Hearn et al. (1981) J. Chromatogr. 218:509-518) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

In preferred embodiments, the serotype 11A glycoconjugates of the invention are prepared using reductive amination. Reductive amination involves two steps, (1) oxidation of the polysaccharide to generate aldehyde functionalities from vicinal diols in individual hexasaccharide unit, (2) reduction of the activated polysaccharide and a carrier protein to form a conjugate.

Before oxidation, the serotype 11A polysaccharide is optionally hydrolized to reduce its viscosity. Mechanical or chemical hydrolysis maybe employed. Chemical hydrolysis maybe conducted using acetic acid. Mechanical sizing maybe conducted using High Pressure Homogenization Shearing.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate). In an embodiment the capsular polysaccharide from serotype 11A of *S. pneumoniae* is oxydized in the presence of metaperiodate, preferably in the presence of sodium periodate ($NaIO_4$). In another embodiment the capsular polysaccharide from serotype 11A is oxydized in the presence of orthoperiodate, preferably in the presence of periodic acid.

Following the oxidation step of the polysaccharide, the polysaccharide is said to be activated and is referred to as "activated polysaccharide" here below. The activated polysaccharide maybe purified and lyophilised (freeze-dried).

The activated polysaccharide and the carrier protein may be lyophilized (freeze-dried), either independently (discrete lyophilization) or together (co-lyophilized). In one embodiment the activated polysaccharide and the carrier protein are co-lyophilized. In another embodiment the activated polysaccharide and the carrier protein are lyophilized independently.

In one embodiment the lyophilization takes place in the presence of a non-reducing sugar, possible non-reducing sugars include sucrose, trehalose, raffinose, stachyose, melezitose, dextran, mannitol, lactitol and palatinit.

The second step of the conjugation process is the reduction of the activated polysaccharide and a carrier protein to form a conjugate (reductive amination), using a reducing agent. Reducing agents which are suitable include the cyanoborohydrides, such as sodium cyanoborohydride, borane-pyridine, or borohydride exchange resin. In one embodiment the reducing agent is sodium cyanoborohydride.

In an embodiment, the reduction reaction is carried out in aqueous solvent, in another embodiment the reaction is carried out in aprotic solvent. In an embodiment, the reduction reaction is carried out in DMSO (dimethylsulfoxide) or in DMF (dimethylformamide) solvent. The DMSO or DMF solvent may be used to reconstitute the activated polysaccharide and carrier protein which has been lyophilised.

In one embodiment between 0.1 and 3.0, between 0.15 and 2.0, between 0.2 and 2.0, or between 0.5 and 1.5 molar equivalents of sodium cyanoborohydride is used in the reduction reaction. In one embodiment about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.9 or 3.0 molar equivalents of sodium cyanoborohydride is used in the reduction reaction.

In one embodiment the reducing agent is sodium triacetoxyborohydride, in a further embodiment between 1.0 and 6.0 molar equivalents, between 2.0 and 5.0 molar equivalents or about 3.0 molar equivalents of sodium triacetoxyborohydride is used in the reduction reaction.

At the end of the reduction reaction, there may be unreacted aldehyde groups remaining in the conjugates, these may be capped using a suitable capping agent. In one embodiment this capping agent is sodium borohydride ($NaBH_4$). In an embodiment capping is achieved by mixing the reduction reaction with between 0.5 and 5.0 molar equivalents of $NaBH_4$, for example about 1, 1.5, 2, 2.5 or 3 molar equivalents of $NaBH_4$.

Following the conjugation (the reduction reaction and optionally the capping), the glycoconjugates may be purified. The glycoconjugates maybe purified by diafiltration and/or ion exchange chromatography and/or size exclusion chromatography. In an embodiment, the glycoconjugates are purified by diafiltration or ion exchange chromatography or size exclusion chromatography.

In one embodiment the glycoconjugates are sterile filtered.

In some embodiments, the serotype 11A glycoconjugates of the present invention are conjugated to the carrier protein (e.g., $CRM_{197}$) and comprise a saccharide having a molecular weight of between 10 kDa and 2,000 kDa. In other such embodiments, the saccharide has a molecular weight of between 50 kDa and 2,000 kDa. In further such embodiments, the saccharide has a molecular weight of between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa between; 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa; between 200 kDa and 400 kDa or between 200 kDa and 300 kDa.

In some embodiments, the serotype 11A glycoconjugate of the invention has a molecular weight of between 50 kDa and 20,000 kDa. In other embodiments, the serotype 11A glycoconjugate has a molecular weight of between 50 kDa and 15,000 kDa. In other embodiments, the serotype 11A glycoconjugate has a molecular weight of between 500 kDa and 10,000 kDa. In other embodiments, the serotype 11A glycoconjugate has a molecular weight of between 200 kDa and 10,000 kDa. In still other embodiments, the serotype 11A glycoconjugate has a molecular weight of between 1,000 kDa and 8,000 kDa or between 2,000 kDa and 8,000 kDa.

In further embodiments, the serotype 11A glycoconjugate of the invention has a molecular weight of between 200 kDa and 20,000 kDa; between 200 kDa and 17,500 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 2,000 kDa; between 200 kDa and 1,000 kDa; between 500 kDa and 20,000 kDa; between 500 kDa and 17,500 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 700 kDa and 20,000 kDa; between 700 kDa and 17,500 kDa; between 700 kDa and 15,000 kDa; between 700 kDa and 12,500 kDa; between 700 kDa and 10,000 kDa; between 700 kDa and 7,500 kDa; between 700 kDa and 6,000 kDa;

between 700 kDa and 5,000 kDa; between 700 kDa and 4,500 kDa; between 700 kDa and 4,000 kDa; between 700 kDa and 3,500 kDa; between 700 kDa and 3,000 kDa; between 700 kDa and 2,000 kDa; between 700 kDa and 1,500 kDa; between 1,000 kDa and 20,000 kDa; between 1,000 kDa and 17,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 20,000 kDa; between 2,000 kDa and 17,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotype 11A glycoconjugate of the invention has a molecular weight of between 3,000 kDa and 20,000 kDa; between 3,000 kDa and 17,500 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 17,500 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa. In further embodiments, the serotype 11A glycoconjugate of the invention has a molecular weight of between 5,000 kDa and 20,000 kDa; between 5,000 kDa and 17,500 kDa; between 5,000 kDa and 15,000 kDa; between 5,000 kDa and 10,000 kDa or between 5,000 kDa and 7,500 kDa.

In an embodiment, said serotype 11A glycoconjugates are prepared using reductive amination.

In a preferred embodiment, the serotype 11A glycoconjugate of the invention comprises at least 0.3, 0.5, 0.6, 1.0, 1.4, 1.8, 2.2, 2.6, 3.0, 3.4, 3.8, 4.2, 4.6 or 5 mM acetate per mM serotype 11A polysaccharide. In a preferred embodiment, the serotype 11A glycoconjugate comprises at least 1.8, 2.2 or 2.6 mM acetate per mM serotype 11A polysaccharide. In an embodiment, the glycoconjugate comprises at least 0.6 mM acetate per mM serotype 11A polysaccharide. In a preferred embodiment, the serotype 11A glycoconjugate of the invention comprises at least 0.6, 1, 1.4, 1.8, 2.2, 2.6, 3, 3.4, 3.8, 4.2 or 4.6 mM acetate per mM serotype 11A polysaccharide and less than about 5 mM acetate per mM serotype 11A polysaccharide. In an embodiment, the serotype 11A glycoconjugate of the invention comprises at least 0.6, 1.0, 1.4, 1.8, 2.2, 2.6, or 3.0 mM acetate per mM serotype 11A polysaccharide and less than about 3.4 mM acetate per mM serotype 11A polysaccharide. In an embodiment, the serotype 11A glycoconjugate of the invention comprises at least 0.6, 1, 1.4, 1.8, 2.2, 2.6, or about 3.0 mM acetate per mM serotype 11A polysaccharide and less than about 3.3 mM acetate per mM serotype 11A polysaccharide. Any of the above number is contemplated as an embodiment of the disclosure.

In a preferred embodiment, the ratio of mM acetate per mM serotype 11A capsular polysaccharide in the serotype 11A glycoconjugate to mM acetate per mM serotype 11A capsular polysaccharide in the isolated polysaccharide is at least 0.6, 0.65, 0.7, 0.75, 0.8, 0.85, 0.9, or 0.95. In a preferred embodiment, the ratio of mM acetate per mM serotype 11A capsular polysaccharide in the serotype 11A glycoconjugate to mM acetate per mM serotype 11A capsular polysaccharide in the isolated polysaccharide is at least 0.7. In a preferred embodiment, the ratio of mM acetate per mM serotype 11A capsular polysaccharide in the serotype 11A glycoconjugate to mM acetate per mM serotype 11A capsular polysaccharide in the isolated polysaccharide is at least 0.9. In a preferred embodiment, the presence of O-acetyl groups is determined by ion-HPLC analysis.

In a preferred embodiment, the ratio of mM acetate per mM serotype 11A capsular polysaccharide in the serotype 11A glycoconjugate to mM acetate per mM serotype 11A capsular polysaccharide in the activated polysaccharide is at least 0.6, 0.65, 0.7, 0.75, 0.8, 0.85, 0.9, or 0.95. In a preferred embodiment, the ratio of mM acetate per mM serotype 11A capsular polysaccharide in the serotype 11A glycoconjugate to mM acetate per mM serotype 11A capsular polysaccharide in the activated polysaccharide is at least 0.7. In a preferred embodiment, the ratio of mM acetate per mM serotype 11A capsular polysaccharide in the serotype 11A glycoconjugate to mM acetate per mM serotype 11A capsular polysaccharide in the activated polysaccharide is at least 0.9. In a preferred embodiment, the presence of O-acetyl groups is determined by ion-HPLC analysis.

In a preferred embodiment, the serotype 11A glycoconjugate of the invention comprises at least 0.1, 0.2, 0.3, 0.4, 0.5, 0.6, 0.7, 0.8, 0.9 or 1.0 mM glycerol per mM serotype 11A polysaccharide. In a preferred embodiment, the serotype 11A glycoconjugate comprises at least 0.2, 0.3 or 0.4 mM glycerol per mM serotype 11A polysaccharide. In a preferred embodiment, the serotype 11A glycoconjugate of the invention comprises at least 0.1, 0.2, 0.3, 0.4, 0.5, 0.6, 0.7, 0.8 or 0.9 mM glycerol per mM serotype 11A polysaccharide and less than about 1.0 mM glycerol per mM serotype 11A polysaccharide. In a preferred embodiment, the serotype 11A glycoconjugate of the invention comprises at least 0.3, 0.4, 0.5, 0.6, or 0.7 mM glycerol per mM serotype 11A polysaccharide and less than about 0.8 mM glycerol per mM serotype 11A polysaccharide. Any of the above number is contemplated as an embodiment of the disclosure.

Another way to characterize the serotype 11A glycoconjugates of the invention is by the number of lysine residues in the carrier protein (e.g., $CRM_{197}$) that become conjugated to the saccharide which can be characterized as a range of conjugated lysines (degree of conjugation).

The evidence for lysine modification of the carrier protein, due to covalent linkages to the polysaccharides, can be obtained by amino acid analysis using routine methods known to those of skill in the art. Conjugation results in a reduction in the number of lysine residues recovered compared to the $CRM_{197}$ protein starting material used to generate the conjugate materials.

In a preferred embodiment, the degree of conjugation of the serotype 11A glycoconjugate of the invention is between 1 and 15, between 1 and 13, between 1 and 10, between 1 and 8, between 1 and 6, between 1 and 5, between 1 and 4, between 2 and 15, between 2 and 13, between 2 and 10, between 2 and 8, between 2 and 6, between 2 and 5, between 2 and 4, between 5 and 15, between 5 and 10, between 8 and 15, between 8 and 12, between 10 and 15 or between 10 and 12. In an embodiment, the degree of conjugation of the serotype 11A glycoconjugate of the invention is about 1, about 2, about 3, about 4, about 5, about 6, about 7, about 8, about 9, about 10, about 11, about 12, about 13, about 14 or about 15. In a preferred embodiment, the degree of conjugation of the serotype 11A glycoconjugate of the invention is between 1 and 6 or between 2 and 5. In some such embodiments, the carrier protein is $CRM_{197}$.

The serotype 11A glycoconjugates of the invention may also be characterized by the ratio (weight/weight) of saccharide to carrier protein. In some embodiments, the saccharide to carrier protein ratio (w/w) is between 0.2 and 4 (e.g., about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the saccharide to carrier protein ratio (w/w) is between 0.7 and 2.5, between 0.8 and 2.0, between 0.7 and 2.0, between 0.8 and 1.5, between 0.7 and 1.5, 0.7 and 1.4, between 0.8 and 1.4, between 0.7 and 1.45 or between 0.8 and 1.45. In further embodiments, the saccharide to carrier protein ratio (w/w) is between 0.8 and 1.6 (e.g., about 0.8, about 0.9 about 1.0, about 1.1, about 1.2, about 1.3, about 1.4, about 1.5 or about 1.6). In some such embodiments, the carrier protein is $CRM_{197}$. In an embodiment, said serotype 11A glycoconjugates are prepared using reductive amination.

The serotype 11A glycoconjugates and immunogenic compositions of the invention may contain free saccharide that is not covalently conjugated to the carrier protein, but is nevertheless present in the glycoconjugate composition. The free saccharide may be noncovalently associated with (i.e., noncovalently bound to, adsorbed to, or entrapped in or with) the glycoconjugate.

In some embodiments, the serotype 11A glycoconjugates of the invention comprise less than about 50% of free serotype 11A capsular polysaccharide compared to the total amount of serotype 11A capsular polysaccharide, less than about 45% free saccharide, less than about 40% free saccharide, less than about 35% free saccharide, less than about 30% free saccharide, less than about 25% free saccharide, less than about 20% free saccharide, less than about 15% free saccharide, less than about 10% free saccharide, or less than about 5% of free serotype 11A capsular polysaccharide compared to the total amount of serotype 11A capsular polysaccharide. Preferably, serotype 11A the glycoconjugate comprises less than 15% free saccharide, more preferably less than 10% free saccharide, and still more preferably, less than 5% of free saccharide.

The serotype 11A glycoconjugates may also be characterized by their molecular size distribution ($K_d$). Size exclusion chromatography media (CL-4B) can be used to determine the relative molecular size distribution of the conjugate, as mentioned above.

In a preferred embodiment, at least 30% of the serotype 11A glycoconjugates of the invention has a $K_d$ below or equal to 0.3 in a CL-4B column. In a preferred embodiment, at least 40%, 45%, 50%, 55%, 60%, 65%, 70%, 75%, 80%, or 85% of the serotype 11A glycoconjugates of the invention has a $K_d$ below or equal to 0.3 in a CL-4B column. In a preferred embodiment, at least 60% of the serotype 11A glycoconjugates of the invention has a $K_d$ below or equal to 0.3 in a CL-4B column. In a preferred embodiment, at least 65% of the serotype 11A glycoconjugates of the invention has a $K_d$ below or equal to 0.3 in a CL-4B column.

1.3.8 Glycoconjugates from *S. pneumoniae* Serotype 8

In an embodiment, the serotype 8 glycoconjugates are obtained by activating polysaccharide with 1-cyano-4-dimethylamino pyridinium tetrafluoroborate (CDAP) to form a cyanate ester. The activated polysaccharide may be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide, SIB, SIAB, sulfo-SIAB, SIA, or SBAP). Preferably, the cyanate ester (optionally made by CDAP chemistry) is coupled with hexane diamine or adipic acid dihydrazide (ADH) and the amino-derivatised saccharide is conjugated to the carrier protein using carbodiimide (e.g., EDAC or EDC) chemistry via a carboxyl group on the protein carrier. Such conjugates are described for example in WO 93/15760, WO 95/08348 and WO 96/29094.

Other suitable techniques use carbodiimides, hydrazides, active esters, norborane, p-nitrobenzoic acid, N-hydroxysuccinimide, S-NHS, EDC, TSTU. Many are described in International Patent Application Publication No. WO 98/42721. Conjugation may involve a carbonyl linker which may be formed by reaction of a free hydroxyl group of the saccharide with CDI (see Bethell et al. (1979) J. Biol. Chem. 254:2572-2574; Hearn et al. (1981) J. Chromatogr. 218:509-518) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

In preferred embodiments, the serotype 8 glycoconjugates of the invention are prepared using reductive amination. Reductive amination involves two steps, (1) oxidation of the polysaccharide to generate aldehyde functionalities from vicinal diols in individual hexasaccharide unit, (2) reduction of the activated polysaccharide and a carrier protein to form a conjugate.

Before oxidation, the serotype 8 polysaccharide is optionally hydrolized to reduce its viscosity. Mechanical or chemical hydrolysis maybe employed. Chemical hydrolysis maybe conducted using acetic acid.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate). In an embodiment the capsular polysaccharide from serotype 8 of *S. pneumoniae* is oxydized in the presence of metaperiodate, preferably in the presence of sodium periodate ($NaIO_4$). In another embodiment the capsular polysaccharide from serotype 8 is oxydized in the presence of orthoperiodate, preferably in the presence of periodic acid.

Following the oxidation step of the polysaccharide, the polysaccharide is said to be activated and is referred to as "activated polysaccharide" here below. The activated polysaccharide maybe purified and lyophilised (freeze-dried).

The activated polysaccharide and the carrier protein may be lyophilised (freeze-dried), either independently (discrete lyophilization) or together (co-lyophilized). In one embodiment the activated polysaccharide and the carrier protein are co-lyophilised. In another embodiment the activated polysaccharide and the carrier protein are lyophilised independently.

In one embodiment the lyophilisation takes place in the presence of a non-reducing sugar, possible non-reducing sugars include sucrose, trehalose, raffinose, stachyose, melezitose, dextran, mannitol, lactitol and palatinit.

The second step of the conjugation process is the reduction of the activated polysaccharide and a carrier protein to form a conjugate (reductive amination), using a reducing agent. Reducing agents which are suitable include the cyanoborohydrides, such as sodium cyanoborohydride, borane-pyridine, or borohydride exchange resin. In one embodiment the reducing agent is sodium cyanoborohydride.

In an embodiment, the reduction reaction is carried out in aqueous solvent, in another embodiment the reaction is carried out in aprotic solvent. In an embodiment, the reduction reaction is carried out in DMSO (dimethylsulfoxide) or in DMF (dimethylformamide) solvent. The DMSO or DMF solvent may be used to reconstitute the activated polysaccharide and carrier protein which has been lyophilised.

In one embodiment between 0.1 and 3.0, between 0.15 and 2.0, between 0.2 and 1.0, or between 0.25 and 0.5 molar equivalents of sodium cyanoborohydride is used in the reduction reaction. In one embodiment about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.9 or 3.0 molar equivalents of sodium cyanoborohydride is used in the reduction reaction.

In one embodiment the reducing agent is sodium triacetoxyborohydride. In a further embodiment between 1.0 and 6.0 molar equivalents, between 2.0 and 5.0 molar equivalents or about 3.0 molar equivalents of sodium triacetoxyborohydride is used in the reduction reaction.

At the end of the reduction reaction, there may be unreacted aldehyde groups remaining in the conjugates, these may be capped using a suitable capping agent. In one embodiment this capping agent is sodium borohydride ($NaBH_4$). In an embodiment capping is achieved by mixing the reduction reaction with between 0.5 and 5.0 molar equivalents of $NaBH_4$, for example about 1.0, 1.5, 2.0, 2.5 or 3.0 molar equivalents of $NaBH_4$.

Following the conjugation (the reduction reaction and optionally the capping), the glycoconjugates may be purified. The glycoconjugates maybe purified by diafiltration and/or ion exchange chromatography and/or size exclusion chromatography. In an embodiment, the glycoconjugates are purified by diafiltration or ion exchange chromatography or size exclusion chromatography.

In one embodiment the glycoconjugates are sterile filtered.

In some embodiments, the serotype 8 glycoconjugates of the present invention are conjugated to the carrier protein (e.g., $CRM_{197}$) and comprise a saccharide having a molecular weight of between 10 kDa and 2,000 kDa. In other such embodiments, the saccharide has a molecular weight of between 50 kDa and 2,000 kDa. In further such embodiments, the saccharide has a molecular weight of between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa; or between 200 kDa and 400 kDa. In an embodiment, said serotype 8 glycoconjugates are prepared using reductive amination.

In some embodiments, the serotype 8 glycoconjugate of the invention has a molecular weight of between 50 kDa and 20,000 kDa. In other embodiments, the serotype 8 glycoconjugate has a molecular weight of between 50 kDa and 15,000 kDa. In other embodiments, the serotype 8 glycoconjugate has a molecular weight of between 500 kDa and 10,000 kDa. In other embodiments, the serotype 8 glycoconjugate has a molecular weight of between 200 kDa and 10,000 kDa. In still other embodiments, the serotype 8 glycoconjugate has a molecular weight of between 1,000 kDa and 8,000 kDa or between 2,000 kDa and 8,000 kDa.

In further embodiments, the serotype 8 glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotype 8 glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa. In further embodiments, the serotype 8 glycoconjugate of the invention has a molecular weight of between 5,000 kDa and 20,000 kDa; between 5,000 kDa and 15,000 kDa; between 5,000 kDa and 10,000 kDa or between 5,000 kDa and 7,500 kDa. In further embodiments, the serotype 8 glycoconjugate of the invention has a molecular weight of between 6,000 kDa and 20,000 kDa; between 6,000 kDa and 15,000 kDa; between 6,000 kDa and 10,000 kDa or between 6,000 kDa and 7,500 kDa.

In further embodiments, the serotype 8 glycoconjugate of the invention has a molecular weight of between 7,000 kDa and 20,000 kDa; between 7,000 kDa and 15,000 kDa; between 7,000 kDa and 10,000 kDa or between 7,000 kDa and 8,000 kDa. In further embodiments, the serotype 8 glycoconjugate of the invention has a molecular weight of between 8,000 kDa and 20,000 kDa; between 8,000 kDa and 15,000 kDa; or between 8,000 kDa and 10,000 kDa.

In an embodiment, said serotype 8 glycoconjugates are prepared using reductive amination.

Another way to characterize the serotype 8 glycoconjugates of the invention is by the number of lysine residues in the carrier protein (e.g., $CRM_{197}$) that become conjugated to the saccharide which can be characterized as a range of conjugated lysines (degree of conjugation).

The evidence for lysine modification of the carrier protein, due to covalent linkages to the polysaccharides, can be obtained by amino acid analysis using routine methods known to those of skill in the art. In frequent embodiments, the carrier protein is covalently conjugated to activated polysaccharide through an amine linkage to one or more ε-amino groups of lysine residues on the carrier protein. In some such embodiments, the carrier protein comprises 2 to 20 lysine residues covalently conjugated to the saccharide. In other such embodiments, the carrier protein comprises 4 to 16 or 6 to 14 lysine residues covalently conjugated to the saccharide.

In a preferred embodiment, the degree of conjugation of the serotype 8 glycoconjugate of the invention is between 2 and 20, between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotype 8 glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotype 8 glycoconjugate of the invention is between 4 and 16 or between 6 and 14.

In some such embodiments, the carrier protein is $CRM_{197}$.

In a preferred embodiment, the carrier protein comprises $CRM_{197}$, which contains 39 lysine residues. In some such embodiments, the $CRM_{197}$ may comprise between 4 and 16 or between 6 and 14 lysine residues out of 39 covalently linked to the saccharide. Another way to express this parameter is that about 10% to about 41% or about 15% to about 36% of $CRM_{197}$ lysines are covalently linked to the saccharide. In another such embodiment, the $CRM_{197}$ may comprise 2 to 20 lysine residues out of 39 covalently linked to the saccharide. Another way to express this parameter is that about 5% to about 50% of $CRM_{197}$ lysines are covalently linked to the saccharide. In some such embodiments, the $CRM_{197}$ may comprise about 4, 5, 6, 7, 8, 9, 10, 11, 12, 13, 14, 15, or 16 lysine residues out of 39 covalently linked to the saccharide.

The serotype 8 glycoconjugates of the invention may also be characterized by the ratio (weight/weight) of saccharide to carrier protein. In some embodiments, the saccharide to carrier protein ratio (w/w) is between 0.2 and 4.0 (e.g., about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the saccharide to carrier protein ratio (w/w) is between 0.7 and 2.5. In further embodiments, the saccharide to carrier protein ratio (w/w) is between 0.8 and 1.5 (e.g., about 0.8, about 0.9 about 1.0, about 1.1, about 1.2, about 1.3, about 1.4 or about 1.5). In some such embodiments, the carrier protein is $CRM_{197}$. In an embodiment, said serotype 8 glycoconjugates are prepared using reductive amination.

The serotype 8 glycoconjugates and immunogenic compositions of the invention may contain free saccharide that is not covalently conjugated to the carrier protein, but is nevertheless present in the glycoconjugate composition. The free saccharide may be noncovalently associated with (i.e., noncovalently bound to, adsorbed to, or entrapped in or with) the glycoconjugate.

In some embodiments, the serotype 8 glycoconjugates of the invention comprise less than about 50% free saccharide, less than about 45% free saccharide, less than about 40% free saccharide, less than about 35% free saccharide, less than about 30% free saccharide, less than about 25% free saccharide, less than about 20% free saccharide, less than about 15% free saccharide, less than about 10% free saccharide, or less than about 5% free saccharide relative to the total amount of serotype 8 saccharide. Preferably, serotype 8 the glycoconjugate comprises less than 15% free saccharide, more preferably less than 10% free saccharide, and still more preferably, less than 5% of free saccharide.

The serotype 8 glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 40% of the serotype 8 glycoconjugates of the invention have a $K_d$ below or equal to 0.3 in a CL-4B column. In a preferred embodiment, at least 30%, 35%, 40%, 45%, 50%, 55%, 60%, 65%, 70%, 75%, 80%, or 85% of the serotype 8 glycoconjugates of the invention have a $K_d$ below or equal to 0.3 in a CL-4B column. In a preferred embodiment, at least 60% of the serotype 8 glycoconjugates of the invention have a $K_d$ below or equal to 0.3 in a CL-4B column. In a preferred embodiment, at least 70% of the serotype 8 glycoconjugates of the invention have a $K_d$ below or equal to 0.3 in a CL-4B column.

In a preferred embodiment, between 40% and 90% of the serotype 8 glycoconjugates have a $K_d$ below or equal to 0.3 in a CL-4B column. In a preferred embodiment, between 50% and 90% of the serotype 8 glycoconjugates have a $K_d$ below or equal to 0.3 in a CL-4B column. In a preferred embodiment, between 65% and 80% of the serotype 8 glycoconjugates have a $K_d$ below or equal to 0.3 in a CL-4B column.

1.4 Combinations of Glycoconjugates of the Invention

In an embodiment the immunogenic composition of the invention comprises any of the glycoconjugates disclosed herein.

In an embodiment the immunogenic composition of the invention comprises at least one glycoconjugate selected from the group consisting of a glycoconjugate from *S. pneumoniae* serotype 15B (such as the glycoconjugates of section 1.3.4 above), a glycoconjugate from *S. pneumoniae* serotype 22F (such as the glycoconjugates of section 1.3.2 above), a glycoconjugate from *S. pneumoniae* serotype 33F (such as the glycoconjugates of section 1.3.3 above), a glycoconjugate from *S. pneumoniae* serotype 12F (such as the glycoconjugates of section 1.3.5 above), a glycoconjugate from *S. pneumoniae* serotype 10A (such as the glycoconjugates of section 1.3.6 above), a glycoconjugate from *S. pneumoniae* serotype 11A (such as the glycoconjugates of section 1.3.7 above) and a glycoconjugate from *S. pneumoniae* serotype 8 (such as the glycoconjugates of section 1.3.8 above).

In an embodiment the immunogenic composition of the invention comprises at least one glycoconjugate from *S. pneumoniae* serotype 15B, such as the glycoconjugate of section 1.3.4 above. In an embodiment the immunogenic composition of the invention comprises at least one glycoconjugate from *S. pneumoniae* serotype 22F, such as the ones disclosed at section 1.3.2 above. In an embodiment the immunogenic composition of the invention comprises at least one glycoconjugate from *S. pneumoniae* serotype 33F such as the ones disclosed at section 1.3.3 above. In an embodiment the immunogenic composition of the invention comprises at least one glycoconjugate from *S. pneumoniae* serotype 12F such as the ones disclosed at section 1.3.5 above. In an embodiment the immunogenic composition of the invention comprises at least one glycoconjugate from *S. pneumoniae* serotype 10A such as the ones disclosed at section 1.3.6 above. In an embodiment the immunogenic composition of the invention comprises at least one glycoconjugate from *S. pneumoniae* serotype 11A such as the ones disclosed at section 1.3.7 above. In an embodiment the immunogenic composition of the invention comprises at least one glycoconjugate from *S. pneumoniae* serotype 8 such as the ones disclosed at section 1.3.8 above.

In an embodiment the immunogenic composition of the invention comprises at least one glycoconjugate of each of the two *S. pneumoniae* serotypes selected from the group consisting of: 15B and 22F, 15B and 33F, 15B and 12F, 15B and 10A, 15B and 11A, 15B and 8, 22F and 33F, 22F and 12F, 22F and 10A, 22F and 11A, 22F and 8, 33F and 12F, 33F and 10A, 33F and 11A, 33F and 8, 12F and 10A, 12F and 11A, 12F and 8, 10A and 11A, 10A and 8, and 11A and 8.

In an embodiment the immunogenic composition of the invention comprises at least one glycoconjugate of each of the three following *S. pneumoniae* serotypes:

15B and 22F and 33F,
15B and 22F and 12F,
15B and 22F and 10A,
15B and 22F and 11A,
15B and 22F and 8,
15B and 33F and 12F,
15B and 33F and 10A,
15B and 33F and 11A,
15B and 33F and 8,
15B and 12F and 10A,
15B and 12F and 11A,
15B and 12F and 8,
15B and 10A and 11A,
15B and 10A and 8,
15B and 11A and 8,
22F and 33F and 12F,
22F and 33F and 10A,
22F and 33F and 11A,
22F and 33F and 8,
22F and 12F and 10A,
22F and 12F and 11A,
22F and 12F and 8,
22F and 10A and 11A,
22F and 10A and 8,
22F and 11A and 8,
33F and 12F and 10A,
33F and 12F and 11A,
33F and 12F and 8,
33F and 10A and 11A,
33F and 10A and 8,
33F and 11A and 8,
12F and 10A and 11A,
12F and 10A and 8,
12F and 11A and 8, or
10A and 11A and 8.

In an embodiment the immunogenic composition of the invention comprises at least one glycoconjugate of each of the four following *S. pneumoniae* serotypes:

15B and 22F and 33F and 12F,
15B and 22F and 33F and 10A,
15B and 22F and 33F and 11A,
15B and 22F and 33F and 8,
15B and 22F and 12F and 10A,
15B and 22F and 12F and 11A,
15B and 22F and 12F and 8,
15B and 22F and 10A and 11A,
15B and 22F and 10A and 8,
15B and 22F and 11A and 8,
15B and 33F and 12F and 10A,
15B and 33F and 12F and 11A,
15B and 33F and 12F and 8,
15B and 33F and 10A and 11A,
15B and 33F and 10A and 8,
15B and 33F and 11A and 8,
15B and 12F and 10A and 11A,
15B and 12F and 10A and 8,
15B and 12F and 11A and 8,
15B and 10A and 11A and 8,
22F and 33F and 12F and 10A,
22F and 33F and 12F and 11A,
22F and 33F and 12F and 8,
22F and 33F and 10A and 11A,
22F and 33F and 10A and 8,
22F and 33F and 11A and 8,
22F and 12F and 10A and 11A,
22F and 12F and 10A and 8,
22F and 12F and 11A and 8,
22F and 10A and 11A and 8,
33F and 12F and 10A and 11A,
33F and 12F and 10A and 8,
33F and 12F and 11A and 8,
33F and 10A and 11A and 8 or
12F and 10A and 11A and 8.

In an embodiment the immunogenic composition of the invention comprises at least one glycoconjugate of each of the five following *S. pneumoniae* serotypes:

15B and 22F and 33F and 12F and 10A,
15B and 22F and 33F and 12F and 11A,
15B and 22F and 33F and 12F and 8,
15B and 22F and 33F and 10A and 11A,
15B and 22F and 33F and 10A and 8,
15B and 22F and 33F and 11A and 8,
15B and 22F and 12F and 10A and 11A,
15B and 22F and 12F and 10A and 8,
15B and 22F and 12F and 11A and 8,
15B and 22F and 10A and 11A and 8,
15B and 33F and 12F and 10A and 11A,
15B and 33F and 12F and 10A and 8,
15B and 33F and 12F and 11A and 8,
15B and 33F and 10A and 11A and 8,
15B and 12F and 10A and 11A and 8, 22F and 33F and 12F and 10A and 11A,
22F and 33F and 12F and 10A and 8,
22F and 33F and 12F and 11A and 8,
22F and 33F and 10A and 11A and 8,
22F and 12F and 10A and 11A and 8 or
33F and 12F and 10A and 11A and 8.

In an embodiment the immunogenic composition of the invention comprises at least one glycoconjugate of each of the six following *S. pneumoniae* serotypes:

15B and 22F and 33F and 12F and 10A and 11A,
15B and 22F and 33F and 12F and 10A and 8,
15B and 22F and 33F and 12F and 11A and 8,
15B and 22F and 33F and 10A and 11A and 8,
15B and 22F and 12F and 10A and 11A and 8,
15B and 33F and 12F and 10A and 11A and 8 or
22F and 33F and 12F and 10A and 11A and 8.

In an embodiment the immunogenic composition of the invention comprises at least one glycoconjugate of each of the seven following *S. pneumoniae* serotypes: 15B and 22F and 33F and 12F and 10A and 11A and 8.

In an embodiment the glycoconjugates from *S. pneumoniae* serotypes 15B, 22F, 33F, 12F, 10A, 11A and/or 8 of any of the immunogenic composition defined in this section are as disclosed at sections 1.3.2 to 1.3.8 above.

In an embodiment any of the immunogenic compositions above comprise in addition glycoconjugates from *S. pneumoniae* serotypes 4, 6B, 9V, 14, 18C, 19F and 23F (such as the glycoconjugates of section 1.3.1 above).

In an embodiment any of the immunogenic compositions above comprise in addition glycoconjugates from *S. pneumoniae* serotypes 1, 5 and 7F (such as the glycoconjugates of section 1.3.1 above).

In an embodiment any of the immunogenic compositions above comprise in addition glycoconjugates from *S. pneumoniae* serotypes 6A and 19A (such as the glycoconjugates of section 1.3.1 above).

In an embodiment any of the immunogenic compositions above comprise in addition glycoconjugates from *S. pneumoniae* serotype 3 (such as the glycoconjugates of section 1.3.1 above).

Preferably, all the glycoconjugates of the above immunogenic compositions are individually conjugated to the carrier protein.

In an embodiment of any of the above immunogenic compositions, the glycoconjugates from *S. pneumoniae* serotype 22F is conjugated to $CRM_{197}$. In an embodiment of any of the above immunogenic compositions, the glycoconjugates from *S. pneumoniae* serotype 33F is conjugated to $CRM_{197}$. In an embodiment of any of the above immunogenic compositions, the glycoconjugates from *S. pneumoniae* serotype 15B is conjugated to $CRM_{197}$. In an embodiment of any of the above immunogenic compositions, the glycoconjugates from *S. pneumoniae* serotype 12F is conjugated to $CRM_{197}$. In an embodiment of any of the above immunogenic compositions, the glycoconjugates from *S. pneumoniae* serotype 10A is conjugated to $CRM_{197}$. In an embodiment of any of the above immunogenic compositions, the glycoconjugates from *S. pneumoniae* serotype 11A is conjugated to $CRM_{197}$. In an embodiment of any of the above immunogenic compositions, the glycoconjugates from *S. pneumoniae* serotype 8 is conjugated to $CRM_{197}$. In an embodiment of any of the above immunogenic compositions, the glycoconjugates from *S. pneumoniae* serotypes 4, 6B, 9V, 14, 18C, 19F and 23F are conjugated to $CRM_{197}$. In an embodiment of any of the above immunogenic compositions, the glycoconjugates from *S. pneumoniae* serotypes 1, 5 and 7F are conjugated to $CRM_{197}$. In an embodiment of any of the above immunogenic compositions, the glycoconjugates from *S. pneumoniae* serotypes 6A and 19A are conjugated to $CRM_{197}$.

In an embodiment of any of the above immunogenic compositions, the glycoconjugates from *S. pneumoniae* serotype 3 is conjugated to $CRM_{197}$.

In an embodiment, the glycoconjugates of any of the above immunogenic compositions are all individually conjugated to $CRM_{197}$.

In an embodiment, the glycoconjugates from *S. pneumoniae* serotypes 1, 4, 5, 6B, 7F, 9V, 14 and/or 23F of any of the above immunogenic compositions are individually conjugated to PD.

In an embodiment, the glycoconjugate from *S. pneumoniae* serotype 18C of any of the above immunogenic compositions is conjugated to TT.

In an embodiment, the glycoconjugate from *S. pneumoniae* serotype 19F of any of the above immunogenic compositions is conjugated to DT.

In an embodiment, the glycoconjugates from *S. pneumoniae* serotypes 1, 4, 5, 6B, 7F, 9V, 14 and/or 23F of any of the above immunogenic compositions are individually conjugated to PD, the glycoconjugate from *S. pneumoniae* serotype 18C is conjugated to TT and the glycoconjugate from *S. pneumoniae* serotype 19F is conjugated to DT.

In an embodiment the above immunogenic compositions comprise from 8 to 20 different serotypes of *S. pneumoniae*. In one embodiment the above immunogenic compositions comprise glycoconjugates from 12, 13, 14, 15, 16, 17, 18, 19 or 20 different serotypes. In one embodiment the above immunogenic compositions comprise glycoconjugates from 16 or 20 different serotypes.

In an embodiment the above immunogenic compositions are 8, 9, 10, 11, 12, 13, 14, 15, 16, 17, 18, 19 or 20-valent pneumococcal conjugate compositions. In an embodiment the above immunogenic compositions are 14, 15, 16, 17, 18 or 19-valent pneumococcal conjugate compositions. In an embodiment the above immunogenic compositions are 16-valent pneumococcal conjugate compositions. In an embodiment the above immunogenic compositions are 19-valent pneumococcal conjugate compositions.

1. In an embodiment the immunogenic composition of the invention comprises at least one glycoconjugate from *S. pneumoniae* serotype 15B, such as the glycoconjugates of section 1.3.4 above.

2. In another embodiment the immunogenic composition of the invention comprises in addition to point 1 above, at least one glycoconjugate from *S. pneumoniae* serotype 22F, such as the ones disclosed at section 1.3.2 above.

3. In another embodiment the immunogenic composition of the invention comprises in addition to point 1 or 2 above, at least one glycoconjugate from *S. pneumoniae* serotype 33F such as the ones disclosed at section 1.3.3 above.

4. In another embodiment the immunogenic composition of the invention comprises in addition to point 1, 2 or 3 above, at least one glycoconjugate from *S. pneumoniae* serotype 12F such as the ones disclosed at section 1.3.5 above.

5. In another embodiment the immunogenic composition of the invention comprises in addition to point 1, 2, 3 or 4 above, at least one glycoconjugate from *S. pneumoniae* serotype 10A such as the ones disclosed at section 1.3.6 above.

6. In another embodiment the immunogenic composition of the invention comprises in addition to point 1, 2, 3, 4 or 5 above, at least one glycoconjugate from *S. pneumoniae* serotype 11A such as the ones disclosed at section 1.3.7 above.

7. In another embodiment the immunogenic composition of the invention comprises in addition to point 1, 2, 3, 4, 5 or 6 above, at least one glycoconjugate from *S. pneumoniae* serotype 8 such as the ones disclosed at section 1.3.8 above.

8. In another embodiment the immunogenic composition of the invention comprises in addition to point 1, 2, 3, 4, 5, 6 or 7 above glycoconjugates from *S. pneumoniae* serotypes 4, 6B, 9V, 14, 18C, 19F and 23F, such as the glycoconjugates of section 1.3.1 above.

9. In another embodiment the immunogenic composition of the invention comprises in addition to point 1, 2, 3, 4, 5, 6, 7 or 8 above glycoconjugates from *S. pneumoniae* serotypes 1, 5 and 7F such as the glycoconjugates of section 1.3.1 above.

10. In another embodiment the immunogenic composition of the invention comprises in addition to point 1, 2, 3, 4, 5, 6, 7, 8 or 9 above glycoconjugates from *S. pneumoniae* serotypes 6A and 19A such as the glycoconjugates of section 1.3.1 above.

11. In another embodiment the immunogenic composition of the invention comprises in addition to point 1, 2, 3, 4, 5, 6, 7, 8, 9 or 10 above glycoconjugates from *S. pneumoniae* serotype 3 such as the glycoconjugates of section 1.3.1 above.

In an embodiment, the immunogenic composition of the invention comprises glycoconjugates from *S. pneumoniae* serotypes 1, 3, 4, 5, 6A, 6B, 7F, 9V, 14, 15B, 18C, 19A, 19F, 22F, 23F and 33F.

In an embodiment, the immunogenic composition of the invention comprises glycoconjugates from *S. pneumoniae* serotypes 1, 4, 5, 6A, 6B, 7F, 9V, 14, 15B, 18C, 19A, 19F, 22F, 23F and 33F.

In an embodiment, the immunogenic composition of the invention comprises conjugated *S. pneumoniae* saccharides from serotypes 1, 3, 4, 5, 6A, 6B, 7F, 8, 9V, 10A, 11A, 12F, 14, 15B, 18C, 19A, 19F, 22F, 23F and 33F.

In an embodiment, the immunogenic composition of the invention comprises conjugated *S. pneumoniae* saccharides from serotypes 1, 4, 5, 6A, 6B, 7F, 8, 9V, 10A, 11A, 12F, 14, 15B, 18C, 19A, 19F, 22F, 23F and 33F.

In an embodiment, the glycoconjugates of the immunogenic composition of the invention consist of glycoconjugates from *S. pneumoniae* serotypes 1, 3, 4, 5, 6A, 6B, 7F, 9V, 14, 15B, 18C, 19A, 19F, 22F, 23F and 33F. In an embodiment, the glycoconjugates of the immunogenic composition of the invention consist of glycoconjugates from serotypes 1, 4, 5, 6A, 6B, 7F, 9V, 14, 15B, 18C, 19A, 19F, 22F, 23F and 33F. In an embodiment, the glycoconjugates of the immunogenic composition of the invention consist of glycoconjugates from serotypes 1, 3, 4, 5, 6A, 6B, 7F, 8, 9V, 10A, 11A, 12F, 14, 15B, 18C, 19A, 19F, 22F, 23F and 33F. In an embodiment, the glycoconjugates of the immunogenic composition of the invention consist of glycoconjugates from 1, 4, 5, 6A, 6B, 7F, 8, 9V, 10A, 11A, 12F, 14, 15B, 18C, 19A, 19F, 22F, 23F and 33F.

Preferably, all the glycoconjugates of the immunogenic composition of the invention (e.g., of any of points 1 to 11 above) are individually conjugated to the carrier protein.

In an embodiment, the glycoconjugates from *S. pneumoniae* serotypes 1, 4, 5, 6B, 7F, 9V, 14 and/or 23F of any of points 8 to 11 above are individually conjugated to PD.

In an embodiment, the glycoconjugate from *S. pneumoniae* serotype 18C of any of points 8 to 11 above is conjugated to TT.

In an embodiment, the glycoconjugate from *S. pneumoniae* serotype 19F of any of points 8 to 11 above is conjugated to DT.

In an embodiment of any of points 8 to 11 above, the glycoconjugates from *S. pneumoniae* serotypes 1, 4, 5, 6B, 7F, 9V, 14 and/or 23F are individually conjugated to PD, the glycoconjugate from *S. pneumoniae* serotype 18C is conjugated to TT and the glycoconjugate from *S. pneumoniae* serotype 19F is conjugated to DT.

In an embodiment of any of points 1 to 11 above, the glycoconjugate from *S. pneumoniae* serotype 22F is conjugated to $CRM_{197}$. In an embodiment of any of points 2 to 11 above, the glycoconjugate from *S. pneumoniae* serotype 33F is conjugated to $CRM_{197}$. In an embodiment of any of points 3 to 11 above, the glycoconjugate from *S. pneumoniae* serotype 15B is conjugated to $CRM_{197}$. In an embodiment of any of points 4 to 11 above, the glycoconjugate from *S. pneumoniae* serotype 12F is conjugated to $CRM_{197}$. In an embodiment of any of points 5 to 11 above, the glycoconjugate from *S. pneumoniae* serotype 10A is conjugated to $CRM_{197}$. In an embodiment of any of points 6 to 11 above, the glycoconjugate from *S. pneumoniae* serotype 11A is conjugated to $CRM_{197}$. In an embodiment of any of points 7 to 11 above, the glycoconjugate from *S. pneumoniae* serotype 8 is conjugated to $CRM_{197}$. In an embodiment of any of points 8 to 11 above, the glycoconjugates from *S. pneumoniae* serotypes 4, 6B, 9V, 14, 18C, 19F and 23F are conjugated to $CRM_{197}$. In an embodiment of any of points 9 to 11 above, the glycoconjugates from *S. pneumoniae* serotypes 1, 5 and 7F are conjugated to $CRM_{197}$.

In an embodiment of any of points 10 to 11 above, the glycoconjugates from *S. pneumoniae* serotypes 6A and 19A are conjugated to $CRM_{197}$. In an embodiment of point 11 above, the glycoconjugate from *S. pneumoniae* serotype 3 is conjugated to $CRM_{197}$. In an embodiment, the glycoconjugates of immunogenic composition of points 1 to 11 above are individually conjugated to $CRM_{197}$.

In an embodiment the immunogenic composition of the invention comprises from 12 to 20 different serotypes of *S. pneumoniae*. In one embodiment the immunogenic composition of the invention comprises glycoconjugates from 12, 13, 14, 15, 16, 17, 18, 19 or 20 different serotypes. In one embodiment the immunogenic composition of the invention comprises glycoconjugates from 16 or 20 different serotypes.

In an embodiment the immunogenic composition of points 1 to 11 above is a 8, 9, 10, 11, 12, 13, 14, 15, 16, 17, 18, 19 or 20-valent pneumococcal conjugate composition. In an embodiment the immunogenic composition of points 1 to 11 above is a 15, 16, 17, 18 or 19-valent pneumococcal conjugate composition. In an embodiment the immunogenic composition of points 1 to 11 above is a 16-valent pneumococcal conjugate composition. In an embodiment the immunogenic composition of points 1 to 11 above is a 19-valent pneumococcal conjugate composition.

After conjugation of the capsular polysaccharide to the carrier protein, the glycoconjugates are purified (enriched with respect to the amount of polysaccharide-protein conjugate) by a variety of techniques. These techniques include concentration/diafiltration operations, precipitation/elution, column chromatography, and depth filtration (see for example U.S. Patent App. Pub. No. 2007/0184072 or WO 2008/079653). After the individual glycoconjugates are purified, they are compounded to formulate the immunogenic composition of the present invention.

1.5 Further Combinations of Glycoconjugates of the Invention

In an embodiment any of the immunogenic compositions defined at section 1.4 above further comprise, at least one glycoconjugate from *S. pneumoniae* serotype 9V.

In an embodiment any of the immunogenic compositions defined at section 1.4 above further comprise, at least one glycoconjugate of each of the two *S. pneumoniae* serotypes selected from the group consisting of: 9V and 4, 9V and 6B, 9V and 14, 9V and 18C, 9V and 19F, 9V and 23F.

In an embodiment any of the immunogenic compositions defined at section 1.4 above further comprise, at least one glycoconjugate of each of the seven following *S. pneumoniae* serotypes: 9V, 4, 6B, 14, 18C, 19F and 23F.

In an embodiment any of the immunogenic compositions defined at section 1.4 above further comprise, at least one glycoconjugate of each of the eight following *S. pneumoniae* serotypes:

9V and 1 and 4 and 6B and 14 and 18C and 19F and 23F, 9V and 4 and 5 and 6B and 14 and 18C and 19F and 23F, or 9V and 4 and 6B and 7F and 14 and 18C and 19F and 23F.

In an embodiment any of the immunogenic compositions defined at section 1.4 above further comprise, at least one glycoconjugate of each of the ten following *S. pneumoniae* serotypes: 9V, 1, 5, 4, 6B, 7F, 14, 18C, 19F and 23F.

In an embodiment any of the immunogenic compositions defined at section 1.4 above further comprise, at least one glycoconjugate of each of the eleven following *S. pneumoniae* serotypes:

9V and 1 and 4 and 5 and 6A and 6B and 7F and 14 and 18C and 19F and 23F or 9V and 1 and 4 and 5 and 6B and 7F and 14 and 18C and 19A and 19F and 23F.

In an embodiment any of the immunogenic compositions defined at section 1.4 above further comprise, at least one glycoconjugate of each of the twelve following *S. pneumoniae* serotypes: 9V, 1, 4, 5, 6A, 6B, 7F, 14, 18C, 19A, 19F and 23F.

In an embodiment any of the immunogenic compositions defined at section 1.4 above further comprise, at least one glycoconjugate of each of the thirteen following *S. pneumoniae* serotypes: 9V, 1, 3, 4, 5, 6A, 6B, 7F, 14, 18C, 19A, 19F and 23F.

In an embodiment any of the immunogenic compositions defined at section 1.4 above comprise in addition at least one glycoconjugate from *S. pneumoniae* serotype 2.

In an embodiment any of the immunogenic compositions defined at section 1.4 above comprise in addition at least one glycoconjugate from *S. pneumoniae* serotype 17F.

In an embodiment any of the immunogenic compositions defined at section 1.4 above comprise in addition at least one glycoconjugate from *S. pneumoniae* serotype 20.

In an embodiment any of the immunogenic compositions defined at section 1.4 above comprise in addition at least one glycoconjugate from *S. pneumoniae* serotype 15C.

In an embodiment any of the immunogenic compositions defined at section 1.4 above comprise in addition at least one glycoconjugate from *S. pneumoniae* serotype 9N.

Preferably, all the glycoconjugates of the above immunogenic compositions are individually conjugated to the carrier protein.

In an embodiment of any of the above immunogenic compositions, the glycoconjugate from *S. pneumoniae* serotype 9V is conjugated to $CRM_{197}$. In an embodiment of any of the above immunogenic compositions, the glycoconjugates from *S. pneumoniae* serotypes 4, 6B, 14, 18C, 19F and 23F are conjugated to $CRM_{197}$. In an embodiment of any of the above immunogenic compositions, the glycoconjugates from *S. pneumoniae* serotypes 1, 5 and 7F are conjugated to $CRM_{197}$. In an embodiment of any of the above immunogenic compositions, the glycoconjugates from *S. pneumoniae* serotypes 6A and 19A are conjugated to $CRM_{197}$. In an embodiment of any of the above immunogenic compositions, the glycoconjugate from *S. pneumoniae* serotype 3 is conjugated to $CRM_{197}$. In an embodiment of any of the above immunogenic compositions, the glycoconjugate from *S. pneumoniae* serotype 2 is conjugated to $CRM_{197}$. In an embodiment of any of the above immunogenic compositions, the glycoconjugate from *S. pneumoniae* serotype 17F is conjugated to $CRM_{197}$. In an embodiment of any of the above immunogenic compositions, the glycoconjugate from *S. pneumoniae* serotype 20 is conjugated to $CRM_{197}$. In an embodiment of any of the above immunogenic compositions, the glycoconjugate from *S. pneumoniae* serotype 15C is conjugated to $CRM_{197}$. In an embodiment of any of the above immunogenic compositions, the glycoconjugate from *S. pneumoniae* serotype 9N is conjugated to $CRM_{197}$.

In an embodiment, the glycoconjugates of the above immunogenic compositions are all individually conjugated to $CRM_{197}$.

In another embodiment, the glycoconjugate from *S. pneumoniae* serotype 9V of any of the above immunogenic compositions is individually conjugated to PD.

In an embodiment, the glycoconjugates from *S. pneumoniae* serotypes 1, 4, 5, 6B, 7F, 9V, 14 and/or 23F of any of the above immunogenic compositions are individually conjugated to PD.

In an embodiment, the glycoconjugate from *S. pneumoniae* serotype 18C of any of the above immunogenic compositions is conjugated to TT.

In an embodiment, the glycoconjugate from *S. pneumoniae* serotype 19F of any of the above immunogenic compositions is conjugated to DT.

In an embodiment, the glycoconjugates from *S. pneumoniae* serotypes 1, 4, 5, 6B, 7F, 9V, 14 and/or 23F of any of the above immunogenic compositions are individually conjugated to PD, the glycoconjugate from *S. pneumoniae* serotype 18C is conjugated to TT and the glycoconjugate from *S. pneumoniae* serotype 19F is conjugated to DT.

In an embodiment the above immunogenic compositions comprises from 7 to 25 different serotypes of *S. pneumoniae*. In one embodiment the above immunogenic compositions comprise glycoconjugates from 7, 8, 9, 10, 11, 12, 13, 14, 15, 16, 17, 18, 19, 20, 21, 22, 23, 24 or 25 different serotypes. In one embodiment the above immunogenic compositions comprise glycoconjugates from 16 or 20 different serotypes.

In an embodiment the above immunogenic compositions are 8, 9, 10, 11, 12, 13, 14, 15, 16, 17, 18, 19 or 20-valent pneumococcal conjugate compositions. In an embodiment the above immunogenic compositions are 14, 15, 16, 17, 18 or 19-valent pneumococcal conjugate compositions. In an embodiment the above immunogenic compositions are 16-valent pneumococcal conjugate compositions. In an embodiment the above immunogenic compositions are 19-valent pneumococcal conjugate compositions. In an embodiment the above immunogenic compositions are 20-valent pneumococcal conjugate compositions.

After conjugation of the capsular polysaccharide to the carrier protein, the glycoconjugates are purified (enriched with respect to the amount of polysaccharide-protein conjugate) by a variety of techniques. These techniques include concentration/diafiltration operations, precipitation/elution, column chromatography, and depth filtration (see for example U.S. Patent App. Pub. No. 2007/0184072 or WO 2008/079653. After the individual glycoconjugates are purified, they are compounded to formulate the immunogenic composition of the present invention.

1.6 Particular Combinations of Glycoconjugates of the Invention

In an embodiment any of the immunogenic compositions defined at section 1.4 or 1.5 above do not comprise capsular saccharide from *S. pneumoniae* serotype 9N.

In an embodiment any of the immunogenic compositions defined at section 1.4 or 1.5 above do not comprise capsular saccharide from *S. pneumoniae* serotype 9A.

In an embodiment any of the immunogenic compositions defined at section 1.4 or 1.5 above do not comprise capsular saccharide from *S. pneumoniae* serotype 9L.

In an embodiment any of the immunogenic compositions defined at section 1.4 or 1.5 above do not comprise capsular saccharide from *S. pneumoniae* serotypes 9N and 9A.

In an embodiment any of the immunogenic compositions defined at section 1.4 or 1.5 above do not comprise capsular saccharide from *S. pneumoniae* serotypes 9N and 9L.

In an embodiment any of the immunogenic compositions defined at section 1.4 or 1.5 above do not comprise capsular saccharide from *S. pneumoniae* serotypes 9A and 9L.

In an embodiment any of the immunogenic compositions defined at section 1.4 or 1.5 above do not comprise capsular saccharide from *S. pneumoniae* serotypes 9N, 9A and 9L.

2 Dosage of the Immunogenic Compositions

The amount of glycoconjugate(s) in each dose is selected as an amount which induces an immunoprotective response without significant, adverse side effects in typical vaccinees. Such amount will vary depending upon which specific immunogen is employed and how it is presented.

2.1 Glycoconjugate Amount

The amount of a particular glycoconjugate in an immunogenic composition can be calculated based on total polysaccharide for that conjugate (conjugated and nonconjugated). For example, a glycoconjugate with 20% free polysaccharide will have about 80 μg of conjugated polysaccharide and about 20 μg of nonconjugated polysaccharide in a 100 μg polysaccharide dose. The amount of glycoconjugate can vary depending upon the pneumococcal serotype. The saccharide concentration can be determined by the uronic acid assay.

The “immunogenic amount” of the different polysaccharide components in the immunogenic composition, may diverge and each may comprise about 1 μg, about 2 μg, about 3 μg, about 4 μg, about 5 μg, about 6 μg, about 7 μg, about 8 μg, about 9 μg, about 10 μg, about 15 μg, about 20 μg, about 30 μg, about 40 μg, about 50 μg, about 60 μg, about 70 μg, about 80 μg, about 90 μg, or about 100 μg of any particular polysaccharide antigen.

Generally, each dose will comprise 0.1 μg to 100 μg of polysaccharide for a given serotype, particularly 0.5 μg to 20 μg, more particularly 1.0 μg to 10 μg, and even more particularly 2.0 μg to 5.0 μg. Any whole number integer within any of the above ranges is contemplated as an embodiment of the disclosure.

In an embodiment, each dose will comprise about 1.0 μg, about 1.2 μg, about 1.4 μg, about 1.6 μg, about 1.8 μg, about 2.0 μg, about 2.2 μg, about 2.4 μg, about 2.6 μg, about 2.8 μg, about 3.0 μg, about 3.2 μg, about 3.4 μg, about 3.6 μg, about 3.8 μg, about 4.0 μg, about 4.2 μg, about 4.4 μg, about 4.6 μg, about 4.8 μg, about 5.0 μg, about 5.2 μg, about 5.4 μg, about 5.6 μg, about 5.8 μg or about 6.0 μg of polysaccharide for each particular glycoconjugate.

In an embodiment, each dose will comprise about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, or about 3.0 μg μg of polysaccharide for glycoconjugates from *S. pneumoniae* serotype 1, 3, 4, 5, 6A, 7F, 8, 9V, 10A, 11A, 12F, 14, 15B, 18C, 19A, 19F, 22F, 23F and/or 33F.

In an embodiment, each dose will comprise about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, or about 3.0 μg of polysaccharide for glycoconjugates from *S. pneumoniae* serotype 1, 4, 5, 6A, 7F, 8, 9V, 10A, 11A, 12F, 14, 15B, 18C, 19A, 19F, 22F, 23F and/or 33F.

In an embodiment, each dose will comprise about 2.0 μg, about 2.2 μg, about 2.4 μg, about 2.6 μg, about 2.8 μg, about 3.0 μg, about 3.2 μg, about 3.4 μg, about 3.6 μg, about 3.8 μg, about 4.0 μg, about 4.2 μg, about 4.4 μg, about 4.6 μg, about 4.8 μg, about 5.0, about 5.2 μg, about 5.4 μg, about 5.6 μg, about 5.8 μg or about 6.0 μg of polysaccharide for glycoconjugates from *S. pneumoniae* serotype 6B.

In an embodiment, each dose will comprise about 1.5 μg to about 3.0 μg of polysaccharide for each glycoconjugate from *S. pneumoniae* serotype 1, 3, 4, 5, 6A, 7F, 8, 9V, 10A, 11A, 12F, 14, 15B, 18C, 19A, 19F, 22F, 23F and 33F, and about 3.0 μg to about 6.0 μg of polysaccharide for glycoconjugate from *S. pneumoniae* serotype 6B.

In an embodiment, each dose will comprise about 2.0 μg to about 2.5 μg of polysaccharide for each glycoconjugate from *S. pneumoniae* serotype 1, 3, 4, 5, 6A, 7F, 8, 9V, 10A, 11A, 12F, 14, 15B, 18C, 19A, 19F, 22F, 23F and 33F, and about 4.0 μg to about 4.8 μg of polysaccharide for glycoconjugate from *S. pneumoniae* serotype 6B.

In an embodiment, each dose will comprise about 2.2 μg of polysaccharide from each glycoconjugate from *S. pneumoniae* serotype 1, 3, 4, 5, 6A, 7F, 8, 9V, 10A, 11A, 12F, 14, 15B, 18C, 19A, 19F, 22F, 23F and 33F, and about 4.4 μg of polysaccharide for glycoconjugate from *S. pneumoniae* serotype 6B.

In an embodiment, each dose will comprise about 1.5 μg to about 3.0 μg of polysaccharide for each glycoconjugate from *S. pneumoniae* serotype 1, 3, 4, 5, 6A, 7F, 9V, 14, 15B, 18C, 19A, 19F, 22F, 23F and 33F, and about 3 μg to about 6 μg of polysaccharide for glycoconjugate from *S. pneumoniae* serotype 6B.

In an embodiment, each dose will comprise about 2.0 μg to about 2.5 μg of polysaccharide for each glycoconjugate from *S. pneumoniae* serotype 1, 3, 4, 5, 6A, 7F, 9V, 14, 15B, 18C, 19A, 19F, 22F, 23F and 33F, and about 4.0 μg to about 4.8 μg of polysaccharide for glycoconjugate from *S. pneumoniae* serotype 6B.

In an embodiment, each dose will comprise about 2.2 μg of polysaccharide from each glycoconjugate from *S. pneumoniae* serotype 1, 3, 4, 5, 6A, 7F, 9V, 14, 15B, 18C, 19A, 19F, 22F, 23F and 33F, and about 4.4 μg of polysaccharide for glycoconjugate from *S. pneumoniae* serotype 6B.

In an embodiment, each dose will comprise about 1.5 μg to about 3.0 μg of polysaccharide for each glycoconjugate from *S. pneumoniae* serotype 1, 4, 5, 6A, 7F, 8, 9V, 10A, 11A, 12F, 14, 15B, 18C, 19A, 19F, 22F, 23F and 33F, and about 3.0 μg to about 6.0 μg of polysaccharide for glycoconjugate from *S. pneumoniae* serotype 6B.

In an embodiment, each dose will comprise about 2.0 μg to about 2.5 μg of polysaccharide for each glycoconjugate from *S. pneumoniae* serotype 1, 4, 5, 6A, 7F, 8, 9V, 10A, 11A, 12F, 14, 15B, 18C, 19A, 19F, 22F, 23F and 33F, and about 4.0 μg to about 4.8 μg of polysaccharide for glycoconjugate from *S. pneumoniae* serotype 6B.

In an embodiment, each dose will comprise about 2.2 μg of polysaccharide from each glycoconjugate from *S. pneumoniae* serotype 1, 4, 5, 6A, 7F, 8, 9V, 10A, 11A, 12F, 14, 15B, 18C, 19A, 19F, 22F, 23F and 33F, and about 4.4 μg of polysaccharide for glycoconjugate from *S. pneumoniae* serotype 6B.

In an embodiment, each dose will comprise about 1.5 μg to about 3.0 μg of polysaccharide for each glycoconjugate from *S. pneumoniae* serotype 1, 4, 5, 6A, 7F, 9V, 14, 15B, 18C, 19A, 19F, 22F, 23F and 33F, and about 3.0 μg to about 6.0 μg of polysaccharide for glycoconjugate from *S. pneumoniae* serotype 6B.

In an embodiment, each dose will comprise about 2.0 μg to about 2.5 μg of polysaccharide for each glycoconjugate from *S. pneumoniae* serotype 1, 4, 5, 6A, 7F, 9V, 14, 15B, 18C, 19A, 19F, 22F, 23F and 33F, and about 4.0 μg to about 4.8 μg of polysaccharide for glycoconjugate from *S. pneumoniae* serotype 6B.

In an embodiment, each dose will comprise about 2.2 μg of polysaccharide from each glycoconjugate from *S. pneumoniae* serotype 1, 4, 5, 6A, 7F, 9V, 14, 15B, 18C, 19A, 19F, 22F, 23F and 33F, and about 4.4 μg of polysaccharide for glycoconjugate from *S. pneumoniae* serotype 6B.

2.2 Carrier Amount

Generally, each dose will comprise 10 μg to 150 μg of carrier protein, particularly 15 μg to 100 μg of carrier protein, more particularly 25 μg to 75 μg of carrier protein, and even more particularly 40 μg to 60 μg of carrier protein. In an embodiment, said carrier protein is $CRM_{197}$.

In an embodiment, each dose will comprise about 25 μg, about 26 μg, about 27 μg, about 28 μg, about 29 μg, about 30 μg, about 31 μg, about 32 μg, about 33 μg, about 34 μg, about 35 μg, about 36 μg, about 37 μg, about 38 μg, about 39 μg, about 40 μg, about 41 μg, about 42 μg, about 43 μg, about 44 μg, about 45 μg, about 46 μg, about 47 μg, about 48 μg, about 49 μg, about 50 μg, about 51 μg, about 52 μg, about 53 μg, about 54 μg, about 55 μg, about 56 μg, about 57 μg, about 58 μg, about 59 μg, about 60 μg, about 61 μg, about 62 μg, about 63 μg, about 64 μg, about 65 μg, about 66 μg, about 67 μg, about 68 μg, about 69 μg, about 70 μg, about 71 μg, about 72 μg, about 73 μg, about 74 μg or about 75 μg of carrier protein. In an embodiment, said carrier protein is $CRM_{197}$.

3 Further Antigens

Immunogenic compositions of the invention comprise conjugated *S. pneumoniae* saccharide antigens (glycoconjugates). They may also further include antigens from other pathogens, particularly from bacteria and/or viruses. Preferred further antigens are selected from: a diphtheria toxoid (D), a tetanus toxoid (T), a pertussis antigen (P), which is typically acellular (Pa), a hepatitis B virus (HBV) surface antigen (HBsAg), a hepatitis A virus (HAV) antigen, a conjugated *Haemophilus influenzae* type b capsular saccharide (Hib), inactivated poliovirus vaccine (IPV).

In an embodiment, the immunogenic compositions of the invention comprise D-T-Pa. In an embodiment, the immunogenic compositions of the invention comprise D-T-Pa-Hib, D-T-Pa-IPV or D-T-Pa-HBsAg. In an embodiment, the immunogenic compositions of the invention comprise D-T-Pa-HBsAg-IPV or D-T-Pa-HBsAg-Hib. In an embodiment, the immunogenic compositions of the invention comprise D-T-Pa-HBsAg-IPV-Hib.

Pertussis antigens: *Bordetella pertussis* causes whooping cough. Pertussis antigens in vaccines are either cellular (whole cell, in the form of inactivated *B. pertussis* cells) or acellular. Preparation of cellular pertussis antigens is well documented (e.g., it may be obtained by heat inactivation of phase I culture of *B. pertussis*). Preferably, however, the invention uses acellular antigens. Where acellular antigens are used, it is preferred to use one, two or (preferably) three of the following antigens: (1) detoxified pertussis toxin (pertussis toxoid, or PT); (2) filamentous hemagglutinin (FHA); (3) pertactin (also known as the 69 kiloDalton outer membrane protein). FHA and pertactin may be treated with formaldehyde prior to use according to the invention. PT is preferably detoxified by treatment with formaldehyde and/or glutaraldehyde. Acellular pertussis antigens are preferably adsorbed onto one or more aluminum salt adjuvants. As an alternative, they may be added in an unadsorbed state. Where pertactin is added then it is preferably already adsorbed onto an aluminum hydroxide adjuvant. PT and FHA may be adsorbed onto an aluminum hydroxide adjuvant or an aluminum phosphate. Adsorption of all of PT, FHA and pertactin to aluminum hydroxide is most preferred.

Inactivated poliovirus vaccine: Poliovirus causes poliomyelitis. Rather than use oral poliovirus vaccine, preferred embodiments of the invention use IPV. Prior to administration to patients, polioviruses must be inactivated, and this can be achieved by treatment with formaldehyde. Poliomyelitis can be caused by one of three types of poliovirus. The three types are similar and cause identical symptoms, but they are antigenically different and infection by one type does not protect against infection by others. It is therefore preferred to use three poliovirus antigens in the invention: poliovirus Type 1 (e.g., Mahoney strain), poliovirus Type 2 (e.g., MEF-1 strain), and poliovirus Type 3 (e.g., Saukett strain). The viruses are preferably grown, purified and inactivated individually, and are then combined to give a bulk trivalent mixture for use with the invention.

Diphtheria toxoid: *Corynebacterium diphtheriae* causes diphtheria. Diphtheria toxin can be treated (e.g., using formalin or formaldehyde) to remove toxicity while retaining the ability to induce specific anti-toxin antibodies after injection. These diphtheria toxoids are used in diphtheria vaccines. Preferred diphtheria toxoids are those prepared by formaldehyde treatment. The diphtheria toxoid can be obtained by growing *C. diphtheriae* in growth medium, followed by formaldehyde treatment, ultrafiltration and precipitation. The toxoided material may then be treated by a process comprising sterile filtration and/or dialysis. The diphtheria toxoid is preferably adsorbed onto an aluminum hydroxide adjuvant.

Tetanus toxoid: *Clostridium tetani* causes tetanus. Tetanus toxin can be treated to give a protective toxoid. The toxoids are used in tetanus vaccines. Preferred tetanus toxoids are those prepared by formaldehyde treatment. The tetanus toxoid can be obtained by growing *C. tetani* in growth medium, followed by formaldehyde treatment, ultrafiltration and precipitation. The material may then be treated by a process comprising sterile filtration and/or dialysis.

Hepatitis A virus antigens: Hepatitis A virus (HAV) is one of the known agents which causes viral hepatitis. A preferred HAV component is based on inactivated virus, and inactivation can be achieved by formalin treatment.

Hepatitis B virus (HBV) is one of the known agents which causes viral hepatitis. The major component of the capsid is a protein known as HBV surface antigen or, more commonly, HBsAg, which is typically a 226-amino acid polypeptide with a molecular weight of ~24 kDa. All existing hepatitis B vaccines contain HBsAg, and when this antigen is administered to a normal vaccinee it stimulates the production of anti-HBsAg antibodies which protect against HBV infection.

For vaccine manufacture, HBsAg has been made in two ways: purification of the antigen in particulate form from the plasma of chronic hepatitis B carriers or expression of the protein by recombinant DNA methods (e.g., recombinant expression in yeast cells). Unlike native HBsAg (i.e., as in the plasma-purified product), yeast-expressed HBsAg is generally non-glycosylated, and this is the most preferred form of HBsAg for use with the invention.

Conjugated *Haemophilus influenzae* type b antigens: *Haemophilus influenzae* type b (Hib) causes bacterial meningitis. Hib vaccines are typically based on the capsular saccharide antigen, the preparation of which is well documented. The Hib saccharide can be conjugated to a carrier protein in order to enhance its immunogenicity, especially in children. Typical carrier proteins are tetanus toxoid, diphtheria toxoid, $CRM_{197}$, *H. influenzae* protein D, and an outer membrane protein complex from serogroup B meningococcus. The saccharide moiety of the conjugate may comprise full-length polyribosylribitol phosphate (PRP) as prepared from Hib bacteria, and/or fragments of full-length PRP. Hib conjugates may or may not be adsorbed to an aluminum salt adjuvant.

In an embodiment the immunogenic compositions of the invention further include a conjugated *N. meningitidis* serogroup Y capsular saccharide (MenY), and/or a conjugated *N. meningitidis* serogroup C capsular saccharide (MenC).

In an embodiment the immunogenic compositions of the invention further include a conjugated *N. meningitidis* serogroup A capsular saccharide (MenA), a conjugated *N. meningitidis* serogroup W135 capsular saccharide (MenW135), a conjugated *N. meningitidis* serogroup Y capsular saccharide (MenY), and/or a conjugated *N. meningitidis* serogroup C capsular saccharide (MenC).

In an embodiment the immunogenic compositions of the invention further include a conjugated *N. meningitidis* serogroup W135 capsular saccharide (MenW135), a conjugated *N. meningitidis* serogroup Y capsular saccharide (MenY), and/or a conjugated *N. meningitidis* serogroup C capsular saccharide (MenC).

4 Adjuvant(s)

In some embodiments, the immunogenic compositions disclosed herein may further comprise at least one, two or three adjuvants. The term "adjuvant" refers to a compound or mixture that enhances the immune response to an antigen. Antigens may act primarily as a delivery system, primarily as an immune modulator or have strong features of both. Suitable adjuvants include those suitable for use in mammals, including humans.

Examples of known suitable delivery-system type adjuvants that can be used in humans include, but are not limited to, alum (e.g., aluminum phosphate, aluminum sulfate or aluminum hydroxide), calcium phosphate, liposomes, oil-in-water emulsions such as MF59 (4.3% w/v squalene, 0.5% w/v polysorbate 80 (Tween 80), 0.5% w/v sorbitan trioleate (Span 85)), water-in-oil emulsions such as Montanide, and poly(D,L-lactide-co-glycolide) (PLG) microparticles or nanoparticles.

In an embodiment, the immunogenic compositions disclosed herein comprise aluminum salts (alum) as adjuvant (e.g., aluminum phosphate, aluminum sulfate or aluminum hydroxide). In a preferred embodiment, the immunogenic compositions disclosed herein comprise aluminum phosphate or aluminum hydroxide as adjuvant. In an embodiment, the immunogenic compositions disclosed herein comprise from 0.1 mg/mL to 1 mg/mL or from 0.2 mg/mL to 0.3 mg/mL of elemental aluminum in the form of aluminum phosphate. In an embodiment, the immunogenic compositions disclosed herein comprise about 0.25 mg/mL of elemental aluminum in the form of aluminum phosphate.

Examples of known suitable immune modulatory type adjuvants that can be used in humans include, but are not limited to, saponin extracts from the bark of the Aquilla tree (QS21, Quil A), TLR4 agonists such as MPL (Monophosphoryl Lipid A), 3DMPL (3-O-deacylated MPL) or GLA-AQ, LT/CT mutants, cytokines such as the various interleukins (e.g., IL-2, IL-12) or GM-CSF, and the like.

Examples of known suitable immune modulatory type adjuvants with both delivery and immune modulatory features that can be used in humans include, but are not limited to, ISCOMS (see, e.g., Sjölander et al. (1998) J. Leukocyte Biol. 64:713; WO 90/03184, WO 96/11711, WO 00/48630, WO 98/36772, WO 00/41720, WO 2006/134423 and WO 2007/026190) or GLA-EM which is a combination of a TLR4 agonist and an oil-in-water emulsion.

For veterinary applications including but not limited to animal experimentation, one can use Complete Freund's Adjuvant (CFA), Freund's Incomplete Adjuvant (IFA), Emulsigen, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants to enhance effectiveness of the pneumococcal vaccines as disclosed herein include, but are not limited to: (1) oil-in-water emulsion formulations (with or without other specific immunostimulating agents such as muramyl peptides (see below) or bacterial cell wall components), such as for example (a) SAF, containing 10% Squalane, 0.4% Tween 80, 5% pluronic-blocked polymer L121, and thr-MDP either microfluidized into a submicron emulsion or vortexed to generate a larger particle size emulsion, and (b) RIBI™ adjuvant system (RAS), (Ribi Immunochem, Hamilton, MT) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21, STIMULON™ (Cambridge Bioscience, Worcester, MA), ABISCO® (Isconova, Sweden), or ISCOMATRIX® (Commonwealth Serum Laboratories, Australia), may be used or particles generated therefrom such as ISCOMs (immunostimulating complexes), which ISCOMS may be devoid of additional detergent (e.g., WO 00/07621); (3) Complete Freund's Adjuvant (CFA) and Incomplete Freund's Adjuvant (IFA); (4) cytokines, such as interleukins (e.g., IL-1, IL-2, IL-4, IL-5, IL-6, IL-7, IL-12 (e.g., WO 99/44636)), interferons (e.g., gamma interferon), macrophage colony stimulating factor (M-CSF), tumor necrosis factor (TNF), etc.; (5) monophosphoryl lipid A (MPL) or 3-O-deacylated MPL (3dMPL) (see, e.g., GB-2220211, EP0689454), optionally in the substantial absence of alum when used with pneumococcal saccharides (see, e.g., WO 00/56358); (6) combinations of 3dMPL with, for example, QS21 and/or oil-in-water emulsions (see, e.g., EP0835318, EP0735898, EP0761231); (7) a polyoxyethylene ether or a polyoxyethylene ester (see, e.g., WO 99/52549); (8) a polyoxyethylene sorbitan ester surfactant in combination with an octoxynol (e.g., WO 01/21207) or a polyoxyethylene alkyl ether or ester surfactant in combination with at least one additional non-ionic surfactant such as an octoxynol (e.g., WO 01/21152); (9) a saponin and an immunostimulatory oligonucleotide (e.g., a CpG oligonucleotide) (e.g., WO 00/62800); (10) an immunostimulant and a particle of metal salt (see, e.g., WO 00/23105); (11) a saponin and an oil-in-water emulsion (e.g., WO 99/11241); (12) a saponin (e.g., QS21)+3dMPL+IM2 (optionally+a sterol) (e.g., WO 98/57659); (13) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc.

In an embodiment of the present invention, the immunogenic compositions as disclosed herein comprise a CpG Oligonucleotide as adjuvant. A CpG oligonucleotide as used herein refers to an immunostimulatory CpG oligodeoxynucleotide (CpG ODN), and accordingly these terms are used interchangeably unless otherwise indicated. Immunostimulatory CpG oligodeoxynucleotides contain one or more immunostimulatory CpG motifs that are unmethylated cytosine-guanine dinucleotides, optionally within certain preferred base contexts. The methylation status of the CpG immunostimulatory motif generally refers to the cytosine residue in the dinucleotide. An immunostimulatory oligonucleotide containing at least one unmethylated CpG dinucleotide is an oligonucleotide which contains a 5' unmethylated cytosine linked by a phosphate bond to a 3' guanine, and which activates the immune system through binding to Toll-like receptor 9 (TLR-9). In another embodiment the immunostimulatory oligonucleotide may contain one or more methylated CpG dinucleotides, which will activate the immune system through TLR9 but not as strongly as if the CpG motif(s) was/were unmethylated. CpG immunostimulatory oligonucleotides may comprise one or more palindromes that in turn may encompass the CpG dinucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068. In an embodiment of the present invention, the immunogenic compositions as disclosed herein comprise any of the CpG Oligonucleotide described at page 3, line 22, to page 12, line 36, of WO 2010/125480.

Different classes of CpG immunostimulatory oligonucleotides have been identified. These are referred to as A, B, C and P class, and are described in greater detail at page 3, line 22, to page 12, line 36, of WO 2010/125480. Methods of the invention embrace the use of these different classes of CpG immunostimulatory oligonucleotides.

In an embodiment of the present invention, the immunogenic compositions as disclosed herein comprise an A class CpG oligonucleotide. Preferably, the "A class" CpG oligonucleotide of the invention has the following nucleic acid sequence: 5' GGGGACGACGTCGTGGGGGGG 3' (SEQ ID NO: 1). Some non-limiting examples of A-Class oligonucleotides include:

```
                                        (SEQ ID NO: 2)
5' G*G*G_G_A_C_G_A_C_G_T_C_G_T_G_G*G*G*G*G*G 3';
```

wherein "*" refers to a phosphorothioate bond and "_" refers to a phosphodiester bond.

In an embodiment of the present invention, the immunogenic compositions as disclosed herein comprise a B class CpG Oligonucleotide. In one embodiment, the CpG oligonucleotide for use in the present invention is a B class CpG oligonucleotide represented by at least the formula: 5' $X_1X_2CGX_3X_4$ 3', wherein X1, X2, X3, and X4 are nucleotides. In one embodiment, $X_2$ is adenine, guanine, or thymine. In another embodiment, $X_3$ is cytosine, adenine, or thymine.

The B class CpG oligonucleotide sequences of the invention are those broadly described above as well as disclosed in WO 96/02555, WO 98/18810 and U.S. Pat. Nos. 6,194,388; 6,207,646; 6,214,806; 6,218,371; 6,239,116 and 6,339,068. Exemplary sequences include but are not limited to those disclosed in these latter applications and patents.

In an embodiment, the "B class" CpG oligonucleotide of the invention has the following nucleic acid sequence:

```
                              (SEQ ID NO: 3)
5' TCGTCGTTTTTCGGTGCTTTT 3',
or

                              (SEQ ID NO: 4)
5' TCGTCGTTTTTCGGTCGTTTT 3',
or

                              (SEQ ID NO: 5)
5' TCGTCGTTTTGTCGTTTTGTCGTT 3',
or

                              (SEQ ID NO: 6)
5' TCGTCGTTTCGTCGTTTTGTCGTT 3',
or

                              (SEQ ID NO: 7)
5' TCGTCGTTTTGTCGTTTTTTTCGA 3'.
```

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

Some non-limiting examples of B-Class oligonucleotides include:

```
                                        (SEQ ID NO: 8)
5' T*C*G*T*C*G*T*T*T*T*T*C*G*G*T*G*C*T*T*T*T 3',
or

                                        (SEQ ID NO: 9)
5' T*C*G*T*C*G*T*T*T*T*T*C*G*G*T*C*G*T*T*T*T 3',
or

                                       (SEQ ID NO: 10)
5' T*C*G*T*C*G*T*T*T*T*G*T*C*G*T*T*T*T*G*T*C*G*T*
T 3',
or

                                       (SEQ ID NO: 11)
5' T*C*G*T*C*G*T*T*T*C*G*T*C*G*T*T*T*T*G*T*C*G*T*
T 3',
or
```

-continued (SEQ ID NO: 12)
5' T*C*G*T*C*G*T*T*T*T*G*T*C*G*T*T*T*T*T*T*T*C*G*A 3' wherein "*" refers to a phosphorothioate bond.

In an embodiment of the present invention, the immunogenic compositions as disclosed herein comprise a C class CpG Oligonucleotide. In an embodiment, the "C class" CpG oligonucleotides of the invention have the following nucleic acid sequence:

(SEQ ID NO: 13)
5' TCGCGTCGTTCGGCGCGCGCCG 3',
or (SEQ ID NO: 14)
5' TCGTCGACGTTCGGCGCGCGCCG 3',
or (SEQ ID NO: 15)
5' TCGGACGTTCGGCGCGCGCCG 3',
or (SEQ ID NO: 16)
5' TCGGACGTTCGGCGCGCCG 3',
or (SEQ ID NO: 17)
5' TCGCGTCGTTCGGCGCGCCG 3',
or (SEQ ID NO: 18)
5' TCGACGTTCGGCGCGCGCCG 3',
or (SEQ ID NO: 19)
5' TCGACGTTCGGCGCGCCG 3',
or (SEQ ID NO: 20)
5' TCGCGTCGTTCGGCGCCG 3',
or (SEQ ID NO: 21)
5' TCGCGACGTTCGGCGCGCGCCG 3',
or (SEQ ID NO: 22)
5' TCGTCGTTTTCGGCGCGCGCCG 3',
or (SEQ ID NO: 23)
5' TCGTCGTTTTCGGCGGCCGCCG 3',
or (SEQ ID NO: 24)
5' TCGTCGTTTTACGGCGCCGTGCCG 3',
or (SEQ ID NO: 25)
5' TCGTCGTTTTCGGCGCGCGCCGT 3'

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide.

Some non-limiting examples of C-Class oligonucleotides include:

(SEQ ID NO: 26)
5' T*C_G*C_G*T*C_G*T*T*C_G*G*C*G*C_G*C*G*C*C*G 3',
or

-continued (SEQ ID NO: 27)
5' T*C_G*T*C_G*A*C_G*T*T*C_G*G*C*G*C_G*C*G*C*C*G 3',
or (SEQ ID NO: 28)
5' T*C_G*G*A*C_G*T*T*C_G*G*C*G*C_G*C*G*C*C*G 3',
or (SEQ ID NO: 29)
5' T*C_G*G*A*C_G*T*T*C_G*G*C*G*C*G*C*C*G 3',
or (SEQ ID NO: 30)
5' T*C_G*C_G*T*C_G*T*T*C_G*G*C*G*C*G*C*C*G 3',
or (SEQ ID NO: 31)
5' T*C_G*A*C_G*T*T*C_G*G*C*G*C_G*C*G*C*C*G 3',
or (SEQ ID NO: 32)
5' T*C_G*A*C_G*T*T*C_G*G*C*G*C*G*C*C*G 3',
or (SEQ ID NO: 33)
5' T*C_G*C_G*T*C_G*T*T*C_G*G*C*G*C*C*G 3',
or (SEQ ID NO: 34)
5' T*C_G*C_G*A*C_G*T*T*C_G*G*C*G*C_G*C*G*C*C*G 3',
or (SEQ ID NO: 35)
5' T*C*G*T*C*G*T*T*T*T*C*G*G*C*G*C*G*C*G*C*C*G 3',
or (SEQ ID NO: 36)
5' T*C*G*T*C*G*T*T*T*T*C*G*G*C*G*G*C*C*G*C*C*G 3',
or (SEQ ID NO: 37)
5' T*C*G*T*C_G*T*T*T*T*A*C_G*G*C*G*C*C_G*T*G*C*C*G 3',
or (SEQ ID NO: 38)
5' T*C_G*T*C*G*T*T*T*T*C*G*G*C*G*C*G*C*G*C*C*G*T 3' wherein "*" refers to a phosphorothioate bond and "_" refers to a phosphodiester bond.

In any of these sequences, an ethyl-uridine or a halogen may substitute for the 5' T, examples of halogen substitutions include but are not limited to bromo-uridine or iodo-uridine substitutions.

In an embodiment of the present invention, the immunogenic compositions as disclosed herein comprise a P class CpG Oligonucleotide. In an embodiment, the CpG oligonucleotide for use in the present invention is a P class CpG oligonucleotide containing a 5' TLR activation domain and at least two palindromic regions, one palindromic region being a 5' palindromic region of at least 6 nucleotides in length and connected to a 3' palindromic region of at least 8 nucleotides in length either directly or through a spacer, wherein the oligonucleotide includes at least one YpR dinucleotide. In an embodiment, said oligonucleotide is not T*C_G*T*C_G*A*C_G*T*T*C_G*G*C*G*C_G*C*G*C*C*G (SEQ ID NO: 27). In one embodiment the P class CpG oligonucleotide includes at least one unmethylated CpG dinucleotide. In another embodiment the TLR activation domain is TCG, TTCG, TTTCG, TYpR, TTYpR, TTTYpR, UCG, UUCG, UUUCG, TTT, or TTTT. In yet another embodiment the TLR activation domain is within the 5' palindromic region. In another embodiment the TLR activation domain is immediately 5' to the 5' palindromic region.

In an embodiment, the "P class" CpG oligonucleotides of the invention have the following nucleic acid sequence: 5' TCGTCGACGATCGGCGCGCGCCG 3' (SEQ ID NO: 39).

In said sequences, all of the linkages may be all phosphorothioate bonds. In another embodiment, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

A non-limiting example of P-Class oligonucleotides include:

```
                                       (SEQ ID NO: 40)
5' T*C_G*T*C_G*A*C_G*A*T*C_G*G*C*G*C_G*C*G*C*C*G 3'
```

wherein "*" refers to a phosphorothioate bond and "_" refers to a phosphodiester bond.

In one embodiment the oligonucleotide includes at least one phosphorothioate linkage. In another embodiment all internucleotide linkages of the oligonucleotide are phosphorothioate linkages. In another embodiment the oligonucleotide includes at least one phosphodiester-like linkage. In another embodiment the phosphodiester-like linkage is a phosphodiester linkage. In another embodiment a lipophilic group is conjugated to the oligonucleotide. In one embodiment the lipophilic group is cholesterol.

In an embodiment, all the internucleotide linkages of the CpG oligonucleotides disclosed herein are phosphodiester bonds ("soft" oligonucleotides, as described in WO 2007/026190). In another embodiment, CpG oligonucleotides of the invention are rendered resistant to degradation (e.g., are stabilized). A "stabilized oligonucleotide" refers to an oligonucleotide that is relatively resistant to in vivo degradation (e.g., via an exo- or endo-nuclease). Nucleic acid stabilization can be accomplished via backbone modifications. Oligonucleotides having phosphorothioate linkages provide maximal activity and protect the oligonucleotide from degradation by intracellular exo- and endo-nucleases.

The immunostimulatory oligonucleotides may have a chimeric backbone, which have combinations of phosphodiester and phosphorothioate linkages. For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. When the phosphodiester linkage is preferentially located within the CpG motif such molecules are called "semi-soft" as described in WO 2007/026190.

Other modified oligonucleotides include combinations of phosphodiester, phosphorothioate, methylphosphonate, methylphosphorothioate, phosphorodithioate, and/or p-ethoxy linkages.

Mixed backbone modified ODN may be synthesized as described in WO 2007/026190.

The size of the CpG oligonucleotide (i.e., the number of nucleotide residues along the length of the oligonucleotide) also may contribute to the stimulatory activity of the oligonucleotide. For facilitating uptake into cells, CpG oligonucleotide of the invention preferably have a minimum length of 6 nucleotide residues. Oligonucleotides of any size greater than 6 nucleotides (even many kb long) are capable of inducing an immune response if sufficient immunostimulatory motifs are present, because larger oligonucleotides are degraded inside cells. In certain embodiments, the CpG oligonucleotides are 6 to 100 nucleotides long, preferentially 8 to 30 nucleotides long. In important embodiments, nucleic acids and oligonucleotides of the invention are not plasmids or expression vectors.

In an embodiment, the CpG oligonucleotide disclosed herein comprise substitutions or modifications, such as in the bases and/or sugars as described at paragraphs 134 to 147 of WO 2007/026190.

In an embodiment, the CpG oligonucleotide of the present invention is chemically modified. Examples of chemical modifications are known to the skilled person and are described, for example in Uhlmann et al. (1990) Chem. Rev. 90:543; S. Agrawal, Ed., Humana Press, Totowa, USA 1993; Crooke et al. (1996) Annu. Rev. Pharmacol. Toxicol. 36:107-129; and Hunziker et al. (1995) Mod. Synth. Methods 7:331-417. An oligonucleotide according to the invention may have one or more modifications, wherein each modification is located at a particular phosphodiester internucleoside bridge and/or at a particular R-D-ribose unit and/or at a particular natural nucleoside base position in comparison to an oligonucleotide of the same sequence which is composed of natural DNA or RNA.

In some embodiments of the invention, CpG-containing nucleic acids might be simply mixed with immunogenic carriers according to methods known to those skilled in the art (see, e.g., WO 03/024480).

In a particular embodiment of the present invention, any of the immunogenic compositions disclosed herein comprise from 2 μg to 100 mg of CpG oligonucleotide, preferably from 0.1 mg to 50 mg CpG oligonucleotide, preferably from 0.2 mg to 10 mg CpG oligonucleotide, preferably from 0.3 mg to 5 mg CpG oligonucleotide, preferably from 0.3 mg to 5 mg CpG oligonucleotide, even preferably from 0.5 to 2 mg CpG oligonucleotide, even preferably from 0.75 to 1.5 mg CpG oligonucleotide. In a preferred embodiment, any of the immunogenic composition disclosed herein comprises about 1 mg CpG oligonucleotide.

5 Formulation

The immunogenic compositions of the invention may be formulated in liquid form (i.e., solutions or suspensions) or in a lyophilized form. Liquid formulations may advantageously be administered directly from their packaged form and are thus ideal for injection without the need for reconstitution in aqueous medium as otherwise required for lyophilized compositions of the invention.

Formulation of the immunogenic composition of the present invention can be accomplished using art-recognized methods. For instance, the individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

The present disclosure provides an immunogenic composition comprising any of combination of glycoconjugates disclosed herein and a pharmaceutically acceptable excipient, carrier, or diluent.

In an embodiment, the immunogenic composition of the invention is in liquid form, preferably in aqueous liquid form.

Immunogenic compositions of the disclosure may comprise one or more of a buffer, a salt, a divalent cation, a non-ionic detergent, a cryoprotectant such as a sugar, and an anti-oxidant such as a free radical scavenger or chelating agent, or any multiple combinations thereof.

In an embodiment, the immunogenic compositions of the invention comprise a buffer. In an embodiment, said buffer has a pKa of about 3.5 to about 7.5. In some embodiments, the buffer is phosphate, succinate, histidine or citrate. In certain embodiments, the buffer is succinate at a final concentration of 1 mM to 10 mM. In one particular embodiment, the final concentration of the succinate buffer is about 5 mM.

In an embodiment, the immunogenic compositions of the invention comprise a salt. In some embodiments, the salt is selected from the groups consisting of magnesium chloride, potassium chloride, sodium chloride and a combination thereof. In one particular embodiment, the salt is sodium chloride. In one particular embodiment, the immunogenic compositions of the invention comprise sodium chloride at 150 mM.

In an embodiment, the immunogenic compositions of the invention comprise a surfactant. In an embodiment, the surfactant is selected from the group consisting of polysorbate 20 (TWEEN™20), polysorbate 40 (TWEEN™40), polysorbate 60 (TWEEN™60), polysorbate 65 (TWEEN™65), polysorbate 80 (TWEEN™80), polysorbate 85 (TWEEN™85), TRITON™ N-101, TRITON™ X-100, oxtoxynol 40, nonoxynol-9, triethanolamine, triethanolamine polypeptide oleate, polyoxyethylene-660 hydroxystearate (PEG-15, Solutol H 15), polyoxyethylene-35-ricinoleate (CREMOPHOR® EL), soy lecithin and a poloxamer. In one particular embodiment, the surfactant is polysorbate 80. In some said embodiment, the final concentration of polysorbate 80 in the formulation is at least 0.0001% to 10% polysorbate 80 weight to weight (w/w). In some said embodiments, the final concentration of polysorbate 80 in the formulation is at least 0.001% to 1% polysorbate 80 weight to weight (w/w). In some said embodiments, the final concentration of polysorbate 80 in the formulation is at least 0.01% to 1% polysorbate 80 weight to weight (w/w). In other embodiments, the final concentration of polysorbate 80 in the formulation is 0.01%, 0.02%, 0.03%, 0.04%, 0.05%, 0.06%, 0.07%, 0.08%, 0.09% or 0.1% polysorbate 80 (w/w). In another embodiment, the final concentration of the polysorbate 80 in the formulation is 1% polysorbate 80 (w/w).

In certain embodiments, the immunogenic composition of the invention has a pH of 5.5 to 7.5, more preferably a pH of 5.6 to 7.0, even more preferably a pH of 5.8 to 6.0.

In one embodiment, the present invention provides a container filled with any of the immunogenic compositions disclosed herein. In one embodiment, the container is selected from the group consisting of a vial, a syringe, a flask, a fermentor, a bioreactor, a bag, a jar, an ampoule, a cartridge and a disposable pen. In certain embodiments, the container is siliconized.

In an embodiment, the container of the present invention is made of glass, metals (e.g., steel, stainless steel, aluminum, etc.) and/or polymers (e.g., thermoplastics, elastomers, thermoplastic-elastomers). In an embodiment, the container of the present invention is made of glass.

In one embodiment, the present invention provides a syringe filled with any of the immunogenic compositions disclosed herein. In certain embodiments, the syringe is siliconized and/or is made of glass.

A typical dose of the immunogenic composition of the invention for injection has a volume of 0.1 mL to 2 mL, more preferably 0.2 mL to 1 mL, even more preferably a volume of about 0.5 mL.

Therefore the container or syringe as defined above is filed with a volume of 0.1 mL to 2 mL, more preferably 0.2 mL to 1 mL, even more preferably a volume of about 0.5 mL of any of the immunogenic compositions defined herein.

6 Uses of the Immunogenic Compositions of the Invention

In an embodiment, the immunogenic compositions disclosed herein are for use as a medicament.

The immunogenic compositions described herein may be used in various therapeutic or prophylactic methods for preventing, treating or ameliorating a bacterial infection, disease or condition in a subject. In particular, immunogenic compositions described herein may be used to prevent, treat or ameliorate a *S. pneumoniae* infection, disease or condition in a subject.

Thus in one aspect, the invention provides a method of preventing, treating or ameliorating an infection, disease or condition associated with *S. pneumoniae* in a subject, comprising administering to the subject an immunologically effective amount of an immunogenic composition of the invention.

In some such embodiments, the infection, disease or condition is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess.

In an embodiment, the invention provides a method of inducing an immune response to *S. pneumoniae* in a subject comprising administering to the subject an immunologically effective amount of an immunogenic composition of the invention In an embodiment, the immunogenic compositions disclosed herein are for use as a vaccine. In such embodiments the immunogenic compositions described herein may be used to prevent a *S. pneumoniae* infection in a subject. Thus in one aspect, the invention provides a method of preventing an infection by *S. pneumoniae* in a subject comprising administering to the subject an immunologically effective amount of an immunogenic composition of the invention. In some such embodiments, the infection is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess. In one aspect, the subject to be vaccinated is a mammal, such as a human, cat, sheep, pig, horse, bovine or dog.

In one aspect, the immunogenic compositions disclosed herein are for use in a method of preventing, treating or ameliorating an infection, disease or condition associated with *S. pneumoniae* in a subject. In some such embodiments, the infection, disease or condition is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess.

In an embodiment, the immunogenic compositions disclosed herein are for use as a vaccine. In such embodiments the immunogenic compositions described herein may be used to prevent a *S. pneumoniae* infection in a subject. Thus in one aspect, the immunogenic compositions disclosed herein are for use in a method of preventing, an infection by *S. pneumoniae* in a subject. In some such embodiments, the infection is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess. In one aspect, the subject to be vaccinated is a mammal, such as a human, cat, sheep, pig, horse, bovine or dog.

The immunogenic compositions of the present invention can be used to protect or treat a human susceptible to pneumococcal infection, by means of administering the immunogenic compositions via a systemic or mucosal route. In an embodiment, the immunogenic compositions disclosed herein are administered by intramuscular, intraperitoneal, intradermal or subcutaneous routes. In an embodiment, the immunogenic compositions disclosed herein are administered by intramuscular, intraperitoneal, intradermal or subcutaneous injection. In an embodiment, the immunogenic compositions disclosed herein are administered by intramuscular or subcutaneous injection.

In an embodiment, the immunogenic composition of the present disclosure comprising at least one glycoconjugate from *S. pneumoniae* serotype 15B (such as the glycoconjugates of section 1.3.4 above), when administered to a subject, are able to induce the formation of antibodies capable of binding to *S. pneumonia* serotype 15B, 15A and/or 15C as measured by a standard ELISA assay. In an embodiment, the immunogenic composition of the present disclosure comprising at least one glycoconjugate from *S. pneumoniae* serotype 15B (such as the glycoconjugates of section 1.3.4 above), when administered to a subject, are able to induce the formation of antibodies capable of binding to *S. pneumonia* serotype 15B, and 15C as measured by a standard ELISA assay.

In the ELISA (Enzyme-linked Immunosorbent Assay) method, antibodies from the sera of vaccinated subjects are incubated with polysaccharides which have been adsorbed to a solid support. The bound antibodies are detected using enzyme-conjugated secondary detection antibodies.

In an embodiment said standard ELISA assay is the standardized (WHO) ELISA assay as defined by the WHO in the 'Training manual for Enzyme linked immunosorbent assay for the quantitation of *Streptococcus pneumoniae* serotype specific IgG (Pn PS ELISA).' (accessible at http://www.vaccine.uab.edu/ELISA%20protocol.pdf; accessed on Mar. 31, 2014).

The ELISA measures type specific IgG anti-*S. pneumoniae* capsular polysaccharide (PS) antibodies present in human serum. When dilutions of human sera are added to type-specific capsular PS-coated microtiter plates, antibodies specific for that capsular PS bind to the microtiter plates. The antibodies bound to the plates are detected using a goat anti-human IgG alkaline phosphatase-labeled antibody followed by a p-nitrophenyl phosphate substrate. The optical density of the colored end product is proportional to the amount of anticapsular PS antibody present in the serum.

In an embodiment, the immunogenic composition of the present disclosure comprising at least one glycoconjugate from *S. pneumoniae* serotype 15B (such as the glycoconjugates of section 1.3.4 above) is able to elicit IgG antibodies in human which are capable of binding *S. pneumoniae* serotype 15B polysaccharide at a concentration of at least 0.05, 0.1, 0.2, 0.3, 0.35, 0.4 or 0.5 μg/ml as determined by ELISA assay.

In an embodiment, the immunogenic composition of the present disclosure comprising at least one glycoconjugate from *S. pneumoniae* serotype 15B (such as the glycoconjugates of section 1.3.4 above) is able to elicit IgG antibodies in human which are capable of binding *S. pneumoniae* serotype 15C polysaccharide at a concentration of at least 0.05, 0.1, 0.2, 0.3, 0.35, 0.4 or 0.5 μg/ml as determined by ELISA assay.

In an embodiment, the immunogenic composition of the present disclosure comprising at least one glycoconjugate from *S. pneumoniae* serotype 15B (such as the glycoconjugates of section 1.3.4 above) is able to elicit IgG antibodies in human which are capable of binding *S. pneumoniae* serotypes 15B and 15C polysaccharide at a concentration of at least 0.05, 0.1, 0.2, 0.3, 0.35, 0.4 or 0.5 μg/ml as determined by ELISA assay.

In an embodiment, the immunogenic composition of the present disclosure comprising at least one glycoconjugate from *S. pneumoniae* serotype 15B (such as the glycoconjugates of section 1.3.4 above), when administered to a subject, are able to induce the formation of antibodies capable of killing *S. pneumonia* serotype 15B in an opsonophagocytosis assay as disclosed herein (such as the OPA assay of Example 12).

In an embodiment, the immunogenic composition of the present disclosure comprising at least one glycoconjugate from *S. pneumoniae* serotype 15B (such as the glycoconjugates of section 1.3.4 above), when tested in an OPA assay as disclosed herein (such as the OPA assay of Example 12), has an OPA titer greater than the OPA titer obtained with an unconjugated native *S. pneumonia* serotype 15B capsular polysaccharide.

In an embodiment, the immunogenic composition of the present disclosure comprising at least one glycoconjugate from *S. pneumoniae* serotype 15B (such as the glycoconjugates of section 1.3.4 above), when administered to a subject, are able to induce the formation of antibodies capable of killing *S. pneumonia* serotype 15C in an opsonophagocytosis assay as disclosed herein (such as the OPA assay of Example 12). In an embodiment, the immunogenic composition of the present disclosure comprising at least one glycoconjugate from *S. pneumoniae* serotype 15B (such as the glycoconjugates of section 1.3.4 above), when tested in an OPA assay as disclosed herein (such as the OPA assay of Example 12), has an OPA titer greater than the OPA titer obtained with an unconjugated native *S. pneumonia* serotype 15B capsular polysaccharide.

The pneumococcal opsonophagocytic assay (OPA), which measures killing of *S. pneumoniae* cells by phagocytic effector cells in the presence of functional antibody and complement, is considered to be an important surrogate for evaluating the effectiveness of pneumococcal vaccines.

Opsonophagocytic assay (OPA) can be conducted by incubating together a mixture of *Streptococcus pneumoniae* cells, a heat inactivated human serum to be tested, differentiated HL-60 cells (phagocytes) and an exogenous complement source (e.g. baby rabbit complement). Opsonophagocytosis proceeds during incubation and bacterial cells that are coated with antibody and complement are killed upon opsonophagocytosis. Colony forming units (cfu) of surviving bacteria that escape from opsonophagocytosis are determined by plating the assay mixture. The OPA titer is defined as the reciprocal dilution that results in a 50% reduction in bacterial count over control wells without test serum. The OPA titer is interpolated from the two dilutions that encompass this 50% killing cut-off.

An endpoint titer of 1:8 or greater is considered a positive result in these killing type OPA. In an embodiment, the immunogenic composition of the present disclosure comprising at least one glycoconjugate from *S. pneumoniae* serotype 15B (such as the glycoconjugates of section 1.3.4 above), is able to elicit a titer of at least 1:8 against *S. pneumoniae* serotype 15B in at least 50% of the subjects as determined by opsonophagocytic killing assay (OPA). In an embodiment, the immunogenic composition of the present disclosure comprising at least one glycoconjugate from *S. pneumoniae* serotype 15B (such as the glycoconjugates of section 1.3.4 above) is able to elicit a titer of at least 1:8 against *S. pneumoniae* serotype 15B in at least 60%, 70%, 80%, 90%, or at least 93% of the subjects as determined by opsonophagocytic killing assay (OPA).

In an embodiment, the immunogenic composition of the present disclosure comprising at least one glycoconjugate from *S. pneumoniae* serotype 15B (such as the glycoconjugates of section 1.3.4 above) is able to elicit a titer of at least 1:8 against *S. pneumoniae* serotype 15C in at least 50% of the subjects as determined by opsonophagocytic killing assay (OPA). In an embodiment, the immunogenic composition of the present disclosure comprising at least one glycoconjugate from *S. pneumoniae* serotype 15B (such as the glycoconjugates of section 1.3.4 above) is able to elicit a titer of at least 1:8 against *S. pneumoniae* serotype 15C in at least 60%, 70%, 80%, 90%, or at least 95% of the subjects as determined by opsonophagocytic killing assay (OPA).

In a further aspect, the present disclosure provides a method of treating or preventing a *S. pneumoniae* infection, disease or condition associated with *S. pneumoniae* serotype 15A, 15B and/or 15C in a subject, the method comprising the step of administering a therapeutically or prophylactically effective amount of any of the immunogenic compositions of the present disclosure comprising at least one glycoconjugate from *S. pneumoniae* serotype 15B (such as the glycoconjugates of section 1.3.4 above). In an embodiment, the immunogenic composition of the present disclosure comprising at least one glycoconjugate from *S. pneumoniae* serotype 15B (such as the glycoconjugates of section 1.3.4 above), when administered to a subject, induces the formation of antibodies capable of binding to *S. pneumoniae* serotype 15B, 15A and/or 15C. In an embodiment, the immunogenic composition of the present disclosure comprising at least one glycoconjugate from *S. pneumoniae* serotype 15B (such as the glycoconjugates of section 1.3.4 above), when administered to a subject, induces the formation of antibodies capable of killing *S. pneumoniae* serotype 15B, 15C and/or 15A in an opsonophagocytosis assay as disclosed herein (such as the OPA assay of Example 12). One embodiment of the disclosure provides a method of protecting a subject against an infection with *S. pneumoniae* serotype 15C, or a method of preventing infection with *S. pneumoniae* serotype 15C, or a method of reducing the severity of or delaying the onset of at least one symptom associated with an infection caused by *S. pneumoniae* serotype 15C, the methods comprising administering to a subject an immunogenic amount of any of the immunogenic composition of the present disclosure comprising at least one glycoconjugate from *S. pneumoniae* serotype 15B (such as the glycoconjugates of section 1.3.4 above). One embodiment of the disclosure provides a method of treating or preventing a *S. pneumoniae* infection, disease or condition associated with *S. pneumoniae* serotype 15A, 15B and/or 15C (preferably 15B and/or 15C, more preferably 15B) in a subject, the method comprising the step of administering a therapeutically or prophylactically effective amount of any of the immunogenic composition of the present disclosure comprising at least one glycoconjugate from *S. pneumoniae* serotype 15B (such as the glycoconjugates of section 1.3.4 above) to the subject. Another embodiment provides a method of treating or preventing a *S. pneumoniae* infection, disease or condition associated with a *S. pneumoniae* serotype 15A, 15B and/or 15C (preferably 15B and/or 15C, more preferably 15B) in a subject, the method comprising generating a polyclonal or monoclonal antibody preparation from any of the immunogenic composition of the present disclosure comprising at least one glycoconjugate from *S. pneumoniae* serotype 15B (such as the glycoconjugates of section 1.3.4 above), and using said antibody preparation to confer passive immunity to the subject.

In one embodiment, the disclosure relates to the use of any of the immunogenic composition of the present disclosure comprising at least one glycoconjugate from *S. pneumoniae* serotype 15B (such as the glycoconjugates of section 1.3.4 above) for the manufacture of a medicament for protecting a subject against an infection with *S. pneumoniae*, and/or preventing infection with *S. pneumoniae*, and/or reducing the severity of or delaying the onset of at least one symptom associated with an infection caused by *S. pneumoniae*, and/or protecting a subject against an infection with *S. pneumoniae* serotype 15A, 15B and/or 15C (preferably 15B and/or 15C, more preferably 15B) and/or preventing infection with *S. pneumoniae* serotype 15A, 15B and/or 15C (preferably 15B and/or 15C, more preferably 15B), and/or reducing the severity of or delaying the onset of at least one symptom associated with an infection caused by *S. pneumoniae* serotype 15A, 15B and/or 15C (preferably 15B and/or 15C, more preferably 15B).

In one embodiment, the disclosure relates to the use of any of the immunogenic composition of the present disclosure comprising at least one glycoconjugate from *S. pneumoniae* serotype 15B (such as the glycoconjugates of section 1.3.4 above) for protecting a subject against an infection with *S. pneumoniae*, and/or preventing infection with *S. pneumoniae*, and/or reducing the severity of or delaying the onset of at least one symptom associated with an infection caused by *S. pneumoniae*, and/or protecting a subject against an infection with *S. pneumoniae* serotype 15A, 15B and/or 15C (preferably 15B and/or 15C, more preferably 15B) and/or preventing infection with *S. pneumoniae* serotype 15A, 15B and/or 15C (preferably 15B and/or 15C, more preferably 15B), and/or reducing the severity of or delaying the onset of at least one symptom associated with an infection caused by *S. pneumoniae* serotype 15A, 15B and/or 15C (preferably 15B and/or 15C, more preferably 15B).

7 Subject to be Treated with the Immunogenic Compositions of the Invention

As disclosed herein, the immunogenic compositions described herein may be used in various therapeutic or prophylactic methods for preventing, treating or ameliorating a bacterial infection, disease or condition in a subject.

In a preferred embodiment, said subject is a human. In a most preferred embodiment, said subject is a newborn (i.e., under three months of age), an infant (i.e., from 3 months to one year of age) or a toddler (i.e., from one year to four years of age).

In an embodiment, the immunogenic compositions disclosed herein are for use as a vaccine.

In such embodiment, the subject to be vaccinated may be less than 1 year of age. For example, the subject to be vaccinated can be about 1, about 2, about 3, about 4, about 5, about 6, about 7, about 8, about 9, about 10, about 11 or about 12 months of age. In an embodiment, the subject to be vaccinated is about 2, about 4 or about 6 months of age. In another embodiment, the subject to be vaccinated is less than 2 years of age. For example the subject to be vaccinated can be about 12 to about 15 months of age. In some cases, as little as one dose of the immunogenic composition according to the invention is needed, but under some circumstances, a second, third or fourth dose may be given (see section 8 below).

In an embodiment of the present invention, the subject to be vaccinated is a human adult 50 years of age or older, more preferably a human adult 55 years of age or older. In an embodiment, the subject to be vaccinated is a human adult 65 years of age or older, 70 years of age or older, 75 years of age or older or 80 years of age or older.

In an embodiment the subject to be vaccinated is an immunocompromised individual, in particular a human. An immunocompromised individual is generally defined as a person who exhibits an attenuated or reduced ability to mount a normal humoral or cellular defense to challenge by infectious agents.

In an embodiment of the present invention, the immunocompromised subject to be vaccinated suffers from a disease or condition that impairs the immune system and results in an antibody response that is insufficient to protect against or treat pneumococcal disease.

In an embodiment, said disease is a primary immunodeficiency disorder. Preferably, said primary immunodeficiency disorder is selected from the group consisting of: combined T- and B-cell immunodeficiencies, antibody deficiencies, well-defined syndromes, immune dysregulation diseases, phagocyte disorders, innate immunity deficiencies, autoinflammatory disorders, and complement deficiencies. In an embodiment, said primary immunodeficiency disorder is selected from the one disclosed on page 24, line 11, to page 25, line 19, of WO 2010/125480.

In a particular embodiment of the present invention, the immunocompromised subject to be vaccinated suffers from a disease selected from the groups consisting of: HIV-infection, acquired immunodeficiency syndrome (AIDS), cancer, chronic heart or lung disorders, congestive heart failure, diabetes mellitus, chronic liver disease, alcoholism, cirrhosis, spinal fluid leaks, cardiomyopathy, chronic bronchitis, emphysema, chronic obstructive pulmonary disease (COPD), spleen dysfunction (such as sickle cell disease), lack of spleen function (asplenia), blood malignancy, leukemia, multiple myeloma, Hodgkin's disease, lymphoma, kidney failure, nephrotic syndrome and asthma.

In an embodiment of the present invention, the immunocompromised subject to be vaccinated suffers from malnutrition.

In a particular embodiment of the present invention, the immunocompromised subject to be vaccinated is taking a drug or treatment that lowers the body's resistance to infection. In an embodiment, said drug is selected from the one disclosed on page 26, line 33, to page 26, line 4, of WO 2010/125480.

In a particular embodiment of the present invention, the immunocompromised subject to be vaccinated is a smoker.

In a particular embodiment of the present invention, the immunocompromised subject to be vaccinated has a white blood cell count (leukocyte count) below $5\times10^9$ cells per liter, or below $4\times10^9$ cells per liter, or below $3\times10^9$ cells per liter, or below $2\times10^9$ cells per liter, or below $1\times10^9$ cells per liter, or below $0.5\times10^9$ cells per liter, or below $0.3\times10^9$ cells per liter, or below $0.1\times10^9$ cells per liter.

White blood cell count (leukocyte count): The number of white blood cells (WBC) in the blood. The WBC is usually measured as part of the CBC (complete blood count). White blood cells are the infection-fighting cells in the blood and are distinct from the red (oxygen-carrying) blood cells known as erythrocytes. There are different types of white blood cells, including neutrophils (polymorphonuclear leukocytes; PMN), band cells (slightly immature neutrophils), T-type lymphocytes (T-cells), B-type lymphocytes (B-cells), monocytes, eosinophils, and basophils. All the types of white blood cells are reflected in the white blood cell count. The normal range for the white blood cell count is usually between 4,300 and 10,800 cells per cubic millimeter of blood. This can also be referred to as the leukocyte count and can be expressed in international units as $4.3\text{-}10.8\times10^9$ cells per liter.

In a particular embodiment of the present invention, the immunocompromised subject to be vaccinated suffers from neutropenia. In a particular embodiment of the present invention, the immunocompromised subject to be vaccinated has a neutrophil count below $2\times10^9$ cells per liter, or below $1\times10^9$ cells per liter, or below $0.5\times10^9$ cells per liter, or below $0.1\times10^9$ cells per liter, or below $0.05\times10^9$ cells per liter.

A low white blood cell count or "neutropenia" is a condition characterized by abnormally low levels of neutrophils in the circulating blood. Neutrophils are a specific kind of white blood cell that help to prevent and fight infections. The most common reason that cancer patients experience neutropenia is as a side effect of chemotherapy. Chemotherapy-induced neutropenia increases a patient's risk of infection and disrupts cancer treatment. In a particular embodiment of the present invention, the immunocompromised subject to be vaccinated has a CD4+ cell count below $500/mm^3$, or CD4+ cell count below $300/mm^3$, or CD4+ cell count below $200/mm^3$, CD4+ cell count below $100/mm^3$, CD4+ cell count below $75/mm^3$, or CD4+ cell count below $50/mm^3$.

CD4 cell tests are normally reported as the number of cells in $mm^3$. Normal CD4 counts are between 500 and 1,600, and CD8 counts are between 375 and 1,100. CD4 counts drop dramatically in people with HIV.

In an embodiment of the invention, any of the immunocompromised subjects disclosed herein is a human male or a human female.

8 Regimen

In some cases, as little as one dose of the immunogenic composition according to the invention is needed, but under some circumstances, such as conditions of greater immune deficiency, a second, third or fourth dose may be given. Following an initial vaccination, subjects can receive one or several booster immunizations adequately spaced.

In an embodiment, the schedule of vaccination of the immunogenic composition according to the invention is a single dose. In a particular embodiment, said single dose schedule is for healthy persons being at least 2 years of age.

In an embodiment, the schedule of vaccination of the immunogenic composition according to the invention is a multiple dose schedule. In a particular embodiment, said multiple dose schedule consists of a series of 2 doses separated by an interval of about 1 month to about 2 months. In a particular embodiment, said multiple dose schedule consists of a series of 2 doses separated by an interval of about 1 month, or a series of 2 doses separated by an interval of about 2 months.

In another embodiment, said multiple dose schedule consists of a series of 3 doses separated by an interval of about 1 month to about 2 months. In another embodiment, said multiple dose schedule consists of a series of 3 doses separated by an interval of about 1 month, or a series of 3 doses separated by an interval of about 2 months.

In another embodiment, said multiple dose schedule consists of a series of 3 doses separated by an interval of about 1 month to about 2 months followed by a fourth dose about 10 months to about 13 months after the first dose. In another embodiment, said multiple dose schedule consists of a series of 3 doses separated by an interval of about 1 month followed by a fourth dose about 10 months to about 13 months after the first dose, or a series of 3 doses separated by an interval of about 2 months followed by a fourth dose about 10 months to about 13 months after the first dose.

In an embodiment, the multiple dose schedule consists of at least one dose (e.g., 1, 2 or 3 doses) in the first year of age followed by at least one toddler dose.

In an embodiment, the multiple dose schedule consists of a series of 2 or 3 doses separated by an interval of about 1 month to about 2 months (for example 28-56 days between doses), starting at 2 months of age, and followed by a toddler dose at 12-18 months of age. In an embodiment, said multiple dose schedule consists of a series of 3 doses separated by an interval of about 1 month to about 2 months (for example 28-56 days between doses), starting at 2 months of age, and followed by a toddler dose at 12-15 months of age. In another embodiment, said multiple dose schedule consists of a series of 2 doses separated by an interval of about 2 months, starting at 2 months of age, and followed by a toddler dose at 12-18 months of age.

In an embodiment, the multiple dose schedule consists of a 4-dose series of vaccine at 2, 4, 6, and 12-15 months of age.

In an embodiment, a prime dose is given at day 0 and one or more boosts are given at intervals that range from about 2 to about 24 weeks, preferably with a dosing interval of 4-8 weeks.

In an embodiment, a prime dose is given at day 0 and a boost is given about 3 months later.

As used herein, the term “about” means within a statistically meaningful range of a value, such as a stated concentration range, time frame, molecular weight, temperature or pH. Such a range can be within an order of magnitude, typically within 20%, more typically within 10%, and even more typically within 5% or within 1% of a given value or range. Sometimes, such a range can be within the experimental error typical of standard methods used for the measurement and/or determination of a given value or range. The allowable variation encompassed by the term “about” will depend upon the particular system under study, and can be readily appreciated by one of ordinary skill in the art. Whenever a range is recited within this application, every whole number integer within the range is also contemplated as an embodiment of the disclosure.

The terms “comprising”, “comprise” and “comprises” herein are intended by the inventors to be optionally substitutable with the terms “consisting essentially of”, “consist essentially of”, “consists essentially of”, “consisting of”, “consist of” and “consists of”, respectively, in every instance.

All references or patent applications cited within this patent specification are incorporated by reference herein.

The invention is illustrated in the accompanying examples. The examples below are carried out using standard techniques, which are well known and routine to those of skill in the art, except where otherwise described in detail. The examples are illustrative, but do not limit the invention.

EXAMPLE

Example 1. General Process for Preparation of eTEC Linked Glycoconjugates

Activation of Saccharide and Thiolation with Cystamine Dihydrochloride

The saccharide is reconstituted in anhydrous dimethylsulfoxide (DMSO). Moisture content of the solution is determined by Karl Fischer (KF) analysis and adjusted to reach a moisture content of between 0.1% and 0.4%, typically 0.2%.

To initiate the activation, a solution of 1,1'-carbonyl-di-1,2,4-triazole (CDT) or 1,1'-carbonyldiimidazole (CDI) is freshly prepared at a concentration of 100 mg/mL in DMSO. The saccharide is activated with various amounts of CDT/CDI (1-10 molar equivalents) and the reaction is allowed to proceed for 1 hour at 23±2° C. The activation level may be determined by HPLC. Cystamine dihydrochloride is freshly prepared in anhydrous DMSO at a concentration of 50 mg/mL. The activated saccharide is reacted with 1 molar equivalents (mol. eq.) of cystamine dihydrochloride. Alternatively, the activated saccharide is reacted with 1 mol. eq. of cysteamine hydrochloride. The thiolation reaction is allowed to proceed for 21±2 hours at 23±2° C., to produce a thiolated saccharide. The thiolation level is determined by the added amount of CDT/CDI.

Residual CDT/CDI in the activation reaction solution is quenched by the addition of 100 mM sodium tetraborate, pH 9.0 solution. Calculations are performed to determine the added amount of tetraborate and to adjust the final moisture content to be up to 1-2% of total aqueous.

Reduction and Purification of Activated Thiolated Saccharide

The thiolated saccharide reaction mixture is diluted 10-fold by addition to pre-chilled 5 mM sodium succinate in 0.9% saline, pH 6.0 and filtered through a 5 μm filter. Dialfiltration of thiolated saccharide is performed against 40-fold diavolume of WFI. To the retentate a solution of tris(2-carboxyethyl)phosphine (TCEP), 1-5 mol. eq., is added after dilution by 10% volume of 0.1 M sodium phosphate buffer, pH 6.0. This reduction reaction is allowed to proceed for 20±2 hours at 5±3° C. Purification of the activated thiolated saccharide is performed preferably by ultrafiltration/dialfiltration of against pre-chilled 10 mM sodium phosphate monobasic, pH 4.3. Alternatively, the thiolated saccharide is purified by standard size exclusion chromatographic (SEC) procedures or ion exchange chromatographic methods. An aliquot of activated thiolated saccharide retentate is pulled to determine the saccharide concentration and thiol content (Ellman) assays.

Alternative Reduction and Purification of Activated Thiolated Saccharide

As an alternative to the purification procedure described above, activated thiolated saccharide was also purified as below.

To the thiolated saccharide reaction mixture a solution of tris(2-carboxyethyl)phosphine (TCEP), 5-10 mol. eq., was added and allowed to proceed for 3±1 hours at 23±2° C. The reaction mixture was then diluted 5-fold by addition to pre-chilled 5 mM sodium succinate in 0.9% saline, pH 6.0 and filtered through a 5 μm filter. Dialfiltration of thiolated saccharide was performed using 40-fold diavolume of pre-chilled 10 mM sodium phosphate monobasic, pH 4.3. An aliquot of activated thiolated saccharide retentate was pulled to determine the saccharide concentration and thiol content (Ellman) assays.

Activation and Purification of Bromoacetylated Carrier Protein

Free amino groups of the carrier protein are bromoacteylated by reaction with a bromoacetylating agent, such as bromoacetic acid N-hydroxysuccinimide ester (BAANS), bromoacetylbromide, or another suitable reagent.

The carrier protein (in 0.1 M Sodium Phosphate, pH 8.0±0.2) is first kept at 8±3° C., at about pH 7 prior to activation. To the protein solution, the N-hydroxysuccinimide ester of bromoacetic acid (BAANS) as a stock dimethylsulfoxide (DMSO) solution (20 mg/mL) is added in a ratio of 0.25-0.5 BAANS: protein (w/w). The reaction is gently mixed at 5±3° C. for 30-60 minutes. The resulting bromoacetylated (activated) protein is purified, e.g., by ultrafiltration/diafiltration using 10 kDa MWCO membrane using 10 mM phosphate (pH 7.0) buffer. Following purification, the protein concentration of the bromoacetylated carrier protein is estimated by Lowry protein assay.

The extent of activation is determined by total bromide assay by ion-exchange liquid chromatography coupled with suppressed conductivity detection (ion chromatography). The bound bromide on the activated bromoacetylated protein is cleaved from the protein in the assay sample preparation and quantitated along with any free bromide that may be present. Any remaining covalently bound bromine on the protein is released by conversion to ionic bromide by heating the sample in alkaline 2-mercaptoethanol.

Activation and Purification of Bromoacetylated $CRM_{197}$ $CRM_{197}$ was diluted to 5 mg/mL with 10 mM phosphate buffered 0.9% NaCl pH 7 (PBS) and then made 0.1 M $NaHCO_3$, pH 7.0, using 1 M stock solution. BAANS was added at a $CRM_{197}$:BAANS ratio 1:0.35 (w:w) using a BAANS stock solution of 20 mg/mL DMSO. The reaction mixture was incubated at between 3° C. and 11° C. for 30 mins-1 hour then purified by ultrafiltration/diafiltration using a 10K MWCO membrane and 10 mM Sodium Phosphate/0.9% NaCl, pH 7.0. The purified activated $CRM_{197}$ was assayed by the Lowry assay to determine the protein concentration and then diluted with PBS to 5 mg/mL. Sucrose was added to 5% wt/vol as a cryoprotectant and the activated protein was frozen and stored at −25° C. until needed for conjugation.

Bromoacetylation of lysine residues of $CRM_{197}$ was very consistent, resulting in the activation of 15 to 25 lysines from 39 lysines available. The reaction produced high yields of activated protein.

Conjugation of Activated Thiolated Saccharide to Bromoacetylated Carrier Protein Before starting the conjugation reaction, the reaction vessels are pre-cooled to 5° C. Bromoacetylated carrier protein and activated thiolated saccharide are subsequently added and mixed at an agitation speed of 150-200 rpm. The saccharide/protein input ratio is 0.9±0.1. The reaction pH is adjusted to 8.0±0.1 with 1 M NaOH solution. The conjugation reaction is allowed to proceed at 5° C. for 20±2 hours.

Capping of Residual Reactive Functional Groups

The unreacted bromoacetylated residues on the carrier protein are quenched by reacting with 2 mol. eq. of N-acetyl-L-cysteine as a capping reagent for 3 hours at 5° C. Residual free sulfhydryl groups are capped with 4 mol. eq. of iodoacetamide (IAA) for 20 hours at 5° C.

Purification of eTEC-Linked Glycoconjugate

The conjugation reaction (post-IAA-capped) mixture is filtered through 0.45 μm filter. Ultrafiltration/dialfiltration of the glycoconjugate is performed against 5 mM succinate-0.9% saline, pH 6.0. The glycoconjugate retentate is then filtered through 0.2 μm filter. An aliquot of glycoconjugate is pulled for assays. The remaining glycoconjugate is stored at 5° C.

Example 2. Preparation of Pn-33F eTEC Conjugates

Activation Process

Activation of Pn33F Polysaccharide

Pn-33F polysaccharide was compounded with 500 mM of 1,2,4-triazole (in WFI) to obtain 10 grams of triazole per gram of polysaccharide. The mixture was shell-frozen in dry ice-ethanol bath and then lyophilized to dryness. The lyophilized 33F polysaccharide was reconstituted in anhydrous dimethylsulfoxide (DMSO). Moisture content of the lyophilized 33F/DMSO solution was determined by Karl Fischer (KF) analysis. The moisture content was adjusted by adding WFI to the 33F/DMSO solution to reach a moisture content of 0.2%.

To initiate the activation, 1,1'-carbonyl-di-1,2,4-triazole (CDT) was freshly prepared as 100 mg/mL in DMSO solution. Pn33F polysaccharide was activated with various amounts of CDT prior to the thiolation step. The CDT activation was carried out at 23±2° C. for 1 hour. The activation level was determined by HPLC (A220/A205). Sodium tetraborate, 100 mM, pH 9.0 solution was added to quench any residual CDT in the activation reaction solution. Calculations are performed to determine the added amount of tetraborate and to allow the final moisture content to be 1.2% of total aqueous. The reaction was allowed to proceed for 1 hour at 23±2° C.

Thiolation of Activated Pn-33F Polysaccharide

Cystamine-dihydrochloride was freshly prepared in anhydrous DMSO and 1 mol. eq. of cystamine dihydrochloride was added to the activated polysaccharide reaction solution. The reaction was allowed to proceed for 21±3 hours at 23±2° C. The thiolated saccharide solution was diluted 10-fold by addition to pre-chilled 5 mM sodium succinate in 0.9% saline, pH 6.0. The diluted reaction solution was filtered through a 5 μm filter. Dialfiltration of thiolated Pn-33F polysaccharide was carried out with 100K MWCO ultrafilter membrane cassettes, using Water for Injection (WFI).

Reduction and Purification of Activated Thiolated Pn-33F Polysaccharide

To the retentate a solution of tris(2-carboxyethyl)phosphine (TCEP), 5 mol. eq., was added after dilution by 10% volume of 0.1 M sodium phosphate buffer, pH 6.0. This reduction reaction was allowed to proceed for 2±1 hours at 23±2° C. Dialfiltration of thiolated 33F polysaccharide was carried out with 100K MWCO ultrafilter membrane cassettes. Diafiltration was performed against pre-chilled 10 mM sodium phosphate, pH 4.3. The thiolated 33F polysaccharide retentate was pulled for both saccharide concentration and thiol (Ellman) assays.

Alternative Reduction and Purification of Activated Thiolated Pn-33F Polysaccharide As an alternative to the purification procedure described above, 33F activated thiolated saccharide was also purified as follows.

Figure 8:
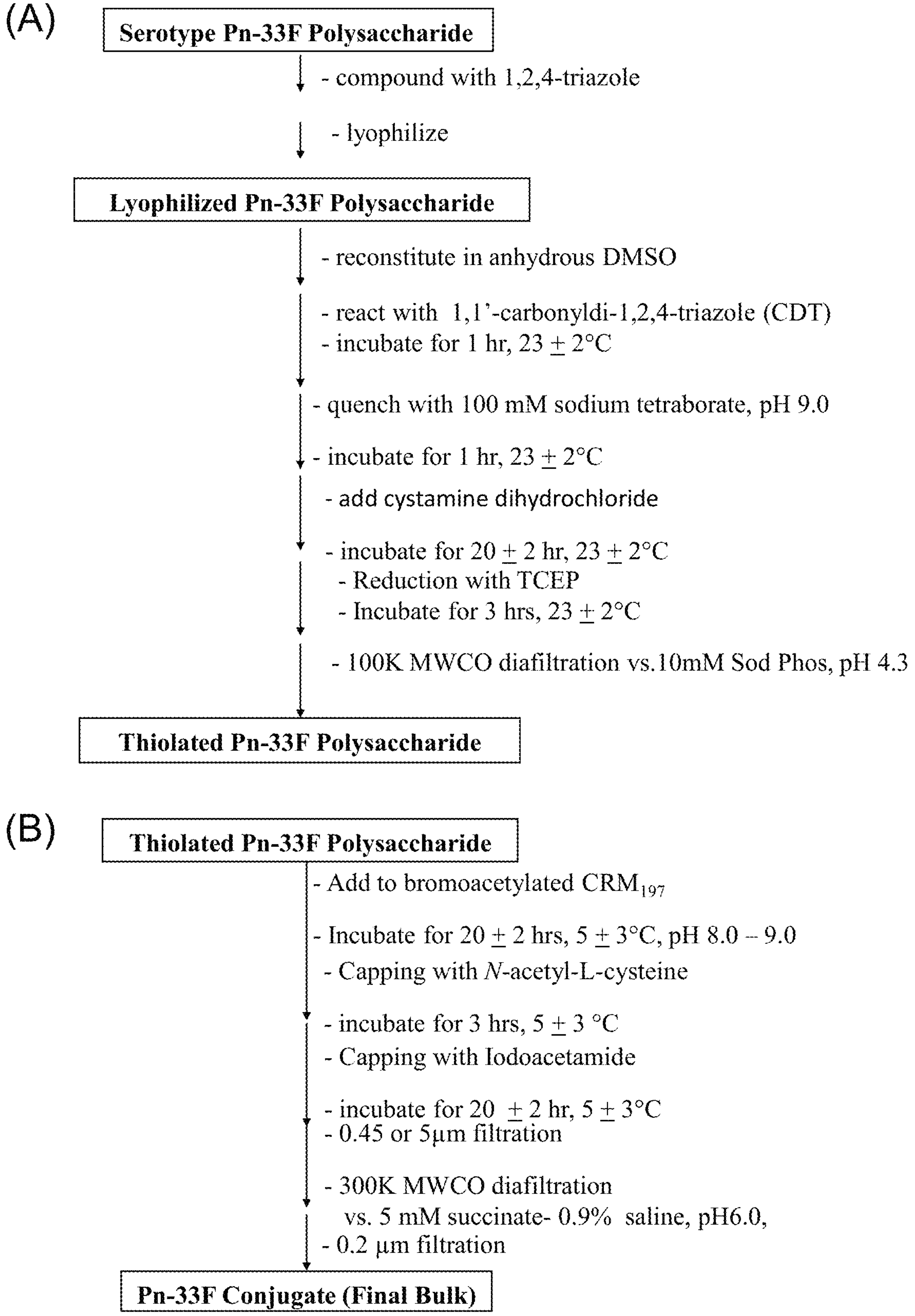
FIG. 8 shows a representative process flow diagram for the activation (A) and conjugation (B) processes which can be used in the preparation of Pn-33F glycoconjugate.

To the thiolated saccharide reaction mixture a solution of tris(2-carboxyethyl)phosphine (TCEP), 5 mol. eq., was added and allowed to proceed for 3±1 hours at 23±2° C. The reaction mixture was then diluted 5-fold by addition to pre-chilled 5 mM sodium succinate in 0.9% saline, pH 6.0 and filtered through a 5 μm filter. Dialfiltration of thiolated saccharide was performed using 40-fold diavolume of pre-chilled 10 mM sodium phosphate monobasic, pH 4.3 with 100K MWCO ultrafilter membrane cassettes. The thiolated 33F polysaccharide retentate was pulled for both saccharide concentration and thiol (Ellman) assays. A flow diagram of the activation process is provided in FIG. 8(A).

Conjugation Process

Conjugation of Thiolated Pn33F Polysaccharide to Bromo-acetylated $CRM_{197}$

The $CRM_{197}$ carrier protein was activated separately by bromoacetylation, as described in Example 1, and then reacted with the activated Pn-33F polysaccharide for the conjugation reaction. Before starting the conjugation reaction, the reaction vessel was pre-cooled to 5° C. Bromo-acetylated $CRM_{197}$ and thiolated 33F polysaccharide were mixed together in a reaction vessel at an agitation speed of 150-200 rpm. The saccharide/protein input ratio was 0.9±0.1. The reaction pH was adjusted to 8.0-9.0. The conjugation reaction was allowed to proceed at 5° C. for 20±2 hours.

Capping of Reactive Groups on Bromoacetylated $CRM_{197}$ and Thiolated Pn33F Polysaccharide The unreacted bromoacetylated residues on $CRM_{197}$ proteins were capped by reacting with 2 mol. eq. of N-acetyl-L-cysteine for 3 hours at 5° C., followed by capping any residual free sulfhydryl groups of the thiolated 33F-polysaccharide with 4 mol. eq. of iodoacetamide (IAA) for 20 hours at 5° C.

Purification of eTEC-Linked Pn-33F Glycoconjugate

The conjugation solution was filtered through a 0.45 μm or 5 μm filter. Dialfiltration of the 33F glycoconjugate was carried out with 300K MWCO ultrafilter membrane cassettes. Diafiltration was performed against 5 mM succinate-0.9% saline, pH 6.0. The Pn-33F glycoconjugate 300K retentate was then filtered through a 0.22 μm filter and stored at 500. A flow diagram of the conjugation process is provided in FIG. 8(B).

Results

The reaction parameters and characterization data for several batches of Pn-33F eTEC glycoconjugates are shown in Table 1. The CDT activation-thiolation with cystamine dihydrochloride generated glycoconjugates having from 63% to 90% saccharide yields and <1% to 13% free saccharides.

TABLE 1

Experimental Parameters and Characterization Data of Pn33F eTEC Conjugates

| Conjugate Batch | 33F-1A | 33F-2B | 33F-3C | 33F-4D | 33F-5E | 33F-6F | 33F-7G |
|---|---|---|---|---|---|---|---|
| Activation level (mol of thiol/mol of polysaccharide) | 0.21 | 0.13 | 0.164 | 0.103 | 0.183 | 0.22 | 0.19 |
| Activation level (% Thiol) | 21 | 13 | 16.4 | 10.3 | 18.3 | 22 | 19 |
| Saccharide/Protein (Input) ratio | 0.75 | 1.0 | 0.75 | 1.0 | 1.0 | 0.75 | 0.80 |
| Saccharide yield (%) | 69% | 63% | 71% | 63% | 69% | 82% | 90% |
| Saccharide/Protein Ratio | 1.3 | 1.7 | 1.2 | 1.9 | 1.6 | 1.1 | 1.5 |
| Free Saccharide | 12.9% | 7.7% | 4.4% | 7.2% | 7.3% | <4% | <4% |
| MW by SEC-MALLS (kDa) | 2627 | 2561 | 4351 | 2981 | 3227 | 3719 | 5527 |
| CMCA/CMC | 14.4/0 | 13.4/0 | 6.8/1.9 | 2.7/0.6 | 5.9/0.6 | 8.2/0 | 11.4/0.6 |
| % $K_d$ (≤0.3) | N/A | 85% | 88% | 75% | 68% | 67% | 76% |
| Acetylation level (mol of acetate/mol of polysaccharide) | 0.89 | 1.16 | 0.99 | 0.85 | 0.81 | 0.85 | 1.01 |

N/A = not available

OPA Titers of Pn-33F eTEC Glycoconjugates to $CRM_{197}$

Pn-33F OPA titers in mice were determined under standard conditions (similar to the OPA procedures described below for 10A and 22F conjugates). OPA titers (GMT with 95% CI) at four and seven weeks are shown in Table 2, demonstrating that the serotype 33F Pn glycoconjugate elicited OPA titers in a murine immunogenicity model.

TABLE 2

Pn-33F OPA Titers (GMT with 95% CI)

| 33F Pn Conjugate | 0.001 μg | 0.01 μg | 0.1 μg |
|---|---|---|---|
| week 4 | 4 (4, 5) | 37 (17, 82) | 414 (234, 734) |
| week 7 | 8 (5, 13) | 131 (54, 314) | 17567 (9469, 32593) |

Example 3. Preparation of Additional Pn-33F eTEC Conjugates

Additional Pn-33F eTEC Conjugates were generated using the process described in Example 2. The reaction parameters and characterization data for these additional batches of Pn-33F eTEC glycoconjugates are shown in Table 3.

TABLE 3

Experimental Parameters and Characterization Data of further Pn33F eTEC Conjugates

| Conjugate Batch | 33F-8H | 33F-9I | 33F-10J | 33F-11K | 33F-12L | 33F-13M | 33F-14N | 33F-15O | 33F-16P |
|---|---|---|---|---|---|---|---|---|---|
| Activation level (mol of thiol/mol of polysaccharide) | 0.22 | 0.11 | 0.11 | 0.13 | 0.14 | 0.13 | 0.06 | 0.13 | 0.11 |
| Saccharide/Protein (Input) ratio | 0.75 | 0.8 | 0.8 | 0.8 | 0.8 | 0.8 | 0.8 | 0.8 | 0.8 |
| Saccharide yield (%) | 78% | 88% | 89% | 67% | 69% | 86% | 81% | 91% | 88% |
| Saccharide/Protein Ratio | 1.0 | 2.2 | 2.1 | 1.4 | 1.4 | 1.4 | 2.2 | 1.9 | 1.9 |
| Free Saccharide | <1% | 6.8% | 5.9% | 2.3% | 3.6% | LOQ | 8.2% | 3.6% | 6.6% |
| MW by SEC-MALLS (kDa) | 4729 | 3293 | 3295 | 2246 | 2498 | 5539 | 3070 | 6009 | 3789 |
| CMCA/CMC | 6.6/LOQ | 14.2/2.1 | 15.4/2.1 | 5.5/1 | 5.4/1.1 | NA/LOQ | 1.7/1.2 | 4.1/2.2 | 2.2/1.2 |
| % $K_d$ (≤0.3) | 69% | N/A | N/A | N/A | N/A | 88% | 87% | 87% | 85% |
| Acetylation level (mol of acetate/mol of polysaccharide) | 0.86 | 0.93 | 0.87 | 1.01 | 0.99 | 0.71 | 0.78 | 0.8 | 0.82 |

LOQ = limit of quantitation;
N/A = not available.

As shown above and in Table 3, several Pn-33F conjugates were obtained using the eTEC conjugation above. The eTEC chemistry allowed preparation of conjugates with high yield, low % free saccharide and high degree of conjugation (conjugated lysines). Additionally, it was possible to preserve more than 80% of acetyl functionality using the eTEC conjugation process.

Example 4. Evaluation of Pn-33F eTEC Glycoconjugates Stability: % Free Saccharide Trends Aliquots of conjugate batch 33F-2B (see table 1) were dispensed into polypropylene tubes and stored at 4° C., 25° C., and 37° C., respectively and monitored for trends in % free saccharide. The data (% free saccharide) are shown in Table 4. As shown in this Table, there were no significant changes in the % free saccharide.

TABLE 4

% Free Saccharide Stability for Pn-33F eTEC Glycoconjugate at 4° C., 25° C. and 37° C.

| Lot# | Free Saccharide (%) | | | | | | |
|---|---|---|---|---|---|---|---|
| | Time | | | | | | |
| 33F-2B | 0 | 1 wk | 3 wks | 1 M | 2 M | 3 M | 6 M |
| | 4° C. | | | | | | |
| | 7.7 | N/A | 8.3 | N/A | 9.7 | 11.2 | 13 |
| | 25° C. | | | | | | |
| | 7.7 | N/A | 10.8 | N/A | 11.8 | N/A | N/A |
| | 37° C. | | | | | | |
| | 7.7 | 12.1 | N/A | 13.4 | N/A | N/A | N/A |

wk = week;
M = month;
N/A = not available.

The accelerated stability of another conjugate lot (Batch 33F-3C) was also conducted at 37° C. up to 1 month. As shown in Table 5, there was no significant change to % free saccharide at 37° C., up to 1 month.

TABLE 5

% Free Saccharide Stability for Pn-33F eTEC Glycoconjugate at 37° C.

| | Free Saccharide (%) Time | | | | |
|---|---|---|---|---|---|
| | 0 | 1 day | 1 wk | 2 wks | 1 M |
| Lot# | | | 37° C. | | |
| 33F-3C | 4.4 | 5.9 | 6.4 | 7.1 | 7.2 |

To further confirm the stability of eTEC conjugates, additional conjugate batches (33F-3C and 33F-5E (see Table 1)) stored at 4° C. were monitored up to approximately one year, for potential trends in % free saccharide. As shown in Table 6, there were no significant changes in % free saccharide levels for the conjugates stored at 4° C. for an extended period up to approximately one year.

TABLE 6

% Free Saccharide Stability Results for Pn-33F eTEC Glycoconjugates at 4° C.

| | Free Saccharide (%) Time | | | | |
|---|---|---|---|---|---|
| | 0 | 3 M | 4 M | 12 M | 14 M |
| Lot# | | | 4° C. | | |
| 33F-3C | 4.4 | N/A | 5.3 | N/A | 7.6 |
| 33F-5E | 7.3 | 6.3 | N/A | 7.4 | N/A |

M = month;
N/A = not available

The Serotype 33F conjugates generated by 33F eTEC chemistry were demonstrated to be stable without noticeable degradation as monitored by the free saccharide trends at various temperatures (real time and accelerated).

Example 5. Preparation of Pn-8 Conjugates to $CRM_{197}$

Preparation of Pn-8 RAC/DMSO Glycoconjugates

Frozen polysaccharide was thawed and transferred to the reaction vessel. 2 M acetic acid and WFI (Water for Injection) was added to the polysaccharide solution to achieve a final polysaccharide concentration of about 2.5 g/L and a final acetic acid concentration of 0.2 M.

Hydrolysis of the Polysaccharide

The native polysaccharide was chemically hydrolyzed prior to activation. The diluted polysaccharide solution was heated to 70° C., and then held this temperature for 3.5 hours.

Oxidation of the Polysaccharide

Oxidation of polysaccharide was initiated by the addition of sodium periodate solution and the reaction kept to proceed for 20 hrs at 23° C.

Purification of Activated Polysaccharide

The activated polysaccharide was concentrated using ultrafiltration cassettes. Diafiltration was performed against 20-fold diavolume of WFI.

Lyophilization

The activated polysaccharide is compounded with sucrose to a ratio of 25 grams of sucrose per gram of activated polysaccharide. The bottles containing the activated saccharide and sucrose are shell frozen in ethanol baths and lyophilized.

Conjugation of Activated Polysaccharide to $CRM_{197}$ and Capping

Lyophilized activated polysaccharide was reconstituted to 2 mg/mL in DMSO. DMSO was added to lyophilized $CRM_{197}$ for reconstitution. Reconstituted $CRM_{197}$ was added to the reconstituted activated polysaccharide. Conjugation was then initiated by adding sodium cyanoborohydride to the reaction mixture and was incubated at 23° C. for 24 hrs. Termination of conjugation reaction is done by adding 2 MEq of sodium borohydride. This capping reaction proceeded for 3 hrs at 23° C.

Purification of Conjugate

The conjugate solution was then diluted into chilled 5 mM succinate-0.9% saline (pH 6.0), filtered, concentrated to 2-4 g/L using 300K cellulose membranes, and a first-stage diafiltration was performed against 5 mM succinate-0.9% saline (pH6.0). A final purification step was done by diafiltration with 5 mM succinate-0.9% saline, pH 6.0 buffer. After the diafiltration is completed, the purified conjugate was transferred to a collection tank through a 0.22 μm filter.

Dilution of the Monovalent Bulk Conjugate

The conjugate was diluted further with 5 mM succinate/0.9% saline (pH 6), to a target saccharide concentration of 0.5 mg/mL. Final 0.22 μm filtration step was completed to prepare the monovalent bulk conjugate (MBC) product for formulation.

Several conjugates were obtained using the above described process by varying different parameters (e.g., saccharide-protein input ratio, reaction concentration and Meq of sodium cyanoborohydride). Characterization for representative Pn-8 glycoconjugates to $CRM_{197}$ is provided in Table 7.

TABLE 7

Characterization of Pn8-$CRM_{197}$ Conjugates

| Sample No. | 1 | 2 | 3 | 4 | 5 | 6 | 7 | 8 | 9 |
|---|---|---|---|---|---|---|---|---|---|
| Activated Saccharide MW by MALLS (kDa) | 267 | 270 | 352 | 65 | 233 | 340 | 113 | 250 | 230 |
| Saccaride/Protein Ratio | 0.81 | 0.84 | 0.5 | 2.7 | 1.15 | 1.0 | 0.81 | 0.64 | 0.42 |
| MW by SEC-MALLS (kDa) | 12200 | 8670 | 3460 | 3379 | 4748 | 4255 | 5470 | 9924 | 6787 |

The Opsonophagocytic activity (OPA) titers for Serotype 8-$CRM_{197}$ conjugates in mice were determined in mice under standard conditions (similar to the OPA procedures described below for 10A and 22F conjugates). OPA titers (geometric mean titer (GMT) with 95% confidence interval (CI)) at four weeks at different doses are shown in Table 8 and 9 (two separate experiments), demonstrating that the serotype 8 conjugate (Samples 1-9; also see Table 7 for characterization data of these conjugates) elicited OPA titers in a murine immunogenicity model.

As shown in Table 8, serotype 8 conjugates were shown to have significantly higher antibody titers, compared to the control unconjugated polysaccharide which had poor antibody titers.

TABLE 8

Immunogenicity of Serotype 8-$CRM_{197}$ Conjugates

| | OPA GMT (95% CI) | | |
|---|---|---|---|
| Sample No. | 0.001 μg | 0.01 μg | 0.1 μg |
| 1 | 17 (10, 30) | 88 (47, 165) | 1344 (896, 2016) |
| 2 | 7 (4, 11) | 184 (87, 387) | 1934 (1313, 2847) |
| 3 | 4 (4, 4) | 17 (9, 30) | 779 (345, 1757) |
| 4 | 5 (4, 7) | 74 (41, 136) | 558 (311, 1001) |
| Unconjugated PS | | | 13 (3, 55) |

TABLE 9

Immunogenicity of Serotype 8-$CRM_{197}$ Conjugates

| Sample | OPA GMT (95% CI) | |
|---|---|---|
| No. | 0.001 μg | 0.01 μg |
| 5 | 8 (5, 12) | 322 (208, 498) |
| 6 | 12 (8, 19) | 264 (129, 537) |
| 7 | 12 (7, 21) | 521 (366, 743) |
| 8 | 19 (10, 38) | 404 (238, 687) |
| 9 | 33 (14, 80) | 686 (380, 1237) |
| 2 | 13 (7, 23) | 177 (94, 336) |

The overall data generated from conjugates prepared by the above reductive amination process demonstrated that it allowed preparing conjugates with good conjugation yield, low % free saccharide and with good stability. Additionally, the prepared conjugates elicited good OPA titers in a murine immunogenicity model.

Example 6. Preparation of Serotype 10A Polysaccharide-$CRM_{197}$ Conjugate

Preparation of isolated *S. pneumoniae* serotype 10A polysaccharide Serotype 10A capsular polysaccharides can be obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/118752). *Streptococcus pneumoniae* serotype 10A were grown in a seed bottle and then transferred to a seed fermentor. Once the targeted optical density was reached, the cells were transferred to a production fermentor. The fermentation broth was inactivated by the addition of N-lauroyl sarcosine and purified by ultrafiltration and diafiltration.

Oxidation of Isolated *Streptococcus pneumoniae* Serotype 10A Capsular Polysaccharide A calculated volume of 0.1 M potassium phosphate buffer (pH 6.0) and water-for-injection (WFI) was added to the polysaccharide solution to achieve a final polysaccharide concentration of 2.5 g/L and a final concentration of 25 mM potassium phosphate buffer, if required pH was adjusted to 6.0, approximately. The diluted polysaccharide was then cooled to 5° C. Oxidation was initiated by the addition of 0.25 molar equivalents (MEq) of sodium periodate solution. The oxidation reaction time was approximately 4 hrs at 5° C. The oxidation reaction was quenched with 1 MEq of 2,3-butanediol under continuous stirring at 5° C. for 1-2 hrs.

After reaching the target reaction time, the activated polysaccharide was concentrated using 30K MWCO Millipore ultrafiltration cassettes. The diafiltration was then performed against 20-fold diavolume of WFI. The purified activated polysaccharide was stored at 5° C. The purified activated saccharide is characterized inter alia by (i) Molecular Weight by SEC-MALLS and (ii) Degree of Oxidation.

Conjugation of Activated *S. pneumoniae* Serotype 10A Polysaccharide with $CRM_{197}$ The conjugation process consisted of the following steps:

a. Compounding with sucrose excipient, and lyophilization;
b. Reconstitution of the lyophilized polysaccharide and $CRM_{197}$;
c. Conjugation of activated polysaccharide to $CRM_{197}$ and capping; and
d. Purification of the conjugate a. Compounding with Sucrose The activated polysaccharide is compounded with sucrose to a ratio of 25 g of sucrose per gram of activated polysaccharide. The bottle of compounded mixture was then lyophilized. Following lyophilization, bottles containing lyophilized activated polysaccharide were stored at −20° C.

b. Reconstitution of Lyophilized Activated Polysaccharide and $CRM_{197}$ Protein Lyophilized activated polysaccharide was reconstituted in anhydrous dimethyl sulfoxide (DMSO). Upon complete dissolution of polysaccharide, the same amount of DMSO was added to the calculated $CRM_{197}$ for reconstitution.

c. Conjugation of Activated Polysaccharide to $CRM_{197}$ and Capping

Reconstituted $CRM_{197}$ (in DMSO) was added to the reconstituted activated polysaccharide in the conjugation reactor. The final polysaccharide concentration is 1 g/L. Conjugation was performed by adding 1.2 MEq of sodium cyanoborohydride to the reaction mixture. The reaction was incubated and at 23° C. for 24 hrs. Termination of conjugation reaction is done by adding 2 MEq of sodium borohydride. The capping reaction was incubated at 23° C. for 3 hrs.

Termination of conjugation reaction is done by adding 2 MEq of sodium borohydride. This capping reaction proceeded for 3 hrs at 23° C.

d. Purification of Conjugate

The conjugate solution was then diluted into 5× (by volume) chilled 5 mM succinate-0.9% saline (pH 6.0) and a 20× diafiltration was performed using 5 mM succinate-0.9% saline (pH6.0). After the initial diafiltration was completed, the conjugate retentate was transferred through a 0.22 μm filter. The conjugate was diluted further with 5 mM succinate/0.9% saline (pH 6), and after the final 0.22 μm filtration step it was stored at 2-8° C.

Several conjugates were obtained using the above described process by varying different parameters (e.g., saccharide-protein input ratio, reaction concentration and MEq of sodium cyanoborohydride). The above chemistry allowed to generate serotype 10A conjugates which were demonstrated to be stable without noticeable degradation as monitored by the free saccharide trends at various temperatures (real time and accelerated). Characterization for representative Pn-10A glycoconjugates to $CRM_{197}$ is provided in Table 10.

TABLE 10

Characterization of Pn-10A-$CRM_{197}$ Conjugates

| Conjugate No. | 1 | 2 | 3 | 4 | 5 | 6 |
|---|---|---|---|---|---|---|
| DO | 12.2 | 19.5 | 5.2 | 10.3 | 10.8 | 10.5 |
| Activated Saccharide MW, kDa | 191 | 240 | 80 | 170 | 170 | 170 |
| Input Ratio | 1.0 | 1.0 | 1.0 | 1.1 | 1.1 | 1.1 |
| % Yield | 56 | 28.5 | 65 | 82 | 73 | 66 |
| % Free Saccharide | 6.8 | 10.0 | 6.7 | 6.8 | 6.4 | 9.7 |
| Conjugate MW, kDa | 3838 | 5810 | 4630 | 4034 | 3463 | 5540 |
| Saccharide/Protein Ratio | 0.82 | 0.88 | 0.85 | 1.1 | 1.2 | 1.0 |
| Lys modification AAA | 7.4 | 3.7 | 13.1 | 6.9 | 6.7 | 6.1 |

The opsonophagocytic activity (OPA) titers for Serotype 10A-$CRM_{197}$ conjugates in mice were determined under standard conditions. Groups of thirty 6-7 week old female Swiss Webster mice were immunized with 0.001 μg, 0.01 μg, or 0.1 μg of test conjugates via the subcutaneous route on week 0. The mice were boosted with the same dose of conjugate on week 3 and then bled at week 4. Serotype-specific OPAs were performed on week 4 sera samples.

Opsonophagocytic activity (OPA) assays are used to measure functional antibodies in murine sera specific for *S. pneumonia* serotype 10A. Test serum is set up in assay reactions that measure the ability of capsular polysaccharide specific immunoglobulin to opsonize bacteria, trigger complement deposition, thereby facilitating phagocytosis and killing of bacteria by phagocytes. The OPA titer is defined as the reciprocal dilution that results in a 50% reduction in bacterial count over control wells without test serum. The OPA titer is interpolated from the two dilutions that encompass this 50% killing cut-off. OPA procedures were based on methods described in Hu et al. (2005) Clin Diagn Lab Immunol 12 (2):287-295 with the following modifications. Test serum was serially diluted 2.5-fold and added to microtiter assay plates. Live serotype 10A target bacterial strains were added to the wells and the plates were shaken at 37° C. for 30 minutes. Differentiated HL-60 cells (phagocytes) and baby rabbit serum (3- to 4-week old, PEL-FREEZ®, 12.5% final concentration) were added to the wells, and the plates were shaken at 37° C. for 60 minutes. To terminate the reaction, 80 μL of 0.9% NaCl was added to all wells, mixed, and a 10 μL aliquot were transferred to the wells of MULTISCREEN® HTS HV filter plates (MILLIPORE®) containing 200 μL of water. Liquid was filtered through the plates under vacuum, and 150 μL of HYSOY® medium was added to each well and filtered through. The filter plates were then incubated at 37° C., 5% $CO_2$ overnight and were then fixed with Destain Solution (Bio-Rad Laboratories, Inc., Hercules, CA). The plates were then stained with Coomassie Blue and destained once. Colonies were imaged and enumerated on a Cellular Technology Limited (CTL) (Shaker Heights, OH) IMMUNOSPOT® Analyzer. Raw colony counts were used to plot kill curves and calculate OPA titers.

OPA titers (geometric mean titer (GMT) with 95% confidence interval (CI)) at four weeks at different doses are shown in Table 11, demonstrating that the serotype 10A conjugate (Samples 1-3; also see Table 10 for characterization data of these conjugates) elicited OPA titers in a murine immunogenicity model. As shown in Table 11, serotype 10A conjugates were shown to have significantly higher OPA titers, compared to the control unconjugated polysaccharide, which had a poor OPA response.

TABLE 11

Immunogenicity of Serotype 10A-$CRM_{197}$ Conjugates

| | OPA GMT (95% CI) | | |
|---|---|---|---|
| Sample No. | 0.001 μg | 0.01 μg | 0.1 μg |
| 1 | 858 (556, 1324) | 1015 (610, 1691) | 4461 (3065, 6494) |
| 2 | 1411 (737, 2703) | 796 (460, 1378) | 2873 (1768, 4842) |
| 3 | 322 (180, 574) | 1062 (528, 2135) | 2618 (1415, 4842) |
| Unconjugated PS | | | 602 (193, 1882) |

Example 7. Conjugation of Pn Serotype-12F Using TEMPO/NCS

In order to improve the stability of serotype 12F-$CRM_{197}$ glycoconjugates, alternate chemistries were explored using 2,2,6,6-Tetramethyl-1-piperidinyloxy free radical (TEMPO) and N-Chlorosuccinimide (NCS) as the cooxidant to oxidize primary alcohols to aldehyde groups. GC/MS analysis showed that the sites of oxidation were different from that of periodate-mediated oxidation. In the case of TEMPO-NCS oxidation, the α-D-Glcp and 2-Glcp were oxidized, whereas α-D-$Gal_p$ was the major site of oxidation when periodate was used (see FIG. 4). As described in further detail herein, TEMPO was used in catalytic amounts (≤0.1 molar equivalents) and the desired degree of oxidation (DO) was achieved by varying the amounts of NCS used. Subsequently several conjugates were synthesized and characterized. In general, the production of Serotype 12F glycoconjugates was carried out in several phases, as follows:

a) Hydrolysis of Serotype 12F polysaccharide to molecular weights 50 kDa to 500 kDa
b) Activation of Serotype 12F polysaccharide with TEMPO/NCS;
c) Purification of the activated polysaccharide;
d) Conjugation of activated Serotype 12F to $CRM_{197}$ protein; and
e) Purification of Serotype 12F-$CRM_{197}$ conjugates.

Hydrolysis and Oxidation of Serotype 12F

The hydrolysis of the polysaccharide was typically performed under acidic conditions with heating to obtain an average molecular weight in the desired range of 100 kDa to 350 kDa. A typical experiment is described below.

Hydrolysis

The Serotype 12F polysaccharide solution was added to a jacketed reaction vessel. To this, the required volume of 0.30 M Acetic acid and water for injection (WFI) were added to maintain ~0.1 M acetic acid concentration. The pH of the solution was adjusted to 3.2±0.3 using 1 N NaOH or Glacial Acetic acid. The temperature of the reaction mixture was increased to 70±5° C. The reaction mixture was stirred at 70±5° C. for 90-120 minutes. The reaction mixture was cooled down to 23±2° C. and neutralized (pH 7.0) by adding 1 M NaOH solution. The hydrolyzed polysaccharide was purified by ultrafiltration/diafiltration against WFI using 30K MWCO membranes. The solution was filtered through a 0.22 μm filter and stored at 2 to 8° C. until oxidation. The molecular weight of the hydrolyzed polysaccharide was analyzed by SEC-MALLS to ensure that the molecular weight met the target range of 100 kDa to 350 kDa.

Partial Oxidation

In one experiment, the serotype 12F polysaccharide was mechanically sized using pressure homogenization using a microfluidiser to reduce the molecular weight to approximately 100 kDa to 500 kDa. The sized polysaccharide was added to a reaction vessel at a concentration of 4.0 mg/mL and mixed with bicarbonate/carbonate buffer (0.5 M $NaHCO_3$/0.05 M $Na_2CO_3$ buffer, pH 8.6) at a ratio of 1:1 v/v. To the stirred mixture was added ≤0.1 mol equivalent of TEMPO. The reaction was started by the addition of 0.6 to 1.0 mol equivalent of NCS. The reaction mixture was stirred at room temperature for 2 hours, after which the activated polysaccharide was purified by diafiltration, with WFI using a 30K ultrafiltration membrane. The purified polysaccharide was collected and the degree of oxidation (DO) was determined by quantitative measurements of aldehyde (using a 3-methyl-2-benzothiazolinone hydrazone (MBTH) assay) and polysaccharide (using an anthrone assay).

In another experiment, the serotype 12F polysaccharide was hydrolyzed to reduce the molecular weight to a molecular weight of approximately 100 kDa to 500 kDa. The serotype 12F polysaccharide was added to a reaction vessel and mixed with 0.5 M $NaHCO_3$/0.05 M $Na_2CO_3$ buffer (pH 8.6) at a ratio of 1:1 v/v. To the stirred mixture was added 0.6 to 1.0 molar equivalents of NCS dissolved in WFI. The activation was initiated by the addition of approximately 0.1 molar equivalents of TEMPO dissolved in WFI. The reaction mixture was stirred at room temperature for 2 hours, after which the activated polysaccharide was purified by diafiltration with WFI using a 30K ultrafiltration membrane. The purified activated polysaccharide was filtered through a 0.2 μm filter and stored at 4° C. before use.

The TEMPO/NCS mediated oxidations were also performed successfully in sodium phosphate buffers of pH 6.5, 7.0, 7.5 and 8.0. In some activation experiments a primary alcohol such as n-propanol was used to quench the reagents in order to avoid saccharide overoxidation. In another set of experiments the chemically hydrolysed polysaccharide was subjected to oxidation directly, without the ultrafiltration/diafiltration purification step.

Conjugation of Serotype 12F Oxidized Polysaccharide

In one experiment, the purified oxidized Serotype 12F polysaccharide was added to a reaction vessel followed by the addition of 0.5 M Sodium phosphate buffer (pH 6.5) to a final buffer concentration of 0.1 M. To this solution, previously lyophilized $CRM_{197}$ was added and mixed thoroughly in order to obtain a homogenous solution. The pH was adjusted to 6.8 using diluted HCl or 1 N NaOH solution. This was followed by the addition of 1.5 molar equivalents of $NaCNBH_3$. The reaction mixture was stirred for 24 hours at room temperature (23° C.) and for 2.5 days at 37° C. The reaction mixture was then diluted with 1×0.9% saline and the unreacted aldehyde groups were "capped" with 2 molar equivalents of sodium borohydride. The capping reaction time was 3 hours.

In another experiment, the purified activated serotype 12F was added to a reaction vessel followed by the addition of 0.5 M sodium phosphate buffer (pH 6.5) to a final buffer concentration of 0.1 M. To this solution, previously lyophilized $CRM_{197}$ was added and mixed thoroughly to obtain a homogenous solution. The pH was adjusted to 6.8 using diluted HCl or 1 N NaOH solution. This was followed by the addition of 3 molar equivalents of $NaCNBH_3$. The reaction mixture was stirred for 24 hours at 23° C. and for 48 hrs at 37° C. The reaction mixture was then diluted with 1×0.9% saline and with stirring, the unreacted aldehyde groups were "capped" with 1 molar equivalent sodium borohydride $NaBH_4$. The capping reaction time was 3 hours.

In another experiment, the purified activated serotype 12F was added to a reaction vessel and mixed with $CRM_{197}$ solution. The mixture was lyophilized and the powder was dissolved in 0.1 M sodium phosphate buffer (pH 6.8) to a final saccharide concentration of 5 mg/mL. If needed the pH was adjusted to 6.8 using diluted HCl or 1 N NaOH solution. This was followed by the addition of 3 molar equivalents $NaCNBH_3$. The reaction mixture was stirred for 24 hours at 23° C. and for 48 hrs at 37° C. The reaction mixture was then diluted with 1×0.9% saline, the unreacted aldehyde groups were "capped" with 1 molar equivalent sodium borohydride $NaBH_4$. The capping reaction time was 3 hours.

Conjugate Purification

The capped reaction mixture was filtered using a 5 μm filter and then purified using 100K MWCO ultra filtration membranes. The conjugate was first diafiltered using 10 mM succinate/0.9% saline, pH 6.0 buffer. The purified conjugate was then filtered through 0.45/0.22 μm filters to obtain the bulk conjugate.

Degree of Oxidation

Figure 9:
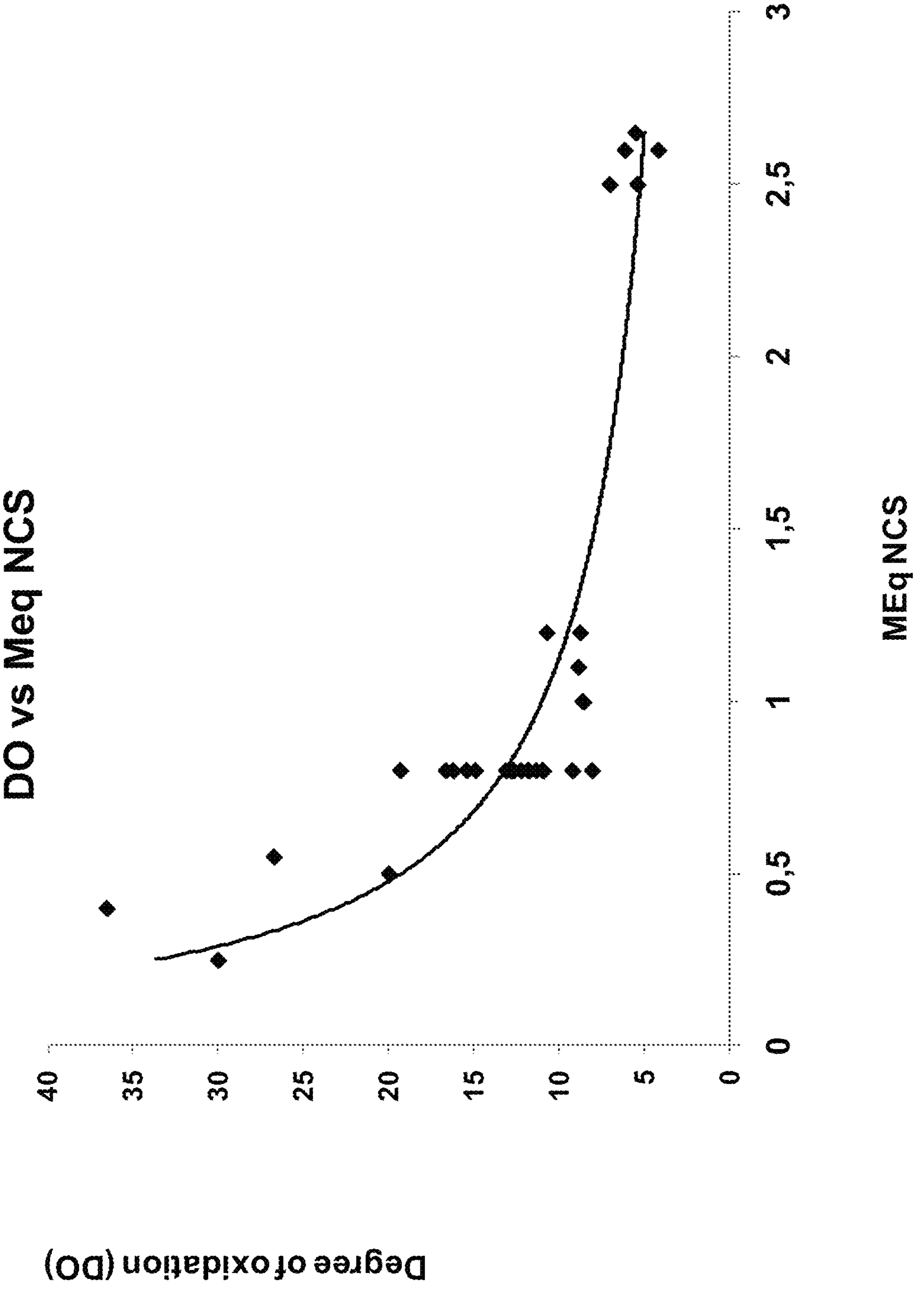
FIG. 9 shows the effect on DO by varying amount of NCS in the TEMPO/NCS oxidation reaction.

Successful oxidation of primary alcohols in the serotype 12F polysaccharide was achieved using the TEMPO/NS system. The hydrolyzed Serotype 12F polysaccharides were oxidized to varying degrees of oxidation (DO) levels by adjusting the amount of NS cooxidant. The effect on DO by varying amounts of NS using different polysaccharide batches and molecular weights is shown in FIG. 9. Typically the oxidation reaction is complete in 2 hours as no significant change in DO was observed after 2 hours.

Several serotype 12F conjugates were generated and characterized using the TEMPO/NCS oxidized polysaccharide. The results are summarized in Table 12.

TABLE 12

| Pneumococcal Serotype 12F-$CRM_{197}$ conjugates | | | | | | |
|---|---|---|---|---|---|---|
| Conjugate Batch | 12F-84A | 12F-97B | 12F-147C | 12F-171D | 12F-177-6E | 12F-181F |
| Oxidation Time (hr) | 2 | 2 | 4 | 2 | 2 | 2 |
| Degree of Oxidation (DO) | 12.0 | 6.0 | 9.6 | 12.0 | 11.5 | 11.5 |
| % Activated Saccharide Yield | 80 | 71 | 70 | 89 | 86 | 86 |
| Activated Saccharide MW by MALLS (kDa) | 137 | 155 | 170 | 190 | 240 | 240 |
| Conjugation process | Lyo-CRM | Lyo-CRM | Lyo-CRM | Lyo-CRM | Lyo-CRM | Co-Lyo |
| Conjugate Results | | | | | | |
| Saccharide yield (%) | 51.6 | 76.8 | 53.6 | 76.3 | 65.8 | 40.7 |
| Saccharide/Protein Ratio | 1.2 | 0.9 | 1.0 | 1.1 | 1.4 | 0.9 |
| % Free Saccharide | 24 | 10 | 17 | 20 | 23 | 14 |
| MW by SEC-MALLS (kDa) | 2050 | 3000 | 3600 | 1500 | 2400 | 2100 |

Example 8. Immunogenicity of Pn-Serotype 12F-$CRM_{197}$ Conjugates Using the TEMPO/NCS Oxidation Method The opsonophagocytic activity (OPA) titers for serotype 12F-$CRM_{197}$ conjugates in mice were determined in mice under standard conditions. OPA titers (geometric mean titer (GMT) with 95% confidence interval (CI)) at four and seven weeks are shown in Table 13, demonstrating that the serotype 12F-$CRM_{197}$ conjugate (Batch 12F-97B; also see Table 12 for characterization data of this conjugate) elicited OPA titers in a murine immunogenicity model. The conjugate generated by the TEMPO-NCS was more immunogenic than the control conjugate (171B) generated from the periodate oxidation.

TABLE 13

| Immunogenicity of Serotype 12F-$CRM_{197}$ Conjugates | | | |
|---|---|---|---|
| | Dose | | |
| Conjugate Sample | 0.001 μg | 0.01 μg | 0.1 μg |
| Periodate Oxidation (171B) Control | 4 | 16 | 172 |
| TEMPO/NCS Oxidation (12F-97B) | 40 | 417 | 880 |

Example 9. Evaluation of Pn-12F Glycoconjugates Stability

Figure 10:
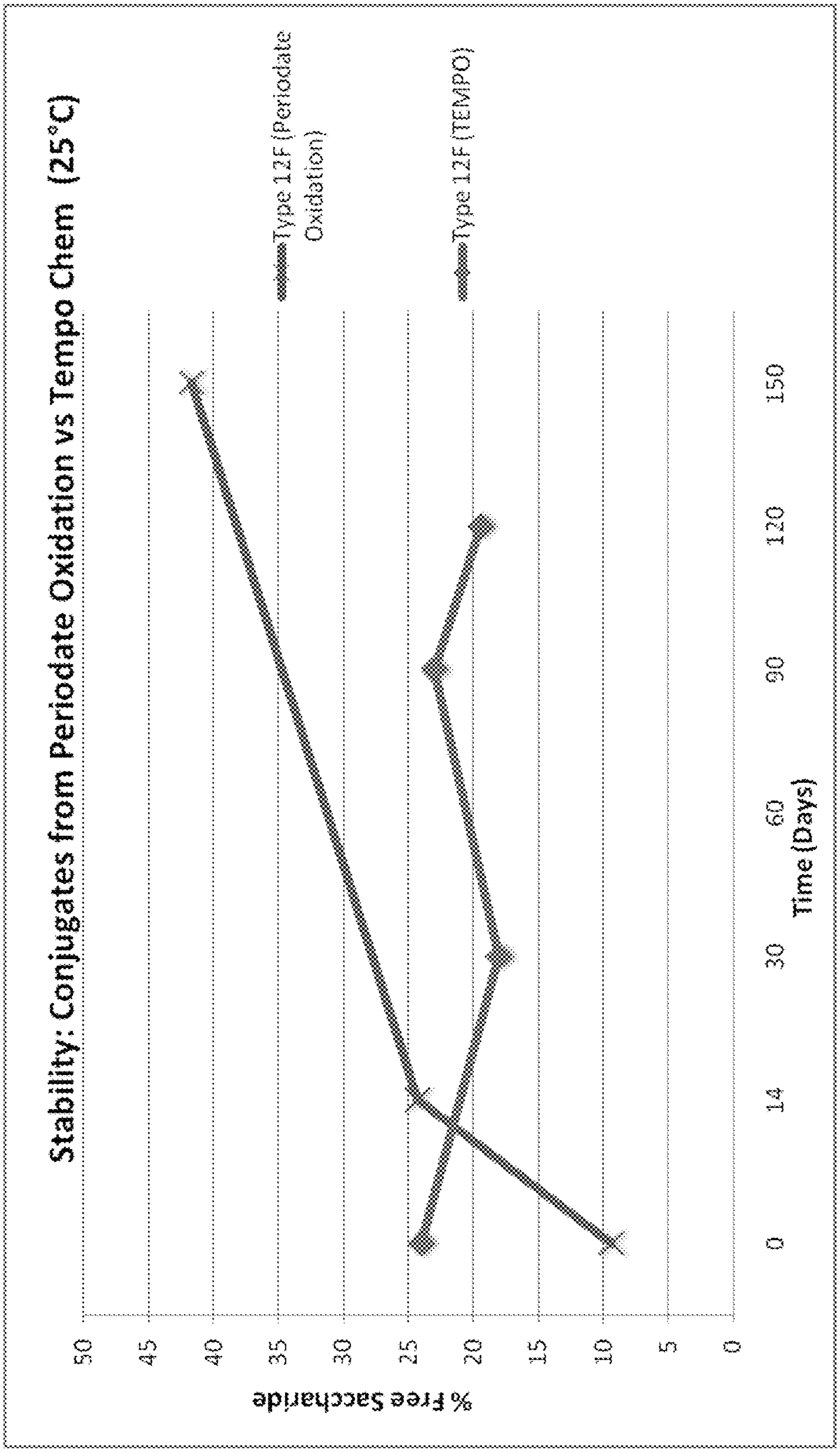
FIG. 10 shows evaluation of Pn-12F glycoconjugates stability.

Comparison of the stability (at 25° C.) of the conjugates generated by periodate oxidation vs. TEMPO/NCS oxidation (see FIG. 10) demonstrated that the conjugate generated by the oxidation of the Pn-12F polysaccharides were relatively more stable. As shown in FIG. 10, an increase in the free saccharide over time was observed for the glycoconjugate generated by the periodate oxidation of the Pn-12F polysaccharide at 25° C. In contrast, the glycoconjugate prepared using the TEMPO/NCS oxidation of the Pn-12F polysaccharide showed no significant trends for the free saccharide under similar conditions.

Example 10. Preparation of Serotype 15B Polysaccharide-$CRM_{197}$ Conjugate

Preparation of isolated *Streptococcus pneumoniae* serotype 15B polysaccharide Serotype 15B capsular polysaccharides can be obtained directly from bacteria using isolation procedures known to one of ordinary skill in the art. The *S. pneumoniae* serotype 15B were grown in a seed bottle and then transferred to a seed fermentor. Once the targeted optical density was reached, the cells were transferred to a production fermentor. The fermentation was broth was inactivated by the addition of N-lauroyl sarcosine and purified by ultrafiltration and diafiltration.

The purified *S. pneumoniae* serotype 15B polysaccharide was then sized by high pressure homogenization using a PANDA 2K® homogenizer (GEA Niro Soavi, Parma, Italy) to produce the isolated *S. pneumoniae* serotype 15B polysaccharide.

Preferably, the isolated *S. pneumoniae* serotype 15B capsular polysaccharide obtained by the above process comprises at least 0.6 mM acetate per mM of serotype 15B capsular polysaccharide and has a molecular weight between 50 kDa and 500 kDa, preferably 150 kDa to 350 kDa.

Oxidation of Isolated *Streptococcus pneumoniae* Serotype 15B Capsular Polysaccharide Polysaccharide oxidation was carried out in 100 mM potassium phosphate buffer (pH 6.0) by sequential addition of calculated amount of 500 mM potassium phosphate buffer (pH 6.0) and WFI to give final polysaccharide concentration of 2.0 g/L. If required, the reaction pH was adjusted to pH 6.0, approximately. After pH adjustment, the reaction temperature was adjusted to 23° C. Oxidation was initiated by the addition of approximately 0.25 molar equivalents of sodium periodate. The oxidation reaction was performed at 23° C. during 16 hrs, approximately.

Concentration and diafiltration of the activated polysaccharide was carried out using 10K MWCO ultrafiltration cassettes. Diafiltration was performed against 20-fold diavolumes of WFI. The purified activated polysaccharide was then stored at 5° C. The purified activated saccharide was characterized inter alia by (i) saccharide concentration by colorimetric assay; (ii) aldehyde concentration by colorimetric assay; (iii) Degree of Oxidation (iv) Molecular Weight by SEC-MALLS and (v) presence of O-acetyl and glycerol.

SEC-MALLS is used for the determination of the molecular weight of polysaccharides and polysaccharide-protein conjugates. SEC is used to separate the polysaccharides by hydrodynamic volume. Refractive index (RI) and multi-angle laser light scattering (MALLS) detectors are used for the determination of the molecular weight. When light interacts with matter, it scatters and the amount of scattered light is related to the concentration, the square of the dn/dc (the specific refractive index increments), and the molar mass of the matter. The molecular weight measurement is calculated based on the readings from the scattered light signal from the MALLS detector and the concentration signal from the RI detector.

The degree of oxidation (DO=moles of sugar repeat unit/moles of aldehyde) of the activated polysaccharide was determined as follows:

The moles of sugar repeat unit is determined by various colorimetric methods, example by using Anthrone method. The polysaccharide is first broken down to monosaccharides by the action of sulfuric acid and heat. The Anthrone reagent reacts with the hexoses to form a yellow green colored complex whose absorbance is read spectrophotometrically at 625 nm. Within the range of the assay, the absorbance is directly proportional to the amount of hexose present.

The moles of aldehyde also are determined simultaneously, using MBTH colorimetric method. The MBTH assay involves the formation of an azine compound by reacting aldehyde groups (from a given sample) with a 3-methyl-2-benzothiazolone hydrazone (MBTH assay reagent). The excess 3-methyl-2-benzothiazolone hydrazone oxidizes to form a reactive cation. The reactive cation and the azine react to form a blue chromophore. The formed chromophore is then read spectroscopically at 650 nm.

Preferably, the activated *S. pneumoniae* serotype 15B capsular polysaccharide obtained by the above process comprises at least 0.6 mM acetate per mM of serotype 15B capsular polysaccharide and has a molecular weight between 50 kDa and 500 kDa, preferably 150 kDa to 350 kDa.

Conjugation of Activated *S. pneumoniae* Serotype 15B Capsular Polysaccharide with $CRM_{197}$ The conjugation process consisted in the following steps:

a) Compounding with sucrose excipient and lyophilization;
b) Reconstitution of the lyophilized activated polysaccharide and $CRM_{197}$;
c) Conjugation of activated polysaccharide to $CRM_{197}$ and capping; and
d) Purification of the conjugate a) Compounding with Sucrose Excipient, and Lyophilization The activated polysaccharide was compounded with sucrose to a ratio of 25 grams of sucrose per gram of activated polysaccharide. The bottle of compounded mixture was then lyophilized. Following lyophilization, bottles containing lyophilized activated polysaccharide were stored at −20° C. Calculated amount of $CRM_{197}$ protein was shell-frozen and lyophilized separately. Lyophilized $CRM_{197}$ was stored at −20° C.

b) Reconstitution of Lyophilized Activated Polysaccharide and $CRM_{197}$ Protein Lyophilized activated polysaccharide was reconstituted in anhydrous dimethyl sulfoxide (DMSO). Upon complete dissolution of polysaccharide, an equal amount of anhydrous DMSO was added to lyophilized $CRM_{197}$ for reconstitution.

c) Conjugation and Capping

Reconstituted activated polysaccharide was combined with reconstituted $CRM_{197}$ in the reaction vessel (input ratio: 0.8:1), followed by mixing thoroughly to obtain a clear solution before initiating the conjugation with sodium cyanoborohydride. The final polysaccharide concentration in reaction solution is approximately 1 g/L. Conjugation was initiated by adding 1.0-1.5 MEq of sodium cyanoborohydride to the reaction mixture and was incubated at 23° C. for 40-48 hrs. Conjugation reaction was terminated by adding 2 MEq of sodium borohydride ($NaBH_4$) to cap unreacted aldehydes. This capping reaction continued at 23° C. for 3 hrs d) Purification of the Conjugate The conjugate solution was diluted 1:10 with chilled 5 mM succinate-0.9% saline (pH 6.0) in preparation for purification by tangential flow filtration using 100-300K MWCO membranes. The diluted conjugate solution was passed through a 5 μm filter and diafiltration was performed using 5 mM succinate-0.9% saline (pH 6.0) as the medium. After the diafiltration was completed, the conjugate retentate was transferred through a 0.22 μm filter.

The conjugate was diluted further with 5 mM succinate/0.9% saline (pH 6), to a target saccharide concentration of approximately 0.5 mg/mL. Final 0.22 μm filtration step was completed to obtain the glycoconjugate.

Preferably, the conjugate obtained by the above process comprises at least 0.6 mM acetate per mM of serotype 15B capsular polysaccharide, has a molecular weight between 3,000 kDa and 20,000 kDa and has a degree of conjugation between 2 and 6.

Example 11. Characterization of Glycoconjugate Comprising *S. pneumoniae* Serotype 15B Capsular Polysaccharide Covalently Linked to a $CRM_{97}$ Conjugate 1 was prepared by the process of Example 10. Conjugates 2 and 3 were prepared by a similar process using different amount of oxidizing agent. Conjugate 4 was prepared by a similar process except that the purified serotype 15B capsular polysaccharide was not sized and was activated to a lower DO (higher oxidation level) and the conjugation was performed in aqueous medium. Conjugate 5 was prepared by a similar process except that the purified serotype 15B capsular polysaccharide was sized by chemical hydrolysis and the conjugation was performed in aqueous medium. Conjugates 6 and 7 were prepared by a similar process except that the purified serotype 15B capsular polysaccharide was not sized.

The obtained conjugates were characterized and the results are summarized in Table 14.

TABLE 14

*Streptococcus pneumoniae* serotype 15B capsular polysaccharide-$CRM_{197}$ conjugates

| Conjugate | 1 | 2 | 3 | 4 | 5 | 6 | 7 |
|---|---|---|---|---|---|---|---|
| Polysaccharide | Sized | Sized | Sized | Native | Hydrolyzed | Native | Native |
| O-Acetyl; activated Polysaccharide (μmol acetate/μmol poly) | 0.69 | 0.69 | 0.69 | 1.01 | 0.66 | 0.76 | N/A |
| Solvent medium | DMSO | DMSO | DMSO | Aqueous | Aqueous | DMSO | DMSO |
| Activated Polysaccharide DO | 11.4 | 5.8 | 9.7 | 4.8 | 8.8 | 5 | 12 |
| Activated Polysaccharide MW | 196 kDa | 218 kDa | 235 kDa | 435 kDa | 270 kDa | 431 kDa | 460 kDa |
| Yield (%) | 87.2 | 64 | 63.7 | 96.2 | 78.8 | 24.2 | 26.2 |
| Saccharide Protein Ratio | 0.68 | 0.65 | 0.71 | 1.22 | 1.29 | 0.9 | 1.5 |
| Free Saccharide (%) | <5 | <5 | 6.1 | 18.1 | 14.2 | 8.8 | 18 |
| Conjugate MW, SEC-MALLS (kDa) | 6190 | 7090 | 7937 | 1766 | 1029 | 6293 | 4466 |
| O-Acetylation, Conjugate (μmol acetate/μmol poly) | 0.68 | 0.7 | 0.68 | 0.61 | 0.44 | 0.85 | N/A |
| <0.3 $K_d$ (%), SEC | N/A | 73 | N/A | N/A | 62 | N/A | N/A |
| Degree of Conj (AAA); Modified Lys | 3.7 | 3.9 | 4.1 | N/A | 3.4 | N/A | N/A |
| % O-Acetyl Retained in Conjugate | 99% | 100% | 99.5% | 60% | 67% | 100% | N/A |

N/A = not available

The percentage of free polysaccharide is measured by a procedure utilizing aluminum hydroxide gel to bind protein and covalently bound saccharide for removal by centrifugation. Samples are mixed with phosphate buffered aluminum hydroxide gel and centrifuged. Bound saccharide is pelleted with the gel and free saccharide remains in the supernatant. The resulting supernatant and controls samples are quantitated by appropriate colorimetric assays to determine the percentage of free saccharide and to confirm sufficient removal of protein and recovery of saccharide.

For the amino acid analysis the polysaccharide-protein sample is first hydrolyzed into its individual components as free amino acids, using 6 N hydrochloric acid (HCl) hydrolysis under vacuum and heat (160° C. for 15 minutes). After hydrolysis, the samples are analyzed using Amino Acid Analyzer. The individual amino acids are separated through ion exchange chromatography using a step gradient of sodium citrate buffer with temperature and flow rate changes. After separation, the amount of each amino acid residual is quantitatively determined using a postcolumn ninhydrin coupling detection system. In this system, the ninhydrin is mixed with the column eluate in the postcolumn reactor system and the mixture passed into the photometer. The reaction of ninhydrin with elated amino acids yields a purple compound that absorbs maximally at 570 nm. This absorbance is a linear response (function) of the amount of α-amino groups present and this reaction provides quantitative colorimetric assay for all organic compounds with α-amino groups. In the reaction with imino acids such as proline and hydroxyproline, which do not have free amino group, a bright yellow compound is generated and monitored at 440 nm. The peak areas for each amino acid are calculated using both 570 nm and 440 nm wavelength outputs.

The yield is calculated as follows: (amount of polysaccharide in the conjugate×100)/amount of activated polysaccharide.

Conjugates (4 and 5) generated using an aqueous medium demonstrated significant loss in O-acetyl levels. Conjugates generated in DMSO solvent, using native polysaccharide without MW sizing (6 and 7) did not demonstrate loss in O-acetyl levels. However, the conjugate yields were very poor in addition to poor filterability characteristics. Conjugates generated in DMSO using polysaccharides that were sized by high pressure homogenization (1, 2 and 3) had high yield and better filterability characteristics with significant preservation of O-acetyl levels. These conjugates also had very low levels of free polysaccharides.

Example 12. Opsonophagocytic Activity (OPA) Assay Using Pn-Serotype 15B-$CRM_{197}$ Conjugates The immunogenicity of the *S. pneumoniae* serotype 15B conjugates of the invention can be assessed using the OPA assay described below.

Groups of 30 6-7 week old female Swiss Webster mice were immunized with 0.001 μg, 0.01 μg, or 0.1 μg of test conjugates via the subcutaneous route on week 0. The mice were boosted with the same dose of conjugate on week 3 and then bled at week 4. Serotype-specific OPAs were performed on week 4 sera samples.

OPAs are used to measure functional antibodies in murine sera specific for *S. pneumoniae* serotype 15B. Test serum is set up in assay reactions that measure the ability of capsular polysaccharide specific immunoglobulin to opsonize bacteria, trigger complement deposition, thereby facilitating phagocytosis and killing of bacteria by phagocytes. The OPA titer is defined as the reciprocal dilution that results in a 50% reduction in bacterial count over control wells without test serum. The OPA titer is interpolated from the two dilutions that encompass this 50% killing cut-off.

OPA procedures were based on methods described in Hu et al. (2005) Clin Diagn Lab Immunol 12 (2):287-295 with the following modifications. Test serum was serially diluted 2.5-fold and added to microtiter assay plates. Live serotype 15B target bacteria were added to the wells and the plates were shaken at 37° C. for 30 minutes. Differentiated HL-60 cells (phagocytes) and baby rabbit serum (3- to 4-week old, PEL-FREEZ®, 6.25% final concentration) were added to the wells, and the plates were shaken at 37° C. for 45 minutes. To terminate the reaction, 80 μL of 0.9% NaCl was added to all wells, mixed, and a 10 μL aliquot were transferred to the wells of MULTISCREEN® HTS HV filter plates (MILLIPORE®) containing 200 μL of water. Liquid was filtered through the plates under vacuum, and 150 μL of HYSOY® medium was added to each well and filtered through. The filter plates were then incubated at 37° C., 5% $CO_2$ overnight and were then fixed with Destain Solution (Bio-Rad Laboratories, Inc., Hercules, CA). The plates were then stained with Coomassie Blue and destained once. Colonies were imaged and enumerated on a Cellular Technology Limited (CTL) (Shaker Heights, OH) IMMUNOSPOT® Analyzer. Raw colony counts were used to plot kill curves and calculate OPA titers.

The immunogenicity of conjugates 1 and 2 has been tested according to the above mentioned assay. One additional conjugate and an unconjugated native *S. pneumoniae* serotype 15B capsular polysaccharide (unconjugated PS) were also tested in the same assay:

Conjugate 9 was prepared by conjugation of native (i.e., not sized) serotype 15B capsular polysaccharide to $CRM_{197}$ by reductive amination in aqueous solution.

The results are shown at Table 15.

TABLE 15

OPA Titers of Animal Testing using Serotype 15B-$CRM_{197}$ Conjugates

| | OPA GMT (95% CI) | | |
|---|---|---|---|
| | 0.001 μg | 0.01 μg | 0.1 μg |
| Conjugate 1 | 485 (413, 569) | 804 (565, 1145) | 1563 (1048, 2330) |
| Conjugate 2 | 556 (438, 707) | 871 (609, 1247) | 1672 (1054, 2651) |
| Conjugate 9 | 395 (329, 475) | 856 (627, 1168) | 1802 (1108, 2930) |
| Unconjugated PS | — | — | 698 (466, 1045) |

As shown in the Table 15 above, conjugates 1 and 2, when administered to mice, generated antibodies capable of opsonizing *S. pneumoniae* serotype 15B, triggering complement deposition, thereby facilitating phagocytosis and killing of bacteria by phagocytes. In addition, despite their lower molecular weight, they also exhibited similar level of immunogenicity as compared to conjugate 9 which has not been sized.

Example 13. Preparation of Serotype 22F Polysaccharide-$CRM_{197}$ Conjugate

Preparation of Isolated *S. pneumoniae* Serotype 22F Polysaccharide

The *S. pneumoniae* serotype 22F were grown in a seed bottle and then transferred to a seed fermentor. Once the targeted optical density was reached, the cells were transferred to a production fermentor. The fermentation was broth was inactivated by the addition of N-lauroyl sarcosine and purified by ultrafiltration and diafiltration.

The purified *S. pneumoniae* serotype 22F polysaccharide was sized by high pressure homogenization using a PANDA 2K® homogenizer (GEA Niro Soavi, Parma, Italy) to produce the isolated *S. pneumoniae* serotype 22F polysaccharide Oxidation of Isolated *S. pneumoniae* Serotype 22F Capsular Polysaccharide Oxidation of polysaccharide was carried out in 100 mM potassium phosphate buffer (pH 5.8) obtained by sequential addition of calculated amount of 500 mM potassium phosphate buffer (pH 5.8) and WFI to give final polysaccharide concentration of 2.0 g/L. If required, the reaction pH was adjusted to 5.8, approximately. After pH adjustment, the reaction temperature was lowered to 5° C. Oxidation was initiated by the addition of 0.10 molar equivalents (MEq) of sodium periodate. The target oxidation reaction time is 16 hrs at 5° C.

The oxidation reaction was quenched with 2 MEq of 2,3-butanediol under continuous stirring at 5° C. for 1-2 hrs.

Concentration and diafiltration of the activated polysaccharide was carried out using 100K MWCO ultrafiltration cassettes. Diafiltration was performed against 35-fold diavolume of WFI. The purified activated polysaccharide was stored at 5° C. The purified activated saccharide is characterized inter alia by (i) Molecular Weight by SEC-MALLS (ii) presence of O-acetyl and (iii) Degree of Oxidation.

SEC-MALLS is used for the determination of the molecular weight of polysaccharides and polysaccharide-protein conjugates. SEC is used to separate the polysaccharides by hydrodynamic volume. Refractive index (RI) and multi-angle laser light scattering (MALLS) detectors are used for the determination of the molecular weight. When light interacts with matter, it scatters and the amount of scattered light is related to the concentration, the square of the dn/dc (the specific refractive index increments), and the molar mass of the matter. The molecular weight measurement is calculated based on the readings from the scattered light signal from the MALLS detector and the concentration signal from the RI detector.

The degree of oxidation (DO=moles of sugar repeat unit/moles of aldehyde) of the activated polysaccharide was determined as follows:

The moles of sugar repeat unit is determined by various colorimetric methods, for example by using Anthrone method. The polysaccharide is first broken down to monosaccharides by the action of sulfuric acid and heat. The Anthrone reagent reacts with the hexoses to form a yellow green colored complex whose absorbance is read spectrophotometrically at 625 nm. Within the range of the assay, the absorbance is directly proportional to the amount of hexose present.

The moles of aldehyde also are determined simultaneously, using MBTH colorimetric method. The MBTH assay involves the formation of an azine compound by reacting aldehyde groups (from a given sample) with a 3-methyl-2-benzothiazolone hydrazone (MBTH assay reagent). The excess 3-methyl-2-benzothiazolone hydrazone oxidizes to form a reactive cation. The reactive cation and the azine react to form a blue chromophore. The formed chromophore is then read spectroscopically at 650 nm.

Conjugation of Activated *S. pneumoniae* Serotype 22F Polysaccharide with $CRM_{197}$ The conjugation process consisted in the following steps:

a. Compounding with sucrose excipient, and lyophilization;
b. Reconstitution of the lyophilized polysaccharide and $CRM_{197}$;
c. Conjugation of activated polysaccharide to $CRM_{197}$ and capping; and
d. Purification of the conjugate a. Compounding with Sucrose and Lyophilization The activated polysaccharide was compounded with sucrose (50% w/v in WFI) to a ratio of 25 grams of sucrose per gram of activated polysaccharide. The bottle of compounded mixture was then lyophilized. Following lyophilization, bottles containing lyophilized activated polysaccharide were stored at −20° C. Calculated amount of $CRM_{197}$ protein (target S/P input ratio=1) was shell frozen and lyophilized separately. Lyophilized $CRM_{197}$ was stored at −20° C.

b. Reconstitution of Lyophilized Activated Polysaccharide and $CRM_{197}$ Protein Lyophilized activated polysaccharide was reconstituted in anhydrous dimethyl sulfoxide (DMSO). Upon complete dissolution of polysaccharide, an equal amount of anhydrous DMSO was added to lyophilized $CRM_{197}$ for reconstitution.

c. Conjugation of Activated Polysaccharide to $CRM_{197}$ and Capping

Reconstituted $CRM_{197}$ (in DMSO) was combined in the conjugation reaction vessel with the reconstituted activated polysaccharide. The final polysaccharide concentration in reaction solution is 1 g/L. Conjugation was initiated by adding 1.5 MEq of sodium cyanoborohydride to the reaction mixture and the reaction was incubated at 23° C. for 20 hrs. Termination of conjugation reaction is done by adding 2 MEq of sodium borohydride. The capping reaction was incubated at 23° C. for 3 hrs.

d. Purification of Conjugate

The conjugate solution was diluted 1:5 with chilled 5 mM succinate-0.9% saline (pH 6.0) in preparation for purification by tangential flow filtration using 100K MWCO membranes and a 20× diafiltration was performed using 5 mM succinate-0.9% saline (pH6.0) as the medium. After the diafiltration was completed, the conjugate retentate was further diluted, filtered through a 0.22 μm filter and stored at 2-8° C.

Several conjugates were obtained using the above described process by varying different parameters (e.g., saccharide-protein input ratio, reaction concentration and Meq of sodium cyanoborohydride). Characterization for representative Pn-22F glycoconjugates to $CRM_{197}$ is provided in Table 16

TABLE 16

| Pneumococcal Serotype 22F-$CRM_{197}$ conjugates | | | | | | | | | | |
|---|---|---|---|---|---|---|---|---|---|---|
| Batch | 1 | 2 | 3 | 4 | 5 | 6 | 7 | 8 | 9 | 10 |
| Degree of Oxidation (D.O) | 12.6 | 19.5 | 17.2 | 14.0 | 12.4 | 14.9 | 11.1 | 14.6 | 14.4 | 13.7 |
| Activated Saccharide MW by MALLS (kDa) | 540 | 697 | 864 | 92 | 866 | 631 | 614 | 639 | 709 | 416 |
| Conjugate Results | | | | | | | | | | |
| Saccharide/ Protein Ratio | 0.75 | 0.87 | 2 | 0.8 | 0.8 | 0.4 | 1.9 | 0.8 | 0.65 | 1.0 |
| O-Ac (%) | 105 | 100 | N/A | N/A | N/A | N/A | N/A | N/A | N/A | N/A |
| % Free Saccharide | <5 | 2 | 15.5 | 35 | <5 | <5 | 33 | <5 | <5 | 8 |
| MW by SEC-MALLS (kDa) | 2787 | 1668 | 2194 | 1419 | 5039 | 10450 | 1577 | 3911 | 3734 | 4453 |

N/A = not available

The % O-Acetyl (preserved) level in the final conjugate was calculated from the ratio of the O-Acetyl content of the conjugate (μmol O-Acetyl per μmol of the serotype 22F saccharide repeat unit) relative to the O-Acetyl content of the polysaccharide (μmol 0-Acetyl per μmol of the serotype 22F saccharide repeat unit).

The immunogenicity of the conjugates obtained above have been assessed using the opsonophagocytic assay (OPA) described below.

Groups of thirty 6-7 week old female Swiss Webster mice were immunized with 0.001 μg, 0.005 μg or 0.01 μg of test conjugates via the subcutaneous route on week 0. The mice were boosted with the same dose of conjugate on week 3 and then bled at week 4. Serotype-specific OPAs were performed on week 4 sera samples.

Opsonophagocytic activity (OPA) assays are used to measure functional antibodies in murine sera specific for *S.*

*pneumonia* serotype 22F. Test serum is set up in assay reactions that measure the ability of capsular polysaccharide specific immunoglobulin to opsonize bacteria, trigger complement deposition, thereby facilitating phagocytosis and killing of bacteria by phagocytes. The OPA titer is defined as the reciprocal dilution that results in a 50% reduction in bacterial count over control wells without test serum. The OPA titer is interpolated from the two dilutions that encompass this 50% killing cut-off.

OPA procedures were based on methods described in Hu et al. (2005) Clin Diagn Lab Immunol 12(2):287-295 with the following modifications. Test serum was serially diluted 2.5-fold and added to microtiter assay plates. Live serotype 22F target bacterial strains were added to the wells and the plates were shaken at 25° C. for 30 minutes. Differentiated HL-60 cells (phagocytes) and baby rabbit serum (3- to 4-week old, PEL-FREEZ®, 12.5% final concentration) were added to the wells, and the plates were shaken at 37° C. for 45 minutes. To terminate the reaction, 80 μL of 0.9% NaCl was added to all wells, mixed, and a 10 μL aliquot were transferred to the wells of MULTISCREEN® HTS HV filter plates (MILLIPORE®) containing 200 μL of water. Liquid was filtered through the plates under vacuum, and 150 μL of HYSOY® medium was added to each well and filtered through. The filter plates were then incubated at 37° C., 5% $CO_2$ overnight and were then fixed with Destain Solution (Bio-Rad Laboratories, Inc., Hercules, CA). The plates were then stained with Coomassie Blue and destained once. Colonies were imaged and enumerated on a Cellular Technology Limited (CTL) (Shaker Heights, OH) IMMUNOSPOT® Analyzer. Raw colony counts were used to plot kill curves and calculate OPA titers.

The Opsonophagocytic activity (OPA) titers for Serotype 22F-$CRM_{197}$ conjugates were determined as mentioned above. OPA titers (geometric mean titer (GMT) with 95% confidence interval (CI)) at four weeks at different doses are shown in Tables 17 and 18, (two separate experiments) demonstrating that the serotype 22F conjugate (Batches 1-7; also see Table 16 for characterization data of these conjugates) elicited OPA titers in a murine immunogenicity model.

TABLE 17

Immunogenicity of Serotype 22F-$CRM_{197}$ Conjugates

| | OPA GMT (95% CI) | | |
|---|---|---|---|
| Sample No. | 0.001 μg | 0.005 μg | 0.01 μg |
| 1 | 86 (45, 165) | 597 (285, 1252) | 2519 (1409, 4504) |
| 2 | 98 (51, 191) | 782 (410, 1492) | 2236 (1319, 3790) |
| 3 | 35 (18, 69) | 250 (122, 512) | 509 (273, 950) |

TABLE 18

Immunogenicity of Serotype 22F-$CRM_{197}$ Conjugates

| | OPA GMT (95% CI) | |
|---|---|---|
| Sample No. | 0.001 μg | 0.01 μg |
| 4 | 37 (18, 76) | 3383 (1911, 5987) |
| 5 | 45 (20, 103) | 1773 (1072, 2931) |
| 6 | 235 (108, 513) | 4335 (3018, 6226) |
| 7 | 10 (7, 13) | 252 (138, 457) |

Example 14. Preparation of Pn-11A Conjugates to $CRM_{197}$

Preparation of Pn-11A RAC Glycoconjugates

The frozen sized polysaccharide stored in de-ionized water or 25 mM potassium phosphate buffer (pH 6.0) was thawed at 5° C.

Oxidation of Polysaccharide

Polysaccharide oxidation was carried out in 100 mM potassium phosphate buffer (pH 6.0) by addition of 500 mM potassium phosphate buffer (pH 6.0) and WFI to give final polysaccharide concentration of 2.0 g/L. Oxidation reaction was carried out at 23° C. Oxidation was initiated by the addition of sodium periodate. The agitation rate ranges from 100-140 rpm.

Purification of Activated 11A Polysaccharide

Concentration and diafiltration of the activated polysaccharide was carried out using ultrafiltration cassettes. Diafiltration was performed against 20-fold diavolume of WFI. After 0.22 μm filtration, the purified activated polysaccharide was stored at 5° C.

Conjugation Process Description

The conjugation process consisted in the following steps:

a. Shell freezing and lyophilization of $CRM_{197}$ protein;
b. Reconstitution of the activated polysaccharide and $CRM_{197}$;
c. Conjugation of activated polysaccharide to $CRM_{197}$; and
d. Purification and dilution of the conjugate a. Shell Freezing and Lyophilization of $CRM_{197}$ Protein $CRM_{197}$ protein was shell-frozen and lyophilized.

b. Reconstitution of Activated Polysaccharide and $CRM_{197}$ Protein

Activated polysaccharide solution (~10 g/L) was charged into reactor followed by addition of calculated amount 0.5 N sodium phosphate buffer (pH 7.2). Under stirring, lyophilized $CRM_{197}$ was added and the reaction mixture was stirred for 2-4 hours in order to reach complete dissolution of $CRM_{197}$.

c. Conjugation and Capping

Conjugation was initiated by adding cyanoborohydride. The reaction mixture was incubated at 23° C. for 72-96 hrs. Termination of conjugation reaction was done by adding 0.5×WFI followed by 2 MEq of sodium borohydride. This capping reaction was kept at 23° C. for 3-4 hrs.

d. Dilution and Initial Purification of Conjugate

The conjugate solution was diluted 1:5 (reaction volume) with 0.15 N sodium phosphate buffer (pH 8.0) in preparation for purification by tangential flow filtration (TFF). Diluted conjugate was mixed in the dilution vessel and then passed through a 5 μm filter. The filtered conjugate solution was then concentrated down to 1-2 g/L. A two-steps diafiltration process was performed. In step one, TFF was carried out using 30× (diafiltration volume) of 0.15 N sodium phosphate buffer (pH 8.0) followed by 20× of 5 mM succinate-0.9% NaCl (pH6.0). After the initial diafiltration was completed, the conjugate retentate was transferred through a 0.45 μm filter into a collection tank.

Final Diafiltration of Conjugate

The final purification step was a 20× diafiltration with 5 mM succinate-0.9% NaCl, pH 6.0 medium using regenerated cellulose membranes.

Dilution of the Monovalent Bulk Conjugate (MBC)

The conjugate was diluted further with 5 mM succinate/0.9% NaCl, pH 6, to a target saccharide concentration of 0.5 mg/mL. Final 0.22 μm filtration step was completed to prepare the monovalent bulk conjugate (MBC) product for formulation.

Several conjugates were obtained using the above described process by varying different parameters (e.g., saccharide-protein input ratio, reaction concentration and Meq of sodium cyanoborohydride). Characterization for representative Pn-11A glycoconjugates to $CRM_{197}$ is provided in Table 19 (batches 1 to 5).

d. Purification and Dilution of the Conjugate

The conjugate solution was purified and diluted using a similar process as described above.

Several conjugates were obtained using the above described process by varying different parameters (e.g., saccharide-protein input ratio, reaction concentration and Meq of sodium cyanoborohydride). Characterization for representative Pn-11A glycoconjugates to $CRM_{197}$ obtained by the above process is provided at Table 19 (batches 6 to 8).

TABLE 19

Pneumococcal Serotype 11A-$CRM_{197}$ conjugates

| Batch | 1 | 2 | 3 | 4 | 5 | 6 | 7 | 8 |
|---|---|---|---|---|---|---|---|---|
| Activated Saccharide MW by MALLS (kDa) | 207 | 129 | 103 | 199 | 183 | 232 | 113 | 113 |
| Conjugate Results | | | | | | | | |
| Saccharide/Protein Ratio | 1.24 | 1.09 | 1.32 | 1.47 | 1.31 | 1 | 0.78 | 0.68 |
| Acetate (mol/mol PS) | 2.72 | 2.89 | 2.72 | 3.2 | 3.13 | N/A | N/A | N/A |
| Glycerol (mol/mol PS)* | 0.62 | 0.68 | 0.75 | 0.51 | 0.41 | N/A | N/A | N/A |
| MW by SEC-MALLS kDa) | 3224 | 837 | 623 | 827 | 994 | 12200 | 6543 | 15730 |

N/A = not available

*Glycerol was quantitated by High Performance Anion Exchange Chromatography with Pulsed Amperometric Detection (HPAEC-PAD) after its release from the polysaccharide by hydrofluoric acid (HF).

Preparation of Pn-11A Glycoconjugates using RAC/DMSO

Oxidized polysaccharide was prepared and purified as described above (see Preparation of Pn-11A RAC Glycoconjugates).

Conjugation Via Reductive Amination in DMSO (RAC/DMSO)

Conjugation of 11A through RAC/DMSO consisted of the following steps:

a. Compounding with sucrose, shell freezing and lyophilization;
b. Reconstitution of the lyophilized polysaccharide and $CRM_{197}$;
c. Conjugation of activated polysaccharide to $CRM_{197}$; and
d. Purification and dilution of the conjugate.

a. Compounding with Sucrose, Shell Freezing and Lyophilization

The activated polysaccharide prepared from sized polysaccharide was compounded with sucrose (50% w/v in WFI) to a ratio of 25 grams of sucrose per gram of activated polysaccharide. The components were mixed the shell-frozen bottle of compounded mixture was then lyophilized. $CRM_{197}$ protein was shell-frozen and lyophilized separately.

b. Reconstitution of Lyophilized Activated Polysaccharide and $CRM_{197}$ Protein Lyophilized activated polysaccharide was reconstituted in DMSO at 2 mg/mL concentration. Upon the complete dissolution of polysaccharide, DMSO was added to lyophilized $CRM_{197}$ for reconstitution c. Conjugation and Capping Reconstituted $CRM_{197}$ (in DMSO) was combined in the conjugation reaction vessel with the reconstituted activated polysaccharide. The final polysaccharide concentration in reaction solution is 1 g/L. Conjugation was initiated by adding cyanoborohydride to the reaction mixture and was incubated at 23° C. for 22 hours. Termination of conjugation reaction is done by adding 2 MEq of sodium borohydride. This capping reaction was kept at 23° C. for 3-4 hrs.

The overall data generated from conjugates prepared by the above reductive amination processes demonstrated that it allowed preparing conjugates with good conjugation yield, low % free saccharide and with good stability.

The immunogenicity of the conjugates obtained above have been assessed using the opsonophagocytic assay (OPA) described below.

Groups of thirty 6-7 week old female Swiss Webster mice were immunized with 0.001 μg, 0.005 μg, 0.01 μg, or 0.1 μg of test conjugates via the subcutaneous route on week 0. The mice were boosted with the same dose of conjugate on week 3 and then bled at week 4. Serotype-specific OPAs were performed on week 4 sera samples.

Opsonophagocytic activity (OPA) assays are used to measure functional antibodies in murine sera specific for *S. pneumonia* serotype 11A. Test serum is set up in assay reactions that measure the ability of capsular polysaccharide specific immunoglobulin to opsonize bacteria, trigger complement deposition, thereby facilitating phagocytosis and killing of bacteria by phagocytes. The OPA titer is defined as the reciprocal dilution that results in a 50% reduction in bacterial count over control wells without test serum. The OPA titer is interpolated from the two dilutions that encompass this 50% killing cut-off. OPA procedures were based on methods described in Hu et al. (2005) Clin Diagn Lab Immunol 12 (2):287-295 with the following modifications. Test serum was serially diluted 2.5-fold and added to microtiter assay plates. Live serotype 22F target bacterial strains were added to the wells and the plates were shaken at 25° C. for 30 minutes. Differentiated HL-60 cells (phagocytes) and baby rabbit serum (3- to 4-week old, PEL-FREEZ®, 12.5% final concentration) were added to the wells, and the plates were shaken at 37° C. for 60 minutes. To terminate the reaction, 80 μL of 0.9% NaCl was added to all wells, mixed, and a 10 μL aliquot were transferred to the wells of MULTISCREEN® HTS HV filter plates (MILLIPORE®) containing 200 μL of water. Liquid was filtered through the plates under vacuum, and 150 μL of HYSOY® medium was added to each well and filtered through. The filter plates were then incubated at 37° C., 5% $CO_2$ overnight and were then fixed with Destain Solution (Bio-Rad Laboratories, Inc., Hercules, CA). The plates were then stained with Coomassie Blue and destained once. Colonies were imaged and enumerated on a Cellular Technology Limited (CTL) (Shaker Heights, OH) IMMUNOSPOT® Analyzer. Raw colony counts were used to plot kill curves and calculate OPA titers.

The Opsonophagocytic activity (OPA) titers for serotype 11A-$CRM_{197}$ conjugates in mice were determined as mentioned above. OPA titers (geometric mean titer (GMT) with 95% confidence interval (CI)) at four weeks at different doses are shown in Table 20, demonstrating that the serotype 11A conjugate (Batches 2-4 and 8; also see Table 19 for characterization data of these conjugates) elicited OPA titers in a murine immunogenicity model.

TABLE 20

Immunogenicity of Serotype 11A-$CRM_{197}$ Conjugates

| | OPA GMT (95% CI) | | |
|---|---|---|---|
| Batch No. | 0.001 μg | 0.01 μg | 0.1 μg |
| 2 | 326 (260, 408) | 1391 (794, 2437) | 4366 (3063, 6223) |
| 3 | 389 (316, 478) | 1113 (690, 1795) | 5527 (3698, 8260) |
| 4 | 192 (149, 248) | 926 (661, 1298) | 2800 (1975, 3970) |
| 8 | 303 (224, 411) | 1099 (624, 1935) | 3861 (2629, 5669) |

Example 15. Formulation of a 16-Valent Pneumococcal Conjugate Vaccine

A 16-valent conjugates composition comprising glycoconjugates from *S. pneumoniae* serotypes 1, 3, 4, 5, 6A, 6B, 7F, 9V, 14, 15B, 18C, 19A, 19F, 22F, 23F and 33F (16vPnC) all individually conjugated to $CRM_{197}$ was formulated.

Glycoconjugates from *S. pneumoniae* from serotypes 15B, 22F and 33F were produced as disclosed above and *S. pneumoniae* glycoconjugates from serotypes 1, 3, 4, 5, 6A, 6B, 7F, 9V, 14, 18C, 19A, 19F and 23F were produced as disclosed in WO 2006/110381. The required volumes of bulk concentrates were calculated based on the batch volume and the bulk saccharide concentrations. The formulated bulk vaccine was prepared by adding the required volume of NaCl/succinate buffer (pH 5.8) to obtain a final target buffer concentration of succinate 5.0 mM and 150 mM NaCl. Polysorbate 80 to a final concentration of 0.02% and the 16 pneumococcal conjugates were added. The preparation was filtered through a 0.2 μm Millipore PES membrane, followed by the addition of AIPO4. The formulation was mixed to allow for binding and to achieve homogeneity.

The formulation was then filled into glass syringes to deliver a dose volume of 0.5 mL.

The final dosage form consisted in 2.2 μg of each of glycoconjugates from *S. pneumoniae* serotypes 1, 3, 4, 5, 6A, 7F, 9V, 14, 15B, 18C, 19A, 19F, 22F, 23F and 33F individually conjugated to $CRM_{197}$, 4.4 μg of glycoconjugate from *S. pneumoniae* serotype 6B, 5 mM succinate buffer pH 5.8, 0.02 PS80, 150 mM NaCl and 0.25 mg/mL aluminum as AIPO4 for a dose of 0.5 mL. $CRM_{197}$, content was about 38 μg for a dose of 0.5 mL.

Example 16. Formulation of a 20-valent Pneumococcal Conjugate Vaccine

A 20 valent conjugates composition comprising glycoconjugates from *S. pneumoniae* serotypes 1, 3, 4, 5, 6A, 6B, 7F, 8, 9V, 10A, 11A, 12F, 14, 15B, 18C, 19A, 19F, 22F, 23F and 33F (20vPnC) all individually conjugated to $CRM_{197}$ was formulated.

Glycoconjugates from *S. pneumoniae* from serotypes 8, 10A, 11A, 12F, 15B, 22F and 33F were produced as disclosed above and *S. pneumoniae* glycoconjugates from serotypes 1, 3, 4, 5, 6A, 6B, 7F, 9V, 14, 18C, 19A, 19F and 23F were produced as disclosed in WO 2006/110381.

The required volumes of bulk concentrates were calculated based on the batch volume and the bulk saccharide concentrations. The formulated bulk vaccine was prepared by adding the required volume of NaCl/succinate buffer (pH 5.8) to obtain a final target buffer concentration of succinate 5.0 mM and 150 mM NaCl. Polysorbate 80 to a final concentration of 0.02% and the 20 pneumococcal conjugates are added. The preparation was filtered through a 0.2 μm Millipore PES membrane, followed by the addition of AIPO4. The formulation was mixed well to obtain maximum binding of the conjugates to the aluminum.

The formulation is then filled into glass syringes to deliver a dose volume of 0.5 mL.

The final dosage form consisted in 2.2 μg of each of glycoconjugates from *S. pneumoniae* serotypes 1, 3, 4, 5, 6A, 7F, 8, 9V, 10A, 11A, 12F, 14, 15B, 18C, 19A, 19F, 22F, 23F and 33F individually conjugated to $CRM_{197}$, 4.4 μg of glycoconjugate from *S. pneumoniae* serotype 6B, 5 mM succinate buffer pH 5.8, 0.02 PS80, 150 mM NaCl and 0.25 mg/mL aluminum as AIPO4 for a dose of 0.5 mL. $CRM_{197}$, content was about 46 μg for a dose of 0.5 mL.

Example 17. Immunogenicity of a 16-Valent Immunogenic Composition

The immunogenicity of the 16-valent immunogenic composition (see Example 15) was assessed in Rabbits using multiplexed direct Luminex immunoassays (dLIAs) to measure serotype-specific IgG concentrations in sera and serotype-specific OPAs.

Groups of ten 2.5 kg to 3.5 kg female New Zealand white rabbits were immunized with the proposed human clinical dose (2.2 μg of conjugate except serotype 6B which was at 4.4 μg; plus 0.1 mg aluminum as AIPO4) via the intramuscular route on week 0. The rabbits were boosted with the same dose of conjugate vaccine on week 2 and then bled at week 4. Serotype-specific dLIAs and OPAs were performed on week 0 and week 4 sera samples.

To quantify the total polysaccharide binding antibody (IgG) specific to each pneumococcal polysaccharide (PnPS), rabbit sera were evaluated in two direct Luminex immunoassays (dLIAs; 13-plex dLIA, PREVNAR 13® serotypes and 7-plex dLIA, additional serotypes). The 13-plex assay measures anti-PnPS antibodies specific to the 13 serotypes included in the 13-valent pneumococcal conjugate (PnC) vaccine (1, 3, 4, 5, 6A, 6B, 7F, 9V, 14, 18C, 19A, 19F, and 23F) and the 7-plex assay measures anti-PnPS antibodies to the additional serotypes (15B, 22F, 33F). Each assay contains a combination of 13 or 7 spectrally distinct magnetic microspheres coupled to PnPS conjugates (PnPS-PLL conjugates: PnPS conjugated to poly-L-Lysine).

Briefly, reference standard, controls and test sera were first pre-adsorbed with two Pn absorbents; CWPS1 (cell wall polysaccharide from PnA containing C-polysaccharide) and CWPS2 (CWP from acapsular *S. pneumoniae* serotype 2) to block non-specific antibodies from binding to the PnPS coating antigen. Following preadsorption, the PnPS-coupled microspheres were incubated with appropriately diluted reference standard serum, controls or rabbit test sera. After incubation, each mixture was washed and an R-Phycoerythrin-conjugated goat anti-rabbit IgG secondary antibody was added.

Fluorescent signals (expressed as median fluorescence intensities (MFIs)) were measured using a Bio-Plex reader and correlated to the amount of bound PnPS-specific IgG. Values for test sera are reported as (Units/mL, U/mL).

Serotype-specific OPAs were performed as described above. The OPA titer is the reciprocal of the highest serum dilution resulting in 50% reduction in the number of bacterial colony forming units (CFUs) when compared to the control without serum (defined as the background CFU). The titer is interpolated from the two dilutions that encompass this 50% killing cut-off.

TABLE 21

16vPnC Total IgG Concentrations and OPA Titers

| | Total IgG (Pn dLIA) | | | | Opsonophagocytic Antibody (OPA) | | | |
|---|---|---|---|---|---|---|---|---|
| Sero type | Wk 0 GMC (μg/ml) | Wk 4 GMC (μg/ml) | Wk 4 95% CI (LCI-UCI) | IgG GMC Ratio Wk 4:Wk 0 | Wk 0 GMT | W k4 GMT | Wk 4 95% CI (LCI-UCI) | OPA GMT Ratio Wk 4:Wk 0 |
| 1 | 0.08 | 28 | 17-44 | 369 | 4 | 87 | 55-139 | 22 |
| 3 | 0.08 | 88 | 60-128 | 1062 | 4 | 214 | 151-304 | 54 |
| 4 | 0.08 | 30 | 14-67 | 402 | 4 | 934 | 551-1583 | 233 |
| 5 | 0.08 | 34 | 18-64 | 449 | 4 | 368 | 232-584 | 87 |
| 6A | 0.03 | 46 | 15-142 | 1835 | 4 | 3026 | 1607-5696 | 756 |
| 6B | 0.08 | 89 | 33-241 | 1182 | 4 | 6156 | 3043-12453 | 1539 |
| 7F | 0.01 | 50 | 31-78 | 3969 | 6 | 2917 | 2013-4227 | 528 |
| 9V | 0.03 | 24 | 15-38 | 881 | 5 | 613 | 426-883 | 112 |
| 14 | 0.08 | 28 | 20-39 | 368 | 19 | 449 | 331-610 | 24 |
| 18C | 0.05 | 79 | 45-139 | 1587 | 4 | 1847 | 1003-3401 | 462 |
| 19A | 0.08 | 120 | 71-205 | 1605 | 4 | 1410 | 851-2336 | 352 |
| 19F | 0.08 | 156 | 96-255 | 2083 | 4 | 3207 | 1783-5771 | 802 |
| 23F | 0.05 | 33 | 13-84 | 668 | 4 | 997 | 487-2042 | 249 |
| 15B | 0.05 | 54 | 40-71 | 1073 | 6 | 741 | 514-1069 | 116 |
| 22F | 0.08 | 158 | 95-262 | 2103 | 5 | 1078 | 661-1756 | 211 |
| 33F | 0.10 | 11 | 6-20 | 115 | 49 | 1337 | 829-2154 | 27 |

Abbreviations:
GMC, geometric mean concentration;
CI, confidence interval;
LCI, lower confidence interval;
UCI, upper confidence interval.

Results showed a significant increase in serotype-specific IgG and functional OPA antibody responses following two immunizations with 16vPnC (Table 21). Serum IgG levels increased more than 2-logs above baseline. Similarly, a robust functional OPA antibody response was elicited with a minimum of a 22-fold increase in OPA GMT above baseline. Pre-immune sera (Wk 0) showed undetectable levels of PnPS-specific IgG and functional OPA antibody for the majority of the 16v Pn serotypes with the exception of serotypes 14 and 33F. Low level OPA titers were present for these serotypes but these baseline responses did not adversely affect the antibody response following vaccination.

Example 18. Immunogenicity of a 20-Valent Immunogenic Composition

The immunogenicity of the 20-valent immunogenic composition (as prepared at example 16) was assessed in rabbits using multiplexed direct Luminex immunoassays (dLIAs) to measure serotype-specific IgG concentrations in sera and serotype-specific OPAs.

Groups of ten 2.5 kg to 3.5 kg female New Zealand white rabbits were immunized with the proposed human clinical dose (2.2 μg of conjugate except serotype 6B which was at 4.4 μg; plus 0.1 mg aluminum as AIPO4) via the intramuscular route on week 0. The rabbits were boosted with the same dose of conjugate vaccine on week 2 and then bled at week 4. Serotype-specific dLIAs and OPAs were performed on week 0 and week 4 sera samples.

To quantify the total polysaccharide binding antibody (IgG) specific to each pneumococcal polysaccharide (PnPS), rabbit sera were evaluated in two direct Luminex immunoassays (dLIAs; 13-plex dLIA, PREVNAR 13® serotypes and 7-plex dLIA, additional serotypes). The 13-plex assay measures anti-PnPS antibodies specific to the 13 serotypes included in the 13-valent pneumococcal conjugate (PnC) vaccine (1, 3, 4, 5, 6A, 6B, 7F, 9V, 14, 18C, 19A, 19F, and 23F) and the 7-plex assay measures anti-PnPS antibodies to the additional serotypes (15B, 22F, 33F). Each assay contains a combination of 13 or 7 spectrally distinct magnetic microspheres coupled to PnPS conjugates (PnPS-PLL conjugates: PnPS conjugated to poly-L-Lysine).

Briefly, reference standard, controls and test sera were first pre-adsorbed with two Pn absorbents; CWPS1 (cell wall polysaccharide from PnA containing C-polysaccharide) and CWPS2 (CWP from acapsular *S. pneumoniae* serotype 2) to block non-specific antibodies from binding to the PnPS coating antigen. Following preadsorption, the PnPS-coupled microspheres were incubated with appropriately diluted reference standard serum, controls or rabbit test sera. After incubation, each mixture was washed and an R-Phycoerythrin-conjugated goat anti-rabbit IgG secondary antibody was added. Fluorescent signals (expressed as median fluorescence intensities (MFIs)) were measured using a Bio-Plex reader and correlated to the amount of bound PnPS-specific IgG. Values for test sera are reported as (Units/mL, U/mL).

Serotype-specific OPAs were performed as described above. The OPA titer is the reciprocal of the highest serum dilution resulting in 50% reduction in the number of bacterial colony forming units (CFUs) when compared to the control without serum (defined as the background CFU). The titer is interpolated from the two dilutions that encompass this 50% killing cut-off.

Rabbits immunized with the 20vPnC also demonstrated significant increases in total IgG and functional OPA antibody titers against serotypes common to the 16v and 20v formulations as well as to the additional four serotypes (8, 10A, 11A, and 12F) (Table 22). A 2-log increase in serum IgG levels across the 20 serotypes was induced following two immunizations. OPA GMTs elicited with the vaccine were at least 27-fold above baseline. Low level OPA titers in pre-immune sera for serotypes 14 and 33F were similarly observed following 20vPnC vaccination, but again did not alter the robustness of the post-vaccination antibody responses.

The 16vPnC and 20vPnC formulations elicited a robust humoral response that was both specific for Pneumococcal polysaccharides and associated with functional killing of the bacterium (see Tables 21 and 22). In conclusion, studies shown in Examples 17 and 18 demonstrated good immunogenicity of both the 16vPnC and 20vPnC formulations.

TABLE 22

20vPnC Total IgG Concentrations and OPA Titers

| Sero type | Total IgG (Pn dLIA) Wk 0 GMC (μg/ml) | Wk 4 GMC (μg/ml) | Wk 4 95% CI (LCI-UCI) | IgG GMC Ratio Wk 4:Wk 0 | Opsonophagocytic Antibody (OPA) Wk 0 GMT | Wk 4 GMT | Wk 4 95% CI (LCI-UCI) | OPA GMT Ratio Wk4:Wk 0 |
|---|---|---|---|---|---|---|---|---|
| 1 | 0.08 | 28 | 19-43 | 379 | 4 | 106 | 69-164 | 27 |
| 3 | 0.08 | 116 | 76-176 | 1542 | 4 | 286 | 193-425 | 72 |
| 4 | 0.08 | 62 | 39-97 | 821 | 4 | 1477 | 954-2287 | 369 |
| 5 | 0.08 | 49 | 33-71 | 648 | 4 | 509 | 350-742 | 127 |
| 6A | 0.03 | 30 | 14-66 | 1209 | 4 | 3682 | 2743-4944 | 849 |
| 6B | 0.08 | 58 | 36-94 | 775 | 4 | 4469 | 3002-6653 | 1117 |
| 7F | 0.02 | 62 | 39-101 | 3681 | 6 | 3226 | 2226-4675 | 500 |
| 9V | 0.05 | 30 | 19-48 | 644 | 6 | 956 | 634-1442 | 150 |
| 14 | 0.08 | 34 | 20-60 | 457 | 12 | 506 | 348-736 | 42 |
| 18C | 0.05 | 106 | 67-166 | 2115 | 4 | 1942 | 1263-2986 | 485 |
| 19A | 0.08 | 112 | 73-171 | 1493 | 4 | 1580 | 1071-2332 | 395 |
| 19F | 0.08 | 178 | 119-266 | 2372 | 4 | 3392 | 2085-5519 | 848 |
| 23F | 0.05 | 48 | 23-103 | 960 | 4 | 1514 | 889-2577 | 378 |
| 15B | 0.05 | 70 | 51-98 | 1410 | 6 | 1332 | 949-1869 | 210 |
| 22F | 0.10 | 172 | 118-250 | 1811 | 5 | 1304 | 1000-1700 | 279 |
| 33F | 0.12 | 14 | 10-20 | 120 | 54 | 1490 | 1117-1989 | 28 |
| 8 | 0.13 | 144 | 100-207 | 1149 | 4 | 1388 | 988-1949 | 333 |
| 10A | 0.13 | 54 | 31-94 | 433 | 5 | 1129 | 732-1741 | 236 |
| 11A | 0.13 | 178 | 125-254 | 1423 | 7 | 10483 | 6373-17241 | 1434 |
| 12F | 0.08 | 31 | 15-63 | 408 | 4 | 828 | 608-1127 | 191 |

Abbreviations:
GMC, geometric mean concentration;
CI, confidence interval;
LCI, lower confidence interval;
UCI, upper confidence interval.

Example 19. Evaluation of Cross-Reactive Opsonophagocytic Immune Responses within Serogroup 9 of *Streptococcus pneumoniae*

The pneumococcal opsonophagocytic assay (OPA), which measures killing of *S. pneumoniae* cells by phagocytic effector cells in the presence of functional antibody and complement, is considered to be an important surrogate for evaluating the effectiveness of pneumococcal vaccines.

Materials and Methods

Two randomly selected subsets of immune sera from adults vaccinated with a 13-valent pneumococcal conjugate vaccine (13v PnC) were tested in OPA assays for the serotypes 9V, 9A, 9L and 9N. The sera were collected from U.S. clinical trials 6115A1-004 (N=59, post-vaccinated) and 6115A1-3005 (N=66, matched pre- and post-vaccination), respectively.

Study 6115A1-3005 (ClinicalTrials.gov Identifier: NCT00546572) was a phase 3, randomized, active-controlled, modified double-blind trial evaluating the safety, tolerability, and immunogenicity of PREVNAR 13® compared with a 23-valent pneumococcal polysaccharide vaccine (23vPS) in ambulatory elderly individuals aged 70 years and older who received 1 dose of 23vPS at least 5 years before study enrollment (see: http://clinicaltrials.gov/ct2/show/NCT00546572; accessed on Mar. 31, 2014). Study 6115A1-004 (ClinicalTrials.gov Identifier: NCT00427895) was a phase 3, randomized, active-controlled, modified double-blind trial evaluating the safety, tolerability, and immunogenicity of a 13-valent pneumococcal conjugate vaccine (13vPnC) compared to a 23-valent pneumococcal polysaccharide vaccine (23vPS) in adults 60 to 64 years old who are naive to 23vPS and the safety, tolerability, and immunogenicity of 13vPnC in adults 18 to 59 years old who are naïve to 23vPS (see: http://clinicaltrials.gov/show/NCT00427895; accessed on Mar. 31, 2014).

The 13-valent pneumococcal conjugate vaccine (13vPnC) tested in these studies contained conjugates from pneumococcal serotypes 1, 3, 4, 5, 6A, 6B, 7F, 9V, 14, 18C, 19A, 19F, and 23F, individually conjugated to diphtheria cross-reacting material 197 ($CRM_{197}$) carrier protein.

OPAs are used to measure functional antibodies in human sera against *S. pneumoniae* serotypes 9V, 9N, 9A and/or 9L. Test serum is set up in assay reactions that measure the ability of capsular polysaccharide specific immunoglobulin to opsonize bacteria, trigger complement deposition, thereby facilitating phagocytosis and killing of bacteria by phagocytes. The OPA titer is defined as the reciprocal dilution that results in a 50% reduction in bacterial count over control wells without test serum. The OPA titer is interpolated from the two dilutions that encompass this 50% killing cut-off.

OPA procedures were based on methods described in Hu et al. (2005) Clin Diagn Lab Immunol 122):287-295. Test heat-inactivated serum was serially diluted 2.5-fold and was added together with the target bacteria in assay plates and incubated for 30 minutes with shaking. Differentiated HL-60 cells (phagocytes) and baby rabbit serum (3- to 4-week old, PEL-FREEZ®, Arkansas, 12.5% final concentration) were then added to the wells, at an approximate effector to target ratio of 200:1, and incubated at 37° C. with shaking. To terminate the reaction, 80 μL of 0.9% NaCl was added to all wells, mixed, and a 10 μL aliquot were transferred to the wells of MULTISCREEN® HTS HV filter plates (MILLIPORE®) containing 200 μL of water. Liquid was filtered through the plates under vacuum, and 150 μL of HYSOY® medium was added to each well and filtered through. The filter plates were then incubated at 37° C., 5% $CO_2$ overnight and were then fixed with Destain Solution (Bio-Rad Laboratories, Inc., Hercules, CA). The plates were then stained with Coomassie Blue and destained once. Colonies were imaged and enumerated on a Cellular Technology Limited (CTL) (Shaker Heights, OH) IMMUNOSPOT® Analyzer.

Statistical Analysis: Pearson two-tailed correlations were calculated.

Results—OPA Responses in 9V, 9A, 9L and 9N

The cross-functional response from immune sera of adults immunized with 13vPnC against serotypes 9A, 9L, and 9N, was evaluated in the respective microcolony Opsonophagocytic Assays (mcOPAs), along with the homologous functional response to serotype 9V. Two randomly selected subsets of immune sera from adults vaccinated with 13vPnC were tested. The sera were collected from U.S. clinical trials 6115A1-004 (N=59, post-vaccinated) and 6115A1-3005 (N=66, matched pre- and post-vaccination), respectively.

Subjects in study 6115A1-004 were previously naïve to any pneumococcal vaccination and received a single dose of 13vPnC as part of the study protocol. The immune sera from study 6115A1-004 shows a similar percentage of responders for all the serogroups with values of 98.3%, 98.3%, 100% and 93.2% for 9V, 9A, 9L and 9N respectively (FIG. 11), supporting the results from 6115A1-3005 (FIG. 12). A relative good OPA titer correlations were observed between serotypes 9V and 9A (Pearson correlation $\rho=0.5456$, $p<0.0001$) or 9L ($\rho=0.7353$, $p<0.0001$), but not with 9N ($\rho=0.1217$, $p<0.3627$).

Subjects in study 6115A1-3005 had previously received 1 dose of 23vPS at least 5 years before study enrollment and received a single dose of 13vPnC as part of the study protocol. Matched pre- and post-vaccination serum panel (N=66) from adults immunized with 13vPnC (study 6115A1-3005) was evaluated on OPA for the homologous response to serotype 9V and for cross-reactivity of anti-9V antibodies to serotypes 9A, 9L, and 9N. As shown in FIG. 12, a relatively high immunity (percentage responders) to 9V (84%), 9A (66%), 9L (82%) and 9N (86%) was detected in the OPA assay likely due to their previous immunization with 23vPS, which includes unconjugated polysaccharides from serotypes 9V and 9N. However, the percentage responders increased to 95% or more for all four serotypes after vaccination with 13vPnC, which only contains serotype 9V conjugate from serogroup 9. The fold-rise in titer values are shown in Table 23 and are similar between the serotypes also suggesting cross-reactivity.

TABLE 23

OPA Titer Fold-Rise Matched Pre- and Post-Vaccination, 13vPnC

| | OPA Titers | | | | | | | |
|---|---|---|---|---|---|---|---|---|
| | 9V | | 9A | | 9L | | 9N | |
| | Pre | Post | Pre | Post | Pre | Post | Pre | Post |
| GMT | 221 | 1323 | 41 | 308 | 165 | 706 | 322 | 693 |
| Fold-rise | 5.9 | | 7.5 | | 4.2 | | 2.1 | |

A more comprehensive analysis of the OPA titer distribution is shown in the reverse cumulative distribution curves (RCDC) in FIGS. 13-16. The RCDCs show an increase in serotype-specific immune response post vaccination for serotypes 9V, 9A, 9L and to a lesser extent 9N. The correlation of the fold-rise of titer of individual matched/samples between 9V 9A, 9V/9L, and 9V/9N were also analyzed using Pearson's correlation. Relatively good correlations of fold-rises of titers were observed between serotypes 9V and 9A (Pearson correlation $\rho=0.8720$, $p<0.0001$) or 9N ($\rho=0.5801$, $p<0.0001$), but to a lesser extent with 9L ($\rho=0.1804$, $p<0.1640$).

Conclusion

Based on these data, the 13vPnC vaccine is likely to provide broader serotype coverage by providing additional protection against serotypes 9A, 9L, and 9N.

Example 20: Cross-Functional OPA Responses Between Serotype 15B and Serotype 15C Pneumococcal serogroup 15 includes four structurally-related serotypes: 15A, 15B, 15C, and 15F. Serotypes 15B and 15C are undistinguishable by genetic typing techniques and have similar capsular polysaccharide (PS) composition, except that the 15B-PS is the O-acetylated variant of 15C-PS. To understand whether anti-capsular PS antibodies for serotype 15B are functionally cross-reacting with serotype 15C, 10 rabbits were immunized with 16vPnC (see example 15) and 20vPnC (see example 16) vaccines both containing an immunogenic conjugate comprising *S. pneumoniae* serotype 15B capsular polysaccharide covalently linked to $CRM_{197}$ as disclosed herein as part of their formulation. Sera from pre- and post-vaccination were tested in OPA assays against serotypes 15B and 15C target pneumococcal strains.

Of the 10 rabbits from each group, 100% had OPA response to serotype 15B following immunization with a serotype 15B conjugate. Of these same samples, 100% had OPA response to serotype 15C as well (Table 24 and Table 25). Low OPA titers were observed in prevaccination sera in 15C OPA. However, over 10-fold GMT OPA titer increase with post vaccination sera compared to pre vaccination demonstrated that the immunogenic conjugates of the invention induces the formation of antibodies capable of killing serotype 15B and 15C *Streptococcus pneumonia* in an OPA.

TABLE 24

OPA Titers Against serotypes 15B and 15C strains in Rabbit Sera Pre and Post vaccination with 16vPnC

| | 15B OPA | | 15C OPA | |
|---|---|---|---|---|
| Animal | wk 0 | wk 4 | wk 0 | wk 4 |
| 1 | 4 | 4129 | 50 | 2524 |
| 2 | 4 | 1645 | 182 | 472 |
| 3 | 4 | 1131 | 126 | 818 |
| 4 | 4 | 3199 | 50 | 1189 |
| 5 | 4 | 2664 | 36 | 727 |
| 6 | 4 | 4589 | 68 | 2492 |
| 7 | 11 | 3601 | 169 | 1137 |
| 8 | 4 | 1838 | 165 | 672 |
| 9 | 4 | 1334 | 98 | 528 |
| 10 | 4 | 1108 | 204 | 2425 |
| GMT | 4 | 2222 | 98 | 1075 |

TABLE 25

OPA Titers Against serotypes 15B and 15C strains in Rabbit Sera Pre and Post vaccination with 20vPnC

| | 15B OPA | | 15C OPA | |
|---|---|---|---|---|
| Animal | wk 0 | wk 4 | wk 0 | wk 4 |
| 1 | 4 | 3784 | indeterminable* | 2353 |
| 2 | 4 | 862 | 480 | 938 |
| 3 | 4 | 3056 | 69 | 1497 |
| 4 | 4 | 1948 | indeterminable* | 1316 |
| 5 | 4 | 2360 | 4 | 4665 |
| 6 | 4 | 1594 | indeterminable* | 1835 |
| 7 | 4 | 4943 | 172 | 4085 |
| 8 | 4 | 2419 | 117 | 1458 |
| 9 | 4 | 1245 | indeterminable* | 527 |
| 10 | 4 | 616 | indeterminable* | 545 |
| GMT | 4 | 1917 | 77 | 1515 |

*Titer cannot be determined due to bad killing curves

All publications and patent applications mentioned in the specification are indicative of the level of those skilled in the art to which this invention pertains. All publications and patent applications are hereby incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

The invention claimed is:

1. A 21-valent immunogenic composition comprising glycoconjugates of capsular polysaccharide from *Streptococcus pneumoniae* serotypes 1, 3, 4, 5, 6A, 6B, 7F, 8, 9N, 9V, 10A, 11A, 12F, 14, 15B, 18C, 19A, 19F, 22F, 23F and 33F individually conjugated to a carrier protein, wherein the carrier protein of the glycoconjugates respectively comprising capsular polysaccharide of serotypes 8, 10A, 11A, 12F and 33F is $CRM_{197}$, and wherein the carrier protein of the glycoconjugates respectively comprising capsular saccharide of serotypes 15B and 22F is tetanus toxoid.

2. The 21-valent immunogenic composition of claim 1, wherein the carrier protein of the glycoconjugates comprising capsular polysaccharide of *Streptococcus pneumoniae* serotypes 3, 4, 6A, 6B, 9V, 14, 18C, 19A, 19F and 23F is $CRM_{197}$.

3. The 21-valent immunogenic composition of claim 2, wherein the carrier protein of the glycoconjugates comprising capsular polysaccharide of *Streptococcus pneumoniae* serotypes 7F and 9N is $CRM_{197}$.

4. The 21-valent immunogenic composition of claim 3, wherein the carrier protein of the glycoconjugates respectively comprising capsular polysaccharide of *Streptococcus pneumoniae* serotypes 1 and 5 is tetanus toxoid.

5. The 21-valent immunogenic composition of claim 4, wherein said glycoconjugates comprising capsular polysaccharide of *Streptococcus pneumoniae* serotypes 15B comprise at least 0.1 mM acetate per 1 mM of the respective capsular polysaccharide.

6. The 21-valent immunogenic composition of claim 5, wherein said glycoconjugates comprising capsular polysaccharide of *Streptococcus pneumoniae* serotypes 15B comprise at least 0.5 mM acetate per 1 mM of the respective capsular polysaccharide.

7. The 21-valent immunogenic composition of claim 6, wherein said glycoconjugates comprising capsular polysaccharide of *Streptococcus pneumoniae* serotypes 15B comprise less than 50% free polysaccharide.

8. The 21-valent immunogenic composition of claim 4, wherein said glycoconjugates comprising capsular polysaccharide of *Streptococcus pneumoniae* serotypes 22F comprise at least 0.1 mM acetate per 1 mM of the respective capsular polysaccharide.

9. The 21-valent immunogenic composition of claim 8, wherein said glycoconjugates comprising capsular polysaccharide of *Streptococcus pneumoniae* serotypes 22F comprise at least 0.5 mM acetate per 1 mM of the respective capsular polysaccharide.

10. The 21-valent immunogenic composition of claim 9, wherein said glycoconjugates comprising capsular polysaccharide of *Streptococcus pneumoniae* serotypes 22F comprise less than 50% free polysaccharide.

11. The 21-valent immunogenic composition of claim 4, wherein said glycoconjugates comprising capsular polysaccharide of *Streptococcus pneumoniae* serotypes 33F comprise at least 0.1 mM acetate per 1 mM of the respective capsular polysaccharide.

12. The 21-valent immunogenic composition of claim 11, wherein said glycoconjugates comprising capsular polysaccharide of *Streptococcus pneumoniae* serotypes 33F comprise at least 0.5 mM acetate per 1 mM of the respective capsular polysaccharide.

13. The 21-valent immunogenic composition of claim 12, wherein said glycoconjugates comprising capsular polysaccharide of *Streptococcus pneumoniae* serotypes 33F comprise less than 50% free polysaccharide.

14. The 21-valent immunogenic composition of claim 4, wherein said glycoconjugates comprising capsular polysaccharide of *Streptococcus pneumoniae* serotypes 15B, 22F and 33F comprise at least 0.5 mM acetate per 1 mM of the respective capsular polysaccharide and comprise less than 50% free polysaccharide of each respective capsular polysaccharide.

15. The multivalent immunogenic composition of claim 4, further comprising an adjuvant and a pharmaceutically acceptable excipient, carrier, or diluent.

16. The multivalent immunogenic composition of claim 15, wherein said multivalent immunogenic composition comprises 2.0 μg to 5.0 μg capsular saccharide of each *Streptococcus pneumoniae* serotype.

17. The multivalent immunogenic composition of claim 16, wherein said multivalent immunogenic composition comprises about 4.4 μg capsular saccharide of *Streptococcus pneumoniae* serotype 6B and about 2.2 μg capsular saccharide of each of the other *Streptococcus pneumoniae* serotypes.

18. The multivalent immunogenic composition of claim 16, wherein said multivalent immunogenic composition comprises 15 μg to 100 μg carrier protein.

19. The multivalent immunogenic composition of claim 16, wherein said multivalent immunogenic composition comprises 40 μg to 100 μg carrier protein.

* * * * *